United States Patent
Morley et al.

(10) Patent No.: US 11,485,731 B2
(45) Date of Patent: Nov. 1, 2022

(54) COMPOUNDS AND METHODS USEFUL IN THE TREATMENT OF A PRMT5-MEDIATED DISORDER

(71) Applicant: ARGONAUT THERAPEUTICS LIMITED, Oxford (GB)

(72) Inventors: Andrew Morley, Cambridge (GB); Rebecca Miller, Oxford (GB); Nicholas La Thangue, Oxford (GB)

(73) Assignee: ARGONAUT THERAPEUTICS LIMITED, Oxford (GB)

( * ) Notice: Subject to any disclaimer, the term of this patent is extended or adjusted under 35 U.S.C. 154(b) by 0 days.

(21) Appl. No.: 16/494,532

(22) PCT Filed: Mar. 16, 2018

(86) PCT No.: PCT/EP2018/056663
§ 371 (c)(1),
(2) Date: Sep. 16, 2019

(87) PCT Pub. No.: WO2018/167269
PCT Pub. Date: Sep. 20, 2018

(65) Prior Publication Data
US 2020/0325128 A1    Oct. 15, 2020

(30) Foreign Application Priority Data
Mar. 17, 2017   (GB) ..................... 1704327

(51) Int. Cl.
| | | |
|---|---|---|
| C07D 413/14 | (2006.01) | |
| A61P 35/00 | (2006.01) | |
| C07D 401/12 | (2006.01) | |
| C07D 409/14 | (2006.01) | |
| C07D 417/12 | (2006.01) | |
| C07D 417/14 | (2006.01) | |
| C07D 495/04 | (2006.01) | |
| C07D 498/08 | (2006.01) | |

(52) U.S. Cl.
CPC ............ *C07D 413/14* (2013.01); *A61P 35/00* (2018.01); *C07D 401/12* (2013.01); *C07D 409/14* (2013.01); *C07D 417/12* (2013.01); *C07D 417/14* (2013.01); *C07D 495/04* (2013.01); *C07D 498/08* (2013.01)

(58) Field of Classification Search
CPC .. C07D 401/12; C07D 401/14; C07D 217/04; C07D 217/06; C07D 491/08; C07D 405/14; C07D 417/12; C07D 409/12; C07D 409/14
See application file for complete search history.

(56) References Cited

FOREIGN PATENT DOCUMENTS

| | | |
|---|---|---|
| CN | 105452226 A | 3/2016 |
| WO | WO 2014/100695 A1 | 6/2014 |
| WO | WO 2014/100719 A2 | 6/2014 |
| WO | WO 2014/100730 A1 | 6/2014 |
| WO | WO 2014100695 A1 | 6/2014 |
| WO | WO 2014100719 A2 | 6/2014 |
| WO | WO 2014100764 A2 | 6/2014 |
| WO | WO 2015/200677 A2 | 12/2015 |
| WO | WO 2015200677 A2 | 12/2015 |
| WO | WO 2015200680 A2 | 12/2015 |
| WO | WO 2016/034673 A1 | 3/2016 |
| WO | WO 2016/034675 A1 | 3/2016 |
| WO | WO 2016034673 A1 | 3/2016 |

OTHER PUBLICATIONS

Combined Search and Examination Report under Sections 17 and 18(3) for Application No. GB1704327.4, dated Nov. 10, 2017; 9 pages.
International Search Report and Written Opinion of the International Searching Authority of PCT/EP2018/056663 dated Jun. 13, 2018, 10 pages.
CA index name 1-Pyrrolidinecarboxamide, N-[3-(3,4-dihydro-2(1H)-isoquinolinyl)propyl]-3-phenyl-; CA registry No. 1333788-94-5; Entered STN Sep. 29, 2011; Supplied by Enamine.
CA index name 1H-1,4-Diazepine-1-carboxamide, N-[3-(3,4-dihydro-2(1H)-isoquinolinyppropyl]hexahydro-4-(2,2,2-trifluoroethyl)-; CA registry No. 1625292-59-2; Entered STN Sep. 24, 2014; Supplied by UkrOrgSyntez Ltd.
CA index name 1-Pyrrolidinecarboxamide, N-[3-(3,4-dihydro-2(1H)-isoquinolinyl)propyl]-; CA registry No. 1626836-54-1; entered STN Sep. 26, 2014; Supplied by UkrOrgSyntez Ltd.
CA index name Cyclopenta[c]pyrrole-3a(1H)-carboxylic acid, 2-[[[3-(3,4-dihydro-2(1H) isoquinolinyl)propyl]amino]carbonyl]hexahydro-, (3aS,6aR)-; CA registry No. 1938575-25-7; Entered STN Jun. 24, 2016; Supplied by FCH group.
Chinese Office Action for CN Application No. 201880032332.4 dated Feb. 24, 2022; and translation.
Aurora Fine Chemicals; "CN 1-Piperidinecarboxamide, N-[3-(3,4-dihydro-2(1H)-isoquinoliny1)-2-hydroxypropy11-2,6-dimethyl— (CA Index Name)", RN 2061832-47-9 Registry; ED Entered STN: Jan. 30, 2017; LC STN Files: Chemcats; SR Chemical Library; MF C20 H31 N3 O2.
Aurora Fine Chemicals; CN 1-Pyrrolidinecarboxamide, N-[3-(3,4-dihydro-2(1H)-isoquinolinyl)propyl]-3-(hydroxymethyl)—(CA Index Name), RN 2072502-51-1 Registry; ED Entered STN: Feb. 20, 2017; LC STN Files: Chemcats; SR Chemical Library; MF C18 H27 N3 O2.
Aurora Fine Chemicals; "CN 1-Piperidinecarboxamide, N-[3-(3,4-dihydro-2(1H)-isoquinolinyl)propyl]-4-(hydroxymethyl)—(CA Index Name)", RN 2072374-01-5 Registry; ED Entered STN: Feb. 19, 2017; LC STN Files: Chemcats; SR Chemical Library; MF C19 H29 N3 O2.

(Continued)

*Primary Examiner* — Noble E Jarrell
(74) *Attorney, Agent, or Firm* — Squire Patton Boggs (US) LLP

(57) ABSTRACT

The present disclosure relates to compounds suitable for the inhibition of protein arginine methyl-transferase (PRMT), in particular PRMT5. These compounds may be for use as therapeutic agents, in particular, agents for use in the treatment and/or prevention of proliferative diseases, such as cancer.

20 Claims, No Drawings

(56) References Cited

OTHER PUBLICATIONS

Aurora Fine Chemicals, "CN 1-Piperidinecarboxamide, N-[3-(3,4-dihydro-2(1H)-isoquinolinyl)propyl]-3-hydroxy—(CA Index Name)", RN 2071765-89-2 Registry; ED Entered STN: Feb. 17, 2017; LC STN Files: Chemcats; SR Chemical Library; MF C18 H27 N3 O2.

Aurora Fine Chemicals; "CN 1-Piperidinecarboxamide, N-[3-(3,4-dihydro-2(1H)-isoquinolinyl)propyl]-3-(hydroxymethyl)—(CA Index Name)", RN 2071765-77-8 Registry; ED Entered STN: Feb. 17, 2017; LC STN Files: Chemcats; MF C19 H29 N3 O2.

Aurora Fine Chemicals, "CN 1-Pyrrolidinecarboxamide, N-[3-(3,4-dihydro-2(1H)-isoquinolinyl)propyl]-2-(hydroxymethyl)—(CA Index Name)", RN 2070287-48-6 Registry; ED Entered STN: Feb. 14, 2017; LC STN Files: Chemcats; MF C18 H27 N3 O2.

Aurora Fine Chemicals, "CN 1-Piperidinecarboxamide, N-[3-(3,4-dihydro-2(1H)-isoquinolinyl)propyl]-3-hydroxy-4-methyl—(CA Index Name)", RN 2061067-68-1 Registry; ED Entered STN: Jan. 29, 2017; LC STN Files: Chemcats; MF C19 H29 N3 O2.

FCH Group, "CN 3-Piperidinecarboxylic acid, 1-[[[3-(3,4-dihydro-2(1H)-isoquinolinyl)propyl]amino]carbonyl]-5-methyl—(CA Index Name)", RN 2031718-64-4 Registry; ED Entered STN: Nov. 15, 2016; LC STN Files: Chemcats; MF C20 H29 N3 O3.

FCH Group, "CN Cyclopenta[c]pyrrole-3a(1H)-carboxylic acid, 2-[[P -(3 ,4-dihydro -2 (1H)-isoquinolinyl)propyl]amino] c arbonyl]hexahydro-, (3aS,6aR)—(CA Index Name)", RN 1938575-25-7 Registry; ED Entered STN: Jun. 24, 2016; LC STN Files: Chemcats; MF C21 H29 N3 O3.

Ukrorgsyntez Ltd., "CN 4-Thiomorpholinecarboxamide, N-[3-(3,4-dihydro-2(1H)-isoquinolinyl)propyl—(CA Index Name)", RN 1825718-36-2 Registry; ED Entered STN: Dec. 9, 2015; LC STN Files: Chemcats; MF C17 H25 N3 O S.

Ukrorgsyntez Ltd., "CN 1H-1,4-Diazepine-l-carboxamide, 4-(4-chlorobenzoyl)-N-[3-(3,4-dihydro-2(1H)-isoquinolinyl)propyl]hexahydro—(CA Index Name)", RN 1647772-79-9 Registry; ED Entered STN: Feb. 15, 2015; LC STN Files: Chemcats; MF C25 H31 Cl N4 O2.

Ukrorgsyntez Ltd., "CN 1H-Indole-l-carboxamide, N-[3-(3,4-dihydro-2(1H)-isoquinolinyl)propyl]-2,3-dihydro-4-methyl—(CA Index Name)", RN 1647583-71-8 Registry; ED Entered STN: Feb. 15, 2015; MF C22 H27 N3 O.

Ukrorgsyntez Ltd., "CN 4-Morpholinecarboxamide, N-[3-(3,4-dihydro-2(1H)-isoquinolinyl)propyl]-2,2-dimethyl—(CA Index Name)", RN 1627182-83-5 Registry; ED Entered STN: Sep. 26, 2014; LC STN Files: Chemcats; MF C19 H29 N3 O2.

Ukrorgsyntez Ltd., "CN 1-Pyrrolidinecarboxamide, N-[3-(3,4-dihydro-2(1H)-isoquinolinyl)propyl—(CA Index Name)", RN 1626836-54-1 Registry; ED Entered STN: Sep. 26, 2014; LC STN Files: Chemcats; MF C17 H25 N3 O.

Ukrorgsyntez Ltd., "CN 1,4-Piperidinedicarboxamide, N143-(3,4-dihydro-2(1H)-isoquinolinyl)propyl]-N4,N4-dimethyl—(CA Index Name)", RN 1626550-16-0 Registry; ED Entered STN: Sep. 26, 2014; LC STN Files: Chemcats; MF C21 H32 N4 O2.

Ukrorgsyntez Ltd., "CN 1H-Azepine-l-carboxamide, N-[3-(3,4-dihydro-2(1H)-isoquinolinyl)propyl]hexahydro-2-(4-pyridinyl)—(CA Index Name)", RN 1626284-87-4 Registry; ED Entered STN: Sep. 25, 2014; LC STN Files: Chemcats; MF C24 H32 N4 O.

Ukrorgsyntez Ltd., "CN 1-Piperidinecarboxamide, N-[3-(3,4-dihydro-2(1H)-isoquinolinyl)propyl]-4-(2-methylpropoxy)—(CA Index Name)", RN 1626235-19-5 Registry; ED Entered STN: Sep. 25, 2014; LC STN Files: Chemcats; MF C22 H35 N3 O2.

Ukrorgsyntez Ltd., "CN Carbamic acid, N-[1-[[[3-(3,4-dihydro-2(1H)-isoquinolinyl)propyl]amino]carbonyl]-3-iperidinyl]-, ethyl ester (CA Index Name)", RN 1625868-58-7 Registry; ED Entered STN: Sep. 25, 2014; LC STN Files: Chemcats; MF C21 H32 N4 O3.

Ukrorgsyntez Ltd., "CN 1H-1,4-Diazepine-l-carboxamide, N-[3-(3,4-dihydro-2(1H)-isoquinolinyl)propyl]hexahydro-4-(2,2,2-trifluoroethyl)—(CA Index Name)", RN 1625292-59-2 Registry; ED Entered STN: Sep. 24, 2014; LC STN Files: Chemcats; MF C20 H29 F3 N4 O.

Ukrorgsyntez Ltd., "CN 1-Piperidinecarboxamide, N-[3-(3,4-dihydro-2(1H)-isoquinolinyl)propyl]-4-phenoxy—(CA Index Name)", RN 1624561-00-7 Registry; ED Entered STN: Sep. 23, 2014; LC STN Files: Chemcats; MF C24 H31 N3 O2.

Enamine, "CN 1-Pyrrolidinecarboxamide, N-[3-(3,4-dihydro-2(1H)-isoquinolinyl)propyl]-3-phenyl—(CA Index Name)", "Other CA Index Names:CN N-[3-(3,4-Dihydro-2(1H)-isoquinolinyl)propyl]-3-phenyl-1-pyrrolidinecarboxamide", RN 1333788-94-5 Registry; ED Entered STN: Sep. 29, 2011; LC STN Files: CA, CAPLUS, Casformultns, Casreact, Chemcats, Toxcenter, Uspatfull; MF C23 H29 N3 O.

COMPOUNDS AND METHODS USEFUL IN THE TREATMENT OF A PRMT5-MEDIATED DISORDER

INTRODUCTION

This application is a national stage filing under 35 USC § 371 of International Application No. PCT/EP2018/056663, which was filed Mar. 16, 2018 and which claims priority to, and the benefit of, GB 1704327.4, which was filed Mar. 17, 2017. The entire contents of each of these applications is herein incorporated by reference in their entirety for all purposes.

The present invention relates to compounds suitable for the inhibition of protein arginine methyl-transferase (PRMT), in particular PRMT5. These compounds may be for use as therapeutic agents, in particular, agents for use in the treatment and/or prevention of proliferative diseases, such as cancer.

BACKGROUND OF THE INVENTION

The transition from G1 into S phase of the cell cycle is tightly regulated in normal cells, but universally deregulated in tumour cells. The pathway involves the retinoblastoma tumour suppressor (pRb) protein, which acts to negatively regulate the G1 to S phase transition through its key target, the E2F family of transcription factors. E2F transcription factors control the expression of a variety of genes that are intimately connected with cell proliferation and cell death, including many involved with DNA synthesis. In tumour cells, normal regulation of E2F is lost (due to oncogenic mutation in the Rb gene or deregulation of Rb activity through other oncogenically-relevant mechanisms), liberating E2F, which subsequently drives cells into S phase and enables cell division to occur. The first member of the family, E2F1, is an important regulator of cell fate. E2F1 both promotes cell proliferation and also causes the opposing outcome, namely apoptosis (cell death).

The protein arginine methyl transferase PRMT5 is elevated in many human malignancies, including lymphomas, lung cancer, breast cancer and colorectal cancer, and its expression level correlates with poor disease prognosis. It is one of the major protein PRMTs in mammalian cells, exhibiting roles in cell death, cell-cycle progression, cell growth and cell proliferation. From the perspective of cancer drug discovery, arginine methylation of E2F1 by PRMT5 is responsible for keeping E2F1 in its growth stimulating mode. This occurs because arginine methylation by PRMT5 suppresses apoptosis driven by E2F-1, and thereby holds E2F-1 and cells expressing methylated E2F1 in their growing state. Thus, inhibiting PRMT5 enzyme activity provides a rational approach to reinstating tumour cell death by reactivating a physiological mechanism, dependent on E2F1 activity, which is responsible for keeping abnormal growth in check.

The relationship between PRMT5 and cancer has been studied extensively, for example, in the references cited below.

There is a need to develop compounds that reduce the expression or activity of PRMT5.

SUMMARY OF THE INVENTION

In one aspect, the present invention provides a compound of Formula I as defined herein, and/or a salt, hydrate or solvate thereof.

In another aspect, the present invention provides a pharmaceutical composition which comprises a compound of Formula I as defined herein, or a pharmaceutically acceptable salt, hydrate or solvate thereof, and one or more pharmaceutically acceptable excipients.

In another aspect, the present invention provides a compound of Formula I as defined herein, or a pharmaceutically acceptable salt, hydrate or solvate thereof, or a pharmaceutical composition as defined herein, for use in therapy.

In another aspect, the present invention provides a compound of Formula I as defined herein, or a pharmaceutically acceptable salt, hydrate or solvate thereof, or a pharmaceutical composition as defined herein, for use in the treatment or prevention of a PRMT5-mediated disorder.

In another aspect, the present invention provides a compound of Formula I as defined herein, or a pharmaceutically acceptable salt, hydrate or solvate thereof, or a pharmaceutical composition as defined herein, for use in the treatment of a proliferative disorder.

In another aspect, the present invention provides a compound of Formula I as defined herein, or a pharmaceutically acceptable salt, hydrate or solvate thereof, or a pharmaceutical composition as defined herein, for use in the treatment cancer.

In another aspect, the present invention provides the use of a compound of Formula I as defined herein, or a pharmaceutically acceptable salt, hydrate or solvate thereof, in the manufacture of a medicament for the treatment or prevention of a PRMT5-mediated disorder.

In another aspect, the present invention provides the use of a compound of Formula I as defined herein, or a pharmaceutically acceptable salt, hydrate or solvate thereof, in the manufacture of a medicament for the treatment of a proliferative disorder.

In another aspect, the present invention provides the use of a compound of Formula I as defined herein, or a pharmaceutically acceptable salt, hydrate or solvate thereof, in the manufacture of a medicament for the treatment of cancer.

In another aspect, the present invention provides a method of treating or preventing a PRMT5-mediated disorder, said method comprising administering to a subject in need thereof an effective amount of a compound of Formula I as defined herein, or a pharmaceutically acceptable salt, hydrate or solvate thereof.

In another aspect, the present invention provides a method of treating a proliferative disorder, said method comprising administering to a subject in need thereof an effective amount of a compound of Formula I as defined herein, or a pharmaceutically acceptable salt, hydrate or solvate thereof.

In another aspect, the present invention provides a method of treating cancer, said method comprising administering to a subject in need thereof a therapeutically effective amount of a compound of Formula I as defined herein, or a pharmaceutically acceptable salt, hydrate or solvate thereof, or a pharmaceutical composition as defined herein.

In another aspect, the present invention provides a method of inhibiting the activity of PRMT5 in vivo or in vitro, said method comprising administering to a subject in need thereof a therapeutically effective amount of a compound of Formula I as defined herein, or a pharmaceutically acceptable salt, hydrate or solvate thereof, or a pharmaceutical composition as defined herein.

In another aspect, the present invention provides a method of altering gene expression in a cell which comprises contacting a cell with an effective amount of a compound of Formula I as defined herein, or a pharmaceutically acceptable salt, hydrate or solvate thereof, or a pharmaceutical composition as defined herein.

In another aspect, the present invention provides a combination comprising a compound of Formula I, or a pharmaceutically acceptable salt, hydrate or solvate thereof, as defined herein, with one or more additional therapeutic agents.

Preferred, suitable, and optional features of any one particular aspect of the present invention are also preferred, suitable, and optional features of any other aspect.

DETAILED DESCRIPTION OF THE INVENTION

Definitions

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I" and the more general term "compounds" refer to and include any and all compounds described by and/or with reference to Formula I. It should also be understood that these terms encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formula I, either by themselves or in combination with additional agents.

The various hydrocarbon-containing moieties provided herein may be described using a prefix designating the minimum and maximum number of carbon atoms in the moiety, e.g. "$(C_{a-b})$" or "$C_a$-$C_b$" or "(a-b)C". For example, $(C_{a-b})$alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene (—$CH_2$—), the ethylene isomers (—$CH(CH_3)$— and —$CH_2CH_2$—), the propylene isomers (—$CH(CH_3)CH_2$—, —$CH(CH_2CH_3)$—, —$C(CH_3)_3$—, and —$CH_2CH_2CH_2$—), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl and naphthyl, suitably phenyl.

As used herein by themselves or in conjunction with another term or terms, "arylene" and "arylene group" refer to a phenylene (—$C_6H_4$—) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group"

refer to an alkyl group in which a hydrogen atom is replaced by an aryl group, wherein alkyl group and aryl group are as previously defined, such as, for example, $C_{1-6}$alkyl$C_{6-12}$aryl, preferably benzyl ($C_6H_5CH_2$—). Alkylaryl groups can be substituted or unsubstituted.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydronaphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. Suitably, cycloalkyl groups are selected from cyclopropyl, cyclobutyl, cyclopentyl and cyclohexyl groups.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2$—). Alkylcycloalkyl groups can be substituted or unsubstituted.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —Cl=$CH_2$, —C≡C—$CF_3$, —$CHFCH_2CH_3$ and —$CHFCH_2CF_3$. Haloalkyl groups can be substituted or unsubstituted. Suitably, a haloalkyl group is selected from $CHF_2$ and $CF_3$, suitably $CF_3$.

As used herein by themselves or in conjunction with another term or terms, "haloalkoxy" and "haloalkoxy group" refer to alkoxy groups (i.e. O-alkyl groups) in which one or more hydrogen atoms are replaced by halogen atoms. Haloalkoxy includes both saturated alkoxy groups as well as unsaturated alkenyl and alkynyl groups. Representative examples include, but are not limited to, —$OCF_3$, —$OCHF_2$, —$OCH_2F$, —$OCF_2CF_3$, —$OCHFCF_3$, —$OCH_2CF_3$, —$OCF_2CH_3$, —$OCHFCH_3$, —$OCF_2CF_2CF_3$, —$OCF_2CH_2CH_3$, —OCF=$CF_2$, —OCCl=$CH_2$, —OCBr=$CH_2$, —$OCHFCH_2CH_3$ and —$OCHFCH_2CF_3$. Haloalkoxy groups can be substituted or unsubstituted. Suitably, a haloalkyoxy group is selected from —$OCHF_2$ and —$OCF_3$, suitably —$OCF_3$.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0$^{2,7}$]dodeca-2(7),3,5-trienyl, 12-oxa-10-aza-tricyclo[6.3.1.0$^{2,7}$]dodeca-2(7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted. Where carbon numbers are provided, e.g. ($C_{n-m}$)alkylheteroaryl, the range refers to the whole group. Suitably, the consitutent alkyl group has 1-6 carbons, suitable 1-3 carbons.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation. Thus, a heterocyclic group should be understood as referring to and including ring systems that are fully saturated (such as, for example, a piperidinyl group), ring systems that are aromatic (such as, for example, a pyrindinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, azetidinyl, azepanyl, diazepanyl (such as 1,4-diazepanyl), oxazepanyl (such as 1,4-oxazepanyl), thiazepanyl (such as 1,4-thiazepanyl), tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo [3.2.1]octanyl, 3,8-diaza-bicyclo[3.2.1]octanyl, 2,5-diazabicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2] nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3] oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo [4,3-d][1,4]diazepin-7-yl and 6,8-dihydro-5H-[1,2,4] triazolo[4,3-a]pyrazin-7-yl. Suitably, a heterocyclylalkyl group as defined herein is a monocyclic, bicyclic or spiro heterocyclyl group comprising one, two or three heteroatoms selected from N, O or S.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl ($C_4H_8NCH_2$—). Alkylheteroyycloalkyl groups can be substituted or unsubstituted. Where carbon numbers are provided, e.g. ($C_{n-m}$)alkylheterocycloalkyl, the range refers to the whole group. Suitably, the consitutent alkyl group has 1-6 carbons, suitable 1-3 carbons.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by itself or in conjunction with another term or terms, "pseudohalogen" refers to —OCN, —SCN, —$CF_3$, and —CN.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety. For example, if $R^1$ is a methyl group (—$CH_3$), it can be optionally substituted by 1 to 3 $R^5$.

As used herein by themselves or in conjunction with another term or terms, "subject(s)" and "patient(s)", suitably refer to mammals, in particular humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder.

As used herein, a "therapeutically active agent", whether used alone or in conjunction with another term or terms, refers to any compound, i.e. a drug, that has been found to be useful in the treatment of a disease, disorder or condition and is not described by Formula I. It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

As used herein, the term "PRMT5-mediated disorder" means any disease, disorder, or other pathological condition in which PRMT5 is known to play a role. Accordingly, in some embodiments, the present disclosure relates to treating or lessening the severity of one or more diseases in which PRMT5 is known to play a role.

The invention will now be further described by way of the following numbered paragraphs:
1. A compound of formula I, or a salt, solvate or hydrate thereof,

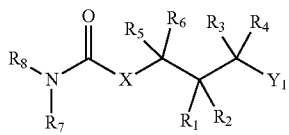

(I)

wherein,
$R_1$, $R_3$, $R_4$, $R_5$ and $R_6$ are each independently selected from hydrogen and $C_{1-3}$ alkyl;
$R_2$ is selected from hydrogen and $R_{14}$;
X is O or $NR_9$, where $R_9$ is hydrogen or a $C_{1-3}$ alkyl;
$Y_1$ is a group selected from one of formula A and B,

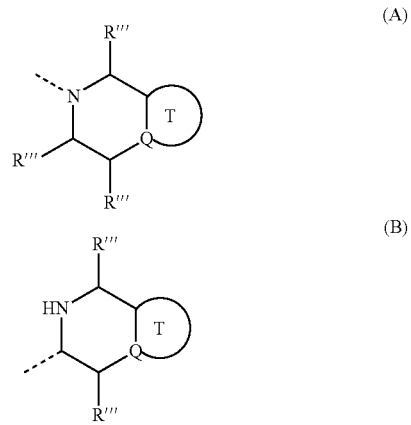

where each R''' is independently selected from H or $C_{1-3}$ alkyl;
Q is C or N;
T is selected from a fused phenyl group and a fused 5- or 6-membered heteroaryl group, wherein each group is optionally substituted with one or more substituents selected from halo and $C_{1-3}$ alkyl; and
$R_7$ and $R_8$ are taken together with the intervening nitrogen atom to form a 3-12 membered heterocycloalkyl ring, wherein the 3-12 membered heterocycloalkyl ring is optionally substituted with one or more $R_{10}$; and/or optionally fused to one or more $C_{6-12}$ aryl, $C_{5-12}$ heteroaryl, $C_{3-8}$ cycloalkyl and 3-12 membered heterocycloalkyl rings, wherein each fused $C_{6-12}$ aryl, $C_{5-12}$ heteroaryl, $C_{3-8}$ cycloalkyl and 3-12 membered heterocycloalkyl ring is optionally substituted with one or more $R_{14}$;
$R_{10}$ is selected from a group of the formula $L_1$-$L_2$-$R_{11}$ or $L_2$-$L_1$-$R_{11}$, where $L_1$ is a linker of the formula —[$CR_{12}R_{13}$]$_n$—, where n is an integer of from 0 to 3 and $R_{12}$ and $R_{13}$ are in each instance each independently selected from H or $C_1$ to $C_2$ alkyl,
where $L_2$ is absent or a linker that is selected from O, S, SO, $SO_2$, N(R'), C(O), C(O)O, [O(CH$_2$)$_r$]$_s$, [(CH$_2$)$_r$O]$_s$, OC(O), CH(OR'), C(O)N(R'), N(R')C(O), N(R')C(O)N(R'), $SO_2$N(R') or N(R')$SO_2$, where R' and R'' are each independently selected from hydrogen and a $C_1$ to $C_2$ alkyl, and where r is 1 or 2 and s is 1 to 4,
$R_{11}$ is independently selected from hydrogen, CN, $NO_2$, hydroxyl, =O, halogen, $C_{1-6}$ haloalkyl, $C_{1-6}$ haloalkoxy, $C_{1-6}$alkyl, O—$C_{1-6}$alkyl, $C_{3-6}$ cycloalkyl, $C_{6-12}$ aryl, $C_{5-12}$ heteroaryl, 3-10 membered (e.g. 3-7 membered) heterocycloalkyl, —C(=O)$R^d$, —C(=O)O$R^d$, —C(=O)NR$^e$R$^d$, —C(O)C(=O)$R^d$, —NR$^e$R$^d$, —NR$^e$C(=O)$R^d$, —NR$^e$C(=O)O$R^d$, —NR$^e$C(=O)NR$^e$R$^d$, —NR$^e$S(=O)$_2$R$^d$, —NR$^e$S(=O)$_2$NR$^e$R$^d$, —OR$^d$, —SR$^d$, —OC(=O)$R^d$, —OC(=O)NR$^e$R$^d$, —OC(=O)O$R^d$, —S(=O)$_2$R$^d$, —S(=O)$R^d$, —OS(=O)$R^d$, —OS(=O)$_2$R$^d$, —OS(=O)$_2$OR$^d$, —S(=O)NR$^e$R$^d$, —OS(=O)$_2$NR$^e$R$^d$, and —S(=O)$_2$NR$^e$R$^d$, wherein, where $R_{11}$ is independently selected from $C_{3-6}$ cycloalkyl, $C_{6-12}$ aryl, $C_{5-12}$ heteroaryl and 3-10 membered (e.g. 3-7 membered) heterocycloalkyl, each $C_{3-6}$ cycloalkyl, $C_{6-12}$ aryl, $C_{5-12}$ heteroaryl and 3-10 membered (e.g. 3-7 membered) heterocycloalkyl is optionally substituted with one or more $R_{14}$;
each $R^a$ and $R^b$ is independently selected from hydrogen and $C_{1-6}$ alkyl;
each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$alkyl, O—$C_{1-6}$alkyl and $C_{6-11}$aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, =O, halogen, CN, COR$^a$, NR$^a$Rb, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl;

each R$^e$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl; or R$^e$ and R$^d$, when attached to the same atom, together with the atom to which they are attached form a 3-7 membered heterocycloalkyl ring, optionally substituted with one or more substituent selected from hydroxyl, =O, halogen, CN, COR$^a$, NR$^a$R$^b$, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl;

and $R^{14}$ is independently selected from halo, CN, NO$_2$, hydroxyl, =O, halogen, $C_{1-6}$ haloalkyl, $C_{1-6}$ haloalkoxy, $C_{1-6}$ alkyl, O—$C_{1-6}$ alkyl, $C_{3-6}$ cycloalkyl, $C_{6-12}$ aryl, 5-6 membered heteroaryl, 3-7 membered heterocycloalkyl, $C_{1-6}$alkyl$C_{6-12}$aryl, —C(=O)R$^d$, —C(=O)OR$^d$, —C(=O)NR$^e$R$^d$, —C(O)C(=O)R$^d$, —NR$^e$R$^d$, —NR$^e$C(=O)R$^d$, —NR$^e$C(=O)OR$^d$, —NR$^e$C(=O)NR$^e$R$^d$, —NR$^e$S(=O)$_2$R$^d$, —NR$^e$S(=O)$_2$NR$^e$R$^d$, —OR$^d$, —SR$^d$, —OC(=O)R$^d$, —OC(=O)NR$^e$R$^d$, —OC(=O)OR$^d$, —S(=O)$_2$R$^d$, —S(=O)R$^d$, —OS(=O)R$^d$, —OS(=O)$_2$R$^d$, —OS(=O)$_2$OR$^d$, —S(=O)NR$^e$R$^d$, —OS(=O)$_2$NR$^e$R$^d$, and —S(=O)$_2$NR$^e$R$^d$.

2. A compound according to paragraph 1, or a salt, solvate or hydrate thereof, wherein X is NH.

3. A compound according to paragraph 1, or a salt, solvate or hydrate thereof, wherein X is O.

4. A compound according to any preceding paragraph, or a salt, solvate or hydrate thereof, wherein R$_2$ is OH.

5. A compound according to any preceding paragraph, or a salt, solvate or hydrate thereof, wherein R$_1$, R$_3$, R$_4$, R$_5$ and R$_6$ are each hydrogen or $C_1$ alkyl.

6. A compound according to paragraph 5, or a salt, solvate or hydrate thereof, wherein R$_1$, R$_3$, R$_4$, R$_5$ and R$_6$ are each hydrogen.

7. A compound according to any preceding paragraph, or a salt, solvate or hydrate thereof, wherein T is a fused phenyl which is optionally substituted with one or more substituents selected from halo and $C_1$ to $C_3$ alkyl.

8. A compound according to any one of paragraphs 1 to 6, or a salt, solvate or hydrate thereof, wherein the T is a fused 5- or 6-membered heteroaryl group optionally substituted with one or more substituents selected from halo and $C_1$ to $C_3$ alkyl.

9. A compound according to paragraph 8, or a salt, solvate or hydrate thereof, wherein T is a fused 5-membered heteroaryl group optionally substituted with one or more substituents selected from halo and $C_1$ to $C_3$ alkyl.

10. A compound according to paragraph 8 or 9, or a salt solvate or hydrate thereof, wherein T comprises one or two heteroatoms selected from N, S and O.

11. A compound according to paragraph 10, or a salt or solvate or hydrate thereof, wherein T comprises a first heteroatom selected from N, and a second heteroatom selected from N, S and O.

12. A compound according to paragraph 8, or a salt or solvate or hydrate thereof, wherein T comprises a pyridinyl or a diazinyl group optionally substituted with one or more substituents selected from halo and $C_1$ to $C_3$ alkyl.

13. A compound according to paragraph 8, or a salt or solvate or hydrate thereof, wherein T comprises a pyrrolyl, imidazolyl, pyralozyl, oxazolyl, isooxazolyl, thiazolyl and isothiazolyl optionally substituted with one or more substituents selected from halo and $C_1$ to $C_3$ alkyl.

14. A compound according to any preceding paragraph, or a salt or solvate or hydrate thereof, wherein each R'" is hydrogen.

15. A compound according to any preceding paragraph, or a salt or solvate or hydrate thereof, wherein T is optionally substituted with 1-4 substituents.

16. A compound according to paragraph 15, or a salt or solvate or hydrate thereof, wherein T is optionally substituted with 1 or 2 substituents.

17. A compound according to paragraph 15 or 16, or a salt or solvate or hydrate thereof, wherein T is optionally substituted with one or two $C_{1-3}$alkyl.

18. A compound according to paragraph 15, or a salt, solvate or hydrate thereof, wherein T is unsubstituted.

19. A compound according to any preceding paragraph, or a salt, solvate or hydrate thereof, wherein $Y_1$ is a group of the formula B.

20. A compound according to paragraph 19, or a salt, solvate or hydrate thereof, wherein Q is C.

21. A compound according to paragraph 19 or 20, or a salt, solvate or hydrate thereof, wherein T is a fused phenyl group.

22. A compound according to paragraph 21, or a salt, solvate or hydrate thereof, wherein $Y_1$ is of the formula

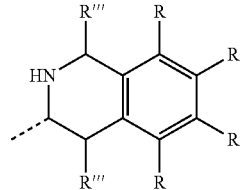

where each R and each R'" is independently selected from H and $C_{1-3}$ alkyl.

23. A compound according to any one of paragraphs 1 to 19, or a salt, solvate or hydrate thereof, wherein $Y_1$ is a group of the formula A.

24. A compound according to paragraph 23, or a salt, solvate or hydrate thereof, wherein Q is N.

25. A compound according to paragraph 23, or a salt, solvate or hydrate thereof, wherein Q is C.

26. A compound according to any preceding paragraph, or a salt, solvate or hydrate thereof, wherein $Y_1$ is selected from:

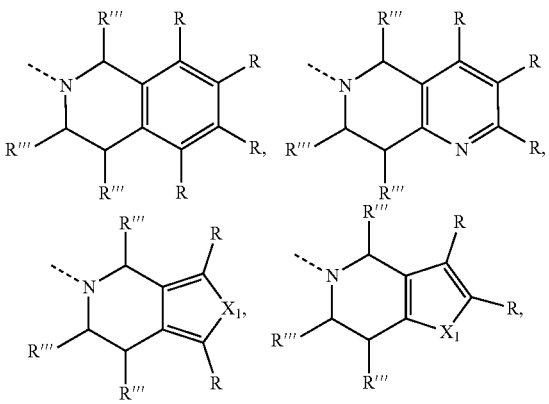

-continued

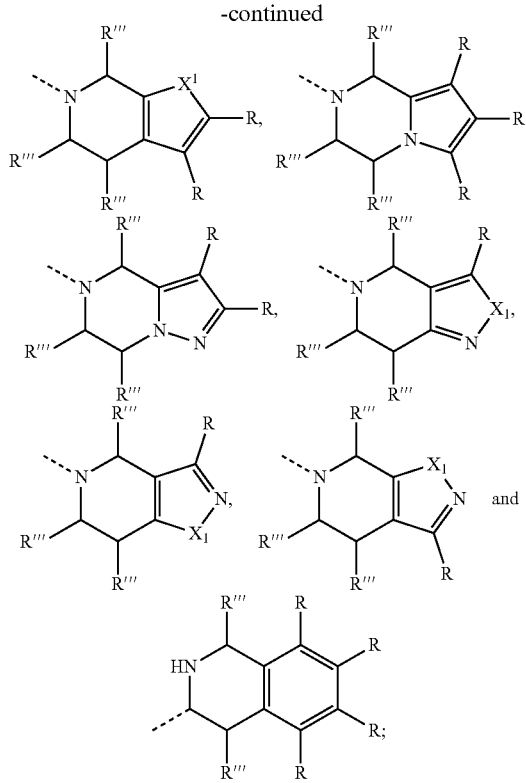

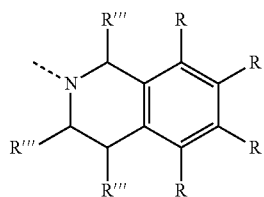

wherein each R and R''' is independently selected from one of H, $C_{1-3}$ alkyl or halo and $X_1$ is selected from N(R'), S or O, wherein R' is H or $C_{1-3}$ alkyl.

27. A compound according to paragraph 26, or a salt, solvate or hydrate thereof, wherein $Y_1$ is selected from:

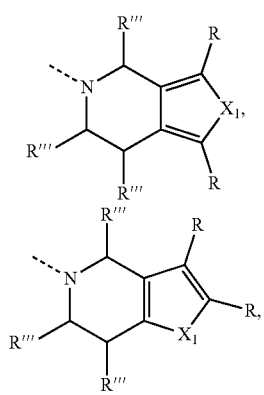

28. A compound according to paragraph 26, or a salt, solvate or hydrate thereof, wherein $Y_1$ is selected from:

-continued

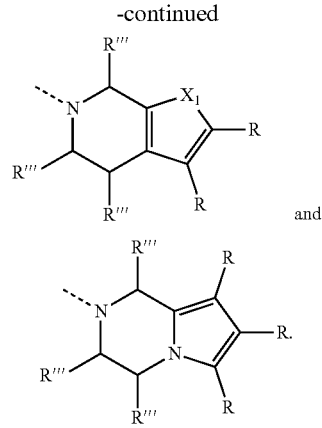

and

29. A compound according to paragraph 26, or a salt, solvate or hydrate thereof, wherein $Y_1$ is selected from:

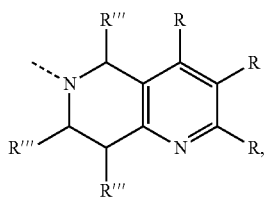

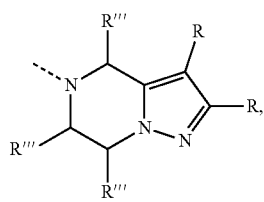

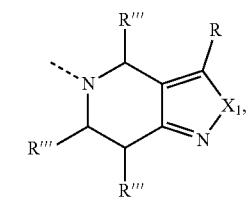

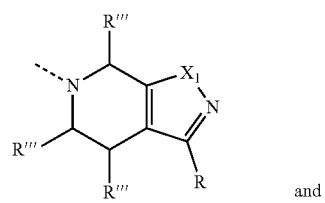

and

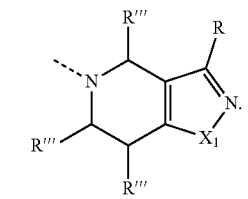

30. A compound according to any preceding paragraph, or a salt, solvate or hydrate thereof, wherein $Y_1$ is selected from

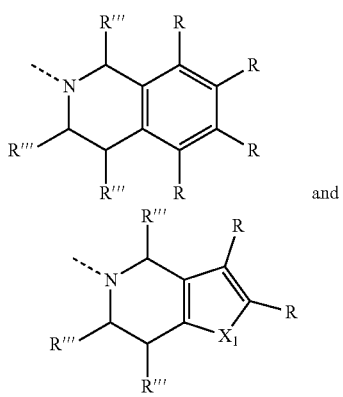

wherein each R and R''' is selected from H and $C_1$ to $C_3$ alkyl, and $X_1$ is S.

31. A compound according to any preceding paragraph, wherein $R_2$ is hydroxyl.

32. A compound according to any preceding paragraph, or a salt, solvate or hydrate thereof, wherein the 3-12 membered heterocycloalkyl ring formed from $R_7$ and $R_8$ taken together with the intervening nitrogen atom is a monocyclic ring.

33. A compound according to any preceding paragraph, or a salt, solvate or hydrate thereof, wherein the 3-12 membered heterocycloalkyl ring formed from $R_7$ and $R_8$ taken together with the intervening nitrogen atom is a 4-10, preferably 5-8, more preferably 5-7 membered heterocycloalkyl ring.

34. A compound according to any preceding paragraph, or a salt, solvate or hydrate thereof, wherein, in the 3-12 membered heterocycloalkyl ring formed from $R_7$ and $R_8$ taken together with the intervening nitrogen atom, the intervening nitrogen atom is the sole heteroatom in the 3-12 membered heterocycloalkyl ring.

35. A compound according to paragraph 34, or a salt, solvate or hydrate thereof, wherein the 3-12 membered heterocycloalkyl ring formed from $R_7$ and $R_8$ taken together with the intervening nitrogen atom is a 4, 5, 6 or 7 membered heterocycloalkyl ring.

36. A compound according to paragraph 35, or a salt, solvate or hydrate thereof, wherein the 4, 5, 6 or 7 membered heterocycloalkyl ring is selected from a pyrrolidinyl, piperidinyl, azepanyl ring.

37. A compound according to any one of paragraphs 1 to 33, or a salt, solvate or hydrate thereof, wherein the 3-12 membered heterocycloalkyl ring formed from $R_7$ and $R_8$ taken together with the intervening nitrogen atom comprises at least two heteroatoms, the first of which is the intervening nitrogen between $R_7$ and $R_8$.

38. A compound according to paragraph 37, or a salt, solvate or hydrate thereof, wherein the 3-12 membered heterocycloalkyl ring comprises a second heteroatom is selected from O, S and N.

39. A compound according to paragraph 38, wherein the 3-12 membered heterocycloalkyl ring comprises S as the second heteroatom, and wherein the S is substituted with one or two =O groups.

40. A compound according to any one of paragraphs 37 to 39, or a salt solvate or hydrate thereof, wherein the 3-12 membered heterocycloalkyl ring formed from $R_7$ and $R_8$ taken together with the intervening nitrogen atom is a 4, 5, 6 or 7 membered heterocycloalkyl ring.

41. A compound according to paragraph 40, or a salt, solvate or hydrate thereof, wherein the 4, 5, 6 or 7 membered heterocycloalkyl ring is selected from a piperizinyl, morpholinyl and diazepanyl ring.

42. A compound according to any preceding paragraph, or a salt, solvate or hydrate thereof, wherein the 3-12 membered heterocycloalkyl ring formed from $R_7$ and $R_8$ taken together with the intervening nitrogen atom that is unsubstituted or substituted with one or more $R_{10}$.

43. A compound according to paragraph 42, or a salt, solvate or hydrate thereof, wherein the 3-12 membered heterocycloalkyl ring formed from $R_7$ and $R_8$ taken together with the intervening nitrogen atom that is unsubstituted or substituted with a single $R_{10}$ substituent.

44. A compound according to paragraph 42 or 43, or a salt, solvate or hydrate thereof, wherein the 3-12 membered heterocycloalkyl ring formed from $R_7$ and $R_8$ taken together with the intervening nitrogen atom that is substituted with one or more $R_{10}$.

45. A compound according to paragraph 44, or a salt, solvate or hydrate thereof, wherein wherein $R_{11}$ is independently selected from hydroxyl, $C_{1-6}$ alkyl, $C_{6-12}$ aryl, $C_{5-12}$ heteroaryl and —C(=O)$R^d$, wherein, where $R_{11}$ is $C_{6-12}$ aryl and/or $C_{5-12}$ heteroaryl, the $C_{6-12}$ aryl and/or $C_{5-12}$ heteroaryl is optionally substituted with one or more $R_{14}$.

46. A compound according to paragraph 45, or a salt, solvate or hydrate thereof, wherein $R_{11}$ is $C_{6-12}$ aryl and/or $C_{5-12}$ heteroaryl that is optionally substituted with one or more $R_{14}$.

47. A compound according to paragraph 45, or a salt, solvate or hydrate thereof, wherein $R_{11}$ is independently selected from hydroxyl, $C_{1-3}$ alkyl, phenyl and —C(=O)$R^d$, wherein $R^d$ is H or $C_{1-6}$ alkyl, wherein where $R_{11}$ is phenyl, the phenyl is optionally substituted with one or more $R_{14}$.

48. A compound according to paragraph 47, or salt, solvate or hydrate thereof, wherein $R_{11}$ is selected from phenyl that is optionally substituted with one or more $R_{14}$.

49. A compound according to any preceding paragraph, or a salt, solvate or hydrate thereof, wherein $L_1$ is a linker of the formula —[$CR_{12}R_{13}$]$_n$—, where n is an integer of from 0 to 3, and $R_{12}$ and $R_{13}$ are in each instance each independently selected from H or $C_1$ to $C_2$ alkyl.

50. A compound according to paragraph 49, or a salt, solvate or hydrate thereof, where $R_{12}$ and $R_{13}$ are in each instance each independently selected from H or methyl.

51. A compound according to paragraph 50, or a salt, solvate or hydrate thereof, where $R_{12}$ and $R_{13}$ are in each instance each independently selected from H.

52. A compound according to any preceding paragraph, or a salt, solvate or hydrate thereof, wherein where $L_2$ is absent or a linker that is selected from O, C(O) and N(R'), where R' is H or $C_1$ to $C_2$ alkyl.

53. A compound according to any preceding paragraph, or a salt, solvate or hydrate thereof, wherein $R_{10}$ is selected from a group of the formula $L_1$-$L_2$-$R_{11}$ or $L_2$-$L_1$-$R_{11}$, where $L_1$ is a linker of the formula —[$CH_2$]$_n$—, where n is 0, 1 or 2, and where $L_2$ is absent or a linker that is selected from O, C(O) and N(R'), where R' is H or $C_1$ to $C_2$ alkyl.

54. A compound according to any preceding paragraph, or a salt, solvate or hydrate thereof, wherein $R_{10}$ is selected from $C_{1-3}$alkyl, phenyl, hydroxyl, —C(=O)$CH_3$, benzyl, phenoxy and —$CH_2OH$.

55. A compound according to paragraph 54, or a salt, solvate or hydrate thereof, wherein $R_{10}$ is selected from phenyl, benzyl and phenoxy.

56. A compound according to paragraph 54 or 55, or a salt, solvate or hydrate thereof, wherein the 3-12 membered heterocycloalkyl ring formed by $R_7$ and $R_8$ taken together with the intervening nitrogen atom is selected from a pyrrolidinyl, piperidinyl, azepanyl and piperizinyl ring.

57. A compound according to any preceding paragraph, or a salt, solvate or hydrate thereof, wherein the 3-12 membered heterocycloalkyl ring formed from $R_7$ and $R_8$ taken together with the intervening nitrogen atom is fused to one or more $C_{6-12}$ aryl, $C_{5-12}$ heteroaryl, $C_{3-8}$ cycloalkyl and 3-12 membered heterocycloalkyl rings, wherein each fused $C_{6-12}$ aryl, $C_{5-12}$ heteroaryl, $C_{3-8}$ cycloalkyl and 3-12 membered heterocycloalkyl ring is optionally substituted with $R_{14}$.

58. A compound according to paragraph 57, or a salt, solvate or hydrate thereof, wherein the 3-12 membered heterocycloalkyl ring formed by $R_7$ and $R_8$ taken together with the intervening nitrogen atom is not substituted with any $R_{10}$ groups but is fused to one or more $C_{6-12}$ aryl, $C_{5-12}$ heteroaryl, $C_{3-8}$ cycloalkyl and 3-12 membered heterocycloalkyl rings, wherein each fused $C_{6-12}$ aryl, $C_{5-12}$ heteroaryl, $C_{3-8}$ cycloalkyl and 3-12 membered heterocycloalkyl ring is optionally substituted with $R_{14}$.

59. A compound according to paragraph 57 or 58, or a salt, solvate or hydrate thereof, wherein the 3-12 membered heterocycloalkyl ring formed by $R_7$ and $R_8$ taken together with the intervening nitrogen is fused to a single ring selected from $C_{6-12}$ aryl, $C_{5-12}$ heteroaryl, $C_{3-8}$ cycloalkyl and 3-12 membered heterocycloalkyl rings, wherein the fused $C_{6-12}$ aryl, $C_{5-12}$ heteroaryl, $C_{3-8}$ cycloalkyl or 3-12 membered heterocycloalkyl ring is optionally substituted with $R_{14}$.

60. A compound according to any one of paragraphs 57 to 59, or a salt, solvate or hydrate thereof, wherein the 3-12 membered heterocycloalkyl ring formed by $R_7$ and $R_8$ taken together with the intervening nitrogen is fused to at least one $C_{6-12}$ aryl ring and/or at least one $C_{5-12}$ heteroaryl ring, wherein each fused $C_{6-12}$ aryl ring and/or $C_{5-12}$ heteroaryl ring is optionally substituted with $R_{14}$.

61. A compound according to paragraph 60, or a salt, solvate or hydrate thereof, wherein the 3-12 membered heterocycloalkyl ring formed by $R_7$ and $R_8$ taken together with the intervening nitrogen is fused to at least one phenyl group that is optionally substituted with $R_{14}$.

62. A compound according to any one of paragraphs 57 to 61, or a salt, solvate or hydrate thereof, wherein the 3-12 membered heterocycloalkyl ring formed by $R_7$ and $R_8$ taken together with the intervening nitrogen is selected from a pyrrolidinyl, piperidinyl, azepanyl and piperizinyl ring.

63. A compound according to paragraph 62, or a salt, solvate or hydrate thereof, wherein the 3-12 membered heterocycloalkyl ring formed by $R_7$ and $R_8$ are taken together with the intervening nitrogen is selected from a piperidinyl or azepanyl ring.

64. A compound according to any preceding paragraph, or a salt, solvate or hydrate thereof, wherein $R_{14}$ is absent or selected from $C_{1-3}$ alkyl, halo or hydroxyl.

65. A compound according to any preceding paragraph, or a salt, solvate or hydrate thereof, wherein $R_7$ and $R_8$ are taken together with the intervening nitrogen atom to form a group selected from:

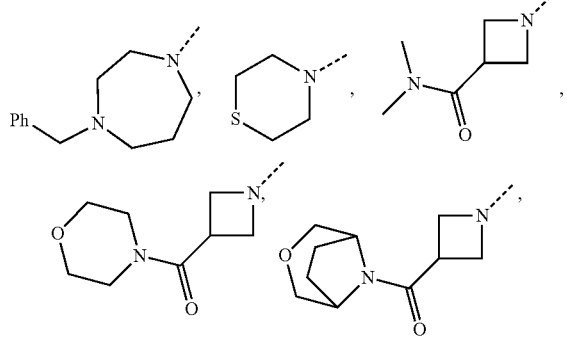

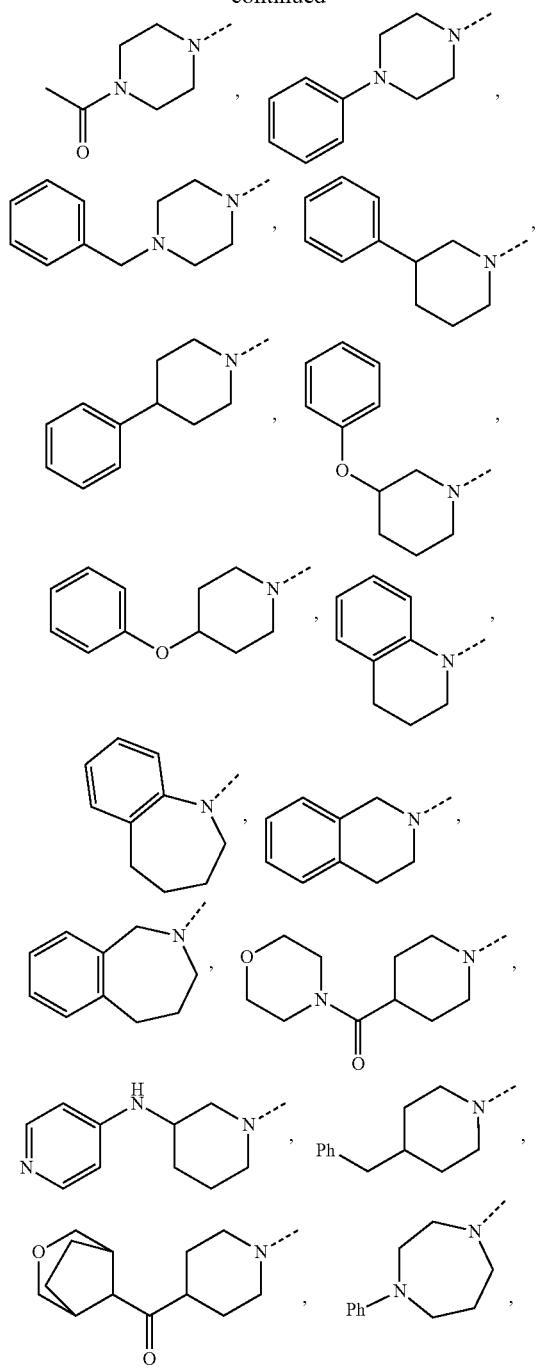

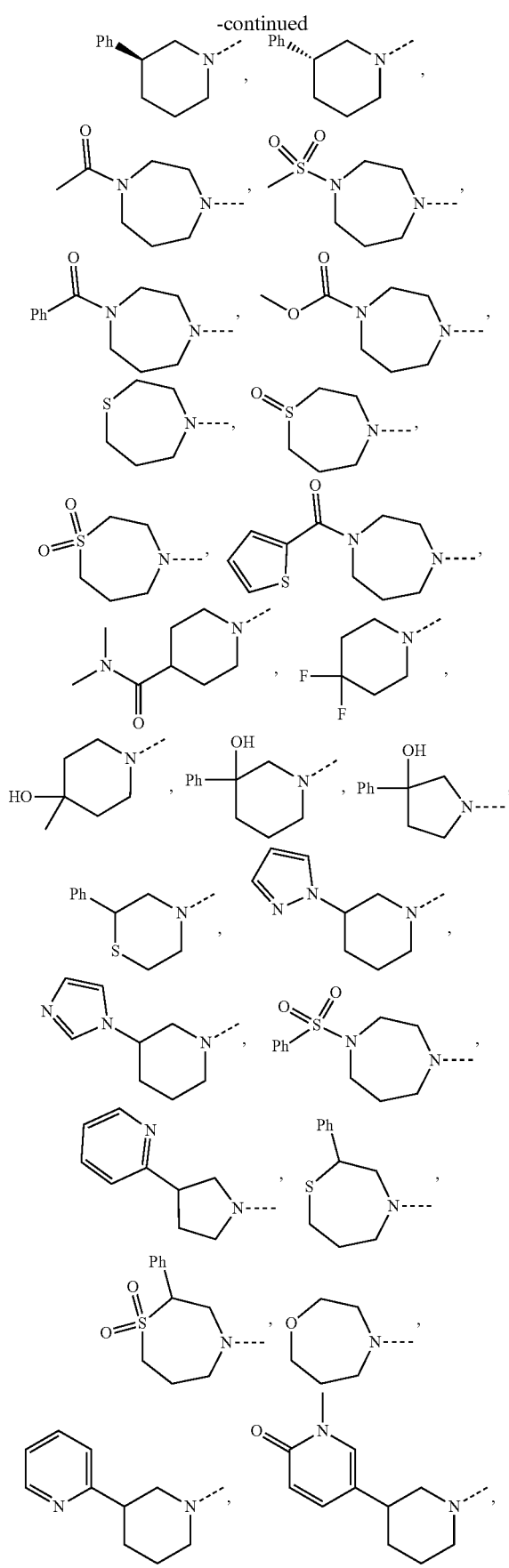
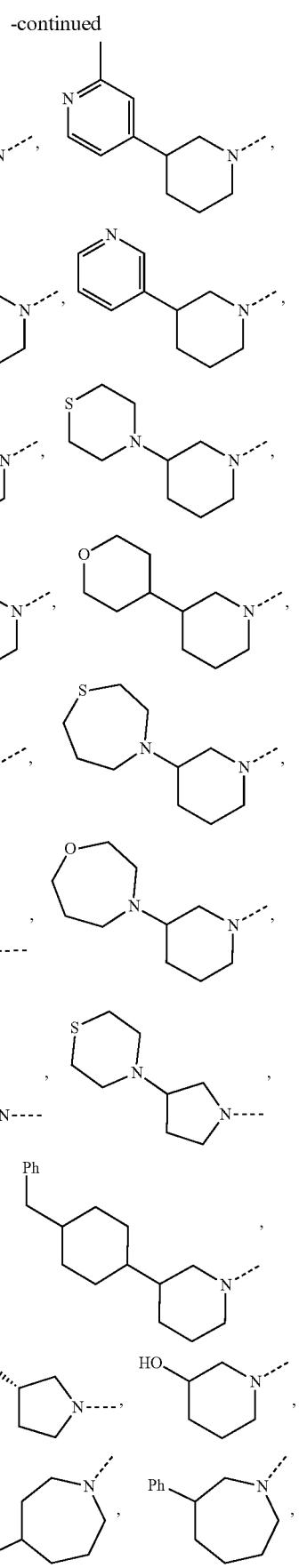

-continued

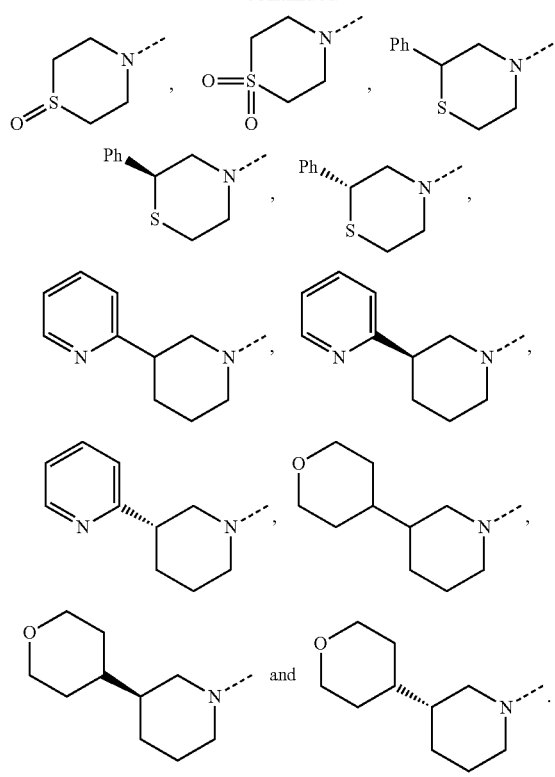

66. A Compound according to paragraph 63, or a salt, solvate or hydrate thereof, wherein $R_7$ and $R_8$ are taken together with the intervening nitrogen atom to form a group selected from:

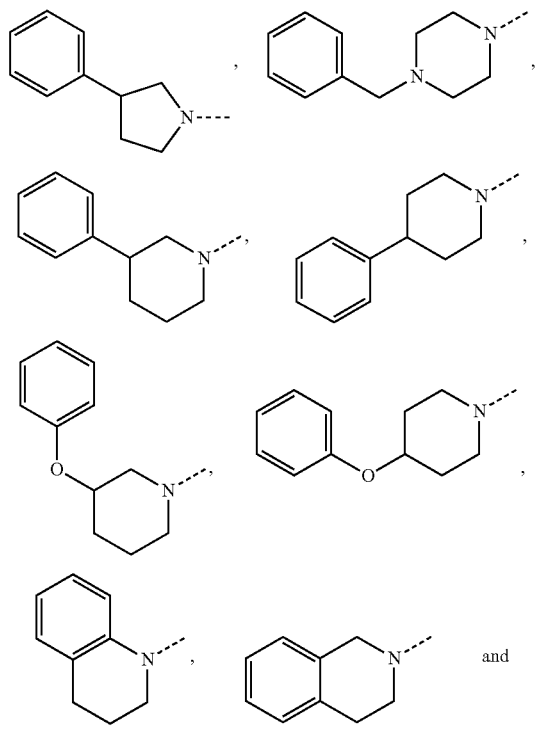

-continued

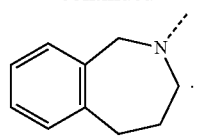

67. A compound according to paragraph 64, or a salt, solvate or hydrate thereof, wherein $R_7$ and $R_8$ are taken together with the intervening nitrogen atom to form a group selected from:

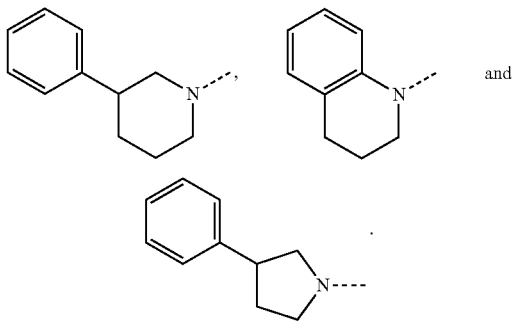

68. A compound according to any one of paragraphs 1 to 64, or a salt, solvate or hydrate thereof, wherein $R_7$ and $R_8$ are taken together with the intervening nitrogen atom to form a group selected from:

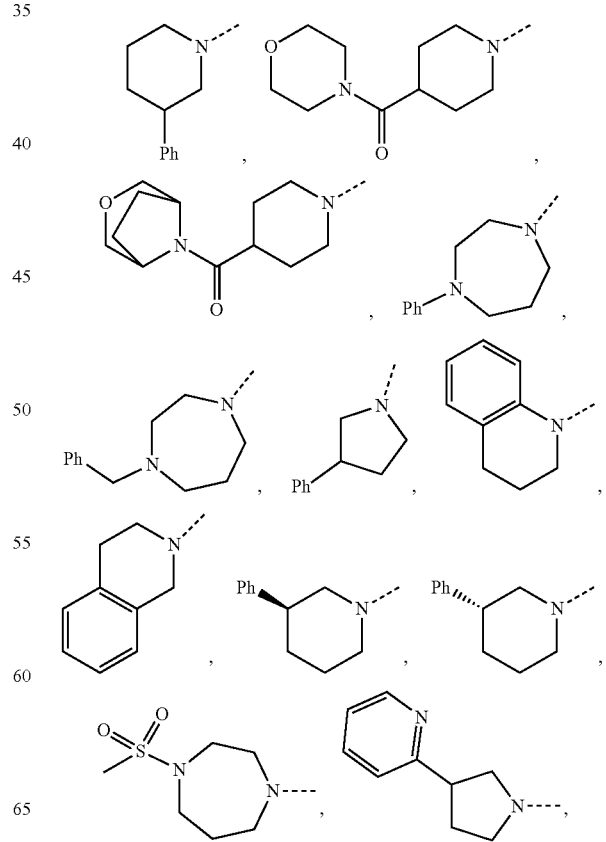

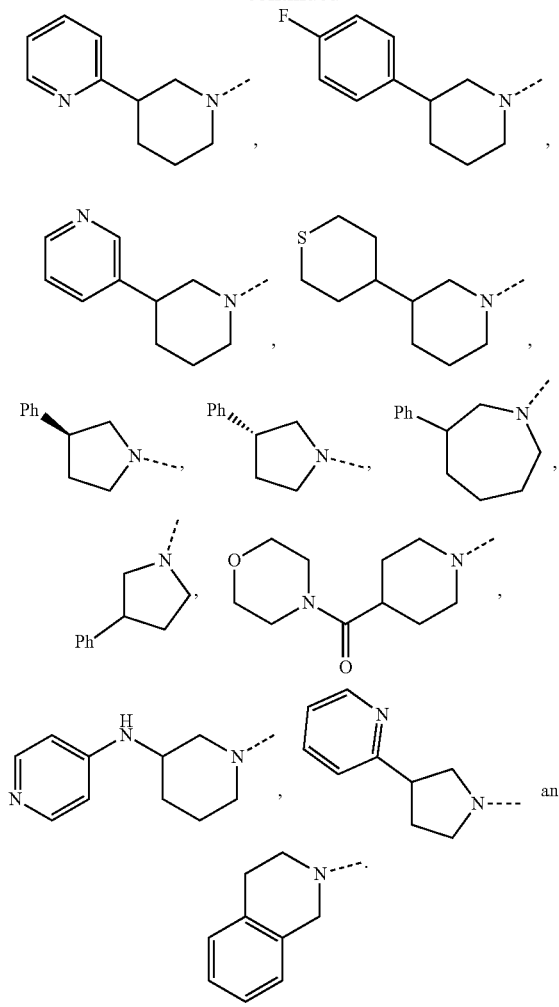

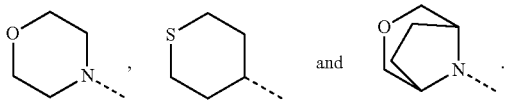

wherein said heterocycloalkyl is optionally substituted with one or more $R_{14}$.

71. A compound according to paragraph 69 or 70, or a salt, solvate or hydrate thereof, wherein the $C_{6-12}$ aryl is a phenyl, and wherein the $C_{5-12}$ heteroaryl is pyridinyl, said phenyl or pyridinyl being optionally substituted with one or more $R_{14}$.

72. A compound according to paragraph 69 or 70, wherein $Y_1$ is selected from

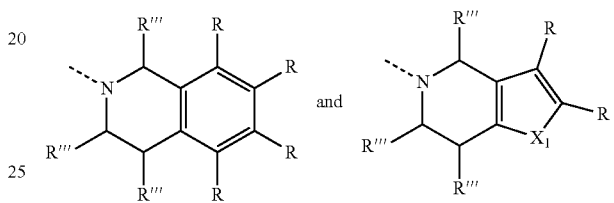

wherein each R and R''' is selected from H and $C_1$ to $C_3$ alkyl, and $X_1$ is S; and $R_2$ is hydroxyl.

73. A compound, or a salt, solvate or hydrate thereof, selected from:

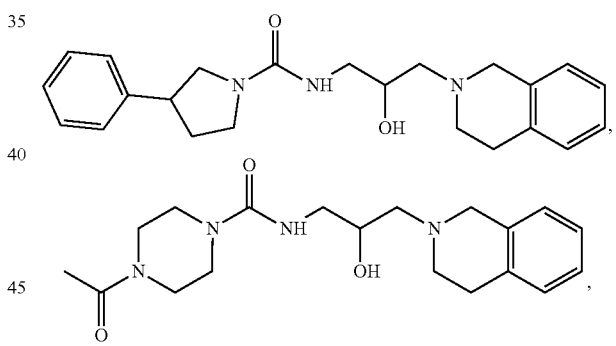

69. A compound according to any preceding paragraph, or a salt, solvate or hydrate thereof, wherein $R_7$ and $R_8$ are taken together with the intervening nitrogen atom to form a 4-7 membered heterocycloalkyl ring, wherein the 4 to 7 membered heterocycloalkyl ring is
   (i) unsubstituted, or either
   (ii) substituted with at least one $R_{10}$, where $R_{10}$ is $L_1$-$L_2$-$R_{11}$ or $L_2$-$L_1$-$R_{11}$, where L is a linker of the formula —[$CR_{12}R_{13}$]$_n$—, where n is an integer of from 0 to 3 and $R_{12}$ and $R_{13}$ are in each instance each independently selected from H or $C_1$ to $C_2$ alkyl, and where $L_2$ is absent or a linker that is selected from O, C(O) or N(R'), where R' is H or $C_1$ to $C_2$ alkyl, and $R_1$ is —S(=O)$_2$$R_d$, $C_{6-12}$ aryl (e.g. phenyl), 3-10 membered heterocycloalkyl or $C_{5-12}$ heteroaryl, wherein the $C_{6-12}$ aryl, 3-10 membered heterocycloalkyl and/or $C_{5-12}$ heteroaryl is optionally substituted with one or more $R_{14}$; and/or
   (iii) fused to at least one $C_{6-12}$ aryl (e.g. phenyl), or $C_{5-12}$ heteroaryl; wherein the $C_{6-12}$ aryl and/or $C_{5-12}$ heteroaryl is optionally substituted with one or more $R_4$.

70. A compound according to paragraph 69, or a salt, solvate or hydrate thereof, wherein the 3-10 membered heterocycloalkyl is selected from:

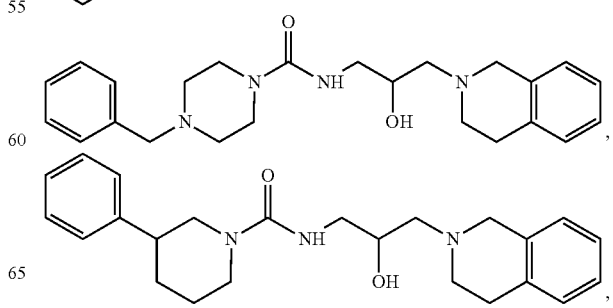

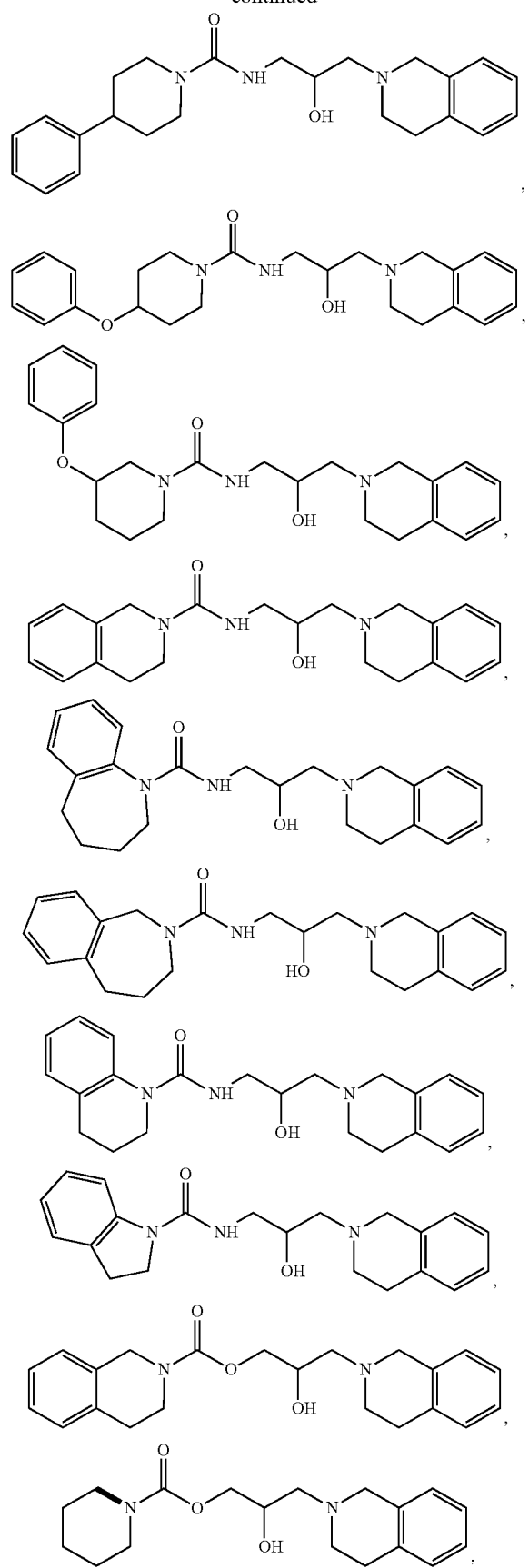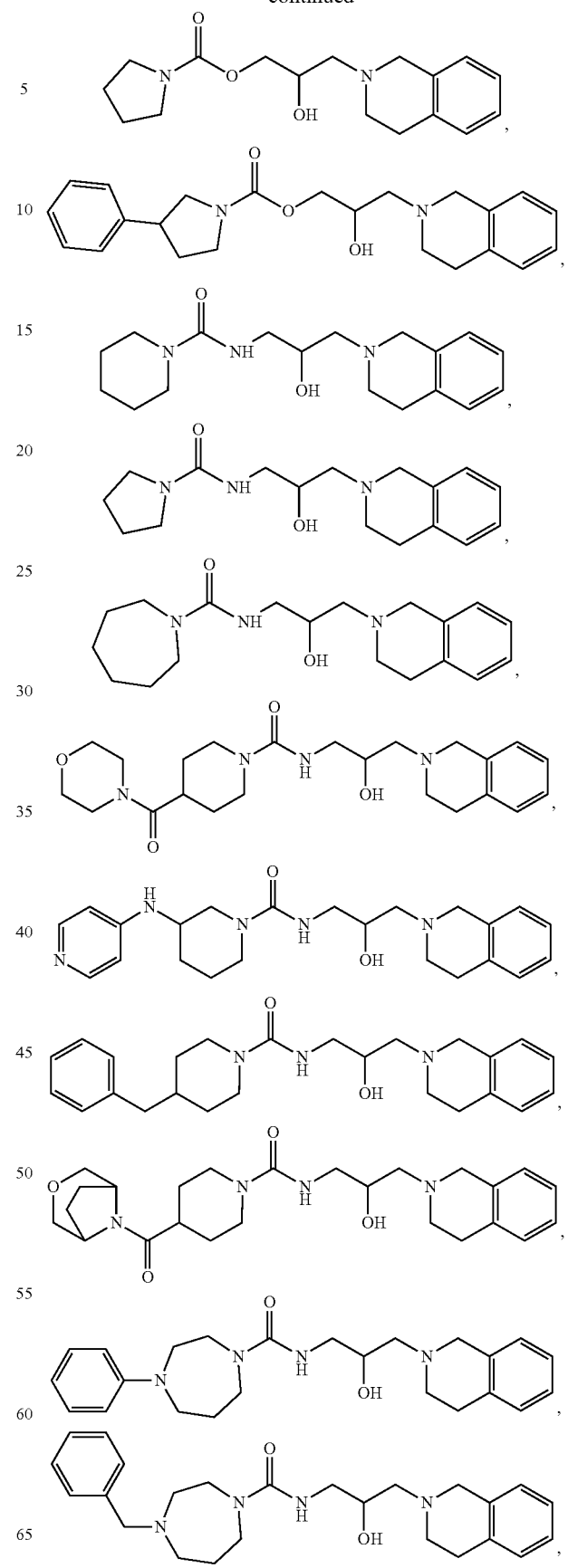

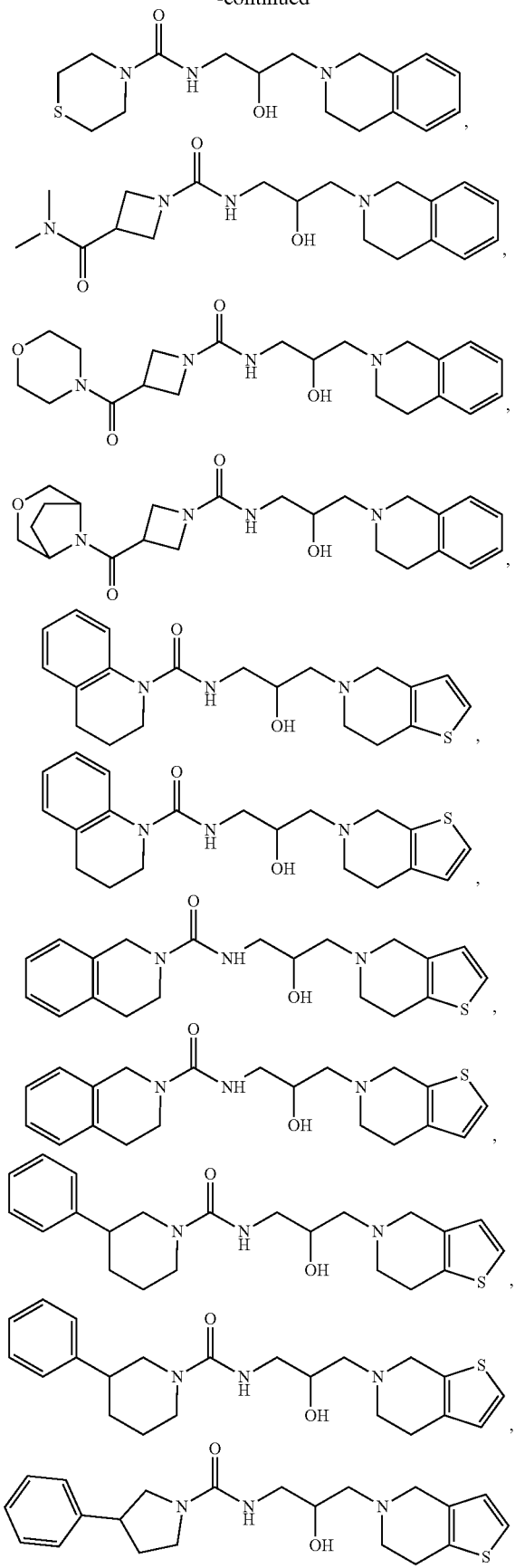
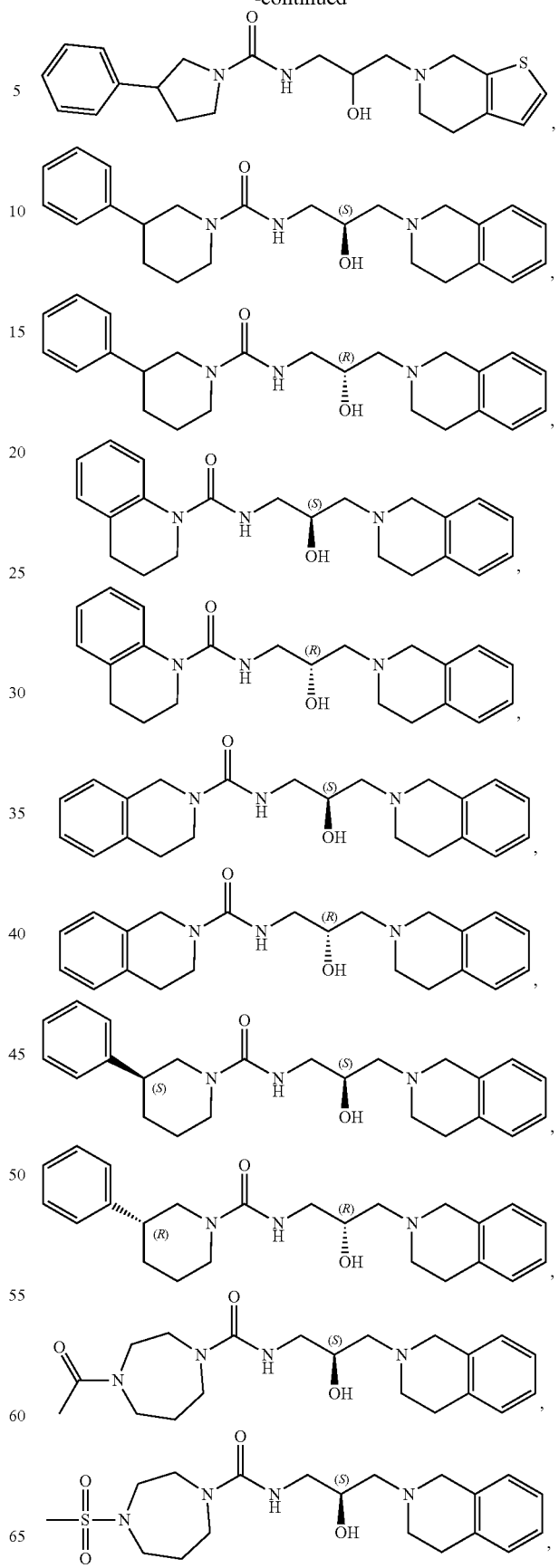

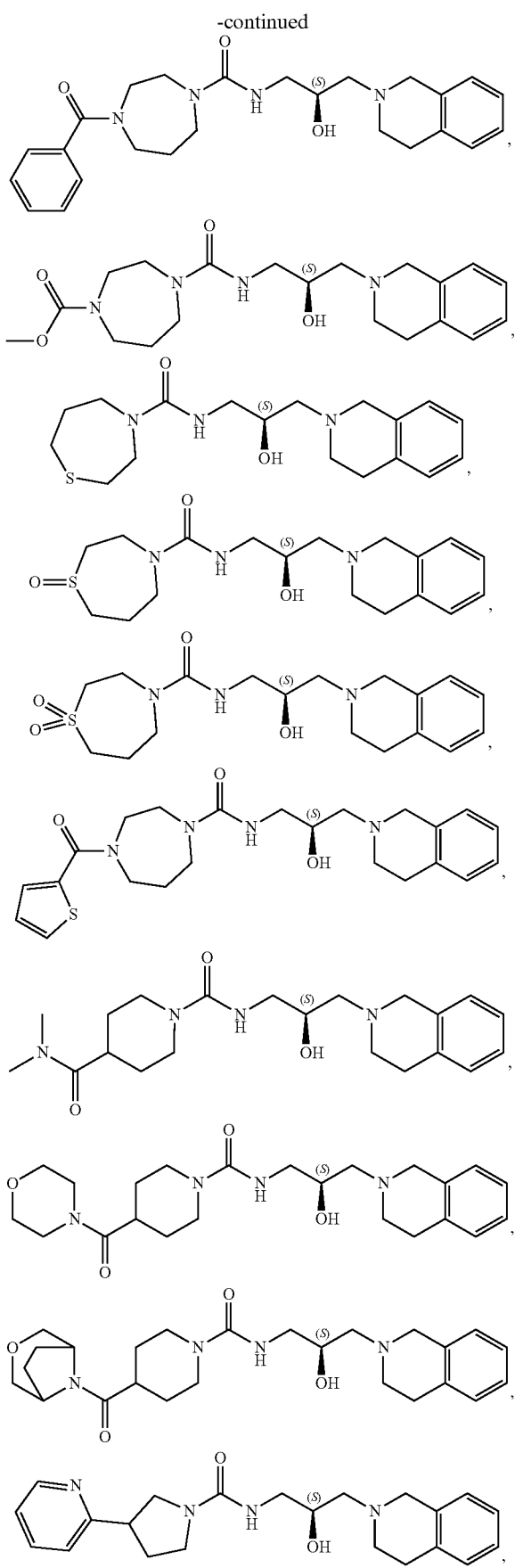
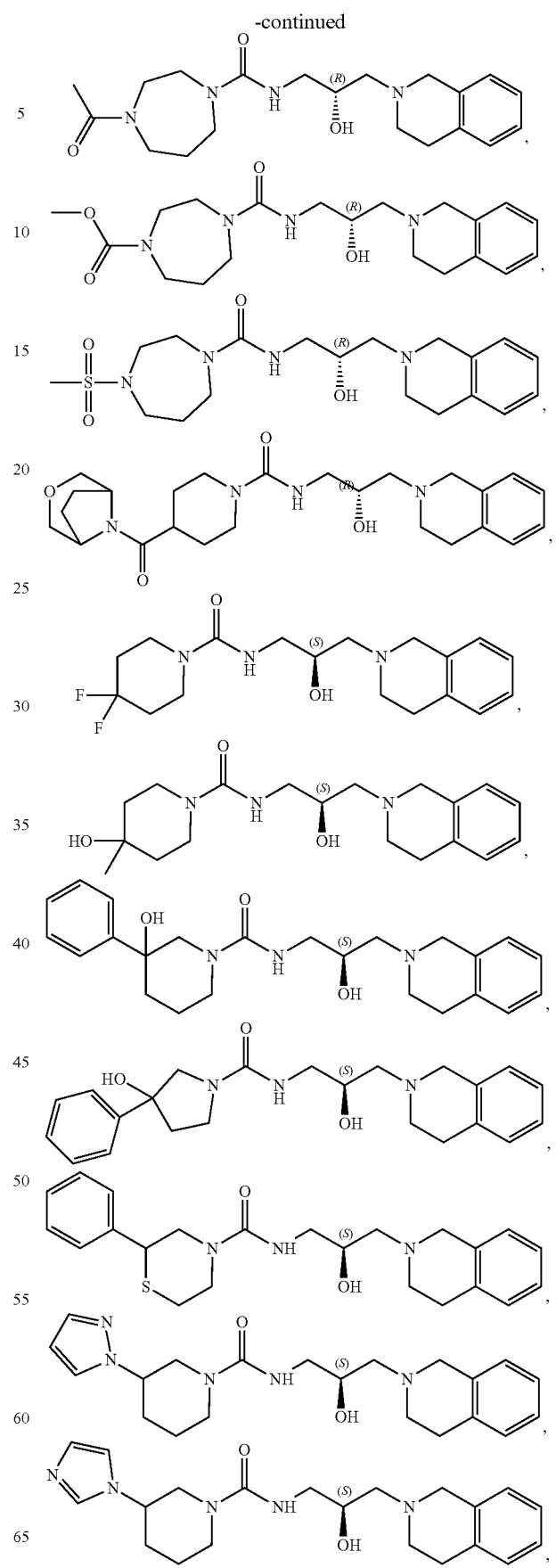

31
-continued
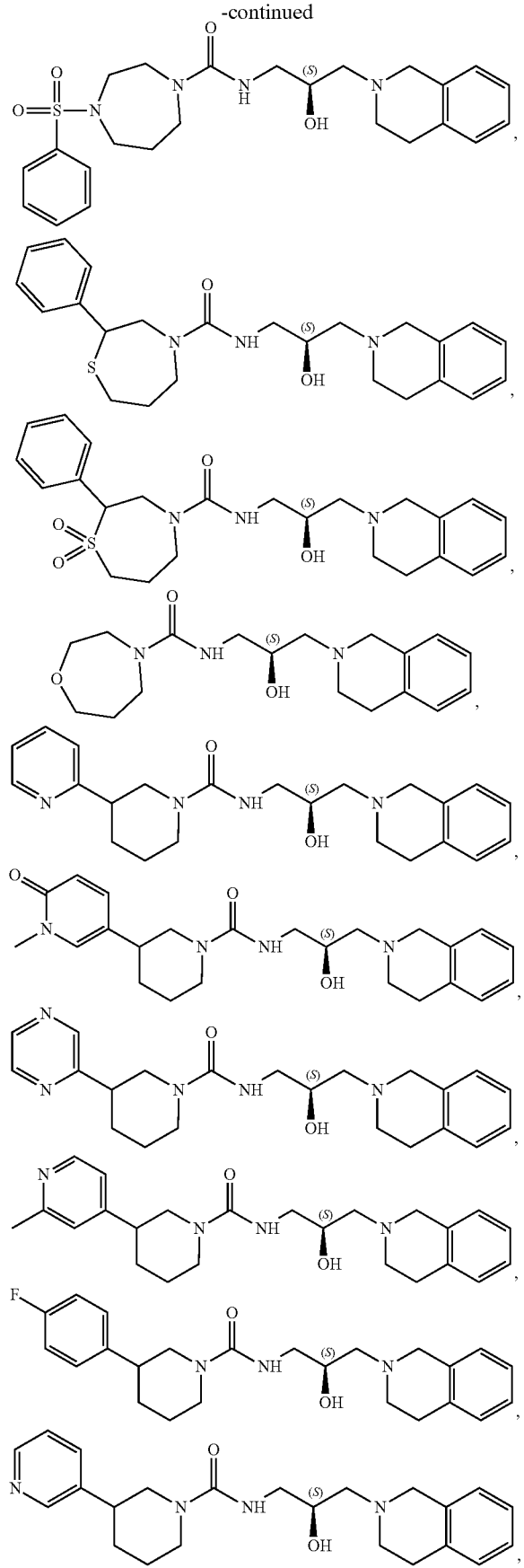
32
-continued
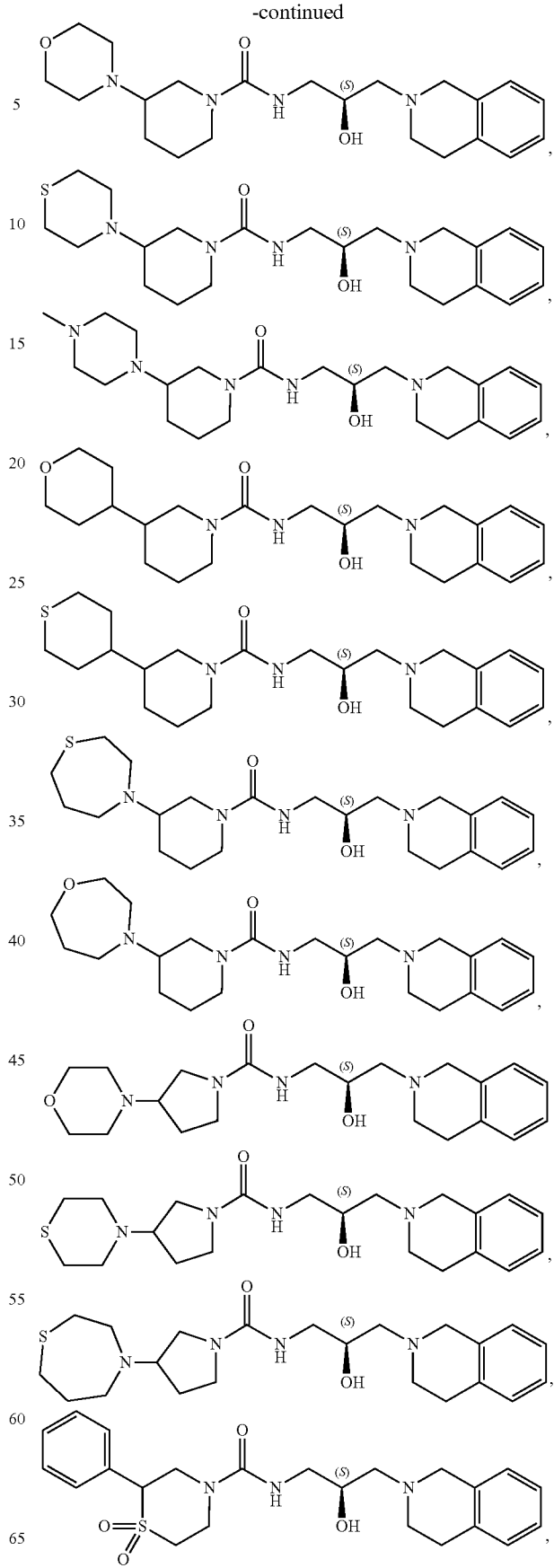

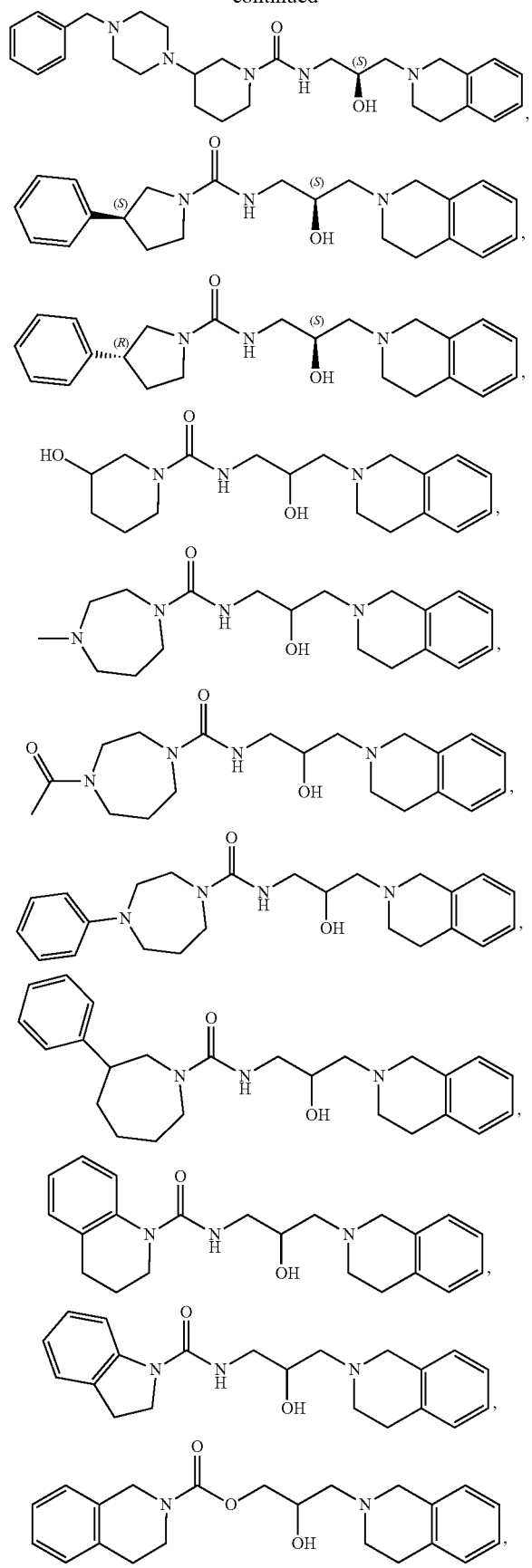
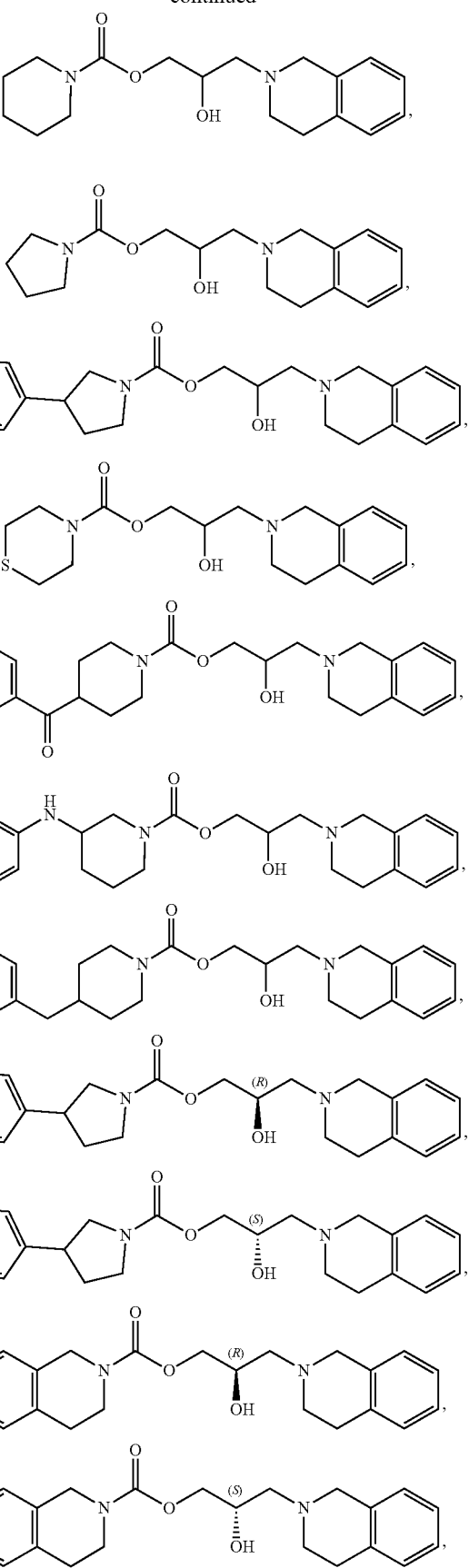

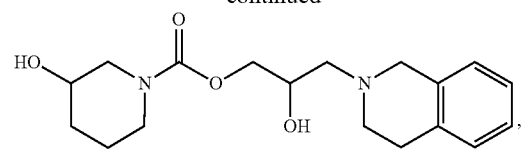
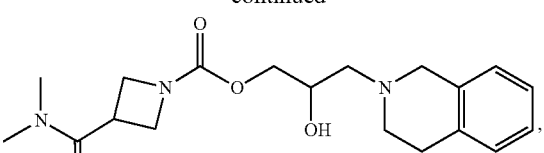

-continued
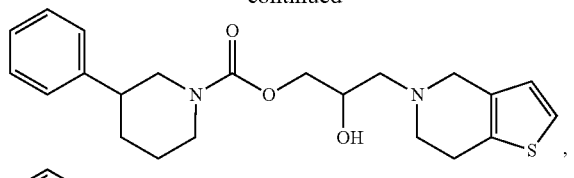
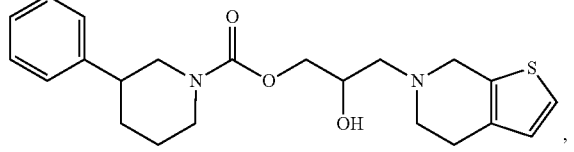
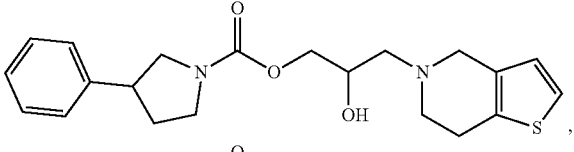
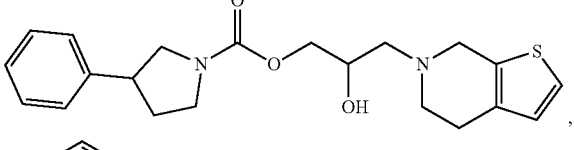
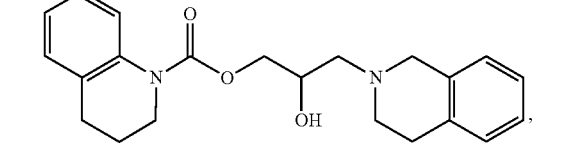
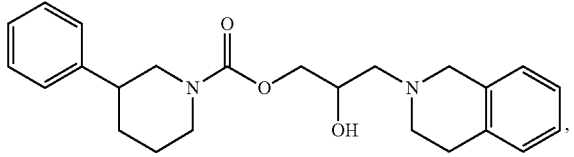
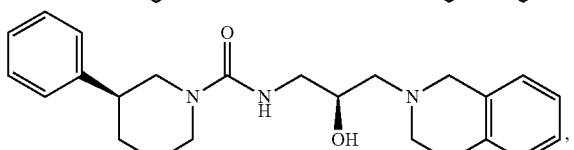
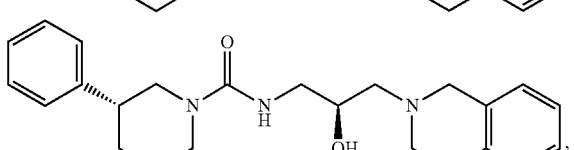
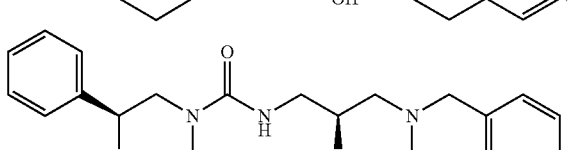
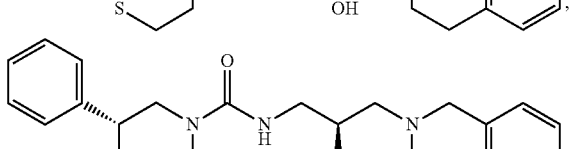
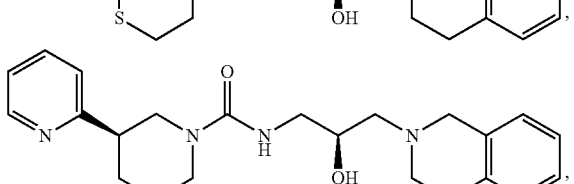
-continued
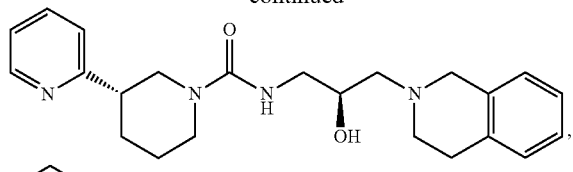
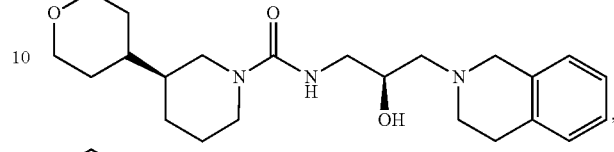
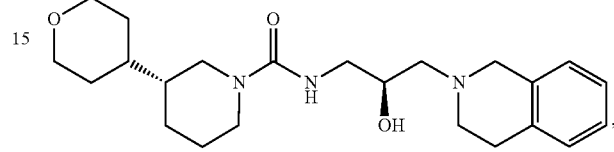
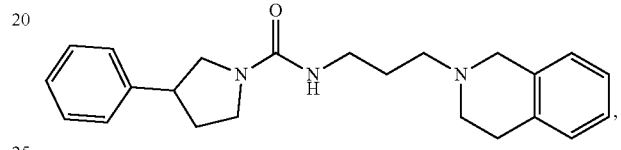
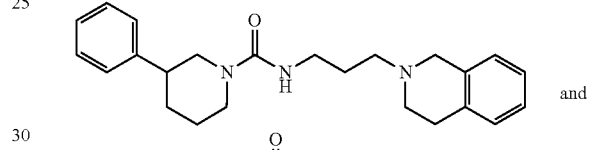
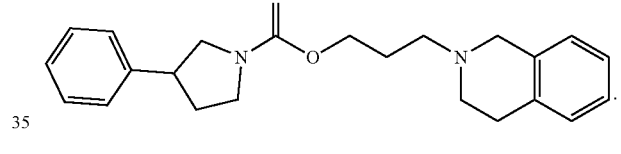
and
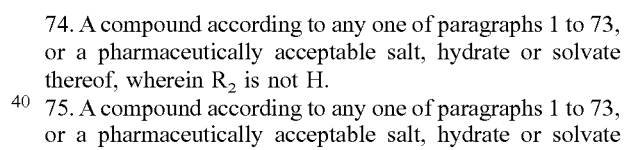
74. A compound according to any one of paragraphs 1 to 73, or a pharmaceutically acceptable salt, hydrate or solvate thereof, wherein $R_2$ is not H.
75. A compound according to any one of paragraphs 1 to 73, or a pharmaceutically acceptable salt, hydrate or solvate thereof, wherein the compound is not any of the following compounds:
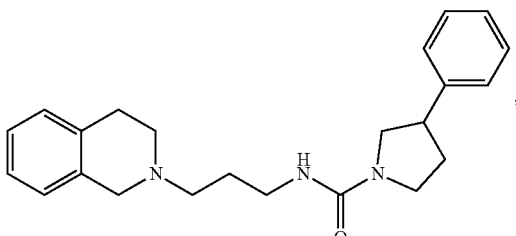
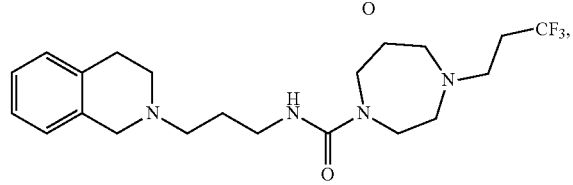
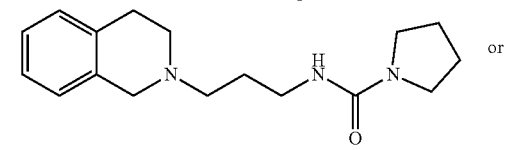
or -continued

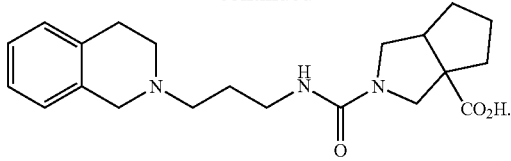

76. A pharmaceutical composition which comprises a compound according to any one of paragraphs 1 to 75, or a pharmaceutically acceptable salt, hydrate or solvate thereof, and one or more pharmaceutically acceptable excipients.

77. A compound according to any one of paragraphs 1 to 75, or a pharmaceutically acceptable salt, hydrate or solvate thereof, or a pharmaceutical composition according to claim 76, for use in therapy.

78. A method of treating or preventing a PRMT5-mediated disorder, said method comprising administering to a subject in need thereof an effective amount of a compound according to any one of paragraphs 1 to 75, or a pharmaceutically acceptable salt, hydrate or solvate thereof, or a pharmaceutical composition according to paragraph 76.

79. A method of treating a proliferative disorder, said method comprising administering to a subject in need thereof an effective amount of a compound according to any one of claims 1 to 75, or a pharmaceutically acceptable salt, hydrate or solvate thereof, or a pharmaceutical composition according to paragraph 76.

80. A method of treating a cancer, said method comprising administering to a subject in need thereof an effective amount of a compound according to any one of paragraphs 1 to 75, or a pharmaceutically acceptable salt, hydrate or solvate thereof, or a pharmaceutical composition according to paragraph 76.

81. A method of inhibiting the activity of PRMT5 in vivo or in vitro, said method comprising administering to a subject in need thereof a therapeutically effective amount of a compound according to any one of paragraphs 1 to 75, or a pharmaceutically acceptable salt, hydrate or solvate thereof, or a pharmaceutical composition according to claim 76.

82. A method of altering gene expression in a cell which comprises contacting a cell with an effective amount of a compound according to any one of paragraphs 1 to 75, or a pharmaceutically acceptable salt, hydrate or solvate thereof, or a pharmaceutical composition according to claim 76.

83. A compound according to any one of paragraphs 1 to 75, or a pharmaceutically acceptable salt, hydrate or solvate thereof, or a pharmaceutical composition according to paragraph 76, for use in the treatment or prevention of a PRMT5-mediated disorder.

84. A compound according to any one of paragraphs 1 to 75, or a pharmaceutically acceptable salt, hydrate or solvate thereof, or a pharmaceutical composition according to paragraph 76, for use in the treatment of a proliferative disorder.

85. A compound according to any one of paragraphs 1 to 75, or a pharmaceutically acceptable salt, hydrate or solvate thereof, or a pharmaceutical composition according to paragraph 76, for use in the treatment cancer.

86. A compound for use according to paragraph 80, wherein the cancer is selected from colorectal, ovarian, prostate, lung, breast, lymphoma/leukaemis, oesophageal, gastric, hepatocellular and brain cancer.

87. Use of a compound according to any one of paragraphs 1 to 75, or a pharmaceutically acceptable salt, hydrate or solvate thereof, or a pharmaceutical composition according to paragraph 76, in the manufacture of a medicament for the treatment or prevention of a PRMT5-mediated disorder.

88. Use of a compound according to any one of paragraphs 1 to 75, or a pharmaceutically acceptable salt, hydrate or solvate thereof, or a pharmaceutical composition according to paragraph 76, in the manufacture of a medicament for the treatment of a proliferative disorder.

89. Use of a compound according to any one of paragraphs 1 to 75, or a pharmaceutically acceptable salt, hydrate or solvate thereof, or a pharmaceutical composition according to paragraph 76, in the manufacture of a medicament for the treatment of cancer.

90. Use according to paragraph 89, wherein the cancer is selected from colorectal, ovarian, prostate, lung, breast, lymphoma/leukaemis, oesophageal, gastric, hepatocellular and brain cancer.

Though the present invention may relate to any compound or particular group of compounds defined herein by way of optional, preferred or suitable features or otherwise in terms of particular embodiments, the present invention mat also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of Formula I are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the Formula I may exist in solvated as well as unsolvated forms such as, for example, hydrated forms. It is to be understood that the invention encompasses all such solvated forms that possess antiproliferative activity.

Polymorphs

It is also to be understood that certain compounds of the Formula I may exhibit polymorphism, and that the invention encompasses all such forms that possess antiproliferative activity.

N-Oxides

Compounds of the Formula I containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

Tautomers

Compounds of the Formula I may exist in a number of different tautomeric forms and references to compounds of the Formula I include all such forms. For the avoidance of doubt, where a compound can exist in one of several tautomeric forms, and only one is specifically described or shown, all others are nevertheless embraced by Formula I. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/aci-nitro.

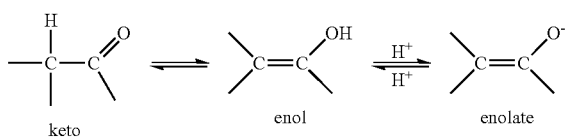

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of Formula I may have one or more asymmetric centers and therefore can exist in a number of stereoisomeric configurations. Consequently, such compounds can be synthesized and/or isolated as mixtures of enantiomers and/or as individual (pure) enantiomers, and, in the case of two or more asymmetric centers, single diastereomers and/or mixtures of diastereomers. It should be understood that the present application includes all such enantiomers and diastereomers and mixtures thereof in all ratios.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^3$H; etc. Preferably, the constituent atoms in the compounds of the present invention are present in their naturally occurring ratios of isotope forms.

Prodrugs and Metabolites

The compounds of Formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in-vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.,* 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_4$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula I that possesses a carboxy group is, for example, an in vivo cleavable amide thereof, for example an amide formed with an amine such as ammonia, a $C_{1-4}$alkylamine such as methylamine, a $(C_{1-4}alkyl)_2$amine such as dimethylamine, N-ethyl-N-methylamine or diethylamine, a $C_{1-4}$ alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the Formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In another aspect, the present invention provides a compound of Formula I as defined herein, or a pharmaceutically acceptable salt or solvate thereof, or a pharmaceutical composition as defined herein, for use in therapy.

In another aspect, the present invention provides a compound of Formula I as defined herein, or a pharmaceutically acceptable salt or solvate thereof, or a pharmaceutical composition as defined herein, for use in the treatment or prevention of a PRMT5-mediated disorder.

In another aspect, the present invention provides a compound of Formula I as defined herein, or a pharmaceutically acceptable salt or solvate thereof, or a pharmaceutical composition as defined herein, for use in the treatment of a proliferative disorder.

In another aspect, the present invention provides a compound of Formula I as defined herein, or a pharmaceutically acceptable salt or solvate thereof, or a pharmaceutical composition as defined herein, for use in the treatment cancer.

In another aspect, the present invention provides the use of a compound of Formula I as defined herein, or a pharmaceutically acceptable salt or solvate thereof, in the manufacture of a medicament for the treatment or prevention of a PRMT5-mediated disorder.

In another aspect, the present invention provides the use of a compound of Formula I as defined herein, or a pharmaceutically acceptable salt or solvate thereof, in the manufacture of a medicament for the treatment of a proliferative disorder.

In another aspect, the present invention provides the use of a compound of Formula I as defined herein, or a pharmaceutically acceptable salt or solvate thereof, in the manufacture of a medicament for the treatment of cancer.

In another aspect, the present invention provides a method of treating or preventing a PRMT5-mediated disorder, said method comprising administering to a subject in need thereof an effective amount of a compound of Formula I as defined herein, or a pharmaceutically acceptable salt or solvate thereof.

In another aspect, the present invention provides a method of treating a proliferative disorder, said method comprising administering to a subject in need thereof an effective amount of a compound of Formula I as defined herein, or a pharmaceutically acceptable salt or solvate thereof.

In another aspect, the present invention provides a method of treating cancer, said method comprising administering to a subject in need thereof a therapeutically effective amount of a compound of Formula I as defined herein, or a pharmaceutically acceptable salt or solvate thereof, or a pharmaceutical composition as defined herein.

In another aspect, the present invention provides a method of inhibiting the activity of PRMT5 in vivo or in vitro, said method comprising administering to a subject in need thereof a therapeutically effective amount of a compound of Formula I as defined herein, or a pharmaceutically acceptable salt or solvate thereof, or a pharmaceutical composition as defined herein.

In another aspect, the present invention provides a combination comprising a compound of Formula I, or a pharmaceutically acceptable salt or solvate thereof, as defined herein, with one or more additional therapeutic agents.

In another aspect, the present invention provides a method of altering gene expression in a cell which comprises contacting a cell with an effective amount of a compound of Formula I as defined herein, or a pharmaceutically acceptable salt or solvate thereof, or a pharmaceutical composition as defined herein.

In each of the above aspects, in one embodiment, the PRMT5 disorder is selected from a proliferative disorder, a metabolic disorder or a blood disorder. Suitably, the PRMT5 disorder is a proliferative disorder or a metabolic disorder.

Suitably the blood disorder is sickle cell disease or β-thalassemia.

Suitably the metabolic disorder is diabetes or obesity.

Suitably the proliferative disorder is cancer, an autoimmune disorder or an inflammatory disorder. Suitably, the proliferative disorder is cancer.

In each of the above aspects, in one embodiment, the cancer is selected from breast cancer, esophageal cancer, bladder cancer, lung cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma, brain tumors, hepatocellular carcinoma, renal cell carcinoma, melanoma, oligodendroglioma, ovarian clear cell carcinoma, and ovarian serous.

Suitably, the cancer is selected from breast cancer, esophageal cancer, bladder cancer, lung cancer, hematopoietic cancer, lymphoma, medulloblastoma, rectum adenocarcinoma, colon adenocarcinoma, gastric cancer, pancreatic cancer, liver cancer, head and neck squamous cell carcinoma and brain tumors.

In one embodiment, the cancer is a cancer in which high expression of PRMT5 occurs. Examples of such cancers include colorectal, ovarian, prostate, lung, breast, lymphoma/leukaemis, oesophageal, gastric, hepatocellular and brain cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination. In one embodiment, a combination refers to a combination product.

According to a further aspect of the invention there is provided a combination comprising a compound of formula I as defined herein, or a pharmaceutically acceptable salt, hydrate or solvate thereof, in combination with an further therapeutic agent (optionally selected from one listed herein above.

In one embodiment, there is provided a pharmaceutical composition which comprises a compound of formula I, or a pharmaceutically acceptable salt, hydrate or solvate thereof, in combination with a therapeutic agent (optionally selected from one listed herein above), in association with a pharmaceutically acceptable diluent or carrier.

Suitably, the additional therapeutic agent is an anti-cancer agent (optionally selected from one listed herein above).

EXAMPLES

The following examples are provided solely to illustrate the present invention and are not intended to limit the scope of the invention, as described herein.

The compounds of the invention may be prepared using synthetic techniques that are known in the art (as illustrated by the examples herein).

Several methods for the chemical synthesis of the compounds of the present application are described herein. These and/or other well-known methods may be modified and/or adapted in various ways in order to facilitate the synthesis of additional compounds within the scope of the present application and claims. Such alternative methods and modifications should be understood as being within the spirit and scope of this application and claims. Accordingly, it should be understood that the methods set forth in the following descriptions, schemes and examples are intended for illustrative purposes and are not to be construed as limiting the scope of the disclosure.

Methods of Analysis used in Synthetic Examples

LCMS Methods
Method-A
Method Name: 0.1_FA_WATER_ACN_pH 2.5
LC Parameters
  Instrument: UPLC AQUITY with PDA detector and QDA
  Column: C18, 50*2.1 mm, 1.6 µm
  Mobile Phase: (A) 0.1% Formic acid in Milli Q water (pH=2.70)
  (B) Acetonitrile:0.1% Formic acid (90:10)
  Flow Rate: 0.800 ml/Min
  Column Temperature: 35° C.
  Autosampler Temperature: 5° C.
  Run Time: 6 min
  Gradient:

| TIME (Minute) | (%) A | (%) B |
| --- | --- | --- |
| 0.00 | 90 | 10 |
| 0.75 | 90 | 10 |
| 2.80 | 10 | 90 |
| 4.50 | 00 | 100 |

| TIME (Minute) | (%) A | (%) B |
| --- | --- | --- |
| 4.60 | 00 | 100 |
| 4.70 | 90 | 10 |
| 6.00 | 90 | 10 |

Mass Parameters
Probe: ESI capillary
Source Temperature: 120° C.
Probe Temperature: 600° C.
Capillary Voltage: 0.8 KV (+Ve and −Ve)
Cone Voltage: 10 & 30 V
Mode of Ionization: +Ve and −Ve
Method-B
Method Name: $NH_4HCO_3$_WATER_MEOH pH_7.35
LC Parameters
    Instrument: Waters Alliance 2690 and 996 PDA detector with Micromass ZQ
    Column: C18, 50×4.6 mm, 3.5 μm
    Mobile Phase: (A) 10 mM Ammonium Bicarbonate in Milli-Qwater (pH=7.35)
    (B) Methanol
    Flow Rate: 1.200 ml/Min
    Run Time: 7 min
    Gradient:

| TIME (Minute) | (%) A | (%) B |
| --- | --- | --- |
| 0.00 | 90 | 10 |
| 1.00 | 90 | 10 |
| 4.00 | 00 | 100 |
| 6.00 | 00 | 100 |
| 6.50 | 90 | 10 |
| 7.00 | 90 | 10 |

Mass Parameters
Probe: ESI capillary
Source Temperature: 100° C.
Desolvation Temperature: 200° C.
Capillary Voltage: 3 KV (+Ve and −Ve)
Cone Voltage: 10 & 30 V
Extractor Voltage: 2.0 V
$R_f$ Lens: 0.1
Desolvation Gas Flow: 800.0 L/h
Cone Gas Flow: 100.0 L/h
Mode of Ionization: +Ve and −Ve
Method-C
Method Name: 0.1_FA_WATER_ACN_pH 2.5
LC Parameters
    Instrument: UPLC AQUITY with PDA detector and QDA
    Column: C18, 50*2.1 mm, 1.6 μm
    Mobile Phase: (A) 0.1% Formic acid in Milli Q water (pH=2.70)
    (B) Acetonitrile:0.1% Formic acid (90:10)
    Flow Rate: 0.300 ml/Min
    Column Temperature: 35° C.
    Auto sampler Temperature: 5° C.
    Run Time: 9 min
    Gradient:

| TIME (Minute) | (%) A | (%) B |
| --- | --- | --- |
| 0.00 | 99 | 1.0 |
| 1.00 | 99 | 1.0 |
| 2.50 | 50 | 50 |
| 3.50 | 50 | 50 |
| 4.50 | 2.5 | 97.5 |
| 6.00 | 2.5 | 97.5 |
| 6.50 | 99 | 1.0 |
| 9.00 | 99 | 1.0 |

Mass Parameters
Probe: ESI capillary
Source Temperature: 120° C.
Probe Temperature: 600° C.
Capillary Voltage: 0.8 KV (+Ve and −Ve)
Cone Voltage: 10 & 30 V
Mode of Ionization: +Ve and −Ve
HPLC Method
Method-A
    COLUMN:—Waters X-Bridge C18 150*4.6 mm, 3.5 μm
    MOBILE PHASE:—A) 10 mM Ammonium bicarbonate in water (HPLC) pH-7.35
    B) 100% ACN
    Flow Rate:—1.00 ml/min
    Gradient:—(B) 10% at 0.01 min, 10% (B) to 90% (B) in 7 min, 100% (B) from 7 min to 9 min, holding 100% (B) for 5 min and from 14.01 min to 17 min 10% (B).
Chiral HPLC Methods
Method-A
LC Parameters
    Instrument: SHIMADZU LC-20AD
    Column: CHROMEGA CHIRAL CCO, 250*4.6 mm, 5μ
    Mobile Phase: (A) 0.1% TFA in n-HEPTANE
    (B) 50:50(IPA:METHANOL)
    Sample preparation: Approx. 1000 ppm in mobile phase
    Flow Rate: 1 ml/Min
    Column Temperature: Room temperature
    Auto sampler Temperature: Room temperature
    Run Time: 60 mins
    ISOCRATIC METHOD:A: B~90:10
Method-B
LC Parameters
    Instrument: SHIMADZU LC-20AD
    Column: CHROMEGA CHIRAL CCO, 250*4.6 mm, 5p
    Mobile Phase: (A) 0.1% DEA in n-HEPTANE
    (B) 70:30(IPA:ACN)
    Sample preparation: Approx. 1000 ppm in mobile phase
    Flow Rate: 1 ml/Min
    Column Temperature: Room temperature
    Auto sampler Temperature: Room temperature
    Run Time: 25 mins
    ISOCRATIC METHOD:A: B~90:10
Method-C
LC Parameters
    Instrument: AGILENT TECHNOLOGIES-1200 SERIES
    Column: CHROMEGA CHIRAL CCO, 250*4.6 mm, 5p
    Mobile Phase: (A) 0.1% TFA in n-HEPTANE
    (B) 50:50(IPA:METHANOL)
    Sample preparation: Approx. 1000 ppm in mobile phase
    Flow Rate: 1 ml/Min
    Column Temperature: Room temperature
    Auto sampler Temperature: Room temperature
    Run Time: 60 mins
    ISOCRATIC METHOD:A: B~90:10

Synthetic Examples

Reagents used in these Schemes were either commercially available, made following procedures already highlighted in the literature or made as outlined below.

Intermediate 1: (3-oxa-8-azabicyclo[3.2.1]octan-8-yl)(piperidin-4-yl)methanone

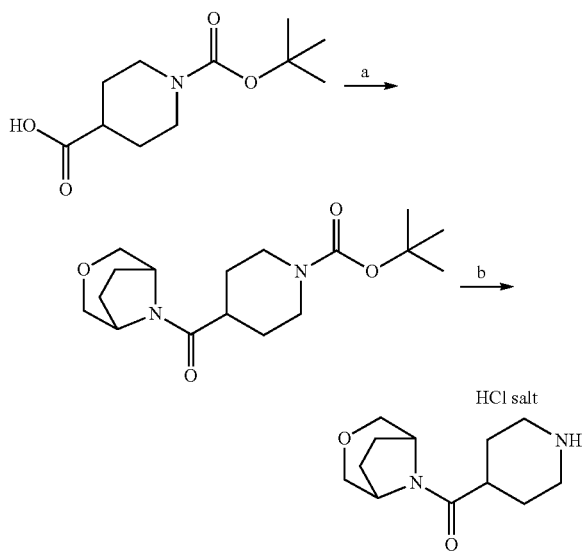

Reagents and conditions: (a) 3-oxa-8-azabicyclo[3.2.1]octane, HATU, DMF, rt, 2 h, (b) HCl in dioxane, DCM, rt, 16.

Step a

To a stirred solution of 1-(tert-butoxycarbonyl)piperidine-4-carboxylic acid (CAS Number 183673-71-4, available from Combi blocks) (5 g, 21.80 mmol) in DMF (30 ml), were added HATU available from Reddy & Reddy chemicals) (12.43 g, 32.70 mmol) and diisopropylethylamine (11.27 g, 87.22 mmol) at 0° C. under nitrogen atmosphere and allowed to stir for 15 min. A solution of 3-oxa-8-azabicyclo[3.2.1]octane (CAS Number 904316-92-3, available from Synthonix) (2.95 g, 26.16 mmol) in DMF (10 ml) was added drop wise and the resulting reaction mixture was allowed to stir at room temperature for 2 h. The reaction mixture was diluted with ice-cold water (500 ml) and extracted with ethyl acetate (4×50 ml). The combined organic layer was brine washed, dried over $Na_2SO_4$ and concentrated under reduced pressure. The crude material, thus obtained was purified by column chromatography (15% ethyl acetate in hexane) to afford tert-butyl 4-(3-oxa-8-azabicyclo[3.2.1]octane-8-carbonyl)piperidine-1-carboxylate (6.0 g, 18.507 mmol) as a white solid. LCMS: Method B, 1.942 min, MS: ES+269.1 (M-56).

Step b

To a stirred solution of tert-butyl 4-(3-oxa-8-azabicyclo [3.2.1]octane-8-carbonyl)piperidine-1-carboxylate (6.0 g, 18.507 mmol) in dichloromethane (20 ml) was added 2.4 N HCl in dioxane drop wise at 0° C. temperature under nitrogen atmosphere. The resulting reaction mixture was stirred at room temperature for 16 h. The mixture was concentrated under reduced pressure and triturated with n-pentane (2×20 ml) to afford (3-oxa-8-azabicyclo[3.2.1] octan-8-yl)(piperidin-4-yl)methanone hydrochloride (4.5 g, 17.265 mmol) as off-white sticky solid. LCMS: Method B, 1.654 min, MS: ES+225.1 (M+1).

Intermediate 2: Azetidin-3-yl(3-oxa-8-azabicyclo[3.2.1]octan-8-yl)methanone

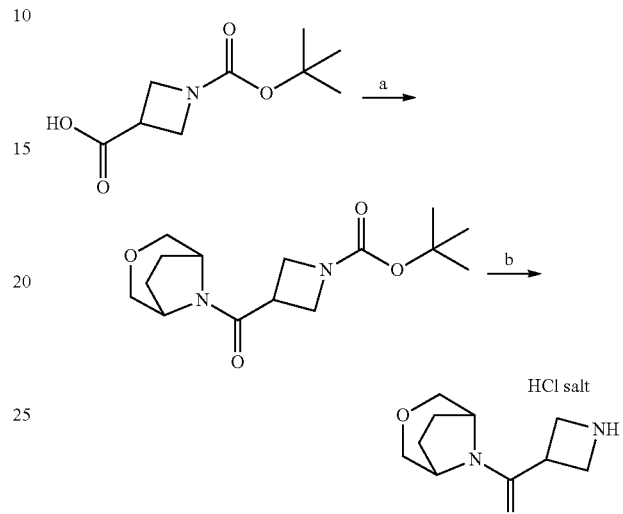

Reagents and conditions: (a) 3-oxa-8-azabicyclo[3.2.1]octane, HATU, DIPEA, DMF, rt, 2 h, (b) HCl in dioxane, Dioxane, rt, 4 h.

Step a

To a stirred solution of 1-(tert-butoxycarbonyl)azetidine-3-carboxylic acid (CAS Number 142253-55-2, available from Combi blocks) (1.7 g, 8.45 mmol) in DMF (5 ml), were added HATU available from Reddy & Reddy chemicals) (3.4 g, 12.68 mmol) and diisopropylethylamine (11.27 g, 25.35 mmol) at 0° C. under nitrogen atmosphere and allowed to stir for 15 min. A solution of 3-oxa-8-azabicyclo [3.2.1]octane (CAS Number 904316-92-3, available from Synthonix) (1.0 g, 8.84 mmol) in DMF (5 ml) was added drop wise and the resulting reaction mixture was allowed to stir at room temperature for 2 h. The reaction mixture was diluted with ice-cold water (500 ml) and extracted with ethyl acetate (4×50 ml). The combined organic layer was brine washed, dried over $Na_2SO_4$ and concentrated under reduced pressure. The crude material, thus obtained was purified by column chromatography (20% ethyl acetate in hexane) to afford crude tert-butyl 3-(3-oxa-8-azabicyclo[3.2.1]octane-8-carbonyl)azetidine-1-carboxylate (2.9 g, 9.79 mmol) as a white solid. LCMS: Method B, 2.062 min, MS: ES+241.1 (M-56).

Step b

To a stirred solution of tert-butyl 3-(3-oxa-8-azabicyclo [3.2.1]octane-8-carbonyl)azetidine-1-carboxylate (2.9 g, 9.79 mmol) in dioxane (10 ml) was added 4 N HCl in dioxane (10 ml) drop wise at 0° C. temperature under nitrogen atmosphere. The resulting reaction mixture was stirred at room temperature for 4 h. The mixture was concentrated under reduced pressure and triturated with n-pentane (2×20 ml) to afford azetidin-3-yl(3-oxa-8-azabicyclo[3.2.1]octan-8-yl)methanone hydrochloride (1.8 g, 7.74 mmol) as off-white sticky solid. MS: ES+197.2 (M+1).

Intermediate 3:
3-(tetrahydro-2H-pyran-4-yl)piperidine

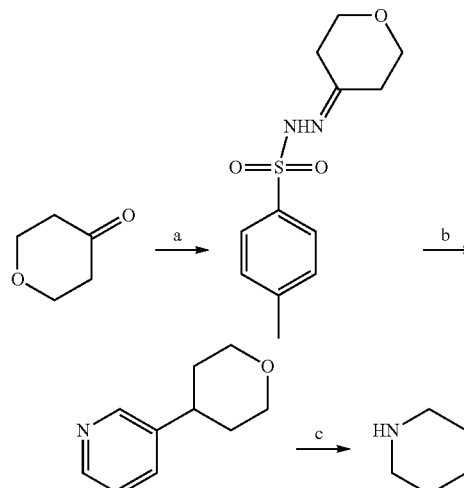

Reagents and conditions: a) 4-Methylbenzenesulfonohydrazide, Ethanol, 90° C., 2 h; b) Pyridin-3-ylboronic acid, $K_2CO_3$, 1,4-Dioxane, 110° C., 48 h; c) Dimethylphenylsilane, Diphenylamine, Tris(pentafluorotriphenyl)borane, Toluene, 120° C., 24 h.

Step a

To a solution of tetrahydro-4H-pyran-4-one (CAS Number 29943-42-8, available from Combi blocks) (5 g, 50.00 mmol) in ethanol (50 ml) were added 4-methylbenzenesulfonohydrazide (CAS Number 1576-35-8, available from Spectrochem) (9.31 g, 50.00 mmol) at room temperature and the resulting reaction mixture was refluxed for 2 h. The reaction mixture was allowed to cool to room temperature; filtered and washed with cold ethanol (2×20 mL). The residues collected were dried under reduced pressure to afford 4-methyl-N'-(tetrahydro-4H-pyran-4-ylidene)benzenesulfonohydrazide (11.0 g, 41.03 mmol). LCMS: Method-B, 2.240 min, MS: ES+268.9 (M+1).

Step b

To a solution 4-methyl-N'-(tetrahydro-4H-pyran-4-ylidene)benzenesulfonohydrazide (11.0 g, 41.03 mmol) in dioxane (300 ml) was added pyridin-3-ylboronic acid (CAS Number 1692-25-7, available from Combi blocks) (5.04 g, 41.03 mmol) and potassium carbonate (CAS Number 584-08-7, available from Spectrochem) (17.04 g, 123.09 221.82 mmol). The resulting reaction mixture was stirred at 120° C. for 48 h. The reaction mixture was filtered through celite and the filtrate was concentrated under reduced pressure. The crude material thus obtained was purified by column chromatography (70% ethyl acetate in hexane) to afford 3-(tetrahydro-2H-pyran-4-yl)pyridine (2.5 g, 15.33 mmol). LCMS: Method-B, 0.235 min, MS: ES+164.1 (M+1).

Step c

To a solution of 3-(tetrahydro-2H-pyran-4-yl)pyridine (2.5 g, 15.33 mmol) in toluene (10 ml) were added dimethylphenylsilane (CAS Number 766-77-8, available from Combi blocks) (10.45 g, 76.65 mmol) and diphenylamine (CAS Number 122-39-4, available from Spectrochem) (10.38 g, 61.32 mmol) and tris(pentafluorotriphenyl)borane (CAS Number 1109-15-5, available from TCI chemical) (0.785 g, 1.533 mmol) at room temperature under nitrogen atmosphere. The resulting reacting mixture was stirred at 120° C. for 24 h. The reaction mixture was concentrated under reduced pressure and the crude material thus obtained was purified by column chromatography (10% diethylamine in ethyl acetate) to afford 3-(tetrahydro-2H-pyran-4-yl)piperidine (3.6 g, 21.28 mmol). MS: ES+170.2 (M+1).

Intermediate 4:
3-(tetrahydro-2H-pyran-4-yl)piperidine

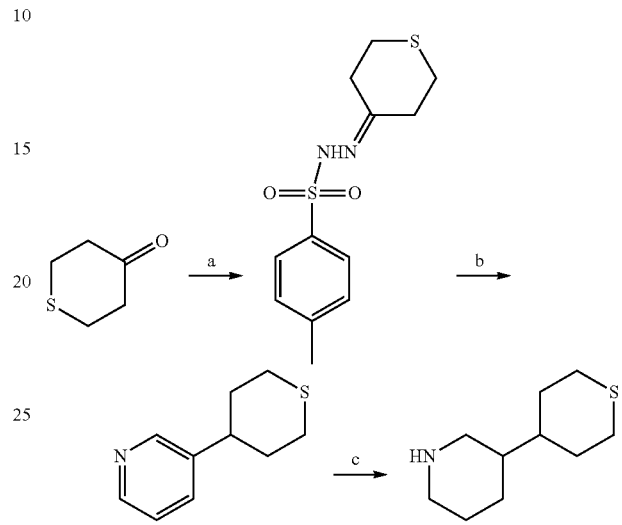

Reagents and conditions: a) 4-Methylbenzenesulfonohydrazide, ethanol, 90° C., 2 h; b) Pyridin-3-ylboronic acid, $K_2CO_3$, 1,4-dioxane, 110° C., 48 h; c) Dimethylphenylsilane, diphenylamine, tris(pentafluorotriphenyl)borane, toluene, 120° C., 24 h.

Step a

To a solution of tetrahydro-4H-thiopyran-4-one (CAS Number 1072-72-6, available from Combi blocks) (10 g, 86.05 mmol) in ethanol (100 ml) was added 4-methylbenzenesulfonohydrazide (CAS Number 1576-35-8, available from Spectrochem) (16.03 g, 86.05 mmol) at room temperature and the resulting reaction mixture was refluxed for 2 h. The reaction mixture was allowed to cool to room temperature; filtered and washed with cold ethanol (2×20 mL). The residues collected were dried under reduced pressure to afford 4-methyl-N'-(tetrahydro-4H-thiopyran-4-ylidene)benzenesulfonohydrazide (21.0 g, 73.94 mmol). LCMS: Method B, 3.287 min, MS: ES+284.8 (M+1).

Step b

To a solution 4-methyl-N'-(tetrahydro-4H-thiopyran-4-ylidene)benzenesulfonohydrazide (21.0 g, 73.94 mmol) in dioxane (200 ml) were added pyridin-3-yl boronic acid (CAS Number 1692-25-7, available from Combi blocks) (9.1 g, 73.94 mmol) and potassium carbonate (CAS Number 584-08-7, available from Spectrochem) (30.7 g, 221.82 mmol). The resulting reaction mixture was stirred at 120° C. for 48 h. The reaction mixture was filtered through celite and the filtrate was concentrated under reduced pressure. The crude material thus obtained was purified by column chromatography (18% ethyl acetate in hexane) to afford 3-(tetrahydro-2H-thiopyran-4-yl)pyridine (4.5 g, 25.13 mmol). LCMS: Method-B, 4.154 min, MS: ES+180.1 (M+1).

Step c

To a solution of 3-(tetrahydro-2H-pyran-4-yl)pyridine (1.0 g, 5.586 mmol) in toluene (10 ml) were added dimethylphenylsilane (CAS Number 766-77-8, available from Combi blocks) (3.8 g, 27.93 mmol) and diphenylamine (CAS Number 122-39-4, available from Spectrochem) (3.8 g, 22.34 mmol) and tris(pentafluorotriphenyl)borane (CAS Number 1109-15-5, available from TCI chemical) (0.29 g, 0.5586 mmol) at room temperature under nitrogen atmosphere. The resulting reacting mixture was stirred at 120° C. for 24 h. The reaction mixture was concentrated under reduced pressure and the crude material thus obtained was purified by column chromatography (10% diethylamine in ethyl acetate) to afford 3-(tetrahydro-2H-pyran-4-yl)piperidine (0.3 g, 1.62 mmol). LCMS: Method-B, 3.194 min, MS: ES+185.9 (M+1).

Intermediate 5

Scheme 1

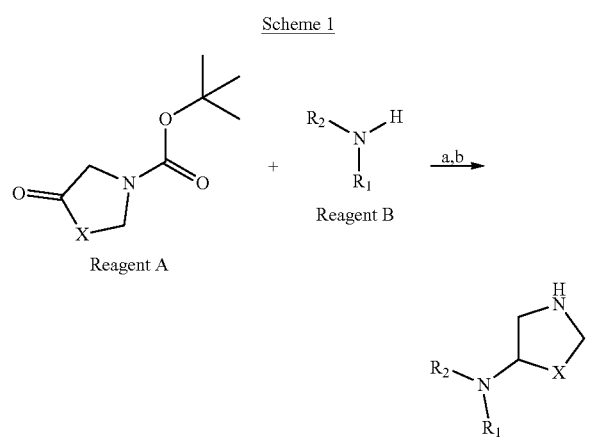

Reagents and conditions: (a) Reagent A, Reagent B, Na(OAc)$_3$BH, glacial acetic acid, 1,2-dichloroethane, rt, 2 h, (b) HCl in dioxane, DCM, rt, 3 h.

Step a

To a solution of tert-butyl 3-oxopiperidine-1-carboxylate (CAS Number 98977-36-7, available from Combi blocks) (1.0 g, 5.02 mmol) and morpholine (CAS Number 110-91-8, available from Spectrochem) (0.4 g, 5.02 mmol) in 1, 2-dichloroethane (20 ml) was added glacial acetic acid (0.03 g, 0.50 mmol) under nitrogen atmosphere at room temperature and allowed to stir for 2 h. Sodium triacetoxyborohydride (CAS Number 56553-60-7, available from Spectrochem) (2.12 g, 10.04 mmol) was then added portion wise at 0° C. under nitrogen atmosphere and the resulting reaction mixture was allowed to stir for 2 h at room temperature. The reaction mixture was poured in 5% aqueous citric acid solution (100 ml) and washed with dichloromethane (2×50 ml). The acidic aqueous layer was then basified up to pH ~8 using saturated sodium bicarbonate solution (100 ml) and extracted with dichloromethane (4×50 ml). The combined organic layers were brine washed, dried over Na$_2$SO$_4$ and concentrated under reduced pressure to afford tert-butyl 3-morpholinopiperidine-1-carboxylate (1.0 g, 3.70 mmol) as pale yellow sticky solid. LSMS: Method B, 1.229 min, MS: ES+271.2 (M+1); $^1$H NMR (CDCl$_3$) δ ppm: 4.235-4.085 (m, 1H), 3.940-3.909 (m, 1H), 3.746-3.724 (t, J=4.4 Hz, 4H), 2.788-2.720 (m, 2H), 2.610-2.599 (m, 4H), 2.229 (br s, 1H), 2.003-1.980 (m, 1H), 1.778-1.737 (m, 1H), 1.478 (s, 9H), 1.435-1.412 (in 2H).

Step b

To a stirred solution of tert-butyl 3-morpholinopiperidine-1-carboxylate (1.0 g, 3.70 mmol) in dichloromethane (5 ml), was added 4 N HCl in dioxane drop wise at 0° C. temperature under nitrogen atmosphere. The resulting reaction mixture was stirred at room temperature for 3 h. The mixture was concentrated under reduced pressure and triturated with n-pentane (2×10 ml) to afford 4-(piperidin-3-yl)morpholine dihydrochloride (0.9 g, 3.70 mmol) as off-white sticky solid. LCMS: Method B, 0.835 min, MS: ES+171.2 (M+1); $^1$H NMR (DMSO-d$_6$) δ ppm: 11.992 (br s, 1H), 9.739 (br s, 1H), 9.403 (br s, 1H), 3.941-3.905 (m, 4H), 3.761-3.628 (m, 1H), 3.381-3.354 (m, 1H), 3.217-3.189 (m, 4H), 2.787-2.761 (m, 1H), 2.548-2.471 (m, 2H), 2.207 (br s, 1H), 1.961-1.931 (m, 1H), 1.742-1.662 (m, 2H).

The following intermediates were made using the same method:

| Int. | Name | Structure | Reagent A | Reagent B | Analytical Data |
|---|---|---|---|---|---|
| 5B | 4-(piperidin-3-yl)thiomorpholine | 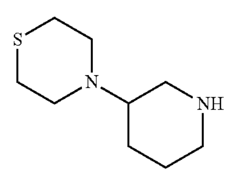 [SMILES: C1CNCC(N2CCSCC2)C1] | | | LCMS: Method B, 1.645 min, MS: ES+ 187.2 (M + 1). |
| 5C | 1-methyl-4-(piperidin-3-yl)piperazine | 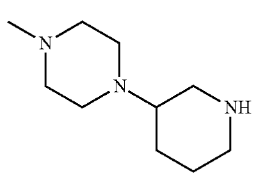 | | | LCMS: Method D, 3.930 min, MS: ES+ 184.3 (M + 1) |
| 5D | 4-(piperidin-3-yl)-1,4-thiazepane | 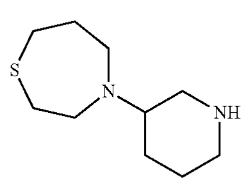 [SMILES: C1CNCC(N2CCCSCC2)C1] | | | LCMS: Method B, 2.798 min, MS: ES+ 201.2 (M + 1) |

-continued

| Int. | Name | Structure | Reagent A | Reagent B | Analytical Data |
|---|---|---|---|---|---|
| 5E | 4-(piperidin-3-yl)-1,4-oxazepane | 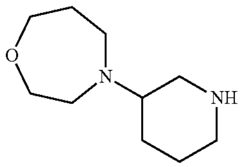 [SMILES: C1CNCC(N2CCCOCC2)C1] | | | LCMS: Method D, 4.299 min, MS: ES+ 185.2 (M + 1) |
| 5F | 4-(pyrrolidin-3-yl)morpholine | 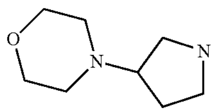 [SMILES: C1CC(N2CCOCC2)CN1] | | | LCMS: Method D, 1.260 min, MS: ES+ 157.2 (M + 1). |
| 5G | 4-(pyrrolidin-3-yl)thiomorpholine | 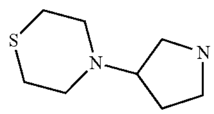 [SMILES: C1CC(N2CCSCC2)CN1] | | | MS: ES+ 173.1 (M + 1); $^1$H NMR: (400 MHz, DMSO-$d_6$) δ ppm: 11.996 (br s, 1H), 9.621-9.496 (m, 1H), 4.002 (br s, 1H), 3.768-3.750 (m, 2H), 3.714-3.698 (m, 2H), 3.466-3.382 (m, 2H), 3.204 (br s, 4H), 2.838 (br s, 2H), 2.331-2.322 (m, 2H). |
| 5H | 4-(pyrrolidin-3-yl)-1,4-thiazepane | 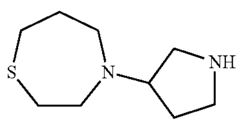 [SMILES: C1CSCCN(C2CCNC2)C1] | | | LCMS: Method B, 1.695 min, MS: ES+ 187.1 (M + 1). |
| 5I | 4-(pyrrolidin-3-yl)-1,4-oxazepane | 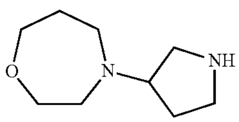 [SMILES: C1COCCN(C2CCNC2)C1] | | | LCMS: Method B, 0.631 min, MS: ES+ 171.2 (M + 1); $^1$H NMR: (400 MHz, DMSO-$d_6$) δ ppm: 11.898 (s, 1H), 9.839 (s, 1H), 9.640 (s, 1H), 4.127-4.071(q, J = 22.4, 1H), 3.927-3.825 (m, 2H), 3.778-3.273 (m, 10H), 3.180-3.170 (m, 1H), 2.490-2.265 (m, 3H), 2.015 (br s, 1H). |

Example 1

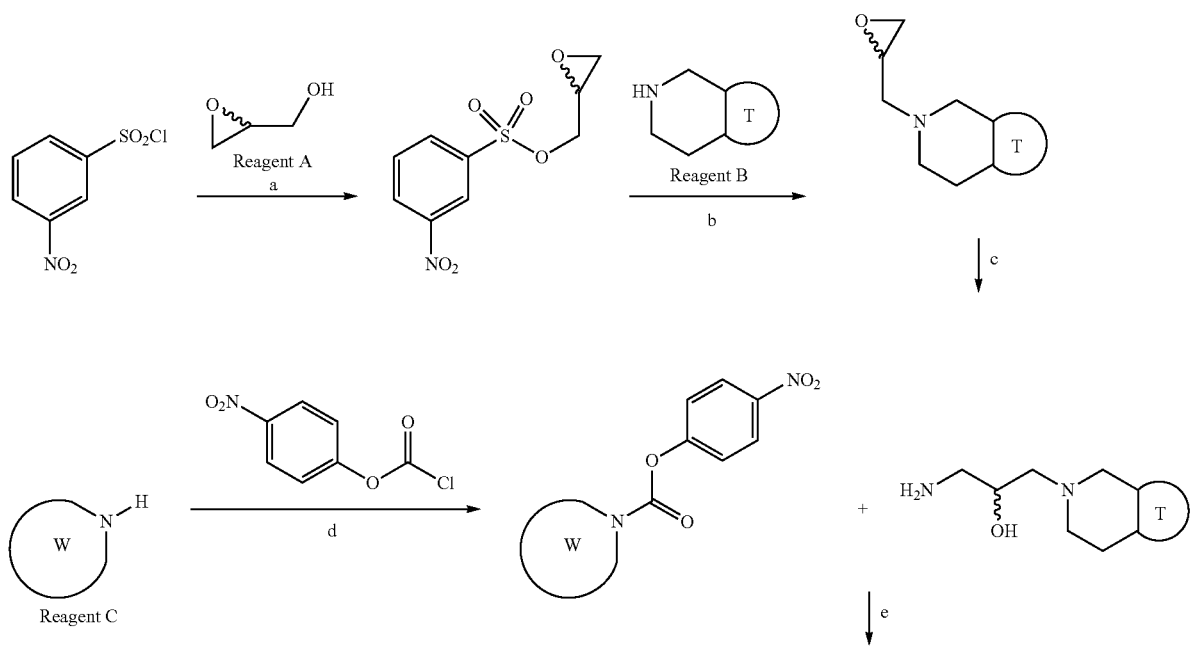

Scheme 2

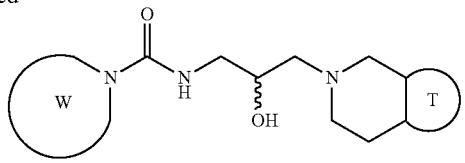

Reagents and conditions: a) Triethylamine, dichloromethane, 0-5° C., 1 h b) KF, THF, 0° C. to rt, 16 h c) NH₃ gas purging at -78° C. in ethanol, followed by heating under hydrogenator at 80° C., 4 h d) diisopropylethylamine, THF, 0° C. to rt, 1 h e) K₂CO₃, DMF, 80° C., 2 h.

Example 1A N-(3-(3,4-dihydroisoquinolin-2(1H)-yl)-2-hydroxypropyl)-3-phenylpyrrolidine-1-carboxamide (Prepared according to Scheme 2)

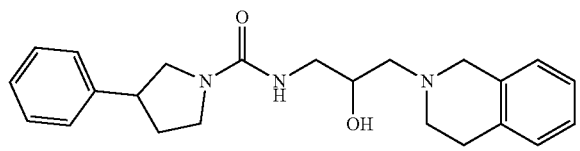 [SMILES: O=C(NCC(O)CN1CCc2ccccc2C1)N1CCC(c2ccccc2)C1]

Step a

To a stirred solution of glycidol (CAS Number 556-52-5, available from Sigma-India) (1.67 g, 22.560 mmol) in dichloromethane (50 ml) was added triethylamine (3.90 ml, 27.070 mmol) at 0° C. for 15 min. To the above reaction mixture was added 3-nitrobenzenesulfonyl chloride (CAS Number 121-51-7, available from combi-blocks) (5.00 g, 22.560 mmol) and the reaction mixture was stirred at same temperature for 1 h. The resulting reaction mixture was poured into water (200 ml) and extracted with dichloromethane (2×100 ml). The combined organic phase was dried over Na₂SO₄, filtered and concentrated under reduced pressure. The resulting crude material was triturated using n-pentane yielding ethyl oxiran-2-ylmethyl 3-nitrobenzenesulfonate (5.00 g, 19.305 mmol).

Step b

To a stirred solution of 1,2,3,4-tetrahydroisoquinoline (2.57 g, 19.300 mmol) in THF (25 ml) at 0° C. was added KF (4.48 g, 77.200 mmol) and allowed to stir at same temperature for 1 h. To the above reaction mixture was added solution of ethyl oxiran-2-ylmethyl 3-nitrobenzenesulfonate (5.00 g, 19.300 mmol) in THF (25 ml) at 0° C. and allowed to stir at room temperature for 16 h. The above reaction mixture filtered to remove excess KF and filtrate collected was concentrated under reduced pressure. The resulting crude material was purified by flash chromatography (2.0% methanol in dichloromethane) yielding 2-(oxiran-2-ylmethyl)-1,2,3,4-tetrahydroisoquinoline (3.50 g, 18.510 mmol). LCMS: Method B, 4.109 min, MS: ES+190.1 (M+1).

Step c

To a stirred solution of 2-(oxiran-2-ylmethyl)-1,2,3,4-tetrahydroisoquinoline (1.50 g, 7.936 mmol) in ethanol (20 ml) was cooled to -78° C. and ammonia gas was purged for 1 h. (Note: Total volume of solution became double after absorption of ammonia gas). The above solution was carefully transferred into Parr hydrogenator (precooled at -78° C.) and sealed it. The hydrogenator was heated at 80° C. for 4 h. After completion of 4 h, the reaction mixture was cooled to ambient temperature and concentrated under reduced pressure yielding 1-amino-3-(3,4-dihydroisoquinolin-2(1H)-yl)propan-2-ol (1.30 g, 6.300 mmol). LCMS: Method B, 4.871 min, MS: ES+324.3 (M+1).

Step d

To a stirred solution of 3-phenyl pyrrolidine (CAS No. 936-44-7; available from Combi Blocks) (0.25 g, 0.619 mmol) in THF (5 ml) was added diisopropylethylamine (0.38 ml, 2.000 mmol) and allowed to stir at 0° C. for 15 min, followed by addition of 4-nitrophenyl chloroformate (CAS No. 7693-46-1; available from Spectrochem) (0.40 g, 2.000 mmol) and allowed to stir at 0° C. for 1 h. After completion of reaction, reaction mixture was poured into water (25 ml). The resulting reaction mixture was extracted with ethyl acetate (2×20 ml). The combined organic phase was dried over Na₂SO₄, filtered and concentrated under reduced pressure. The resulting crude material was purified by flash chromatography (4.5% ethyl acetate in hexane) yielding 4-nitrophenyl 3-phenylpyrrolidine-1-carboxylate (0.40 g, 1.280 mmol). LCMS: Method B, 3.419 min, MS: ES+207.1 (M+1).

Step e

To a stirred solution of 1-amino-3-(3,4-dihydroisoquinolin-2(1H)-yl)propan-2-ol (0.20 g, 0.970 mmol) in DMF (2 ml) was added K₂CO₃ (0.27 g, 1.940 mmol) and stirred at room temperature and stirred for 15 min. 4-nitrophenyl 3-phenylpyrrolidine-1-carboxylate (0.30 g, 0.970 mmol) was added to the above reaction mixture and stirred at 80° C. for 2 h. Reaction mixture was poured into water (25 ml) and extracted with ethyl acetate (2×20 ml). The combined organic phase was dried over Na₂SO₄, filtered and concentrated under reduced pressure. The resulting crude material was purified by reverse-phase flash chromatography (60% acetonitrile in water) yielding N-(3-(3,4-dihydroisoquinolin-2(1H)-yl)-2-hydroxypropyl)-3-phenylpyrrolidine-1-carboxamide (0.1 g crude material), which was further purified by preparative HPLC yielding N-(3-(3,4-dihydroisoquinolin-2(1H)-yl)-2-hydroxypropyl)-3-phenylpyrrolidine-1-carboxamide. (0.04 g, 0.097 mmol) LCMS: Method A, 1.703 min, MS: ES+380.3 (M+1); 1H NMR (400 MHz, DMSO-d6) δ ppm: 7.350-7.301 (m, 2H), 7.256-7.210 (m, 3H), 7.106-7.018 (m, 4H), 6.237-6.228 (d, J=3.6 Hz, 1H), 4.930-4.906 (t, J=4.8 Hz, 1H), 3.794-3.769 (m, 1H), 3.693-3.551 (m, 3H), 3.456-3.411 (m, 1H), 3.307-3.171 (m, 3H), 3.152-3.120 (m, 1H), 3.105-3.032 (m, 1H), 2.724-2.753 (m, 2H), 2.724-2.672 (m, 2H), 2.482-2.394 (m, 1H), 2.181-2.155 (m, 1H), 1.910-1.861 (m, 1H).

Using the route depicted above, the following compounds were also prepared:

| Example | Name | Structure | Reagent A | Reagent B | Reagent C | LC/MS | NMR |
|---|---|---|---|---|---|---|---|
| 1B | 4-acetyl-N-[2-hydroxy-3-(1,2,3,4-tetrahydroisoquinolin-2-yl)propyl]piperazine-1-carboxamide | 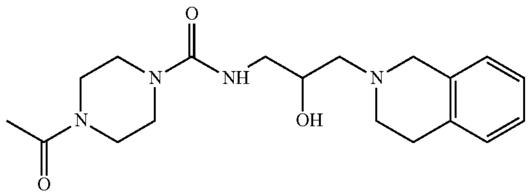 [SMILES: CC(=O)N1CCN(C(=O)NCC(O)CN2CCc3ccccc3C2)CC1] | | | | Method C, Retention Time = 2.256 min, MS: ES+ 361.2 (M + 1) | (400 MHz, CDCl₃) δ ppm: 7.200-7.142 (m, 3H), 7.043-7.028 (m, 1H), 5.364 (br s, 1H), 3.978-3.942 (m, 1H), 3.859-3.822 (m, 1H), 3.663-3.546 (m, 3H), 3.455 (s, 4H) 3.356-3.330 (m, 1H), 3.254-3.330 (m, 1H), 2.971-2.944 (m, 1H), 2.784-2.748 (m, 1H), 2.619-2.532 (m, 2H), 2.121 (s, 4H), 2.030 (s, 3H) |
| 1C | N-[2-hydroxy-3-(1,2,3,4-tetrahydroisoquinolin-2-yl)propyl]-4-phenylpiperazine-1-carboxamide | 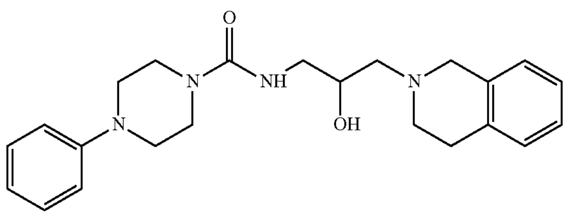 [SMILES: O=C(NCC(O)CN1CCc2ccccc2C1)N1CCN(c2ccccc2)CC1] | | | | Method C, Retention Time = 2.256 min, MS: ES+ 361.2 (M + 1) | (400 MHz, CDCl₃) δ ppm: 7.200-7.028 (m, 2H), 7.205-7.130 (m, 3H), 7.050-7.030 (m, 3H), 6.949-6.900 (m, 1H), 5.350-5.323 (t, J = 5.6 Hz, 1H), 4.019-3.961 (m, 1H), 3.876-3.839 (d, J = 14.0 Hz, 1H), 3.682 (s, 1H), 3.631-3.596 (m, 4H), 3.588-3.534 (m, 1H), 3.286-3.223 (m, 4H), 3.184-3.158 (m, 4H), 3.006-2.938 (m, 3H), 2.651-2.620 (m, 2H), 2.587-2.556 (m, 2H) |

-continued

| Example | Name | Structure | Reagent A | Reagent B | Reagent C | LC/MS | NMR |
|---|---|---|---|---|---|---|---|
| 1D | 4-benzyl-N-[2-hydroxy-3-(1,2,3,4-tetrahydroiso-quinolin-2-yl)propyl]piperazine-1-carboxamide | 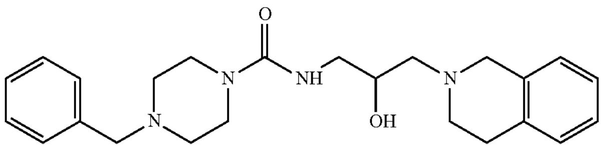 [SMILES: O=C(NCC(O)CN1CCc2ccccc2C1)N1CCN(Cc2ccccc2)CC1] | | | | Method B, Retention Time = 4.668 min, MS: ES+ 409.6 (M + 1) | (400 MHz, CDCl₃) δ ppm: 7.369-7.284 (m, 5H), 7.202-7.128 (m, 3H), 7.051-7.030 (dd, J = 2.8 Hz, 5.6 Hz, 1H), 5.393 (br s, 1H), 4.010 (br s, 1H), 3.997-3.900 (m, 1H), 3.810-3.765 (m, 1H), 3.728-3.712 (m, 1H), 3.611-3.554 (m, 1H), 3.533 (m, 2H), 3.399-3.386 (m, 3H), 3.288-3.225 (m, 1H), 3.169-2.991 (m, 3H), 2.978-2.922 (m, 2H), 2.895-2.614 (m, 2H), 2.440-2.415 (m, 4H) |
| 1E | N-[2-hydroxy-3-(1,2,3,4-tetrahydroiso-quinolin-2-yl)propyl]-3-phenyl-piperidine-1-carboxamide | 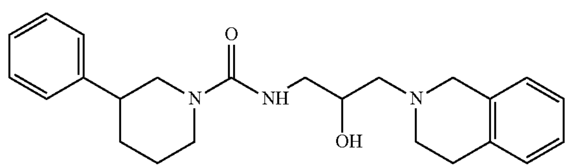 [SMILES: O=C(NCC(O)CN1CCc2ccccc2C1)N1CCCC(c2ccccc2)C1] | | | | Method A, Retention Time = 1.862 min, MS: ES+ 394.2 (M + 1) | (400 MHz, DMSO-d₆) δ ppm: 10.410-10.309 (br d, 1H), 7.402-7.147 (m, 9H), 6.865 (s, 1H), 5.883 (br s, 1H), 4.597-4.519 (m, 1H), 4.242-3-4.354 (dt, J = 2.4 Hz, 8.0 Hz, 1H), 4.115-4.001 (m, 3H), 3.773-3.672 (m, 1H), 3.233-3.152 (m, 5H), 3.038-2.993 (m, 1H), 2.777-2.672 (m, 2H), 2.603-2.563 (m, 1H), 1.899-1.869 (d, J = 12.0 Hz, 1H), 1.703-1.591 (m, 2H), 1.452-1.422 (m, 1H) |

| Example | Name | Structure | Reagent A | Reagent B | Reagent C | LC/MS | NMR |
|---|---|---|---|---|---|---|---|
| 1F | N-[2-hydroxy-3-(1,2,3,4-tetrahydroisoquinolin-2-yl)propyl]-4-phenylpiperidine-1-carboxamide | 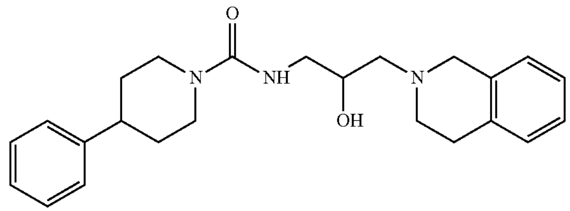 [SMILES: O=C(NCC(O)CN1CCc2ccccc2C1)N1CCC(c2ccccc2)CC1] | | | | Method A, Retention Time = 1.858 min, MS: ES+ 394.2 (M + 1) | (400 MHz, DMSO-d₆) δ ppm: 10.354 (m, 1H), 7.324-7.157 (m, 9H), 6.871 (m, 1H), 5.910 (br s, 1H), 4.607-4.530 (m, 1H), 4.431-4.344 (m, 1H), 4.147-4.115 (m, 3H), 4.783-4.608 (m, 3H), 4.419 (br s, 1H), 3.218-3.141 (m, 2H), 3.116-3.107 (m, 1H), 3.082-2.989 (m, 1H), 2.801-2.655 (m, 3H), 1.758-1.726 (d, J = 12.8 Hz, 2H), 1.527-1.445 (m, 2H) |
| 1G | N-[2-hydroxy-3-(1,2,3,4-tetrahydroisoquinolin-2-yl)propyl]-4-phenoxypiperidine-1-carboxamide | 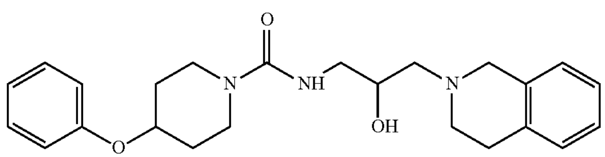 [SMILES: O=C(NCC(O)CN1CCc2ccccc2C1)N1CCC(Oc2ccccc2)CC1] | | | | Method A, Retention Time = 1.718 min, MS: ES+ 410.2 (M + 1) | (400 MHz, DMSO-d₆) δ ppm: 10.354 (m, 1H), 7.324-7.157 (m, 9H), 6.871 (m, 1H), 5.910 (br s, 1H), 4.607-4.530 (m, 1H), 4.431-4.344 (m, 1H), 4.147-4.115 (m, 3H), 4.783-4.608 (m, 3H), 4.419 (br s, 1H), 3.218-3.141 (m, 2H), 3.116-3.107 (m, 1H), 3.082-2.989 (m, 1H), 2.801-2.655 (m, 3H), 1.758-1.726 (d, J = 12.8 Hz, 2H), 1.527-1.445 (m, 2H) |

| Example | Name | Structure | Reagent A | Reagent B | Reagent C | LC/MS | NMR |
|---|---|---|---|---|---|---|---|
| 1H | N-[2-hydroxy-3-(1,2,3,4-tetrahydroisoquinolin-2-yl)propyl]-3-phenoxypiperidine-1-carboxamide | 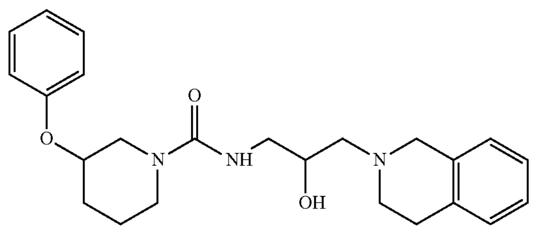 [SMILES: O=C(NCC(O)CN1CCc2ccccc2C1)N1CCCC(Oc2ccccc2)C1] | | | | Method A, Retention Time = 1.722 min, MS: ES+ 410.2 (M + 1) | (400 MHz, DMSO-d₆) δ ppm: 7.299-7.259 (m, 2H), 7.110-7.064 (m, 3H), 7.027-6.908 (m, 4H), 6.661-6.656 (m, 2H), 4.822-4.811 (d, J = 4.4 Hz, 1H), 4.250-4.210 (m, 1 H), 3.939-3.908 (m, 1H), 3.786-3.3.774 (m, 1H), 3.647-3.488 (m, 3H), 3.196-3.148 (m, 1H), 3.059-3.012 (m, 1H), 2.972-2.901 (m, 2H), 2.798-2.677 (m, 4H), 2.478 -2.334 (m, 1H), 1.999-1.968 (m, 1H), 1.585-1.509 (m, 1H), 1.426-1.393 (m, 1H) |
| 1I | N-[2-hydroxy-3-(1,2,3,4-tetrahydroisoquinolin-2-yl)propyl]-1,2,3,4-tetrahydroisoquinoline-2-carboxamide | 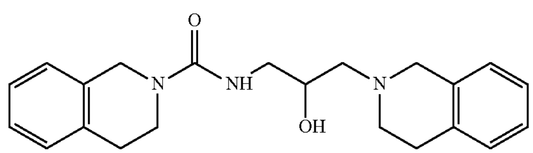 [SMILES: O=C(NCC(O)CN1CCc2ccccc2C1)N1CCc2ccccc2C1] | | | | Method A, Retention Time = 1.639 min, MS: ES+ 366.6 (M + 1) | (400 MHz, DMSO-d₆) δ ppm: 7.157-7.080 (m, 6H), 7.038-7.023 (m, 1H), 6.989-6.970 (m, 1H), 6.725-6.699 (t, J = 5.2 Hz, 1H), 4.887 (br s, 1H), 4.425 (s, 2H), 3.818-3.792 (m, 1H), 3.673-3.567 (m, 2H), 3.512-3.482 (t, J = 6.0 Hz, 2H), 3.238-3.179 (m, 1H), 3.121-3.057 (m, 1H), 2.817-2.776 (m, 2H), 2.724-2.678 (m, 4H), 2.600 (m, 1H), 2.461-2.417 (m, 1H) |

| Example | Name | Structure | Reagent A | Reagent B | Reagent C | LC/MS | NMR |
|---|---|---|---|---|---|---|---|
| 1J | N-[2-hydroxy-3-(1,2,3,4-tetrahydroisoquinolin-2-yl)propyl]-2,3,4,5-tetrahydro-1H-1-benzazepine-1-carboxamide | 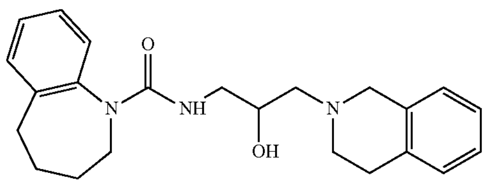 [SMILES: O=C(NCC(O)CN1CCc2ccccc2C1)N1CCCCc2ccccc21] | | | | Method A. Retention Time = 1.858 min. MS: ES+ 380.2 (M + 1) | (400 MHz, DMSO-d$_6$) δ ppm: 10.250-10.180 (br d, 1H), 7.309-7.075 (m, 8H), 5.750 (br s, 1H), 4.581-4.511 (m, 1H), 4.412-4.328 (m, 1H), 4.076 (br s, 1H), 3.757-3.3.656 (m, 1H), 3.436 (m, 1H), 3.257-2.979 (m, 6H), 2.895 (s, 1H), 2.735-2.693 (m, 1H), 2.681-2.621 (m, 2H), 2.094-2.069 (m, 2H), 1.663 (m, 3H) |
| 1K | N-[2-hydroxy-3-(1,2,3,4-tetrahydroisoquinolin-2-yl)propyl]-2,3,4,5-tetrahydro-1H-1-benzazepine-1-carboxamide | 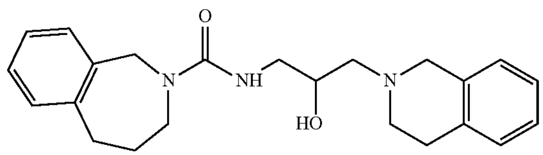 [SMILES: O=C(NCC(O)CN1CCc2ccccc2C1)N1CCCc2ccccc2C1] | | | | Method A. Retention Time = 1.744 min. MS: ES+ 380.2 (M + 1) | (400 MHz, DMSO-d$_6$) δ ppm: 10.360-10.276 (br d, 1H), 7.388 (br s, 1H), 7.306-7.220 (m, 3H), 7.193-7.112 (m, 4H), 6.776-6749 (t, J = 5.6 Hz, 1H), 5.892 (br s, 1H), 4.462-4.416 (m, 3H), 4.286-4.253 (m, 1H), 4.038 (br s, 1H), 3.640 (m, 2H), 3.520 (m, 1H), 3.168 (m, 1H), 3.089-3.055 (m, 3H), 3.013-2.937 (m, 4H), 1.632 (m, 2H) |

| Example | Name | Structure | Reagent A | Reagent B | Reagent C | LC/MS | NMR |
|---|---|---|---|---|---|---|---|
| 1L | N-[2-hydroxy-3-(1,2,3,4-tetrahydroisoquinolin-2-yl)propyl]piperidine-1-carboxamide | 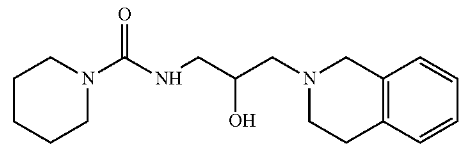 [SMILES: O=C(NCC(O)CN1CCc2ccccc2C1)N1CCCCC1] | | | | Method B, Retention Time = 4.398 min, MS: ES+ 318.6 (M + 1) | (400 MHz, CDCl₃) δ ppm: 7.168-7.136 (m, 3H), 7.052-7.028 (m, 1H), 5.122 (br s, 1H), 3.974-3.963 (m, 1H), 3.866-3.834 (m, 1H), 3.674-3.603 (m, 1H), 3.600-3.556 (m, 1H), 3.352-3.330 (m, 4H), 3.254-3.195 (m, 1H), 2.976-2.945 (m, 3H), 2.794-2.756 (m, 1H), 2.613-2.544 (m, 2H), 1.613-1.555 (m, 6H) |
| 1M | N-[2-hydroxy-3-(1,2,3,4-tetrahydroisoquinolin-2-yl)propyl]pyrrolidine-1-carboxamide | 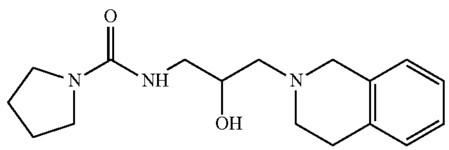 [SMILES: O=C(NCC(O)CN1CCc2ccccc2C1)N1CCCC1] | | | | Method B, Retention Time = 4.162 min, MS: ES+ 304.5 (M + 1) | (400 MHz, CDCl₃) δ ppm: 7.193-7.142 (m, 3H), 7.042-7.027 (m, 1H), 4.085 (br s, 1H), 3.979-3.962 (m, 1H), 3.864-3.642 (m, 2H), 3.623-3.564 (m, 1H), 3.364 (br s, 4H), 3.264-3.189 (m, 1H), 2.973-2.890 (m, 3H), 2.823-2.762 (m, 1H), 2.644-2.552 (m, 2H), 1.923 (br s, 4H) |
| 1N | N-[2-hydroxy-3-(1,2,3,4-tetrahydroisoquinolin-2-yl)propyl]azepane-1-carboxamide | 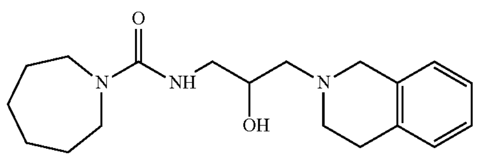 [SMILES: O=C(NCC(O)CN1CCc2ccccc2C1)N1CCCCCC1] | | | | Method B, Retention Time = 4.533 min, MS: ES+ 332.6 (M + 1) | (400 MHz, CDCl₃) δ ppm: 7.176-7.150 (m, 3H), 7.052-7.028 (m, 1H), 5.082 (br s, 1H), 3.972 (br s, 1H), 3.896-3.862 (m, 1H), 3.714-3.583 (m, 2H), 3.434-3.405 (m, 4H), 3.299-3.230 (m, 1H), 2.989-2.972 (m, 3H), 2.811 (br s, 1H), 2.623-2.579 (m, 2H), 1.724 (br s, 8H) |

| Example | Name | Structure | Reagent A | Reagent B | Reagent C | LC/MS | NMR |
|---|---|---|---|---|---|---|---|
| 1O | N-(3-(3,4-dihydroisoquinolin-2(1H)-yl)-2-hydroxypropyl)-4-(morpholine-4-carbonyl)piperidine-1-carboxamide | 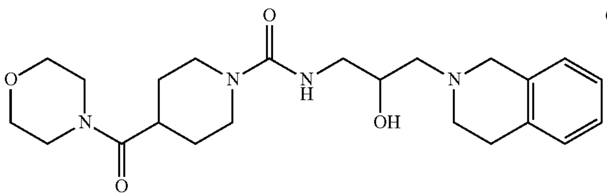 | | | | Method A, Retention Time = 1.293 min, MS: ES+ 431.1 (M + 1) | (400 MHz, DMSO-d$_6$) δ ppm: 7.094-7.043 (m, 4H), 6.627 (br s, 1H), 4.867-4.857 (d, J = 4.0 Hz, 1H), 3.895-3.864 (m, 2H), 3.772 (br s, 1H), 3.657-3.424 (m, 9H), 3.182-3.149 (m, 1H), 3.056-3.010 (m, 1H), 2.808-2.795 (m, 3H), 2.736-2.637 (m, 5H), 2.439-2.335 (m, 2H), 1.500-1.371 (m, 4H) |
| 1P | N-(3-(3,4-dihydroisoquinolin-2(1H)-yl)-2-hydroxypropyl)-3-(pyridin-4-ylamino)piperidine-1-carboxamide | 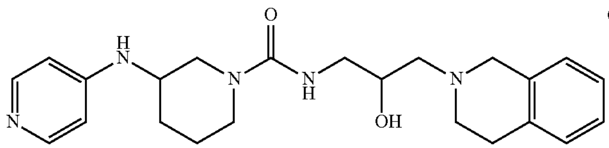 | | | | Method A, Retention Time = 2.034 min, MS: ES+ 410.3 (M + 1) | (400 MHz, DMSO-d$_6$) δ ppm: 8.043-8.028 (d, J = 6.0 Hz, 2H), 7.105-7.082 (m, 3H), 7.035-7.017 (m, 1H), 6.750-6.733 (d, J = 6.8 Hz, 1H), 6.671-6.659 (d, J = 4.8 Hz, 1H), 6.594-6.580 (d, J = 5.6 Hz, 2H), 4.834 (br s, 1H), 4.003-4.001 (m, 1H), 3.973-3.565 (m, 3H), 3.272-3.003 (m, 4H), 2.806-2.683 (m, 6H), 2.477-2.401 (m, 2H), 1.934-1.909 (m, 1H), 1.579 (br s, 1H), 1.397-1.353 (m, 2H) |

| Example | Name | Structure | Reagent A | Reagent B | Reagent C | LC/MS | NMR |
|---|---|---|---|---|---|---|---|
| 1Q | 4-benzyl-N-(3-(3,4-dihydroisoquinolin-2(1H)-yl)-2-hydroxypropyl)piperidine-1-carboxamide | 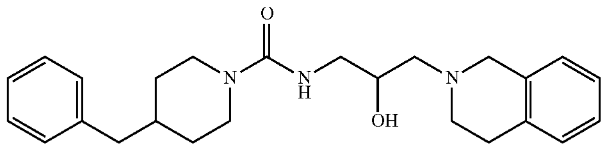 [SMILES: O=C(NCC(O)CN1CCc2ccccc2C1)N1CCC(Cc2ccccc2)CC1] | | | | Method A, Retention Time = 1.901 min, MS: ES+ 408.3 (M+1) | (400 MHz, DMSO-$d_6$) δ ppm: 7.299-7.263 (m, 2H), 7.200-7.134 (m, 3H), 7.104-7.081 (m, 3H), 7.039-7.019 (m, 1H), 6.597-6.571 (t, J = 5.2 Hz, 1 H), 4.875-4.865 (d, J = 4.0 Hz, 1H), 3.783-3.743 (m, 3H), 3.651-3.539 (m, 2H), 3.166-3.107 (m, 1H), 3.070-3.007 (m, 1H), 2.802-2.788 (m, 2H), 2.756-2.647 (m, 2H), 2.552 (br s, 2H), 2.470-2.384 (m, 4H), 1.627-1.573 (m, 1H), 1.435-1.404 (m, 2H), 1.010-0.925 (m, 2H) |
| 1R | 4-(3-oxa-8-azabicyclo[3.2.1]octane-8-carbonyl)-N-(3-(3,4-dihydroisoquinolin-2(1H)-yl)-2-hydroxypropyl)piperidine-1-carboxamide | 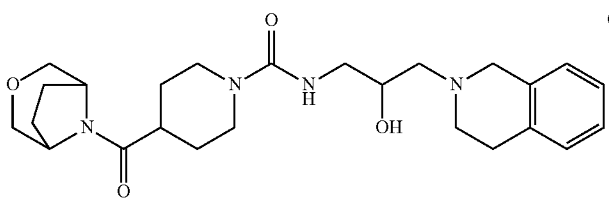 | | | | Method A, Retention Time = 1.435 min, MS: ES+ 457.2 (M+1) | (400 MHz, DMSO-$d_6$) δ ppm: 7.115-7.094 (m, 3H), 7.045-7.029 (m, 1H), 6.641-6.629 (m, 1H), 4.871-4.862 (d, J = 3.6 Hz, 1H), 4.372-4.356 (d, J = 6.4 Hz, 1H), 4.294-4.281 (d, J = 5.2 Hz, 1H), 3.886-3.858 (m, 2H), 3.801-3.760 (q, J = 5.6 Hz, 1H), 3.664-3.424 (m, 6H), 3.181-3.134 (m, 1H), 3.076-3.028 (m, 1H), 2.811-2.797 (m, 2H), 2.768-2.619 (m, 5H), 2.486-2.413 (m, 2H), 1.911-1.811 (m, 3H), 1.738-1.697 (m, 1H), 1.562-1.532 (m, 1H), 1.455-1.239 (m, 3H) |

| Example | Name | Structure | Reagent A | Reagent B | Reagent C | LC/MS | NMR |
|---|---|---|---|---|---|---|---|
| 1S | N-(3,4-dihydro-isoquinolin-2(1H)-yl)-2-hydroxy-propyl)-4-phenyl-1,4-diazepane-1-carboxamide | 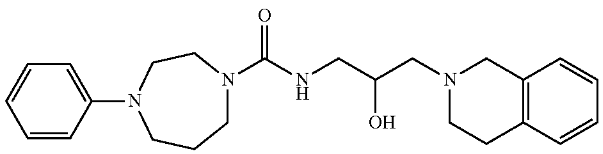 | | | | Method A, Retention Time = 2.592 min, MS: ES+ 409.3 (M + 1) | (400 MHz, DMSO-d₆) δ ppm: 7.156-7.076 (m, 5H), 7.043-7.026 (m, 1H), 6.691-6.671 (d, J = 8.0 Hz, 2H), 6.581-6.545 (t, J = 7.2 Hz, 1H), 6.446-6.420 (t, J = 5.2 Hz, 1H), 4.848-4.837 (d, J = 4.4 Hz, 1H), 3.769-3.729 (m, 1H), 3.631-3.529 (m, 2H), 3.461-3.436 (m, 6H), 3.179-3.029 (m, 4H), 2.802-2.787 (m, 2H), 2.731-2.647 (m, 2H), 2.499-2.359 (m, 2H), 1.816-1.787 (m, 2H) |
| 1T | 4-benzyl-N-(3-(3,4-dihydro-isoquinolin-2(1H)-yl)-2-hydroxy-propyl)-1,4-diazepane-1-carboxamide | 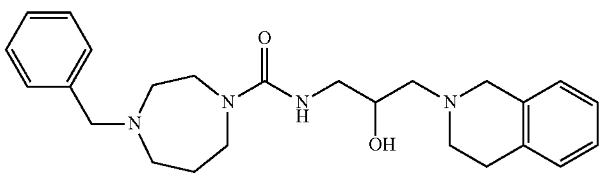 [SMILES: O=C(NCC(O)CN1CCc2ccccc2C1)N1CCCN(Cc2ccccc2)CC1] | | | | Method A, Retention Time = 2.542 min, MS: ES+ 423.3 (M + 1) | (400 MHz, DMSO-d₆) δ ppm: 7.337-7.229 (m, 5H), 7.102-7.004 (m, 4H), 6.419-6.393 (t, J = 5.2 Hz, 1H), 4.930-4.921 (d, J = 3.6 Hz, 1H), 3.785-3.774 (m, 1H), 3.655-3.549 (m, 4H), 3.318-3.287 (m, 5H), 3.163-3.090 (m, 2H), 2.794-2.781 (m, 2H), 2.727-2.679 (m, 2H), 2.478-2.397 (m, 5H), 1.644 (br s, 2H) |

| Example | Name | Structure | Reagent A | Reagent B | Reagent C | LC/MS | NMR |
|---|---|---|---|---|---|---|---|
| 1U | N-(3-(3,4-dihydroisoquinolin-2(1H)-yl)-2-hydroxypropyl)thiomorpholine-4-carboxamide | 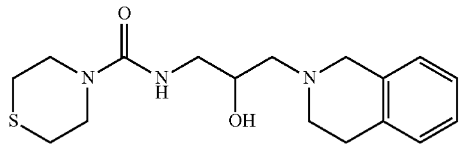 [SMILES: O=C(NCC(O)CN1CCc2ccccc2C1)N1CCSCC1] | | | | Method A, Retention Time = 2.882 min, MS: ES+ 336.2 (M + 1) | (400 MHz, DMSO-d₆) δ ppm: 7.122-7.026 (m, 4H), 6.668-6.642 (t, J = 5.2 Hz, 1H), 4.813-4.802 (d, J = 4.4 Hz, 1H), 3.806-3.766 (m, 1H), 3.656-3.521 (m, 6H), 3.211-3.151 (m, 1H), 3.065-3.016 (m, 1H), 2.810-2.795 (m, 2H), 2.733-2.675 (m, 2H), 2.477-2.391 (m, 6H) |
| 1V | N¹-(3-(3,4-dihydroisoquinolin-2(1H)-yl)-2-hydroxypropyl)-N³,N³-dimethylazetidine-1,3-dicarboxamide | 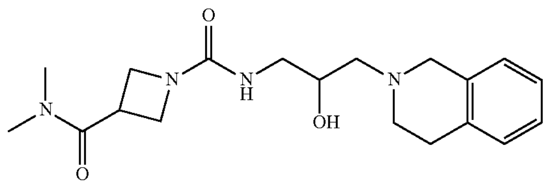 | | | | Method B, Retention Time = 1.194 min, MS: ES+ 361.2 (M + 1) | (400 MHz, DMSO-D₆) δ ppm: 7.125-7.092 (m, 3H), 7.051-7.039 (m, 1H), 6.402-6.376 (t, J = 5.2 Hz, 1H), 3.919-3.749 (m, 5H), 3.654-3.580 (m, 3H), 3.178-3.110 (m, 1H), 2.981-2.923 (m, 1H), 2.827-2.807 (m, 6H), 2.775-2.742 (m, 2H), 2.548-2.438 (m, 4H) |
| 1W | N-(3-(3,4-dihydroisoquinolin-2(1H)-yl)-2-hydroxypropyl)-3-(morpholine-4-carbonyl)azetidine-1-carboxamide | 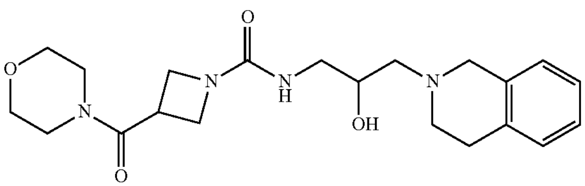 [SMILES: O=C(NCC(O)CN1CCc2ccccc2C1)N1CC(C(=O)N2CCOCC2)C1] | | | | Method A, Retention Time = 2.764 min, MS: ES+ 403.3 (M + 1) | (400 MHz, DMSO-d₆) δ ppm: 7.116-7.084 (m, 3H), 7.040-7.022 (m, 1H), 6.399-6.371 (t, J = 5.6 Hz, 1H), 4.782-4.771 (d, J = 4.4 Hz, 1H), 3.901-3.844 (m, 4H), 3.737-3.723 (m, 1H), 3.602-3.587 (m, 2H), 3.558-3.517 (m, 4H), 3.461-3.437 (m, 2H), 3.243-3.219 (m, 2H), 3.157-3.124 (m, 1H), 2.966-2.949 (m, 1H), 2.802-2.788 (m, 2H), 2.722-2.673 (m, 2H), 2.472-2.377 (m, 3H) |

| Example | Name | Structure | Reagent A | Reagent B | Reagent C | LC/MS | NMR |
|---|---|---|---|---|---|---|---|
| 1X | 3-(3-oxa-8-azabicyclo[3.2.1]octane-8-carbonyl)-N-(3-(3,4-dihydroisoquinolin-2(1H)-yl)-2-hydroxypropyl)azetidine-1-carboxamide | 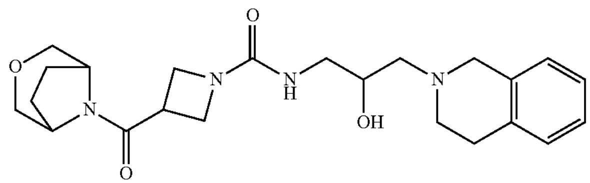 [SMILES: O=C(NCC(O)CN1CCc2ccccc2C1)N1CC(C(=O)N2C3CCC2COC3)C1] | | | | Method A, Retention Time = 2.860 min, MS: ES+ 429.3 (M+1) | (400 MHz, DMSO-d$_6$) δ 7.130-7.084 (m, 3H), 7.042-7.024 (m, 1H), 6.394-6.367 (t, J = 5.2 Hz, 1H), 4.787-4.777 (d, J = 4.0 Hz, 1H), 4.392-4.475 (d, J = 6.8 Hz, 1H), 3.965-3.805 (m, 5H), 3.740-3.727 (m, 1H), 3.605-3.535 (m, 4H), 3.483-3.399 (m, 2H), 3.163-3.130 (m, 1H), 2.965-2.948 (m, 1H), 2.816-2.789 (m, 2H), 2.726-2.673 (m, 2H), 2.458-2.396 (m, 4H), 1.891-1.729 (m, 4H) |
| 1Y | N-(3-(6,7-dihydrothieno[3,2-c]pyridin-5(4H)-yl)-2-hydroxypropyl)-3,4-dihydroquinoline-1(2H)-carboxamide | 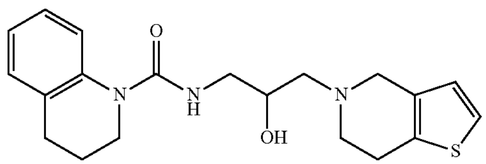 [SMILES: O=C(NCC(O)CN1CCc2sccc2C1)N1CCCc2ccccc21] | | | | Method A, Retention Time = 1.670 min, MS: ES+ 372.2 (M+1) | (400 MHz, DMSO-d$_6$) δ ppm: 7.439-7.418 (d, J = 8.4 Hz, 1H), 7.277-7.264 (d, J = 5.2 Hz, 1H), 7.094-7.047 (m, 2H), 6.939-6.900 (td, J = 1.2, 7.2 Hz, 1H), 6.792-6.779 (d, J = 5.2 Hz, 1H), 6.658-6.632 (t, J = 5.2 Hz, 1H), 4.842-4.831 (d, J = 4.4 Hz, 1H), 3.835-3.779 (q, J = 5.6 Hz, 1H), 3.577-3.479 (m, 4H), 3.280-3.221 (m, 1H), 3.153-3.090 (m, 1H), 2.759 (br s, 4H), 2.666-2.633 (t, J = 6.4 Hz, 2H), 2.485-2.453 (m, 2H), 1.796-1.733 (quin, J = 6.4 Hz, 2H) |

| Example | Name | Structure | Reagent A | Reagent B | Reagent C | LC/MS | NMR |
|---|---|---|---|---|---|---|---|
| 1Z | N-(3-(4,7-dihydrothieno[2,3-c]pyridin-6(5H)-yl)-2-hydroxypropyl)-3,4-dihydroquinoline-1(2H)-carboxamide | 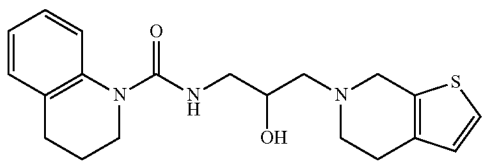 [SMILES: O=C(NCC(O)CN1CCc2ccsc2C1)N1CCCc2ccccc21] | | | | Method A, Retention Time = 1.669 min, MS: ES+ 372.1 (M + 1) | (400 MHz, DMSO-d₆) δ ppm: 7.535-7.523 (d, J = 4.8 Hz, 1H), 7.453 (br s, 1H), 7.117-7.078 (m, 2H), 6.968-6.930 (m, 2H), 6.888-6.862 (t, J = 5.6 Hz, 1H), 5.855 (br s, 1H), 4.712-4.647 (m, 1H), 4.505-4.471 (m, 1H), 4.168 (br s, 1H), 3.759-3.656 (m, 1H), 3.613-3.583 (t, J = 6.4 Hz, 2H), 3.460 (br s, 1H), 3.303-2.903 (m, 6H), 2.699-2.667 (t, J = 6.4 Hz, 2H), 1.859-1.797 (quin, J = 6.4 Hz, 2H) |
| 1AA | N-(3-(6,7-dihydrothieno[3,2-c]pyridin-5(4H)-yl)-2-hydroxypropyl)-3,4-dihydroisoquinoline-2(1H)-carboxamide | 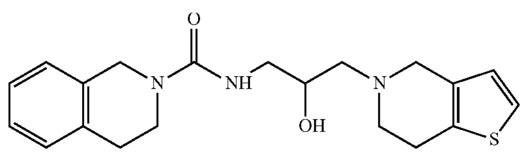 [SMILES: O=C(NCC(O)CN1CCc2sccc2C1)N1CCc2ccccc2C1] | | | | Method A, Retention Time = 1.666 min, MS: ES+ 372.1 (M + 1) | (400 MHz, DMSO-d₆) δ ppm: 7.278-7.266 (d, J = 4.8 Hz, 1H), 7.168-7.130 (m, 3H), 7.054-7.034 (m, 1H), 6.789-6.776 (d, J = 5.2 Hz, 1H), 6.704-6.678 (t, J = 5.2 Hz, 1H), 4.874-4.863 (d, J = 4.4 Hz, 1H), 3.797-3.757 (m, 1H), 3.574-3.474 (m, 4H), 3.233-3.173 (m, 1H), 3.099-3.036 (m, 1H), 2.794-2.771 (m, 3H), 2.741-2.673 (m, 3H), 2.547-2.513 (m, 2H), 2.475-2.428 (m, 2H) |

| Example | Name | Structure | Reagent A | Reagent B | Reagent C | LC/MS | NMR |
|---|---|---|---|---|---|---|---|
| 1AB | N-(3-(4,7-dihydrothieno[2,3-c]pyridin-6(5H)-yl)-2-hydroxypropyl)-3,4-dihydroisoquinoline-2(1H)-carboxamide | 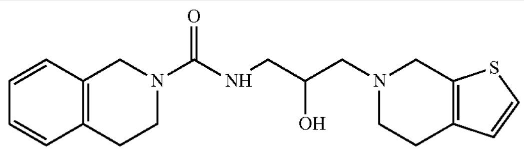 [SMILES: O=C(NCC(O)CN1CCc2ccsc2C1)N1CCc2ccccc2C1] | | | | Method A, Retention Time = 1.599 min, MS: ES+ 372.2 (M + 1) | (400 MHz, CDCl₃) δ ppm: 7.225-7.136 (m, 5H), 6.822-6.810 (d, J = 4.8 Hz, 1H), 5.244 (br s, 1H), 3.970-3.963 (m, 1H), 3.904-3.732 (m, 2H), 3.695-3.552 (m, 4H), 3.319-3.257 (m, 1H), 3.009-2.983 (m, 1H), 2.903-2.796 (m, 6H), 2.716-2.676 (m, 1H), 2.618-2.563 (m, 1H) |
| 1AC | N-(3-(6,7-dihydrothieno[3,2-c]pyridin-5(4H)-yl)-2-hydroxypropyl)-3-phenylpiperidine-1-carboxamide | 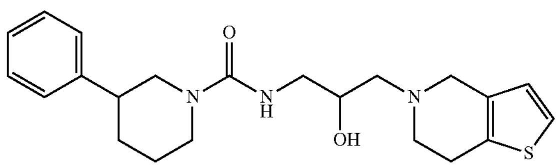 [SMILES: O=C(NCC(O)CN1CCc2sccc2C1)N1CCCC(c2ccccc2)C1] | | | | Method A, Retention Time = 1.821 min, MS: ES+ 400.2 (M + 1) | (400 MHz, DMSO-d₆) δ ppm: 7.368-7.331 (m, 2H), 7.292-7.279 (d, J = 5.2 Hz, 1 H), 7.238-7.202 (t, J = 7.2 Hz, 1H), 7.170-7.157 (m, 2H), 6.799-6.781 (m, 1H), 6.694-6.680 (m, 1H), 5.139 (br s, 1H), 4.980-4.935 (m, 1H), 3.848-3.778 (m, 2H), 3.563-3.510 (m, 2H), 3.210-3.131 (m, 2H), 2.791 (br s, 4H), 2.631-2.514 (m, 4H), 2.275-2.244 (m, 2H), 1.745-1.677 (m, 1H), 1.534-1.444 (m, 2H), 1.371-1.298 (m, 1H) |

| Example | Name | Structure | Reagent A | Reagent B | Reagent C | LC/MS | NMR |
|---|---|---|---|---|---|---|---|
| 1AD | N-(3-(4,7-dihydrothieno[2,3-c]pyridin-6(5H)-yl)-2-hydroxypropyl)-3-phenylpiperidine-1-carboxamide | 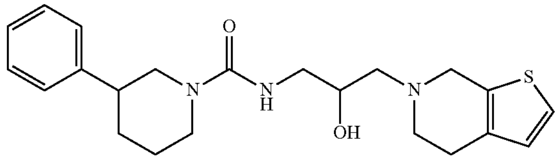 [SMILES: O=C(NCC(O)CN1CCc2ccsc2C1)N1CCCC(c2ccccc2)C1] | | | | Method A, Retention Time = 1.825 min, MS: ES+ 400.1 (M + 1) | (400 MHz, CDCl₃) δ ppm: 7.397-7.353 (m, 2H), 7.263-7.244 (m, 3H), 7.136-7.123 (d, J = 5.2 Hz, 1H), 6.806-6.788 (m, 1H), 5.238-5.167 (m, 2H), 3.956-3.845 (m, 2H), 3.808-3.639 (m, 3H), 3.589-3.530 (m, 1H), 3.289-3.245 (m, 1H), 3.046-2.856 (m, 2H), 2.794-2.703 (m, 3H), 2.630-2.546 (m, 2H), 2.475-2.444 (m, 1H), 2.264-2.231 (m, 1H), 1.958-1.923 (m, 1H), 1.62-1.546 (m, 2H), 1.502-1.443 (m, 1H) |
| 1AE | N-(3-(6,7-dihydrothieno[3,2-c]pyridin-5(4H)-yl)-2-hydroxypropyl)-3-phenylpyrrolidine-1-carboxamide | 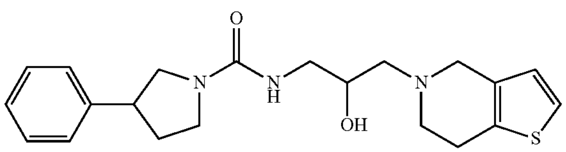 [SMILES: O=C(NCC(O)CN1CCc2sccc2C1)N1CCC(c2ccccc2)C1] | | | | Method A, Retention Time = 1.657 min, MS: ES+ 386.2 (M + 1) | (400 MHz, DMSO-d₆) δ ppm: 7.343-7.213 (m, 6H), 6.796-6.783 (d, J = 5.2 Hz, 1 H), 6.246-6.239 (m, 1H), 4.986 (br s, 1H), 3.781-3.754 (m, 1H), 3.704-3.649 (m, 1H), 3.606-3.506 (m, 2H), 3.438-3.350 (m, 1H), 3.261-3.108 (m, 4H), 3.056 (br s, 1H), 2.831-2.794 (m, 4H), 2.606 (br s, 2H), 2.186-2.175 (m, 1H), 1.930-1.880 (m, 1H) |

| Example | Name | Structure | Reagent A | Reagent B | Reagent C | LC/MS | NMR |
|---|---|---|---|---|---|---|---|
| 1AF | N-(3-(4,7-dihydrothieno[2,3-c]pyridin-6(5H)-yl)-2-hydroxypropyl)-3-phenylpyrrolidine-1-carboxamide | 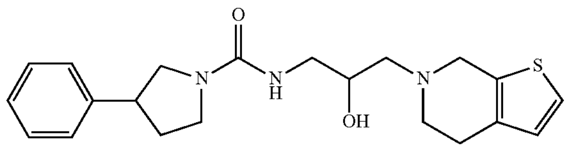 [SMILES: O=C(NCC(O)CN1CCc2ccsc2C1)N1CCC(c2ccccc2)C1] | | | | Method A, Retention Time = 1.723 min, MS: ES+ 386.2 (M + 1) | (400 MHz, CDCl₃) δ ppm: 7.369-7.333 (m, 2H), 7.268-7.247 (m, 3H), 7.142-7.130 (d, J = 4.8 Hz, 1H), 6.812-6.799 (d, J = 5.2 Hz, 1H), 4.932 (br s, 1H), 3.953-3.747 (m, 4H), 3.620-3.531 (m, 2H), 3.456-3.368 (m, 3H), 3.267-3.250 (m, 1H), 3.017-2.991 (m, 1H), 2.877-2.787 (m, 3H), 2.715-2.576 (m, 2H), 2.327 (br s, 1H), 2.114-2.015 (m, 1H) |
| 1AG | (S)-N-((S)-3-(3,4-dihydroisoquinolin-2(1H)-yl)-2-hydroxypropyl)-3-phenylpiperidine-1-carboxamide | 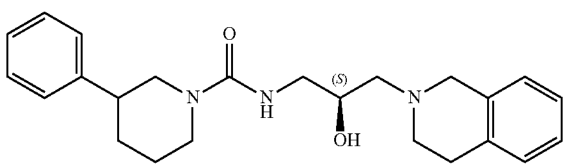 | | | | Method A, Retention Time = 1.836 min, MS: ES+ 394.0 (M + 1) | (400 MHz, DMSO-d₆) δ ppm: 7.365-7.327 (t, J = 8 Hz, 2H), 7.236-7.200 (t, J = 7.2 Hz, 1H), 7.168-7.081 (m, 5H), 7.049-7.034 (m, 1H), 6.706-6.694 (m, 1H), 5.305 (s, 1H), 3.842-3.812 (m, 2H), 3.730-3.604 (m, 2H), 3.216-3.104 (m, 2H), 2.802-2.765 (m, 4H), 2.677-.586 (m, 2H), 2.468-2.467 (m, 2H), 2.231 (br s, 1H), 1.759-1.670 (m, 1H), 1.523-1.285 (m, 3H), 1.240-1.147 (m, 1H) |

| Example | Name | Structure | Reagent A | Reagent B | Reagent C | LC/MS | NMR |
|---|---|---|---|---|---|---|---|
| 1AI | (S)-N-((R)-3-(3,4-dihydroisoquinolin-2(1H)-yl)-2-hydroxypropyl)-3-phenylpiperidine-1-carboxamide | 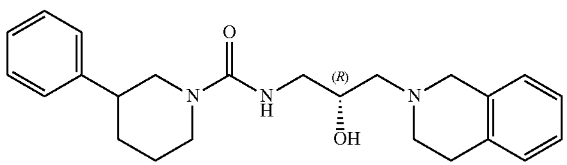 | | | | Method A, Retention Time = 1.827 min, MS: ES+ 394.1 (M + 1) | (400 MHz, DMSO-d₆) δ ppm: 7.363-7.325 (t, J = 7.6 Hz, 2H), 7.235-7.199 (t, J = 7.2 Hz, 1H), 7.164-7.033 (m, 5H), 6.690-6.678 (m, 1H), 5.301 (br s, 1H), 4.854 (br s, 1H), 3.837-3.807 (m, 2H), 3.655-3.520 (m, 2H), 3.202-3.099 (m, 2H), 2.776-2.591 (m, 4H), 2.509-2.373 (m, 4H), 2.225 (br s, 1H), 1.721-1.688 (m, 1H), 1.520-1.175 (m, 4H) |
| 1AJ | (S)-N-(3-(3,4-dihydroisoquinolin-2(1H)-yl)-2-hydroxypropyl)-3,4-dihydroquinoline-1(2H)-carboxamide | 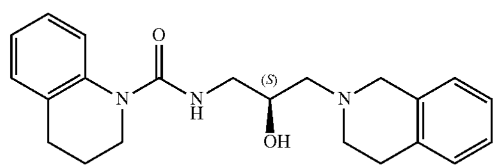 | | | | Method A, Retention Time = 1.671 min, MS: ES+ 366.2 (M + 1) | (400 MHz, DMSO-d₆) δ ppm: 7.438-7.418 (d, J = 8 Hz, 1H), 7.131-7.018 (m, 6H), 6.926-6.889 (m, 1H), 6.664-6.638 (t, J = 5.2 Hz, 1H), 4.847-4.835 (d, J = 4.8 Hz, 1H), 3.860-3.819 (q, J = 5.2 Hz, 1H), 3.656-3.587 (m, 2H), 3.558-3.466 (m, 2H), 3.290-3.230 (m, 1H), 3.166-3.103 (m, 1H), 2.767-2.753 (m, 2H), 2.735-2.665 (m, 2H), 2.646-2.614 (t, J = 6.4 Hz, 2H), 2.5548-2.424 (m, 2H), 1.770-1.723 (m, 2H) |

| Example | Name | Structure | Reagent A | Reagent B | Reagent C | LC/MS | NMR |
|---|---|---|---|---|---|---|---|
| 1AK | (R)-N-(3-(3,4-dihydroisoquinolin-2(1H)-yl)-2-hydroxypropyl)-3,4-dihydroquinoline-1(2H)-carboxamide | 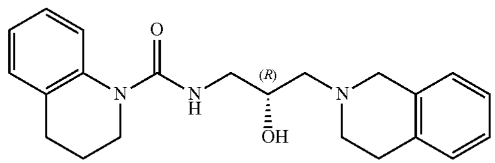 | | | | Method A, Retention Time = 1.744 min, MS: ES+ 366.1 (M + 1) | (400 MHz, CDCl₃) δ ppm: 7.449-7.431 (d, J = 7.2 Hz, 1H), 7.201-7.114 (m, 5H), 7.070-7.020 (m, 2H), 5.747-5.720 (t, J = 5.2 Hz, 1H), 4.007-3.974 (m, 1H), 3.861-3.823 (m, 1H), 3.792-3.761 (t, J = 6.4 Hz, 2H), 3.663-3.630 (m, 1H), 3.616-3.558 (m, 2H), 3.276-3.212 (m, 1H), 2.975-2.910 (m, 3H), 2.811-2.754 (m, 3H), 2.670-2.531 (m, 2H), 1.982-1.917 (quin, J = 6.8 Hz, 2H) |
| 1AL | (S)-N-(3-(3,4-dihydroisoquinolin-2(1H)-yl)-2-hydroxypropyl)-3,4-dihydroisoquinoline-2(1H)-carboxamide | 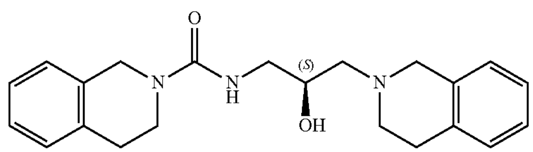 | | | | Method A, Retention Time = 2.406 min, MS: ES+ 366.3 (M + 1) | (400 MHz, DMSO-d₆) δ ppm: 7.156-7.078 (m, 6H), 7.036-7.022 (m, 1H), 6.986-6.968 (m, 1H), 6.720-6.695 (t, J = 5.2 Hz, 1H), 4.875-4.864 (d, J = 4.4 Hz, 1H), 4.424 (s, 2H), 3.827-3.787 (m, 1H), 3.663-3.554 (q, J = 15.2 Hz, 2H), 3.511-3.481 (t, J = 6.0 Hz, 2H), 3.238-3.179 (m, 1H), 3.119-3.056 (m, 1H), 2.813-2.799 (m, 2H), 2.767-2.655 (m, 4H), 2.558-2.405 (m, 2H) |

-continued

| Example | Name | Structure | Reagent A | Reagent B | Reagent C | LC/MS | NMR |
|---|---|---|---|---|---|---|---|
| 1AM | (R)-N-(3-(3,4-dihydroisoquinolin-2(1H)-yl)-2-hydroxypropyl)-3,4-dihydroisoquinoline-2(1H)-carboxamide | [structure] | [epoxide with OH] | [1,2,3,4-tetrahydroisoquinoline] | [1,2,3,4-tetrahydroisoquinoline] | Method A, Retention Time = 1.688 min, MS: ES+ 366.2 (M + 1) | (400 MHz, DMSO-d$_6$) δ ppm: 7.155-7.076 (m, 6H), 7.035-7.020 (m, 1H), 6.985-6.966 (m, 1H), 6.725-6.699 (t, J = 5.2 Hz, 1H), 4.879-4.868 (d, J = 4.4 Hz, 1H), 4.423 (s, 2H), 3.825-3.786 (m, 1H), 3.661-3.552 (q, J = 15.2 Hz, 2H), 3.510-3.480 (t, J = 6.0 Hz, 2H), 3.237-3.178 (m, 1H), 3.117-3.054 (m, 1H), 2.811-2.797 (m, 2H), 2.779-2.651 (m, 4H), 2.547-2.419 (m, 2H) |
| 1AN | (S)-N-((S)-3-(3,4-dihydroisoquinolin-2(1H)-yl)-2-hydroxypropyl)-3-phenylpiperidine-1-carboxamide | [structure] | [epoxide with OH] | [1,2,3,4-tetrahydroisoquinoline] | [3-phenylpiperidine] | Method B, Retention Time = 2.117 min, MS: ES+ 394.3 (M + 1) | (400 MHz, DMSO-d$_6$) δ ppm: 7.333-7.297 (m, 2H), 7.272-7.219 (m, 3H), 7.113-7.036 (m, 4H), 6.616-6.642 (t, J = 5.2 Hz, 1 H), 4.852-4.841 (d, J = 4.4 Hz, 1H), 4.008-3.929 (m, 2H), 3.799-3.759 (q, J = 5.2 Hz, 1H), 3.646-3.554 (m, 2H), 3.206-3.160 (m, 1H), 3.056-3.008 (m, 1H), 2.797-2.783 (m, 2H), 2.763-2.662 (m, 3H), 2.646-2.554 (m, 2H), 2.476-2.378 (m, 2H), 1.875-1.850 (m, 2H), 1.640-1.612 (m, 1H), 1.599-1.587 (m, 1H) |

| Example | Name | Structure | Reagent A | Reagent B | Reagent C | LC/MS | NMR |
|---|---|---|---|---|---|---|---|
| 1AO | (R)-N-((S)-3-(3,4-dihydroisoquinolin-2(1H)-yl)-2-hydroxypropyl)-3-phenylpiperidine-1-carboxamide | 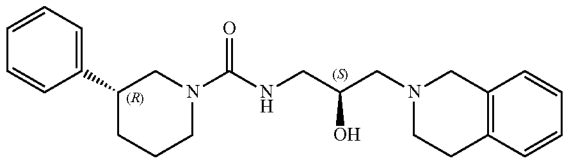 | | | | Method B, Retention Time = 2.146 min, MS: ES+ 394.3 (M + 1) | (400 MHz, DMSO-d$_6$) δ ppm: 7.333-7.296 (m, 2H), 7.265-7.202 (m, 3H), 7.113-7.014 (m, 4H), 6.645-6.617 (t, J = 5.6 Hz, 1H), 4.854-4.843 (d, J = 4.4 Hz, 1H), 3.996-3.930 (m, 2H), 3.810-3.775 (m, 1H), 3.651-3.545 (m, 2H), 3.192-3.145 (m, 1H), 3.055-3.038 (m, 1H), 2.795-2.779 (m, 2H), 2.724-2.653 (m, 3H), 2.612-2.376 (m, 4H), 1.871-1.846 (m, 1H), 1.612-1.583 (m, 2H), 1.416-1.384 (m, 1H) |
| 1AP | (S)-4-acetyl-N-(3-(3,4-dihydroisoquinolin-2(1H)-yl)-2-hydroxypropyl)-1,4-diazepane-1-carboxamide | 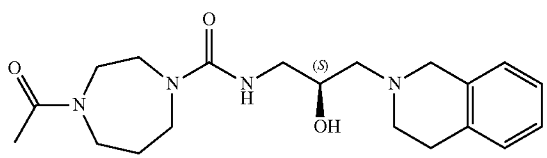 | | | | Method B, Retention Time = 1.152 min, MS: ES+ 375.2 (M + 1) | (400 MHz, DMSO-d$_6$) δ ppm: 7.109-7.045 (m, 4H), 6.501-6.543 (m, 1H), 4.895 (br s, 1H), 3.773 (br s, 3H), 3.671-3.614 (m, 8H), 3.337-3.278 (m, 1H), 3.169-3.141 (m, 1H), 3.050 (br s, 1H), 2.813-2.800 (m, 2H), 2.738-2.723 (m, 2H), 2.440-2.424 (m, 2H), 1.983-1.954 (m, 2H), 1.689 (br s, 1H), 1.581 (br s, 1H) |

| Example | Name | Structure | Reagent A | Reagent B | Reagent C | LC/MS | NMR |
|---|---|---|---|---|---|---|---|
| 1AQ | (S)-N-(3-(3,4-dihydroisoquinolin-2(1H)-yl)-2-hydroxypropyl)-4-(methylsulfonyl)-1,4-diazepane-1-carboxamide | 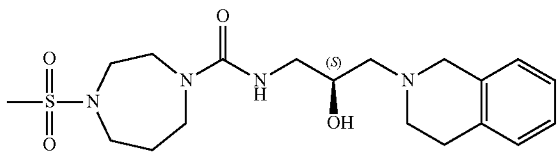 | | | | Method B, Retention Time = 3.809 min, MS: ES+ 411.1 (M + 1) | (400 MHz, DMSO-d₆) δ ppm: 7.118-7.087 (m, 3H), 7.043-7.032 (m, 1H), 6.449 (br s, 1H), 4.841-4.831 (d, J = 4.0 Hz, 1H), 3.778-3.775 (m, 1H), 3.619-3.592 (m, 2H), 3.444-3.417 (m, 2H), 3.389-3.359 (m, 2H), 3.273-3.247 (m, 2H), 3.229-3.200 (m, 2H), 3.174-3.068 (m, 2H), 2.869 (s, 3H), 2.809-2.795 (m, 2H), 2.733-2.690 (m, 2H), 2.483-2.418 (m, 2H), 1.701-1.673 (m, 2H) |
| 1AR | (S)-4-benzoyl-N-(3-(3,4-dihydroisoquinolin-2(1H)-yl)-2-hydroxypropyl)-1,4-diazepane-1-carboxamide | 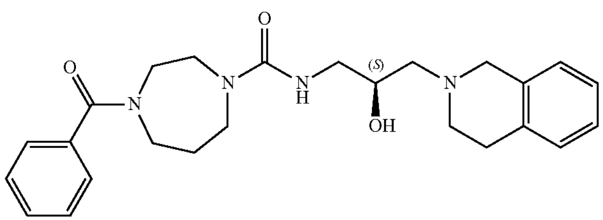 | | | | Method B, Retention Time = 1.545 min, MS: ES+ 437.3 (M + 1) | (400 MHz, DMSO-d₆) δ ppm: 7.427 (br s, 3H), 7.328-7.319 (m, 2H), 7.095-7.083 (m, 3H), 7.013-7.001 (m, 1H), 6.515-6.484 (m, 1H), 4.845 (br s, 1H), 3.788-3.738 (m, 1H), 3.650-3.483 (m, 5H), 3.319-3.209 (m, 5H), 3.175-3.072 (m, 3H), 2.789 (br s, 2H), 2.698-2.682 (m, 2H), 2.419-2.407 (m, 2H), 1.740 (br s, 1H), 1.486 (br s, 1H) |

| Example | Name | Structure | Reagent A | Reagent B | Reagent C | LC/MS | NMR |
|---|---|---|---|---|---|---|---|
| 1AS | Methyl (S)-4-((3-(3,4-dihydroisoquinolin-2(1H)-yl)-2-hydroxypropyl)carbamoyl)-1,4-diazepane-1-carboxylate | 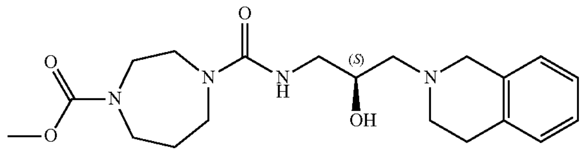 | | | | Method B, Retention Time = 1.445 min, MS: ES+ 391.2 (M + 1) | (400 MHz, CDCl₃) δ ppm: 7.285-7.202 (m, 2H), 7.185-7.166 (m, 1H), 7.094-7.077 (m, 1H), 5.869-5.816 (m, 1H), 4.136-4.119 (m, 2H), 3.712 (s, 3H), 3.666-3.373 (m, 9H), 3.101 (br s, 2H), 2.958-2.824 (m, 2H), 2.347 (br s, 4H), 1.920-1.872 (m, 2H) |
| 1AT | (S)-N-(3-(3,4-dihydroisoquinolin-2(1H)-yl)-2-hydroxypropyl)-1,4-thiazepane-4-carboxamide | 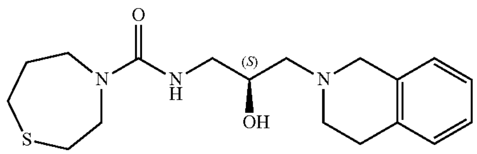 | | | | Method B, Retention Time = 1.524 min, MS: ES+ 350.1 (M + 1) | (400 MHz, DMSO-d₆) δ ppm: 7.121-7.071 (m, 3H), 7.041-7.023 (m, 1H), 6.371-6.345 (t, J = 5.2 Hz, 1H), 4.878-4.869 (d, J = 3.6 Hz, 1H), 3.797-3.757 (m, 1H), 3.660-3.556 (m, 2H), 3.512-3.485 (m, 2H), 3.433-3.404 (t, J = 6.0 Hz, 2H), 3.179-3.133 (m, 1H), 3.098-3.050 (m, 1H), 2.810-2.796 (m, 2H), 2.722-2.677 (m, 2H), 2.627-2.600 (t, J = 5.6 Hz, 2H), 2.547-2.517 (m, 2H), 2.473-2.389 (m, 2H), 1.879-1.819 (quin, J = 6.0 Hz, 2H) |

-continued

| Example | Name | Structure | Reagent A | Reagent B | Reagent C | LC/MS | NMR |
|---|---|---|---|---|---|---|---|
| 1AU | N-((S)-3-(3,4-dihydro-isoquinolin-2(1H)-yl)-2-hydroxy-propyl)-1,4-thiazepane-4-carboxamide 1-oxide | 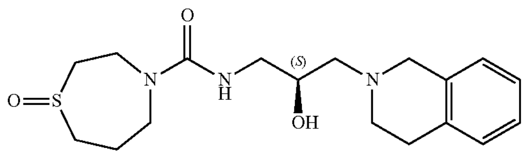 | | | | Method B, Retention Time = 3.757 min, MS: ES+ 366.1 (M + 1) | (400 MHz, DMSO-d₆) δ ppm: 7.112-7.076 (m, 3H), 7.044-7.026 (m, 1H), 6.551-6.525 (t, J = 5.6 Hz, 1H), 4.863 (br s, 1H), 3.787-3.745 (m, 2H), 3.663-3.557 (m, 2H), 3.445-3.398 (m, 2H), 3.203-3.110 (m, 2H), 3.083-3.008 (m, 2H), 2.893-2.572 (m, 7H), 2.448-2.432 (m, 2H), 2.170-2.132 (m, 1H), 1.776-1.732 (m, 1H) |
| 1AV | (S)-N-(3-(3,4-dihydro-isoquinolin-2(1H)-yl)-2-hydroxy-propyl)-1,4-thiazepane-4-carboxamide 1,1-dioxide | 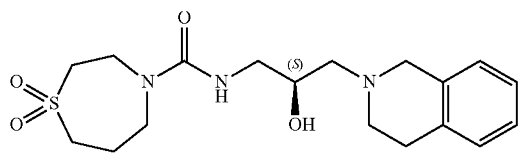 | | | | Method B, Retention Time = 3.759 min, MS: ES+ 382.0 (M + 1) | (400 MHz, DMSO-d₆) δ ppm: 7.108-7.097 (m, 3H), 7.041-7.029 (m, 1H), 6.573 (br s, 1H), 4.829-4.821 (d J = 3.2 Hz, 1H), 3.809-3.798 (m, 1H), 3.624-3.559 (m, 4H), 3.445-3.426 (m, 2H), 3.276 (br s, 2H), 3.209-3.163 (m, 3H), 3.053-3.019 (m, 1H), 2.808-2.795 (m, 2H), 2.722-2.709 (m, 2H), 2.469-2.411 (m, 2H), 1.881-1.852 (m, 2H) |

| Example | Name | Structure | Reagent A | Reagent B | Reagent C | LC/MS | NMR |
|---|---|---|---|---|---|---|---|
| 1AW | (S)-N-(3-(3,4-dihydroisoquinolin-2(1H)-yl)-2-hydroxypropyl)-4-(thiophene-2-carbonyl)-1,4-diazepane-1-carboxamide | 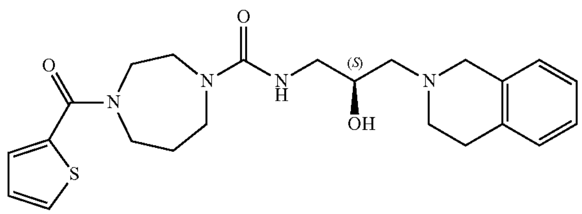 | | | | Method C, Retention Time = 3.105 min, MS: ES+ 443.3 (M + 1) | (400 MHz, DMSO-d₆) δ ppm 7.742-7.730 (d, J = 4.8 Hz, 1H), 7.417-7.410 (d, J = 2.8 Hz, 1H), 7.127-7.063 (m, 4H), 7.024-7.005 (m, 1H), 6.512-6.486 (t, J = 5.2 Hz, 1H), 4.796 (br s, 1H), 3.729-3.671 (m, 3H), 3.574-3.556 (m, 4H), 3.502-3.375 (m, 4H), 3.114-3.037 (m, 2H), 2.787-2.773 (m, 2H), 2.682-2.673 (m, 2H), 2.462-2.335 (m, 2H), 1.723-1.710 (m, 2H) |
| 1AX | (S)-N¹-(3-(3,4-dihydroisoquinolin-2(1H)-yl)-2-hydroxypropyl)-N⁴,N⁴-dimethylpiperidine-1,4-dicarboxamide | 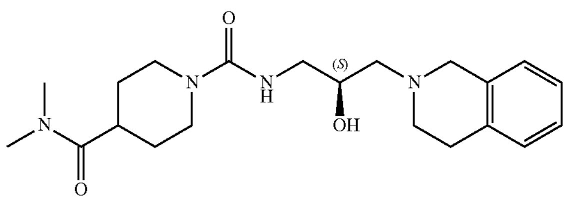 | | | | Method C, Retention Time = 2.879 min, MS: ES+ 389.3 (M + 1) | (400 MHz, DMSO-d₆) δ ppm: 7.104-7.093 (m, 3H), 7.043-7.033 (m, 1H), 6.619 (br s, 1H), 4.872-4.862 (d, J = 4.0 Hz, 1H), 3.905-3.872 (m, 2H), 3.762 (br s, 1H), 3.655-3.550 (m, 2H), 3.191-3.151 (m, 1H), 3.502-3.006 (m, 1H), 3.006 (s, 3H), 2.796-2.635 (m, 9H), 2.476-2.418 (m, 3H), 1.505-1.477 (m, 2H), 1.350-1.319 (m, 2H) |

| Example | Name | Structure | Reagent A | Reagent B | Reagent C | LC/MS | NMR |
|---|---|---|---|---|---|---|---|
| 1AY | (S)-N-(3-(3,4-dihydroisoquinolin-2(1H)-yl)-2-hydroxypropyl)-4-(morpholine-4-carbonyl)piperidine-1-carboxamide | 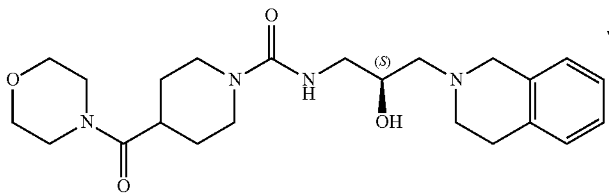 | | | | Method B, Retention Time = 3.877 min, MS: ES+ 431.1 (M + 1) | (400 MHz, DMSO-d$_6$) δ ppm: 7.118-7.085 (m, 3H), 7.043-7.026 (m, 1H), 6.649-6.623 (t, J = 5.2 Hz, 1H), 4.873-4.563 (d, J = 4.4 Hz, 1H), 3.895-3.862 (m, 2H), 3.783-3.770 (m, 1H), 3.656-3.494 (m, 8H), 3.432-3.421 (m, 2H), 3.179-3.133 (m, 1H), 3.069-3.006 (m, 1H), 2.807-2.795 (m, 2H), 2.762-2.633 (m, 5H), 2.477-2.389 (m, 3H), 1.498-1.468 (m, 2H), 1.398-1.338 (m, 2H) |
| 1AZ | 4-(3-oxa-8-azabicyclo[3.2.1]octane-8-carbonyl)-N-((S)-3-(3,4-dihydroisoquinolin-2(1H)-yl)-2-hydroxypropyl)piperidine-1-carboxamide | 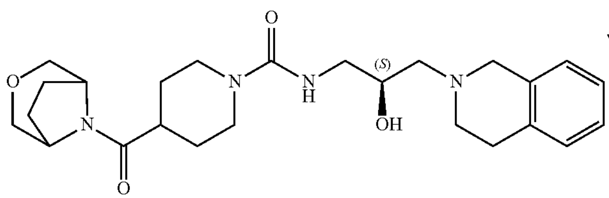 | | | | Method B, Retention Time = 1.515 min, MS: ES+ 457.2 (M + 1) | (400 MHz, DMSO-d$_6$) δ ppm: 7.119-7.038 (m, 4H), 6.652-6.626 (t, J = 5.2 Hz, 1H), 4.890 (br s, 1H), 4.371-4.283 (m, 2H), 3.913-3.790 (m, 3H), 3.675-3.422 (m, 6H), 3.194-3.134 (m, 1H), 3.076-3.013 (m, 1H), 2.815-2.802 (m, 2H), 2.703-2.621 (m, 5H), 2.453-2.439 (m, 2H), 1.914-1.821 (m, 3H), 1.725-1.712 (m, 1H), 1.532-1.359 (m, 4H) |

| Example | Name | Structure | Reagent A | Reagent B | Reagent C | LC/MS | NMR |
|---|---|---|---|---|---|---|---|
| 1BA | N-((S)-3-(3,4-dihydro-isoquinolin-2(1H)-yl)-2-hydroxy-propyl)-3-(pyridin-2-yl)pyrrolidine-1-carbox-amide | 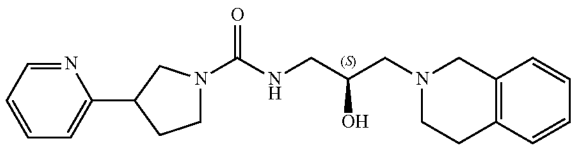 | | | | Method C, Retention Time = 3.033 min, MS: ES+ 381.2 (M + 1) | (400 MHz, DMSO-d₆) δ ppm: 8.523-8.513 (d, J = 4.0 Hz, 1H), 7.760-7.717 (td, J = 2.0, 7.6 Hz, 1H), 7.303-7.284 (d, J = 7.6 Hz, 1H), 7.268-7.235 (m, 1H), 7.104-7.054 (m, 3H), 7.035-7.013 (m, 1H), 6.240-6.233 (m, 1H), 4.927 (br s, 1H), 3.778 (br s, 1H), 3.679-3.589 (m, 3H), 3.500-3.417 (m, 2H), 3.294-3.172 (m, 2H), 3.073-3.024 (m, 1H), 2.799-2.786 (m, 2H), 2.764-2.672 (m, 3H), 2.475-2.389 (m, 2H), 2.198-2.157 (m, 1H), 2.060-2.029 (m, 1H) |
| 1BB | (R)-4-acetyl-N-(3-(3,4-dihydro-isoquinolin-2(1H)-yl)-2-hydroxy-propyl)-1,4-diazepane-1-carbox-amide | 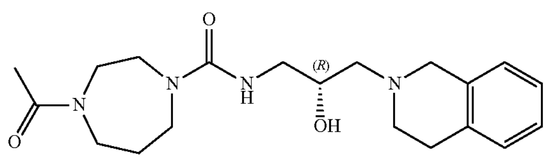 | | | | Method B, Retention Time = 3.863 min, MS: ES+ 375.1 (M + 1) | (400 MHz, DMSO-d₆) δ ppm: 7.120-7.071 (m, 3H), 7.043-7.033 (m, 1H), 6.493-6.417 (br s, 1H), 4.836 (br s, 1H), 3.767 (br s, 1H), 3.653-3.556 (m, 2H), 3.437-3.266 (m, 8H), 3.183-3.129 (m, 1H), 3.083-3.034 (m, 1H), 2.808-2.794 (m, 2H), 2.761-2.677 (m, 2H), 2.468-2.376 (m, 2H), 1.985-1.956 (m, 3H), 1.710-1.680 (m, 1H), 1.600-1.573 (m, 1H) |

| Example | Name | Structure | Reagent A | Reagent B | Reagent C | LC/MS | NMR |
|---|---|---|---|---|---|---|---|
| 1BC | Methyl (R)-4-(3-(3,4-dihydro-isoquin-olin-2(1H)-yl)-2-hydroxy-propyl)carbamoyl)-1,4-diazepane-1-carboxy-late | 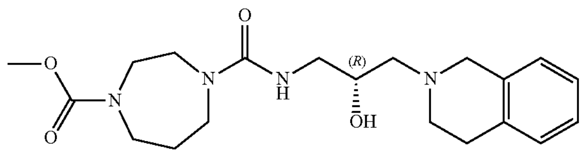 | | | | Method B, Retention Time = 1.687 min, MS: ES+ 391.3 (M + 1) | (400 MHz, DMSO-$d_6$) δ ppm: 7.105-7.094 (m, 3H), 7.040-7.028 (m, 1H), 6.467-6.453 (m, 1H), 4.855-4.823 (m, 1H), 3.772-3.760 (m, 1H), 3.648-3.549 (m, 5H), 3.356-3.305 (m, 8H), 3.171-3.136 (m, 1H), 3.068-3.036 (m, 1H), 2.805-2.792 (m, 2H), 2.725-2.681 (m, 2H), 2.466-2.373 (m, 2H), 1.633-1.620 (m, 2H) |
| 1BD | (R)-N-(3-(3,4-dihydro-isoquin-olin-2(1H)-yl)-2-hydroxy-propyl)-4-(methyl-sulfonyl)-1,4-diazepane-1-carbox-amide | 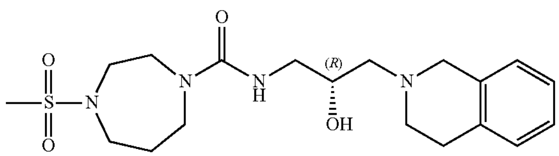 | | | | Method B, Retention Time = 1.569 min, MS: ES+ 411.3 (M + 1) | (400 MHz, DMSO-$d_6$) δ ppm: 7.106-7.094 (m, 3H), 7.041-7.023 (m, 1H), 6.514-6.488 (m, 1H), 4.842-4.832 (d, J = 4.0 Hz, 1H), 3.786-3.772 (m, 1H), 3.651-3.549 (m, 1H), 3.442-3.386 (m, 2H), 3.271-3.146 (m, 4H), 3.079-3.032 (m, 5H), 2.868 (s, 3H), 2.806-2.792 (m, 2H), 2.729-2.672 (m, 2H), 2.478-2.382 (m, 2H), 1.699-1.671 (m, 2H) |

| Example | Name | Structure | Reagent A | Reagent B | Reagent C | LC/MS | NMR |
|---|---|---|---|---|---|---|---|
| 1BE | 4-(3-oxa-8-azabicyclo[3.2.1]octane-8-carbonyl)-N-((R)-3-(3,4-dihydroisoquinolin-2(1H)-yl)-2-hydroxypropyl)piperidine-1-carboxamide | 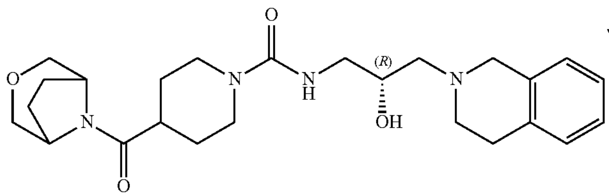 | | | | Method B, Retention Time = 1.388 min, MS: ES+ 457.4 (M + 1) | (400 MHz, DMSO-d₆) δ ppm: 7.114-7.092 (m, 3H), 7.043-7.028 (m, 1H), 6.656-6.630 (t, J = 5.2 Hz, 1H), 4.883-4.872 (d, J = 4.4 Hz, 1H), 4.370-4.281 (m, 2H), 3.910-3.856 (m, 2H), 3.783-3.771 (m, 1H), 3.656-3.498 (m, 1H), 3.471-3.421 (m, 5H), 3.179-3.133 (m, 2H), 3.056-3.040 (m, 1H), 2.807-2.793 (m, 2H), 2.779-2.618 (m, 5H), 2.478-2.388 (m, 2H), 1.911-1.819 (m, 3H), 1.724-1.710 (m, 1H), 1.527-1.428 (m, 4H) |
| 1BF | (S)-N-(3-(3,4-dihydroisoquinolin-2(1H)-yl)-2-hydroxypropyl)-4,4-difluoropiperidine-1-carboxamide | 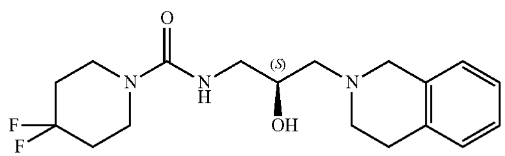 | | | | Method B, Retention Time = 4.316 min, MS: ES+ 354.1 (M + 1) | (400 MHz, DMSO-d₆) δ ppm: 7.123-7.073 (m, 3H), 7.040-7.022 (m, 1H), 6.845-6.819 (t, J = 5.2 Hz, 1H), 4.814-4.806 (d, J = 3.2 Hz, 1H), 3.791 (br s, 1H), 3.652-3.549 (m, 2H), 3.385-3.299 (m, 4H), 3.216-3.157 (m, 1H), 3.046-2.983 (m, 1H), 2.806-2.792 (m, 2H), 2.728-2.671 (m, 2H), 2.472-2.390 (m, 2H), 1.874-1.776 (m, 4H) |

| Example | Name | Structure | Reagent A | Reagent B | Reagent C | LC/MS | NMR |
|---|---|---|---|---|---|---|---|
| 1BG | (S)-N-(3-(3,4-dihydroisoquinolin-2(1H)-yl)-2-hydroxypropyl)-4-hydroxy-4-methylpiperidine-1-carboxamide | 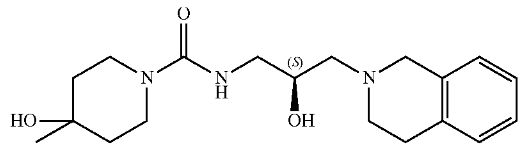 | | | | Method B, Retention Time = 4.012 min, MS: ES+ 348.1 (M + 1) | (400 MHz, DMSO-d₆) δ ppm: 7.106-7.094 (m, 3H), 7.039-7.027 (m, 1H), 6.567 (m, 1H), 4.884-4.874 (d, J = 4.0 Hz, 1H), 4.267 (s, 1H), 3.771-3.757 (m, 1H), 3.651-3.541 (m, 2H), 3.452-3.418 (m, 2H), 3.145-3.132 (m, 1H), 3.080-2.029 (m, 3H), 2.803-2.789 (m, 2H), 2.727-2.677 (m, 2H), 2.425-2.410 (m, 2H), 1.312-1.243 (m, 4H), 1.077 (s, 3H) |
| 1BH | N-((S)-3-(3,4-dihydroisoquinolin-2(1H)-yl)-2-hydroxypropyl)-3-hydroxy-3-phenylpiperidine-1-carboxamide | 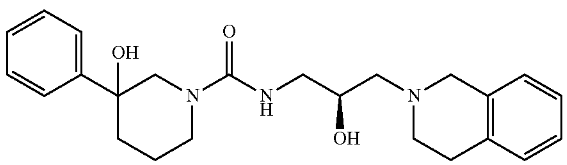 [SMILES: O=C(NC[C@H](O)CN1CCc2ccccc2C1)N1CCCC(O)(c2ccccc2)C1] | | | | Method B, Retention Time = 1.648 min, MS: ES+ 410.3 (M + 1) | (400 MHz, DMSO-d₆) δ ppm: 7.538-7.509 (m, 2H), 7.346-7.308 (m, 2H), 7.252-7.213 (m, 1H), 7.115-7.044 (m, 3H), 7.026-7.005 (m, 1H), 6.462-6.414 (m, 1H), 4.929-4.913 (d, J = 6.4 Hz, 1H), 4.860 (br s, 1H), 3.876-3.844 (m, 1H), 3.771-3.760 (m, 1H), 3.641-3.541 (m, 3H), 3.185-3.122 (m, 2H), 3.096-2.990 (m, 1H), 2.787-2.771 (m, 2H), 2.737-2.675 (m, 3H), 2.416-2.369 (m, 2H), 1.942-1.871 (m, 1H), 1.797-1.768 (m, 1H), 1.680-1.648 (m, 1H), 1.350-1.312 (m, 1H) |

| Example | Name | Structure | Reagent A | Reagent B | Reagent C | LC/MS | NMR |
|---|---|---|---|---|---|---|---|
| 1BI | N-((S)-3-(3,4-dihydroisoquinolin-2(1H)-yl)-2-hydroxypropyl)-3-hydroxy-3-phenylpyrrolidine-1-carboxamide | 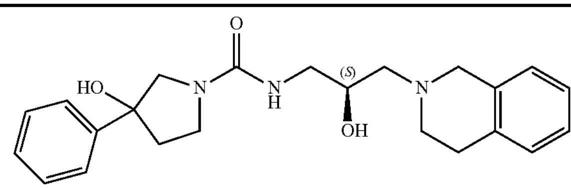 | | | | Method B, Retention Time = 4.329 min, MS: ES+ 396.1 (M + 1) | (400 MHz, DMSO-d₆) δ ppm: 7.503-7.452 (m, 2H), 7.359-7.321 (m, 2H), 7.271-7.232 (m, 1H), 7.109-7.087 (m, 3H), 7.056-7.022 (m, 1H), 6.237-6.226 (m, 1H), 5.370 (s, 1H), 4.985 (br s, 1H), 3.787 (br s, 1H), 3.636 (br s, 2H), 3.513-3.380 (m, 4H), 3.229-3.184 (m, 1H), 3.063-3.001 (m, 1H), 2.806-2.725 (m, 4H), 2.453-2.365 (m, 2H), 2.201-2.123 (m, 1H), 2.011-1.968 (m, 1H) |
| 1BJ | N-((S)-3-(3,4-dihydroisoquinolin-2(1H)-yl)-2-hydroxypropyl)-2-phenylthiomorpholine-4-carboxamide | 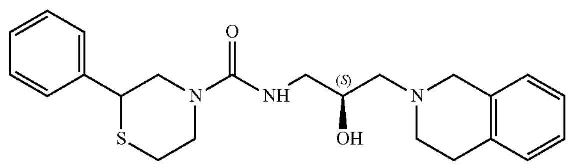 | | | | Method B, Retention Time = 4.748 min, MS: ES+ 412.1 (M + 1) | (400 MHz, DMSO-d₆) δ ppm: 7.355-7.345 (m, 4H), 7.324-7.302 (m, 1H), 7.096-7.084 (m, 3H), 7.028-7.017 (m, 1H), 6.740 (br s, 1H), 4.806 (s, 1H), 4.290-4.259 (d, J = 12.4 Hz, 2H), 3.881-3.790 (m, 3H), 3.644-3.540 (m, 2H), 3.218-3.131 (m, 2H), 3.018-2.927 (m, 2H), 2.787-2.690 (m, 5H), 2.421-2.405 (m, 2H) |

| Example | Name | Structure | Reagent A | Reagent B | Reagent C | LC/MS | NMR |
|---|---|---|---|---|---|---|---|
| 1BK | N-((S)-3-(3,4-dihydroisoquinolin-2(1H)-yl)-2-hydroxypropyl)-3-(1H-pyrazol-1-yl)piperidine-1-carboxamide | 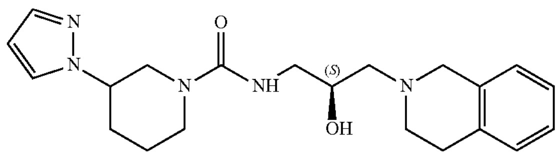 | | | | Method B, Retention Time = 4.247 min, MS: ES+ 384.1 (M + 1) | (400 MHz, DMSO-$d_6$) δ ppm: 7.773-7.767 (d, J = 2.4 Hz, 1H), 7.454-7.451 (d, J = 1.2 Hz, 1H), 7.110-7.061 (m, 3H), 7.035-7.015 (m, 1H), 6.722-6.696 (t, J = 5.2 Hz, 1H), 6.247-6.237 (m, 1H), 4.822 (br s, 1H), 4.149-4.126 (m, 2H), 3.832-3.796 (m, 2H), 3.615-3.597 (m, 2H), 3.223-3.139 (m, 1H), 3.052-2.955 (m, 2H), 2.798-2.786 (m, 2H), 2.742-2.669 (m, 3H), 2.459-2.445 (m, 2H), 2.054-2.025 (m, 1H), 1.959-1.880 (m, 1H), 1.639-1.608 (m, 1H), 1.450-1.372 (m, 1H) |
| 1BL | N-((S)-3-(3,4-dihydroisoquinolin-2(1H)-yl)-2-hydroxypropyl)-3-(1H-imidazol-1-yl)piperidine-1-carboxamide | 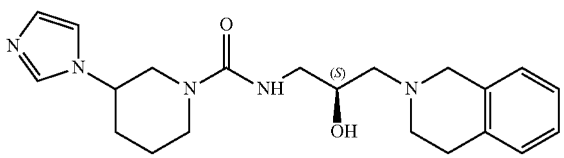 | | | | Method B, Retention Time = 4.073 min, MS: ES+ 384.2 (M + 1) | (400 MHz, DMSO-$d_6$) δ ppm: 7.706 (s, 1H), 7.255 (br s, 1H), 7.122-7.060 (m, 3H), 7.032-7.012 (m, 1H), 6.894 (br s, 1H), 6.734-6.708 (t, J = 5.2 Hz, 1H), 4.807-4.798 (d, J = 3.6 Hz, 1H), 4.057-4.011 (m, 2H), 3.833-3.773 (m, 2H), 3.648-3.552 (q, J = 7.6 Hz, 15.6 Hz, 2H), 3.224-3.142 (m, 1H), 3.057-2.947 (m, 2H), 2.795-2.781 (m, 2H), 2.743-2.669 (m, 3H), 2.427-2.380 (m, 2H), 2.028-2.002 (m, 1H), 1.845-1.808 (m, 1H), 1.638-1.604 (m, 1H), 1.451-1.389 (m, 1H) |

| Example | Name | Structure | Reagent A | Reagent B | Reagent C | LC/MS | NMR |
|---|---|---|---|---|---|---|---|
| 1BM | (S)-N-(3-(3,4-dihydroisoquinolin-2(1H)-yl)-2-hydroxypropyl)-4-(phenylsulfonyl)-1,4-diazepane-1-carboxamide | 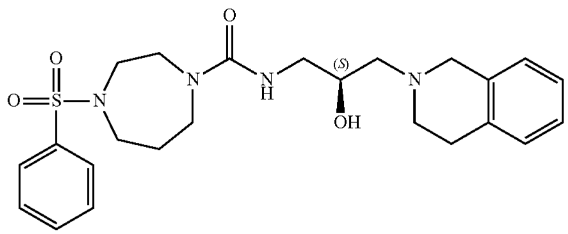 | | | | Method B, Retention Time = 1.699 min, MS: ES+ 473.4 (M + 1) | (400 MHz, DMSO-d$_6$) δ ppm: 7.778-7.757 (m, 2H), 7.690-7.651 (m, 1H), 7.626-7.587 (m, 2H), 7.130-7.067 (m, 3H), 7.019-7.002 (m, 1H), 6.491-6.465 (t, J = 5.2 Hz, 1H), 4.826 (br s, 1H), 3.765-3.750 (m, 1H), 3.620-3.517 (m, 2H), 3.408-3.393 (m, 2H), 3.325-3.310 (m, 2H), 3.183-3.105 (m, 5H), 3.061-2.999 (m, 1H), 2.785-2.771 (m, 2H), 2.690-2.651 (m, 2H), 2.504-2.359 (m, 2H), 1.713-1.671 (m, 2H) |
| 1BN | N-((S)-3-(3,4-dihydroisoquinolin-2(1H)-yl)-2-hydroxypropyl)-2-phenyl-1,4-thiazepane-4-carboxamide | 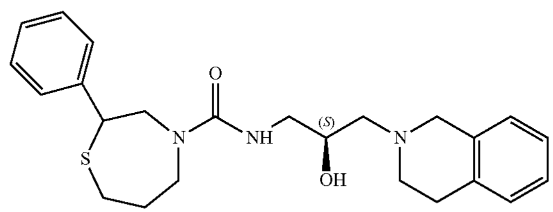 | | | | Method B, Retention Time = 1.785 min, MS: ES+ 426.3 (M + 1) | (400 MHz, DMSO-d$_6$) δ ppm: 7.335-7.324 (m, 4H), 7.305-7.252 (m, 1H), 7.109-7.060 (m, 3H), 7.036-7.015 (m, 1H), 6.436 (br s, 1H), 4.873-4.844 (m, 1H), 4.201-4.172 (m, 1H), 4.035-4.007 (m, 1H), 3.791-3.719 (m, 3H), 3.652-3.557 (m, 2H), 3.499-3.437 (m, 2H), 3.301-3.148 (m, 2H), 3.109-3.047 (m, 1H), 2.876-2.787 (m, 4H), 2.720-2.706 (m, 2H), 2.437-2.384 (m, 2H), 2.244 (br s, 1H), 1.661 (br s, 2H) |

| Example | Name | Structure | Reagent A | Reagent B | Reagent C | LC/MS | NMR |
|---|---|---|---|---|---|---|---|
| 1BO | N-((S)-3-(3,4-dihydroisoquinolin-2(1H)-yl)-2-hydroxypropyl)-2-phenyl-1,4-thiazepane-4-carboxamide 1,1-dioxide | 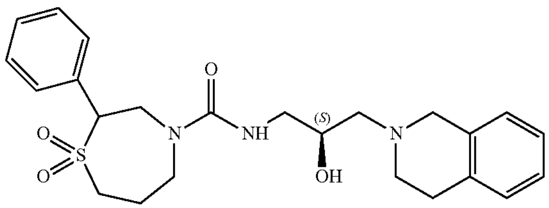 | | | | Method B, Retention Time = 1.813 min, MS: ES+ 458.2 (M + 1) | (400 MHz, DMSO-d₆) δ ppm: 7.409-7.365 (m, 5H), 7.112-7.063 (m, 3H), 7.034-7.022 (m, 1H), 6.685-6.636 (m, 1H), 4.810 (br s, 1H), 4.561-4.499 (m, 1H), 4.121-4.076 (dd, J = 3.2, 14.8 Hz, 1H), 3.832-3.803 (m, 2H), 3.660-3.547 (m, 3H), 3.317-3.166 (m, 4H), 3.075-2.959 (m, 1H), 2.799-2.785 (m, 2H), 2.735-2.663 (m, 2H), 2.472-2.238 (m, 2H), 2.068-2.055 (m, 1H), 1.916-1.868 (m, 1H) |
| 1BP | (S)-N-(3-(3,4-dihydroisoquinolin-2(1H)-yl)-2-hydroxypropyl)-1,4-oxazepane-4-carboxamide | 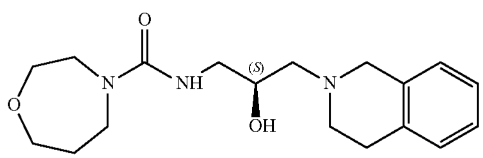 | | | | Method B, Retention Time = 1.190 min, MS: ES+ 334.2 (M + 1) | (400 MHz, DMSO-d₆) δ ppm: 7.123-7.062 (m, 3H), 7.032-7.014 (m, 1H), 6.470-6.444 (t, J = 5.2 Hz, 1H), 4.886-4.876 (d, J = 4.0 Hz, 1H), 3.793-3.754 (m, 1H), 3.649-3.576 (m, 2H), 3.558-3.511 (m, 4H), 3.379-3.363 (m, 1H), 3.190-3.130 (m, 1H), 3.087-3.039 (m, 1H), 2.799-2.784 (m, 2H), 2.723-2.664 (m, 2H), 2.477-2.414 (m, 2H), 1.712-1.655 (m, 2H) |

| Example | Name | Structure | Reagent A | Reagent B | Reagent C | LC/MS | NMR |
|---|---|---|---|---|---|---|---|
| 1BQ | N-((S)-3-(3,4-dihydroisoquinolin-2(1H)-yl)-2-hydroxypropyl)-3-(pyridin-2-yl)piperidine-1-carboxamide | 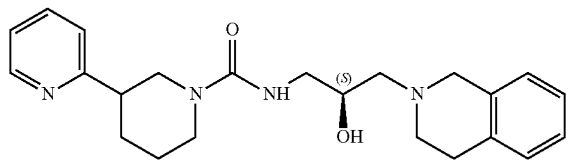 | | | | Method B, Retention Time = 4.319 min, MS: ES+ 395.2 (M + 1) | (400 MHz, DMSO-d₆) δ ppm: 8.506-8.491 (dd, J = 1.2, 4.8 Hz, 1H), 7.743-7.700 (td, J = 1.6, 7.6 Hz, 1H), 7.297-7.279 (d, J = 7.2 Hz, 1H), 7.244-7.211 (m, 1H), 7.101-7.044 (m, 3H), 7.028-7.007 (m, 1H), 6.640-6.613 (t, J = 5.2, 1H), 4.856-4.846 (d, J = 4.0 Hz, 1H), 4.087-4.058 (m, 1H), 3.944-3.911 (m, 1H), 3.770 (br s, 1H), 3.641-3.536 (m, 2H), 3.185-3.151 (m, 1H), 3.052-3.013 (m, 1H), 2.860-2.772 (m, 3H), 2.754-2.584 (m, 4H), 2.448-2.360 (m, 2H), 1.927-1.893 (m, 1H), 1.693-1.576 (m, 2H), 1.429-1.384 (m, 1H) |
| 1BR | N-((S)-3-(3,4-dihydroisoquinolin-2(1H)-yl)-2-hydroxypropyl)-3-(1-methyl-6-oxo-1,6-dihydropyridin-3-yl)piperidine-1-carboxamide | 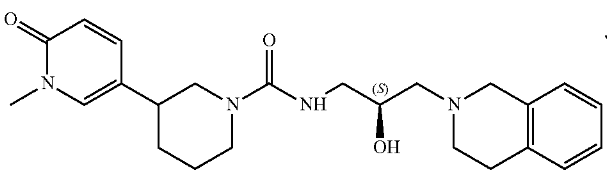 | | | | Method B, Retention Time = 4.109 min, MS: ES+ 425.2 (M + 1) | (400 MHz, DMSO-d₆) δ ppm: 7.537 (s, 1H), 7.413-7.384 (dd, J = 2.4, 9.2 Hz, 1H), 7.241-7.063 (m, 4H), 6.65-6.517 (m, 1H), 6.361-6.338 (d, J = 9.2 Hz, 1H), 4.958 (s, 1H), 4.007-3.991 (m, 4H), 3.934-3.670 (m, 1H), 3.389 (s, 3H), 3.156-3.016 (m, 4H), 2.841 (br s, 2H), 2.603-2.575 (m, 3H), 2.331-2.311 (m, 2H), 1.805-1.778 (m, 1H), 1.611-1.585 (m, 1H), 1.497-1.436 (m, 1H), 1.368-1.336 (m, 1H) |

| Example | Name | Structure | Reagent A | Reagent B | Reagent C | LC/MS | NMR |
|---|---|---|---|---|---|---|---|
| 1BS | N-((S)-3-(3,4-dihydro-isoquin-olin-2(1H)-yl)-2-hydroxy-propyl)-3-(pyrazin-2-yl)piperidine-1-carbox-amide | 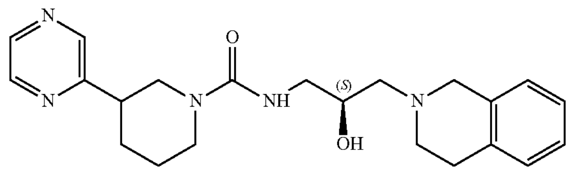 | | | | Method B, Retention Time = 1.438 min, MS: ES+ 396.3 (M + 1) | (400 MHz, CDCl$_3$) δ ppm: 8.541-8.532 (m, 2H), 8.464-8.458 (d, J = 2.4 Hz, 1H), 7.184-7.119 (m, 3H), 7.052-7.031 (m, 1H), 5.546-5.519 (m, 1H), 4.168-4.136 (d, J = 12.8 Hz, 1H), 4.028 (br s, 1H), 3.943-3.908 (m, 2H), 3.765-3.728 (m, 1H), 3.618-3.570 (m, 1H), 3.279-3.230 (m, 1H), 3.189-3.129 (m, 1H), 3.013-2.952 (m, 5H), 2.897-2.857 (m, 1H), 2.695-2.624 (m, 2H), 2.108-2.067 (m, 1H), 1.928-1.765 (m, 2H), 1.696-1.627 (m, 1H) |
| 1BT | N-((S)-3-(3,4-dihydro-isoquin-olin-2(1H)-yl)-2-hydroxy-propyl)-3-(2-methyl-pyridin-4-yl)piperidine-1-carbox-amide | 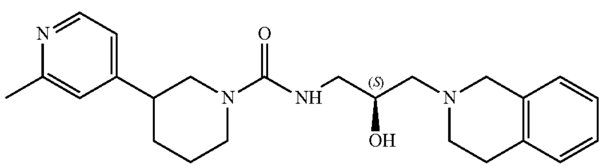 | | | | Method B, Retention Time = 4.401 min, MS: ES+ 409.2 (M + 1) | (400 MHz, DMSO-d$_6$) δ ppm: 8.343-3.330 (d, J = 5.2 Hz, 1H), 7.139 (s, 1H), 7.102-7.045 (m, 4H), 7.026-7.004 (m, 1H), 6.662-6.635 (t, J = 5.2 Hz, 1H), 4.839-4.828 (d, J = 4.4 Hz, 1H), 3.981-3.902 (m, 2H), 3.793-3.755 (m, 1H), 3.643-3.537 (m, 2H), 3.219-3.138 (m, 1H), 3.069-2.981 (m, 1H), 2.787-2.773 (m, 2H), 2.748-2.652 (m, 4H), 2.522-2.430 (m, 6H), 1.859-1.834 (m, 1H), 1.619-1.529 (m, 2H), 1.429-1.363 (m, 1H) |

| Example | Name | Structure | Reagent A | Reagent B | Reagent C | LC/MS | NMR |
|---|---|---|---|---|---|---|---|
| 1BU | N-((S)-3-(3,4-dihydroisoquinolin-2(1H)-yl)-2-hydroxypropyl)-3-(4-fluorophenyl)piperidine-1-carboxamide | 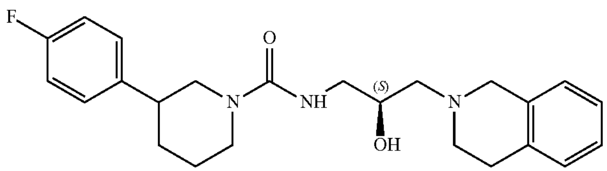 | | | | Method B, Retention Time = 4.754 min, MS: ES+ 412.1 (M + 1) | (400 MHz, DMSO-d$_6$) δ ppm: 7.313-7.258 (m, 2H), 7.235-7.073 (m, 6H), 6.676-6.524 (m, 1H), 4.897 (br s, 1H), 3.970-3.941 (m, 3H), 3.341 (br s, 2H), 3.135-2.995 (m, 5H), 2.860-2.802 (m, 2H), 2.673-2.656 (m, 2H), 2.548-2.474 (m, 2H), 1.854-1.826 (m 1H), 1.618-1.526 (m, 2H), 1.410-1.380 (m, 1H) |
| 1BV | N-((S)-3-(3,4-dihydroisoquinolin-2(1H)-yl)-2-hydroxypropyl)-3-(pyridin-3-yl)piperidine-1-carboxamide | 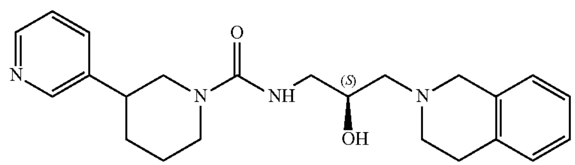 | | | | Method B, Retention Time = 4.277 min, MS: ES+ 395.2 (M + 1) | (400 MHz, DMSO-d$_6$) δ ppm: 8.498-8.493 (d, J = 2.0 Hz, 1H), 8.441-8.426 (dd, J = 1.6, 4.4 Hz, 1H), 7.697-7.663 (m, 1H), 7.349-7.317 (m, 1H), 7.102-7.047 (m, 3H), 7.027-7.006 (m, 1H), 6.664-6.638 (t, J = 5.2, 1H), 4.838-4.828 (d, J = 4.0 Hz, 1H), 3.984-3.925 (m, 2H), 3.796-3.756 (m, 1H), 3.645-3.540 (m, 2H), 3.209-3.141 (m, 1H), 3.069-2.982 (m, 1H), 2.787-2.773 (m, 3H), 2.753-2.608 (m, 5H), 2.457-2.375 (m, 2H), 1.874-1.846 (m, 1H), 1.663-1.602 (m, 2H), 1.448-1.384 (m, 1H), |

| Example | Name | Structure | Reagent A | Reagent B | Reagent C | LC/MS | NMR |
|---|---|---|---|---|---|---|---|
| 1BW | N-((S)-3-(3,4-dihydroisoquinolin-2(1H)-yl)-2-hydroxypropyl)-3-morpholinopiperidine-1-carboxamide | 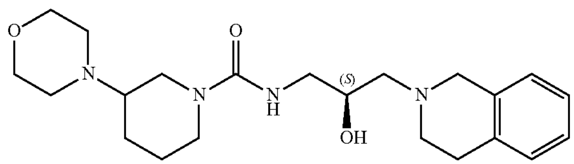 | | | | Method B, Retention Time = 4.041 min, MS: ES+ 403.2 (M + 1) | (400 MHz, DMSO-d$_6$) δ ppm: 7.110-7.063 (m, 3H), 7.031-7.012 (m, 1H), 6.595-6.570 (t, J = 5.2 Hz, 1H), 4.861 (br s, 1H), 3.984-3.952 (m, 1H), 3.766-3.705 (m, 2H), 3.646-3.584 (m, 2H), 3.548-3.525 (m, 4H), 3.192-3.121 (m, 1H), 3.042-2.973 (m, 1H), 2.798-2.785 (m, 2H), 2.767-2.664 (m, 2H), 2.548-2.422 (m, 8H), 2.083-2.075 (m, 1H), 1.819 (br s, 1H), 1.574-1.551 (m, 1H), 1.284-1.255 (m, 2H) |
| 1BX | N-((S)-3-(3,4-dihydroisoquinolin-2(1H)-yl)-2-hydroxypropyl)-3-thiomorpholinopiperidine-1-carboxamide | 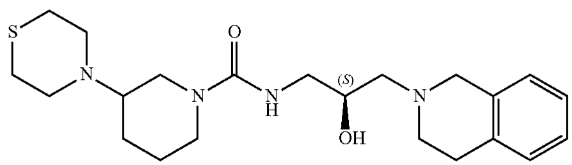 | | | | Method B, Retention Time = 4.420 min, MS: ES+ 419.2 (M + 1) | (400 MHz, DMSO-d$_6$) δ ppm: 7.111-7.062 (m, 3H), 7.028-7.011 (m, 1H), 6.572-6.551 (m, 1H), 4.850-4.833 (m, 1H), 3.927-3.895 (m, 1H), 3.777-3.750 (m, 2H), 3.639-3.534 (m, 2H), 3.179-3.120 (m, 1H), 3.040-2.993 (m, 1H), 2.794-2.755 (m, 6H), 2.737-2.669 (m, 2H), 2.561-2.537 (m, 5H), 2.461-2.363 (m, 3H), 2.261-2.208 (m, 1H), 1.756-1.731 (m, 1H), 1.575-1.535 (m, 1H), 1.361-1.230 (m, 2H) |

| Example | Name | Structure | Reagent A | Reagent B | Reagent C | LC/MS | NMR |
|---|---|---|---|---|---|---|---|
| 1BY | N-((S)-3-(3,4-dihydroisoquinolin-2(1H)-yl)-2-hydroxypropyl)-3-(4-methylpiperazin-1-yl)piperidine-1-carboxamide | 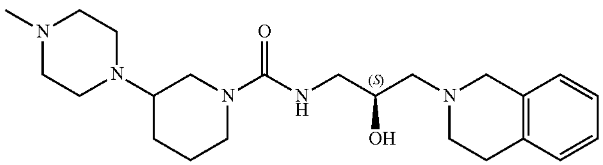 | | | | Method B, Retention Time = 4.074 min, MS: ES+ 416.2 (M + 1) | (400 MHz, DMSO-d₆) δ ppm: 7.107-7.074 (m, 1H), 7.027-7.009 (m, 1H), 6.581-6.556 (t, J = 5.2 Hz, 1H), 4.850-4.833 (m, 1H), 3.980-3.948 (m, 1H), 3.759-3.717 (m, 2H), 3.596-3.574 (m, 2H), 3.177-3.120 (m, 1H), 3.032-2.971 (m, 1H), 2.793-2.779 (m, 2H), 2.748-2.654 (m, 3H), 2.548-2.374 (m, 8H), 2.359-2.309 (m, 4H), 2.116 (s, 3H), 1.805 (br s, 1H), 1.564-1.541 (m, 1H), 1.310-1.231 (m, 2H) |
| 1BZ | N-((S)-3-(3,4-dihydroisoquinolin-2(1H)-yl)-2-hydroxypropyl)-3-(tetrahydro-2H-pyran-4-yl)piperidine-1-carboxamide | 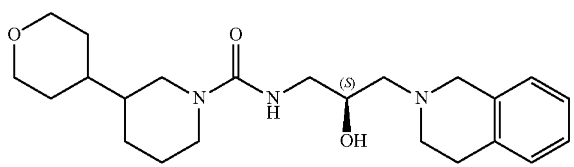 | | | | Method B, Retention Time = 4.518 min, MS: ES+ 402.3 (M + 1) | (400 MHz, DMSO-d₆) δ ppm: 7.109-7.062 (m, 3H), 7.029-7.011 (m, 1H), 6.552-6.528 (t, J = 4.8 Hz, 1H), 4.877-4.859 (m, 1H), 3.878-3.818 (m, 3H), 3.749-3.721 (m, 2H), 3.639-3.539 (m, 2H), 3.249-3.119 (m, 3H), 3.059-2.996 (m, 1H), 2.796-2.782 (m, 2H), 2.723-2.670 (m, 2H), 2.572-2.540 (m, 2H), 2.463-2.415 (m, 2H), 1.742-1.718 (m, 1H), 1.589-1.502 (m, 3H), 1.219-1.021 (m, 6H) |

| Example | Name | Structure | Reagent A | Reagent B | Reagent C | LC/MS | NMR |
|---|---|---|---|---|---|---|---|
| 1CA | N-((S)-3-(3,4-dihydro-isoquinolin-2(1H)-yl)-2-hydroxy-propyl)-3-(tetrahydro-2H-thiopyran-4-yl)piperidine-1-carboxamide | 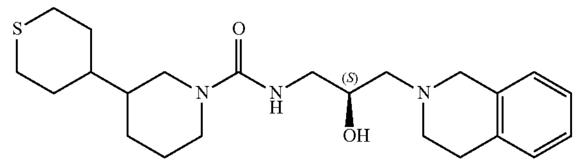 | | | | Method B, 4.737 min, MS: ES+ 417.8 (M + 1) | (400 MHz, DMSO-d₆) δ ppm: 7.111-7.061 (m, 1H), 7.028-7.011 (m, 1H), 6.551-6.525 (t, J = 5.2 Hz, 1H), 4.872-4.855 (m, 1H), 3.849-3.733 (m, 3H), 3.637-3.534 (m, 2H), 3.162-3.116 (m, 1H), 3.039-2.990 (m, 1H), 2.794-2.780 (m, 2H), 2.750-2.654 (m, 2H), 2.574-2.548 (m, 4H), 2.457-2.363 (m, 4H), 1.946-1.870 (m, 2H), 1.672-1.650 (m, 1H), 1.521-1.483 (m, 1H), 1.367-1.288 (m, 2H), 1.228-1.109 (m, 4H) |
| 1CB | N-((S)-3-(3,4-dihydro-isoquinolin-2(1H)-yl)-2-hydroxy-propyl)-3-(1,4-thiazepan-4-yl)piperidine-1-carboxamide | 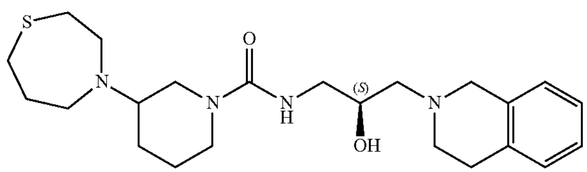 | | | | Method C, Retention Time = 3.319 min, MS: ES+ 433.3 (M + 1) | (400 MHz, DMSO-d₆) δ ppm: 7.098-7.086 (m, 3H), 7.028-7.017 (m, 1H), 6.559 (m, 1H), 4.859 (br s, 1H), 3.945-3.917 (m, 1H), 3.753-3.723 (m, 2H), 3.641-3.542 (m, 1H), 3.168-3.133 (m, 1H), 3.028-2.995 (m, 1H), 2.900-2.873 (m, 2H), 2.835-2.783 (m, 4H), 2.699-2.668 (m, 4H), 2.591-2.565 (m, 2H), 2.463-2.368 (m, 5H), 1.741-1.699 (m, 3H), 1.552-1.522 (m, 1H), 1.332-1.230 (m, 2H) |

| Example | Name | Structure | Reagent A | Reagent B | Reagent C | LC/MS | NMR |
|---|---|---|---|---|---|---|---|
| 1CC | N-((S)-3-(3,4-dihydroisoquinolin-2(1H)-yl)-2-hydroxypropyl)-3-(1,4-oxazepan-4-yl)piperidine-1-carboxamide | 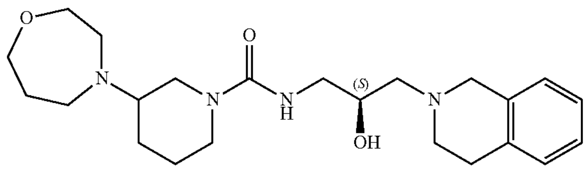 | | | | Method B, Retention Time = 4.263 min, MS: ES+ 417.0 (M + 1) | (400 MHz, DMSO-$d_6$) δ ppm: 7.106-7.059 (m, 3H), 7.026-7.008 (m, 1H), 6.557 (m, 1H), 4.850 (m, 1H), 3.933-3.921 (m, 1H), 3.768-3.739 (m, 2H), 3.652-3.623 (m, 2H), 3.597-3.499 (m, 5H), 3.134-3.122 (m, 1H), 3.039-2.987 (m, 1H), 2.798-2.787 (m, 2H), 2.751-2.668 (m, 6H), 2.463-2.361 (m, 4H), 1.791-1.758 (m, 1H), 1.737-1.679 (m, 2H), 1.562-1.535 (m, 1H), 1.358-1.232 (m, 2H) |
| 1CD | N-((S)-3-(3,4-dihydroisoquinolin-2(1H)-yl)-2-hydroxypropyl)-3-morpholinopyrrolidine-1-carboxamide | 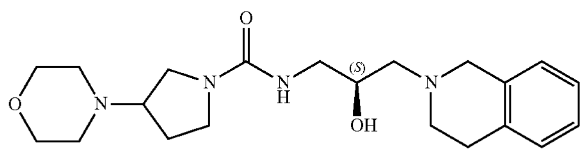 | | | | Method D, Retention Time = 6.739 min, MS: ES+ 389.2 (M + 1) | (400 MHz, DMSO-$d_6$) δ ppm: 7.096-7.084 (m, 3H), 7.031-7.018 (m, 1H), 6.219-6.206 (m, 1H), 4.912-4.902 (m, 1H), 3.763-3.752 (m, 1H), 3.648-3.541 (m, 6H), 3.464-3.458 (m, 1H), 3.170-3.055 (m, 3H), 2.885-2.847 (m, 1H), 2.792-2.672 (m, 6H), 2.422-2.358 (m, 4H), 2.283-2.249 (m, 2H), 1.972-1.958 (m, 1H), 1.602-1.553 (m, 1H) |

| Example | Name | Structure | Reagent A | Reagent B | Reagent C | LC/MS | NMR |
|---|---|---|---|---|---|---|---|
| 1CE | N-(S)-3-(3,4-dihydroisoquinolin-2(1H)-yl)-2-hydroxypropyl)-3-thiomorpholino pyrrolidine-1-carboxamide | 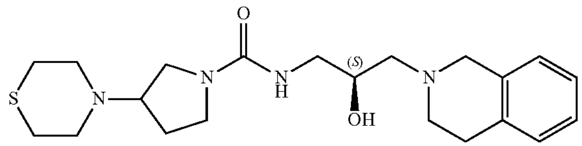 | | | | Method C, Retention Time = 3.046 min, MS: ES+ 405.1 (M + 1) | (400 MHz, DMSO-d$_6$) δ ppm: 7.096-7.084 (m, 3H), 7.031-7.018 (m, 1H), 6.219-6.206 (m, 1H), 4.912-4.902 (m, 1H), 3.763-3.752 (m, 1H), 3.648-3.541 (m, 6H), 3.464-3.458 (m, 1H), 3.170-3.055 (m, 3H), 2.885-2.847 (m, 6H), 2.792-2.672 (m, 6H), 2.422-2.358 (m, 4H), 2.283-2.249 (m, 2H), 1.972-1.958 (m, 1H), 1.602-1.553 (m, 1H) |
| 1CF | N-(S)-3-(3,4-dihydroisoquinolin-2(1H)-yl)-2-hydroxypropyl)-3-(1,4-thiazepan-4-yl)pyrrolidine-1-carboxamide | 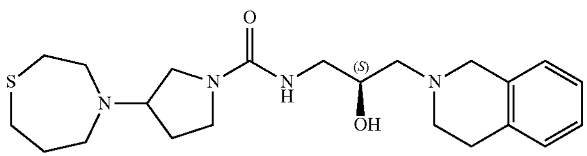 | | | | Method B, Retention Time = 4.470 min, MS: ES+ 419.1 (M + 1) | (400 MHz, DMSO-d$_6$) δ ppm: 7.120-7.060 (m, 3H), 7.029-7.011 (m, 1H), 6.210-6.171 (q, J = 5.2 Hz, 1H), 4.913-4.884 (dd, J = 3.2, 4.4 Hz, 1H), 3.760-3.748 (m, 1H), 3.642-3.532 (m, 2H), 3.438-3.302 (m, 2H), 3.252-3.216 (m, 1H), 3.182-3.135 (m, 1H), 3.077-2.988 (m, 2H), 2.879-2.763 (m, 7H), 2.722-2.667 (m, 4H), 2.648-2.605 (m, 2H), 2.470-2.382 (m, 2H), 1.962-1.932 (m, 1H), 1.808-1.749 (quin, J = 6.0 Hz, 2H), 1.616-1.593 (m, 1H) |

| Example | Name | Structure | Reagent A | Reagent B | Reagent C | LC/MS | NMR |
|---|---|---|---|---|---|---|---|
| 1CG | N-((S)-3-(3,4-dihydroisoquinolin-2(1H)-yl)-2-hydroxypropyl)-2-phenylthiomorpholine-4-carboxamide 1,1-dioxide | 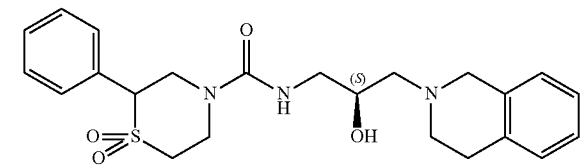 | | | | Method B, Retention Time = 2.105 min, MS: ES+ 444.1 (M + 1) | (400 MHz, DMSO-d₆) δ ppm: 7.428-7.413 (m, 3H), 7.381-7.369 (m, 2H), 7.109-7.060 (m, 3H), 7.034-7.006 (m, 2H), 4.792-4.765 (m, 1H), 4.421-4.334 (m, 3H), 3.813 (br s, 1H), 3.655-3.542 (m, 3H), 3.312-3.157 (m, 4H), 2.986-2.921 (m, 1H), 2.785-2.771 (m, 2H), 2.722-2.669 (m, 2H), 2.452-2.374 (m, 3H) |
| 1CH | 3-(4-benzylpiperazin-1-yl)-N-((S)-3-(3,4-dihydroisoquinolin-2(1H)-yl)-2-hydroxypropyl)piperidine-1-carboxamide | 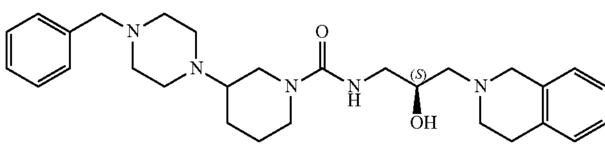 | | | | Method B, Retention Time = 2.024 min, MS: ES+ 492.1 (M + 1) | (400 MHz, CDCl₃) δ ppm: 7.336-7.296 (m, 4H), 7.269-7.257 (m, 1H), 7.178-7.121 (m, 3H), 7.040-7.019 (m, 1H), 5.149-5.139 (m, 1H), 4.138-4.114 (m, 1H), 3.953-3.941 (m, 1H), 3.846-3.809 (m, 2H), 3.647-3.524 (m, 4H), 3.210-3.176 (m, 1H), 2.956-2.907 (m, 2H), 2.687-2.656 (m, 7H), 2.567-2.511 (m, 6H), 2.368-2.314 (m, 1H), 2.038-2.007 (m, 1H), 1.769-1.736 (m, 1H), 1.450-1.362 (m, 2H) |

| Example | Name | Structure | Reagent A | Reagent B | Reagent C | LC/MS | NMR |
|---|---|---|---|---|---|---|---|
| 1CI | (S)-N-((S)-3-(3,4-dihydroisoquinolin-2(1H)-yl)-2-hydroxypropyl)-3-phenylpyrrolidine-1-carboxamide | 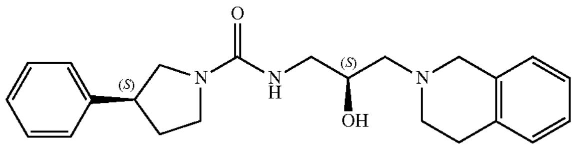 | | | | Method B, Retention Time = 2.406 min, MS: ES+ 380.2 (M + 1) | (400 MHz, DMSO-d₆) δ ppm: 7.329-7.292 (m, 2H), 7.246-7.202 (m, 3H), 7.097-7.054 (m, 3H), 7.040-7.008 (m, 1H), 6.241-6.214 (t, J = 5.2 Hz, 1H), 4.914-4.905 (d, J = 3.6 Hz, 1H), 3.781-3.774 (m, 1H), 3.666-3.536 (m, 3H), 3.440-3.400 (m, 1H), 3.312-3.188 (m, 3H), 3.174-3.094 (m, 1H), 3.075-3.011 (m, 1H), 2.792-2.778 (m, 2H), 2.752-2.660 (m, 2H), 2.471-2.383 (m, 2H), 2.187-2.162 (m, 1H), 1.872 (br s, 1H) |
| 1CJ | (R)-N-((S)-3-(3,4-dihydroisoquinolin-2(1H)-yl)-2-hydroxypropyl)-3-phenylpyrrolidine-1-carboxamide | 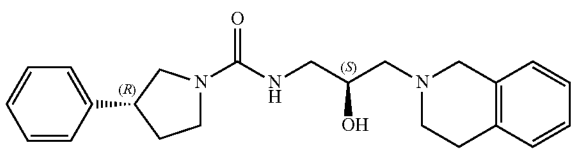 | | | | Method A, Retention Time = 4.677 min, MS: ES+ 380.2 (M + 1) | (400 MHz, DMSO-d₆) δ ppm: 7.329-7.292 (m, 2H), 7.247-7.201 (m, 3H), 7.097-7.009 (m, 3H), 6.252-6.225 (t, J = 5.2 Hz, 1H), 4.930-4.920 (d, J = 4.0 Hz, 1H), 3.795-3.757 (m, 1H), 3.683-3.541 (m, 3H), 3.446-3.408 (m, 1H), 3.277-3.168 (m, 3H), 3.133-3.085 (m, 1H), 3.067-3.017 (m, 1H), 2.793-2.779 (m, 2H), 2.728-2.668 (m, 2H), 2.472-2.381 (m, 2H), 2.183-2.127 (m, 1H), 1.930-1.829 (m, 1H) |

| Example | Name | Structure | Reagent A | Reagent B | Reagent C | LC/MS | NMR |
|---|---|---|---|---|---|---|---|
| 1CK | N-(3,4-dihydroisoquinolin-2(1H)-yl)-2-hydroxypropyl)-3-hydroxypiperidine-1-carboxamide | 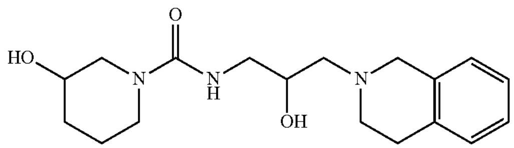 [SMILES: O=C(NCC(O)CN1CCc2ccccc2C1)N1CCCC(O)C1] | | | | Method A, Retention Time = 1.826 min, MS: ES+ 334.2 (M + 1) | (400 MHz, DMSO-d₆) δ ppm: 7.122-7.075 (m, 3H), 7.044-7.026 (m, 1H), 6.542-6.516 (t, J = 5.2 Hz, 1 H), 4.887 (br s, 1H), 4.783-4.772 (d, J = 4.4 Hz, 1H), 3.823-3.792 (m, 2H), 3.635-3.537 (m, 3H), 3.331-3.320 (m, 1H), 3.192-3.134 (m, 1H), 3.038-2.991 (m, 1H), 2.814-2.801 (m, 2H), 2.737-2.645 (m, 3H), 2.548-2.430 (m, 3H), 1.810-1.791 (m, 1H), 1.524 (br s, 1H), 1.252-1.207 (m, 2H) |
| 1CL | N-(3,4-dihydroisoquinolin-2(1H)-yl)-2-hydroxypropyl)-4-methyl-1,4-diazepane-1-carboxamide | 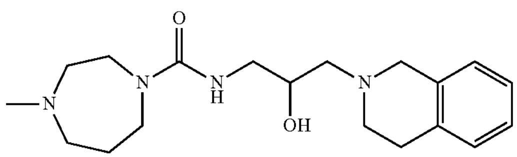 [SMILES: CN1CCCN(C(=O)NCC(O)CN2CCc3ccccc3C2)CC1] | | | | Method B, Retention Time = 4.178 min, MS: ES+ 347.1 (M + 1) | (400 MHz, CDCl₃) δ ppm: 1H 7.191-7.112 (m, 3H), 7.039-7.018 (m, 1H), 5.174-5.147 (t, J = 5.2 Hz, 1H), 3.998-3.930 (m, 1H), 3.841-3.627 (m, 2H), 3.608-3.578 (m, 2H), 3.557-3.534 (m, 1H), 3.461-3.431 (t, J = 6.0 Hz, 2H), 3.264-3.201 (m, 1H), 2.970-2.909 (m, 3H), 2.798-2.721 (m, 1H), 2.638-2.551 (m, 6H), 2.387 (s, 3H), 1.955-1.898 (m, 2H) |

| Example | Name | Structure | Reagent A | Reagent B | Reagent C | LC/MS | NMR |
|---|---|---|---|---|---|---|---|
| 1CM | 4-acetyl-N-(3-(3,4-dihydroisoquinolin-2(1H)-yl)-2-hydroxypropyl)-1,4-diazepane-1-carboxamide | 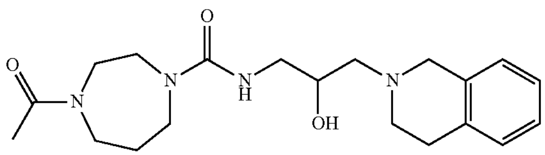 [SMILES: CC(=O)N1CCCN(C(=O)NCC(O)CN2CCc3ccccc3C2)CC1] | | | | Method A, Retention Time = 2.009 min, MS: ES+ 375.32 (M + 1) | (400 MHz, DMSO-d$_6$) δ ppm: 7.105-7.042 (m, 4H), 6.477-6.428 (m, 1H), 4.827 (br s, 1H), 3.768 (br s, 1H), 3.648-3.553 (m, 2H), 3.438 (br s, 4H), 3.396-3.269 (m, 4H), 3.180-3.147 (m, 1H), 3.086-3.038 (m, 1H), 2.807-2.794 (m, 2H), 2.757-2.701 (m, 2H), 2.467-2.375 (m, 2H), 1.986-1.957 (m, 3H), 1.710-1.682 (m, 1H), 1.601-1.589 (m, 1H) |
| 1CN | N-(3-(3,4-dihydroisoquinolin-2(1H)-yl)-2-hydroxypropyl)-4-phenylazepane-1-carboxamide | 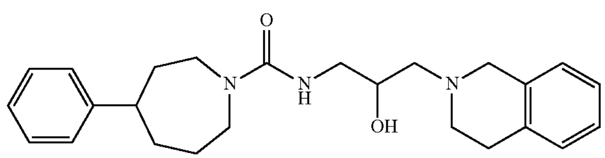 [SMILES: O=C(NCC(O)CN1CCc2ccccc2C1)N1CCCC(c2ccccc2)CC1] | | | | Method B, Retention Time = 4.086 min, MS: ES+ 408.15 (M + 1) | (400 MHz, MeOD), δ ppm: 7.345-7.146 (m, 9H), 4.698-4.618 (m, 1H), 4.473-4.420 (m, 1H), 4.251 (br s, 1H), 3.879 (br s, 1H), 3.766-3.707 (m, 2H), 3.634-3.590 (m, 2H), 3.525-3.428 (m, 2H), 3.391-3.367 (m, 3H), 3.241 (m, 1H), 3.221-3.160 (m, 1H), 2.697-2.645 (t, J = 10.6 Hz, 1 H), 2.025-1.921 (m, 3H), 1.841-1.687 (m, 3H) |

| Example | Name | Structure | Reagent A | Reagent B | Reagent C | LC/MS | NMR |
|---|---|---|---|---|---|---|---|
| 1CO | N-(3-(3,4-dihydroisoquinolin-2(1H)-yl)-2-hydroxypropyl)-3-phenylazepane-1-carboxamide | 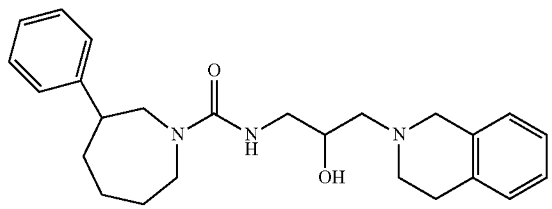 [SMILES: O=C(NCC(O)CN1CCc2ccccc2C1)N1CCCCC(c2ccccc2)C1] | | | | Method A, Retention Time = 2.251 min, MS: ES+ 408.3 (M + 1) | (400 MHz, CDCl₃) δ ppm: 7.339-7.150 (m, 8H), 7.074-7.057 (d, J = 6.8 Hz, 1H), 5.475-5.370 (m, 1H), 4.116-4.078 (m, 1H), 3.968-3.930 (m, 1H), 3.693-3.585 (m, 2H), 3.390-3.341 (m, 2H), 3.282-3.180 (m, 3H), 3.135-3.069 (m, 4H), 2.962-2.831 (m, 3H), 2.029-1.948 (m, 3H), 1.767-1.624 (m, 2H), 1.526-1.448 (m, 1H) |

Example 2

Scheme 3

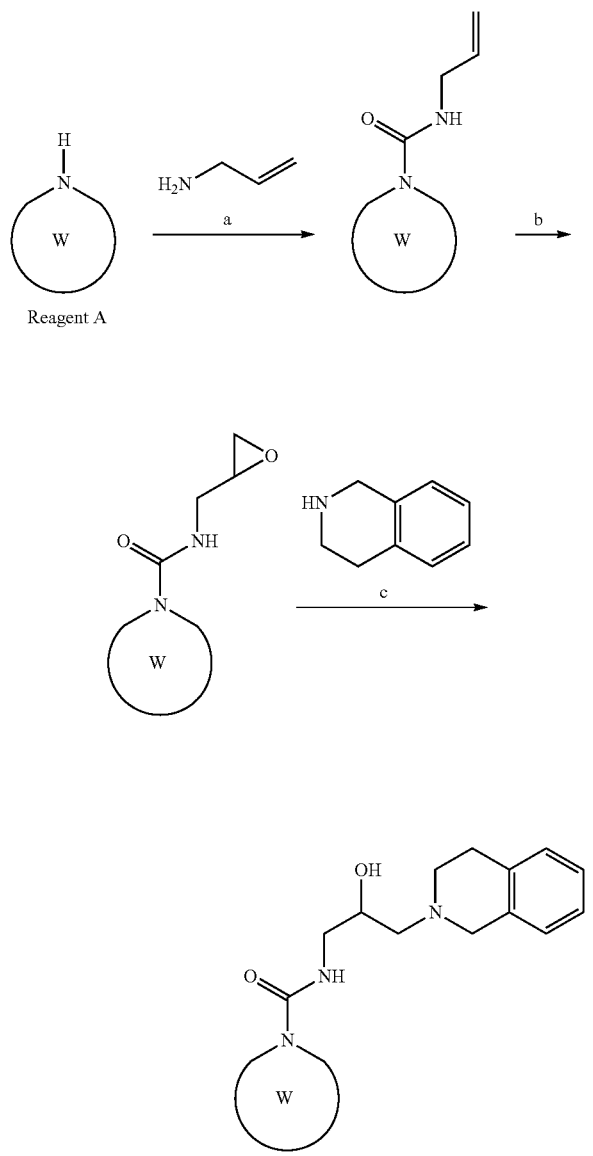

Reagents and conditions: a) i) Triethylamine, triphosgene, toluene 50° C., 3 h,
ii) Triethylamine, allylamine, rt, 16 h. b) m-CPBA, dichloromethane, rt, 1 h
c) triethylamine, IPA, reflux, 16 h.

Example 2A N-(3-(3,4-dihydroisoquinolin-2(1H)-yl)-2-hydroxypropyl)-3,4-dihydroquinoline-1(2H)-carboxamide (Prepared according to Scheme 3)

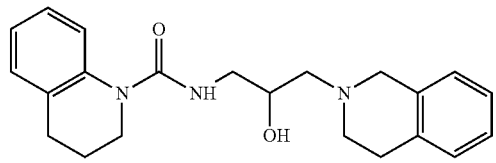 [SMILES: O=C(NCC(O)CN1CCc2ccccc2C1)N1CCCc2ccccc21]

Step a

To a solution of 1,2,3,4-tetrahydroquinoline (CAS Number 635-46-1, available from Spectrochem) (1.00 g, 7.518 mmol) in toluene (5 ml) were added triethylamine (CAS Number 121-44-8, available from Spectrochem) (1.20 ml, 8.646 mmol) and bis(trichloromethyl)carbonate (CAS Number 32315-10-9, available from Spectrochem) (1.00 g, 3.384 mmol). The resulting reaction mixture was stirred at 50° C. for 3 h and then allowed to cool down to room temperature. To this reaction mixture were added triethylamine (1.93 ml, 13.909 mmol) and allylamine (CAS Number 107-11-9, available from Spectrochem) (1.09 g, 18.790 mmol) and the resulting reaction mixture was stirred at room temperature for 16 h. Reaction mixture was poured into saturated $NaHCO_3$ solution (100 ml). The resulting reaction mixture was extracted with ethyl acetate (3×50 ml). The combined organic phase was dried over $Na_2SO_4$, filtered and concentrated under reduced pressure. The resulting crude material was purified by gradient flash chromatography (30% ethyl acetate in hexane) to obtain N-allyl-3,4-dihydroquinoline-1(2H)-carboxamide (0.74 g, 3.424 mmol) MS: ES+217.5 (M+1).

Step b

To a solution of N-allyl-3,4-dihydroquinoline-1(2H)-carboxamide (0.70 g, 3.240 mmol) in dichloromethane (5 ml) at 0° C. was added m-chloroperbenzoic acid (CAS Number 937-14-4, available from Spectrochem) (0.84 g, 4.861 mmol) and allowed to stir at room temperature for 1 h. The above reaction mixture was diluted with dichloromethane (15 ml) and washed with water (2×20 ml). The combined organic phase was dried over $Na_2SO_4$, filtered and concentrated under reduced pressure yielding N-(oxiran-2-ylmethyl)-3,4-dihydroquinoline-1(2H)-carboxamide (0.32 g, 1.379 mmol) which was used in to the next step without further purification. MS: ES+233.6 (M+1).

Step c

To a solution of N-(oxiran-2-ylmethyl)-3,4-dihydroquinoline-1(2H)-carboxamide (0.30 g, 1.293 mmol) in isopropyl alcohol (3 ml) was added triethylamine (0.36 ml, 2.586 mmol) and refluxed for 16 h. The reaction mixture was cooled to room temperature and concentrated under reduced pressure. The obtained crude was purified using preparative HPLC yielding N-(3-(3,4-dihydroisoquinolin-2(1H)-yl)-2-hydroxypropyl)-3,4-dihydroquinoline-1(2H)-carboxamide (Title compound) (0.08 g, 0.219 mmol). LCMS: Method A, 1.624 min, MS: ES+366.3 (M+1). 1H NMR (400 MHz, DMSO-$d_6$) δ ppm: 7.436-7.415 (d, J=8.4 Hz, 1H), 7.154-7.018 (m, 6H), 6.925-6.885 (dt, J=1.2 Hz, 7.2 Hz, 1H), 6.661-6.635 (t, J=5.2 Hz, 1H), 4.845-4.834 (d, J=4.4 Hz, 1H), 3.859-3.817 (q, J=5.6 Hz, 1H), 3.658-3.465 (m, 4H), 3.287-3.227 (m, 1H), 3.164-3.100 (m, 1H), 2.767-2.753 (d, J=5.6 Hz, 2H), 2.719-2.762 (m, 2H), 2.674-2.614 (m, 2H), 2.484-2.424 (m, 1H), 2.082 (s, 1H), 1.770-1.707 (m, 2H).

Using the route depicted above, the following compound was also prepared:

| Example | Name | Structure | Reagent A | LC/MS | NMR |
|---|---|---|---|---|---|
| 2B | N-[2-hydroxy-3-(1,2,3,4-tetrahydroisoquinolin-2-yl)propyl]-2,3-dihydro-1H-indole-1-carboxamide | 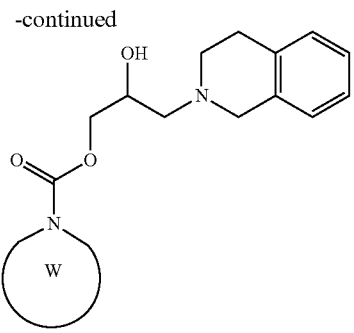 | | Method A, Retention Time = 1.636 min, MS: ES+ 352.2 (M + 1) | (400 MHz, DMSO-$d_6$) δ ppm: 7.827-7.807 (d, J = 8.0 Hz, 1H), 7.127-7.071 (m, 4H), 7.053-7.002 (m, 2H), 6.834-6.795 (dt, J = 0.8 Hz, 7.6 Hz, 1H), 6.686-6.660 (t, J = 5.2 Hz, 1H), 4.852 (s, 1H), 3.881-3.837 (m, 1H), 3.732-3.578 (m, 2H), 3.311-3.251 (m, 1H), 3.165-3.102 (m, 1H), 3.030-2.986 (t, J = 9.0 Hz, 2H), 2.820-2.805 (d, J = 6.0 Hz, 2H), 2.782-2.698 (m, 2H), 2.576-2.530 (m, 1H), 2.576-2.508 (m, 1H) |

Using the route depicted above, the following compounds were also prepared, by replacing 1,2,3,4-tetrahydroquinoline, in Step a, with the requisite amine:

Carbamate derivatives were synthesized via two separate schemes, as explained below.

Example 3

Scheme 4

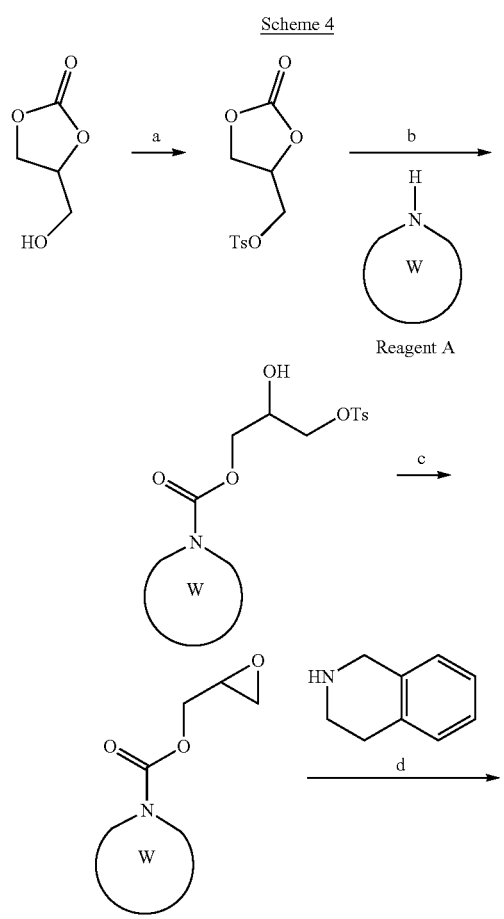

Reagents and conditions: a) p-toluenesulfonyl chloride, 4-dimethylaminopyridine, pyridine, dichloromethane, 3 h b) 1° or 2° amine, triethylamine, THF, rt, 15 h c) Sodium methoxide, methanol, rt, 5 h d) 1,2,3,4-tetrahydroisoquinoline, isopropyl alcohol, rt, 8 h.

Example 3A 3-(3,4-dihydroisoquinolin-2(1H)-yl)-2-hydroxypropyl 3,4-dihydroisoquinoline-2(1H)-carboxylate (Prepared according to Scheme 4)

Step a

To a stirred solution of glycerol 1, 2-carbonate (CAS Number 931-40-8; available from TCI Channel) (3.00 g, 25.420 mmol), 4-dimethylaminopyridine (0.15 g, 1.270 mmol), pyridine (3.07 ml, 38.100 mmol) in dichloromethane (45 ml) at 0° C. temperature in $N_2$ atmosphere for 5 min was added p-toluenesulfonyl chloride (5.33 g, 27.940 mmol) in dichloromethane (20 ml). The resulting reaction mixture was stirred for 2 h, then diluted with dichloromethane (30 ml) & washed with water (2×30 ml). The combined organic phase was washed with saturated solution of potassium hydrogen sulphate (10 ml) & dried over anhydrous $Na_2SO_4$, filtered and concentrated under reduced pressure. The resulting crude material was purified by flash chromatography (20% ethyl acetate in hexane) yielding (2-oxo-1,3-dioxolan- 4-yl)methyl 4-methylbenzenesulfonate as white solid (4.20 g, 15.430 mmol). 1H NMR: (400 MHz, DMSO-$d_6$) δ ppm: 7.823-7.802 (d, J=8.4 Hz, 2H), 7.528-7.508 (d, J=8.0 Hz, 2H), 5.052-4.981 (m, 1H), 4.547-4.503 (t, J=8.8 Hz, 1H), 4.379-4.264 (m, 2H), 4.194-4.158 (dd, J=6.0 Hz, 8.4 Hz, 1H), 2.439 (s, 3H).

Step b

To a stirred solution of (2-oxo-1,3-dioxolan-4-yl)methyl 4-methylbenzenesulfonate (0.70 g, 2.574 mmol) and triethylamine (0.35 ml, 2.574 mmol) in THF (14 ml) was added 1,2,3,4-tetrahydroisoquinoline (CAS Number 91-21-5; available from Alfa Aesar) (0.41 g, 3.080 mmol) at 0° C. and the resulting reaction mixture was allowed to stir at room temperature for 15 h. The reaction mixture was poured in water (15 ml) and extracted with ethyl acetate (2×30 ml). The organic phase was dried over anhydrous $Na_2SO_4$, filtered and concentrate under reduced pressure. The crude compound was purified by silica gel flash chromatography (68% ethyl acetate in hexane) yielding crude 2-hydroxy-3-(((4-methylbenzene)sulfonyl)oxy)propyl 1,2,3,4-tetrahydroisoquinoline-2-carboxylate as yellow sticky solid (0.61 g, 1.506 mmol), which was used in the next step without further purification. LCMS: Method A, 2.378 min, MS: ES+406.1 (M+1).

Step c

To a stirred solution of 2-hydroxy-3-(((4-methylbenzene)sulfonyl)oxy)propyl 1,2,3,4-tetrahydroisoquinoline-2-carboxylate (crude) (0.61 g, 1.508 mmol) in methanol (10 ml) was added sodium methoxide (0.09 g, 1.660 mmol) under $N_2$ atmosphere at 0° C. and stirred for 10 min. The resulting reaction mixture was allowed to stir at room temperature for 7 h. Solvent was removed under reduced pressure. The resulting crude material was suspended in water (10 ml) and extracted with ethyl acetate (3×25 ml). The organic phase was dried over anhydrous $Na_2SO_4$, filtered and concentrate under reduced pressure. The crude compound was purified by silica gel flash chromatography (10% ethyl acetate in hexane) yielding oxiran-2-ylmethyl 1,2,3,4-tetrahydroisoquinoline-2-carboxylate as sticky solid (0.15 g, 0.626 mmol). LCMS: Method A, 2.067 min, MS: ES+234.1 (M+1).

Step d

To a stirred solution of oxiran-2-ylmethyl 1,2,3,4-tetrahydroisoquinoline-2-carboxylate (0.15 g, 0.625 mmol) in isopropyl alcohol (3 ml) was added 1,2,3,4-tetrahydroisoquinoline (CAS-91-21-5, available from Alfa Aesar) (0.09 g, 0.688 mmol) at ambient temperature under $N_2$ atmosphere and the resulting reaction mixture was allowed to stir at room temperature for 7 h. Solvent was removed under reduced pressure. The resulting crude material was purified by reverse phase flash chromatography (84% acetonitrile in water) yielding (Title compound, T-261) 3-(3,4-dihydroisoquinolin-2(1H)-yl)-2-hydroxypropyl-3,4-dihydroisoquinoline-2(1H)-carboxylate as off white solid (0.07 g, 0.186 mmol). LCMS: Method A, 1.717 min, MS: ES+367.2 (M+1); 1H NMR: (400 MHz, DMSO-$d_6$) δ ppm: 7.172 (br s, 4H), 7.110-7.061 (m, 3H), 7.027-7.015 (m, 1H), 4.931-3.920 (d, J=4.4 Hz, 1H), 4.608 (br s, 1H), 4.521 (br s, 1H), 4.137-4.120 (m, 1H), 3.983-3.920 (m, 2H), 3.644-3.608 (m, 4H), 2.788 (br s, 4H), 2.734-2.677 (m, 2H), 2.549-2.530 (m, 2H).

Using the route depicted above, the following compounds were also prepared:

| Example | Name | Structure | Reagent A |
| --- | --- | --- | --- |
| 3B | 2-hydroxy-3-(1,2,3,4-tetrahydro-isoquinolin-2-yl)propyl piperidine-1-carboxylate | 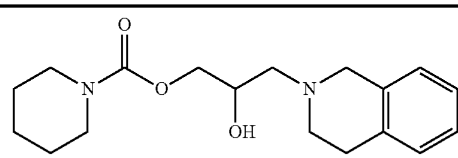 | piperidine (NH) |
| 3C | 2-hydroxy-3-(1,2,3,4-tetrahydro-isoquinolin-2-yl)propyl pyrrolidine-1-carboxylate | 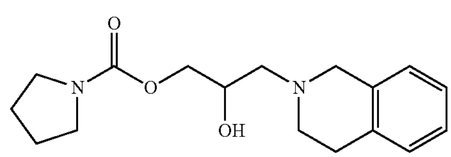 [SMILES: O=C(OCC(O)CN1CCc2ccccc2C1)N1CCCC1] | pyrrolidine (NH) |
| 3D | 2-hydroxy-3-(1,2,3,4-tetrahydro0 isoquinolin-2-yl)propyl 3-phenylpyrrolidine-1-carboxylate | 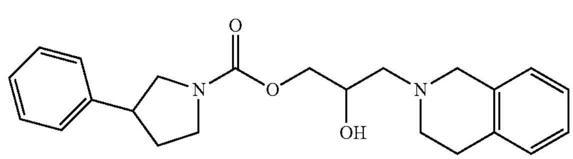 [SMILES: O=C(OCC(O)CN1CCc2ccccc2C1)N1CCC(c2ccccc2)C1] | 3-phenylpyrrolidine (NH) |

| Example | LCMS | NMR |
| --- | --- | --- |
| 3B | Method A, Retention Time = 1.538 min, MS: ES+ 319.5 (M + 1) | (400 MHz, CDCl$_3$) δ ppm: 7.222-7.124 (m, 3H), 7.051-7.031 (m, 1H), 4.278-4.203 (m, 1H), 4.131-4.060 (m, 2H), 3.882-3.845 (d, J = 14.8 Hz, 1H), 3.690-3.653 (d, J = 14.8 Hz, 1H), 3.476-3.449 (m, 4H), 3.008-2.883 (m, 3H) 2.803-2.753 (m, 1H), 2.619-2.603 (d, J = 6.4 Hz, 2H), 1.640-1.560 (m, 6H) |
| 3C | Method A, Retention Time = 1.360 min, MS: ES+ | (400 MHz, DMSO-d$_6$) δ ppm: 7.115-7.068 (m, 3H), 7.039-7.020 (m, 1H), 4.837 (br s, 1H), 4.075-4.042 (dd, J = 2.8 Hz, 10.0 Hz, 1H), 3.930-3.855 (m, 2H), 3.605 (m, 2H), |

| | | |
|---|---|---|
| 3D | Method A, Retention Time = 1.774 min, MS: ES+ 381.3 (M + 1) | 305.3 (M + 1) 3.307-3.213 (m, 4H), 2.794-2.763 (m, 2H), 2.751-2.667 (m, 2H), 2.513-2.440 (m, 2H), 1.814-1.749 (t, J = 13.2 Hz, 4H) (400 MHz, DMSO-$d_6$) δ ppm: 7.356-7.338 (m, 2H), 7.314-7.254 (m, 3H), 7.173-7.134 (m, 3H), 7.057-7.027 (m, 1H), 4.318-4.265 (dt, J = 5.2 Hz, 10.8 Hz, 1H), 4.166-4.098 (m, 2H), 3.959-3.642 (m, 4H), 3.594-3.522 (m, 2H), 3.472-3.375 (m, 2H), 3.016-2.926 (m, 2H), 2.811-2.769 (m, 1H), 2.646-2.612 (t, J = 6.8 Hz, 2H), 2.370-2.285 (m, 1H), 2.010-1.985 (m, 1H) |

Example 4

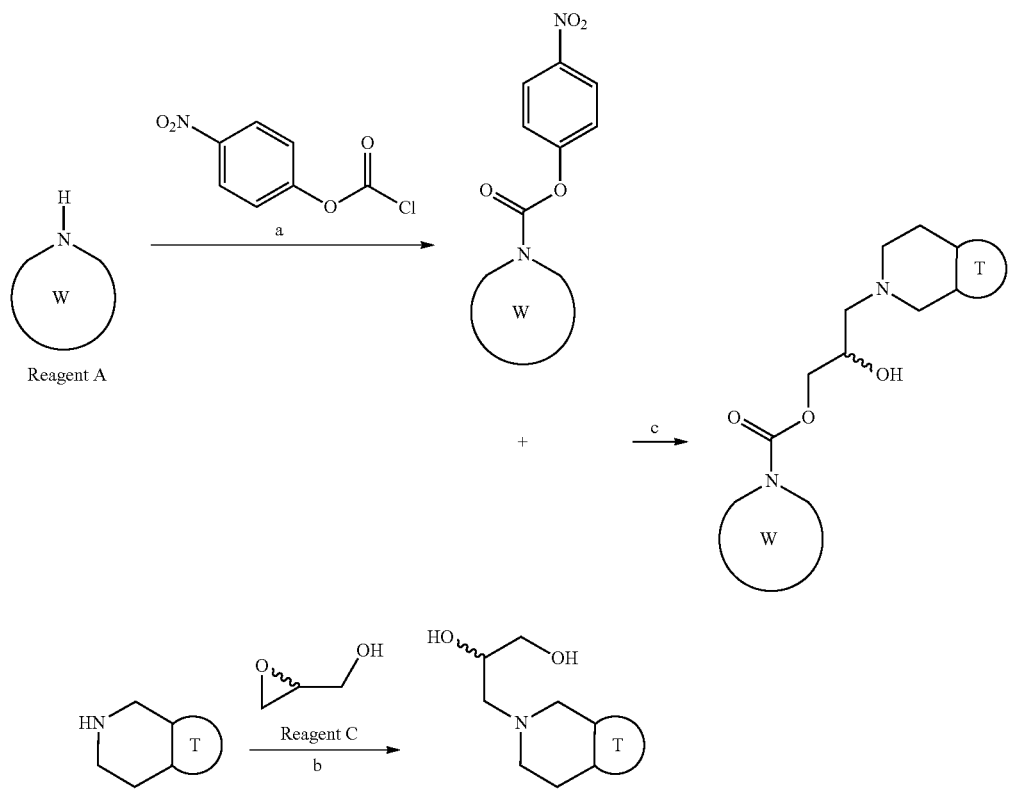

Scheme 5

Reagents and conditions: a) Diisopropylethylamine, dichloromethane, 0° C., to rt, 1 h b) NaH, THF, 0° C. to rt, 2 h (c) THF, 80° C., 2 h Example 4A 3-(3,4-dihydroisoquinolin-2(1H)-yl)-2-hydroxypropyl thiomorpholine-4-carboxylate (Prepared according to Scheme 5)

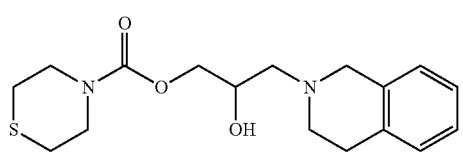 [SMILES: O=C(OCC(O)CN1CCc2ccccc2C1)N1CCSCC1]

Step a

To a stirred solution of thiomorpholine (CAS No. 123-90-0; available from Combi Blocks) (0.8 g, 7.76 mmol) in dichloromethane (16 ml) was added diisopropylethylamine (4 ml, 23.28 mmol) and allowed to stir at 0° C. for 15 min, followed by addition of 4-nitrophenyl chloroformate (CAS No. 7693-46-1; available from Spectrochem) (1.72 g, 8.54 mmol) and allowed to stir at 0° C. for 1 h. After completion of reaction, reaction mixture was poured into water (50 ml). The resulting reaction mixture was extracted with ethyl acetate (2×50 ml). The combined organic phase was dried over $Na_2SO_4$, filtered and concentrated under reduced pressure. The resulting crude material was purified by flash chromatography (6% ethyl acetate in hexane) yielding 4-nitrophenyl thiomorpholine-4-carboxylate (1.46 g, 5.44 mmol). $^1$H-NMR (400 MHz, CDCl$_3$) δ ppm: 8.304-8.265 (m 2H), 7.337-7.298 (m 2H), 3.982-3.863 (m 4H), 2.751-2.726 (m 4H).

Step b

To a stirred suspension of sodium hydride (60% dispersion in mineral oil) (0.032 g, 0.777 mmol) in THF (2 ml) at 0° C. was added glycidol (0.058 g, 0.777 mmol) at 0° C. temperature under nitrogen atmosphere. The reaction mixture was allowed to stir for 15 min. Solution of 4-nitrophenyl thiomorpholine-4-carboxylate (0.25 g, 0.932 mmol) in THF (3 ml) was added drop wise to above reaction mixture at 0° C. temperature and the resulting reaction mixture was stirred at room temperature for 2 h. To this reaction mixture was added 1,2,3,4-tetrahydroisoquinoline (0.31 g, 2.33 mmol) at room temperature and resulting reaction mixture was stirred at 80° C. for 2 h. Reaction mixture was poured into water (25 ml) and extracted with ethyl acetate (3×20 ml). The combined organic phase was dried over Na$_2$SO$_4$, filtered and concentrated under reduced pressure. The resulting crude material was purified by reverse-phase flash chromatography (80% acetonitrile in water) yielding 3-(3,4-dihydroisoquinolin-2(1H)-yl)-2-hydroxypropyl thiomorpholine-4-carboxylate (0.4 g crude material), which was further purified by preparative HPLC yielding 3-(3,4-dihydroisoquinolin-2 (1H)-yl)-2-hydroxypropyl thiomorpholine-4-carboxylate (title compound 4A). (0.049 g, 0.146 mmol) LCMS: Method A, Retention Time=1.703 min, MS: ES+337.2 (M+1); $^1$H NMR (400 MHz, DMSO-d$_6$) δ ppm: 7.144-7.081 (m, 3H), 7.052-7.033 (m, 1H), 4.106-4.072 (m, 1H), 3.972-3.892 (m, 2H), 3.712-3.628 (m, 6H), 2.812-2.733 (m, 5H), 2.597-2.539 (m, 6H).

Using the route depicted above, the following compounds (Examples 4B to 4AH) were also prepared.

| Example | Name | Structure | Reagent A | Reagent B | Reagent C | LC/MS | NMR |
|---|---|---|---|---|---|---|---|
| 4B | 3-(3,4-dihydroisoquinolin-2(1H)-yl)-2-hydroxypropyl 4-(morpholine-4-carbonyl)-piperidine-1-carboxylate | 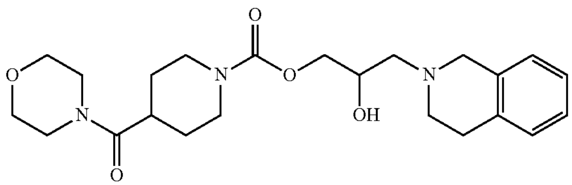 [SMILES: O=C(OCC(O)CN1CCc2ccccc2C1)N1CCC(C(=O)N2CCOCC2)CC1] | | | | Method B, Retention Time = 1.436 min, MS: ES+ 432.1 (M + 1) | (400 MHz, DMSO-d₆) δ ppm: 7.116-7.069 (m, 3H), 7.041-7.022 (m, 1H), 4.895-4.887 (d, J = 3.2 Hz, 1H), 4.070-3.914 (m, 5H), 3.611-3.534 (m, 8H), 3.444-3.432 (m, 2H), 2.850-2.677 (m, 7H), 2.479-2.462 (m, 2H), 1.622-1.592 (m, 2H), 1.431-1.405 (m, 2H) |
| 4C | 3-(3,4-dihydroisoquinolin-2(1H)-yl)-2-hydroxypropyl 3-(pyridin-4-ylamino)piperidine-1-carboxylate | 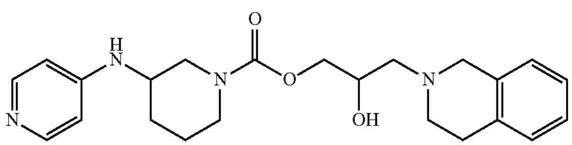 [SMILES: O=C(OCC(O)CN1CCc2ccccc2C1)N1CCCC(Nc2ccncc2)C1] | | | | Method B, Retention Time = 1.142 min and 1.202 min (as mixture of diastereomers), MS: ES+ 411.2 (M + 1) | (400 MHz, DMSO-d₆) δ ppm: 8.031-8.17 (d, J = 5.6 Hz, 2H), 7.112-7.020 (m, 4H), 6.536-6.454 (m, 3H), 4.896-4.888 (m, 2H), 4.085-3.654 (m, 5H), 3.596-3.532 (m, 2H), 3.331 (br s, 1H), 2.949-2.673 (m, 6H), 2.530-2.485 (m, 1H), 1.951-1.928 (m, 1H), 1.708 (br s, 1H), 1.494-1.444 (m, 2H) |

| Example | Name | Structure | Reagent A | Reagent B | Reagent C | LC/MS | NMR |
|---|---|---|---|---|---|---|---|
| 4D | 3-(3,4-dihydroisoquinolin-2(1H)-yl)-2-hydroxypropyl 4-benzylpiperidine-1-carboxylate | 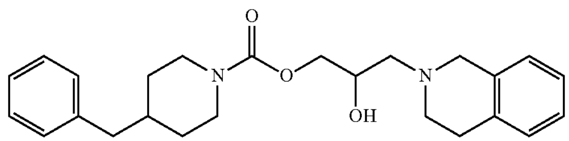 [SMILES: O=C(OCC(O)CN1CCc2ccccc2C1)N1CCC(Cc2ccccc2)CC1] | 4-benzylpiperidine (NH, Ph) | 1,2,3,4-tetrahydroisoquinoline (HN) | glycidol (epoxide-CH2OH) | Method B, Retention Time = 2.042 min, MS: ES+ 409.2 (M + 1) | (400 MHz, DMSO-d6) δ ppm: 7.303-7.266 (m, 2H), 7.203-7.157 (m, 3H), 7.119-7.070 (m, 3H), 7.037-7.018 (m, 1H), 4.886 (br s, 1H), 4.057-3.855 (m, 6H), 3.608 (br s, 2H), 2.795-2.678 (m, 7H), 2.548-2.492 (m, 2H), 1.708-1.653 (m, 1H), 1.557-1.527 (m, 2H), 1.086-1.0542 (m, 2H) |
| 4E | (R)-3-(3,4-dihydroisoquinolin-2(1H)-yl)-2-hydroxypropyl 3-phenylpyrrolidine-1-carboxylate | 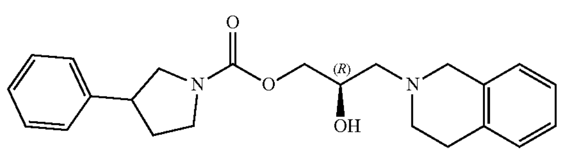 | 3-phenylpyrrolidine (H-N, Ph) | 1,2,3,4-tetrahydroisoquinoline (HN) | (R)-glycidol | Method C, Retention Time = 1.834 min, MS: ES+ 381.2 (M + 1) | (400 MHz, DMSO-d6) δ ppm: 7.350-7.239 (m, 5H), 7.098-7.028 (m, 4H), 4.871 (br s, 1H), 4.095-4.068 (m, 1H), 3.924-3.887 (m, 2H), 3.827-3.713 (m, 1H), 3.615-3.409 (m, 4H), 3.342-3.162 (m, 4H), 2.802-2.608 (m, 4H), 2.209 (br s, 1H), 1.978-1.910 (m, 1H) |

| Example | Name | Structure | Reagent A | Reagent B | Reagent C | LC/MS | NMR |
|---|---|---|---|---|---|---|---|
| 4F | (S)-3-(3,4-dihydroisoquinolin-2(1H)-yl)-2-hydroxypropyl 3-phenyl-pyrrolidine-1-carboxylate | 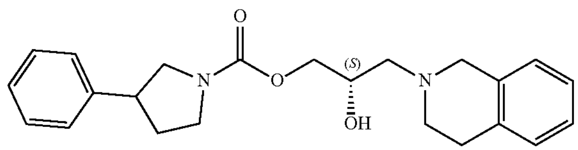 | | | | Method A, Retention Time = 1.802 min, MS: ES+ 381.1 (M + 1) | (400 MHz, DMSO-d$_6$) δ ppm: 7.351-7.224 (m, 5H), 7.109-7.027 (m, 4H), 4.871-4.848 (m, 1H), 4.112-4.068 (m, 1H), 3.927-3.889 (m, 2H), 3.807-3.717 (m, 1H), 3.618-3.602 (m, 2H), 3.342-3.162 (m, 4H) 2.802-2.608 (m, 4H), 2.210-2.196 (m, 1H), 1.957-1.910 (m, 1H) |
| 4G | (R)-3-(3,4-dihydroisoquinolin-2(1H)-yl)-2-hydroxypropyl 3,4-dihydroisoquinoline-2(1H)-carboxylate | 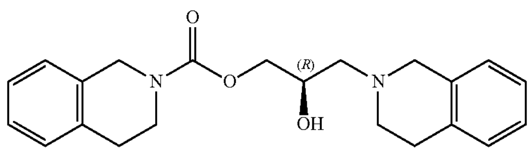 | | | | Method A, Retention Time = 1.802 min, MS: ES+ 367.1 (M + 1) | (400 MHz, DMSO-d$_6$) δ ppm: 7.223-7.173 (m, 4H), 7.125-7.027 (m, 4H), 4.926-4.916 (d, J = 4.0 Hz, 1H), 4.604-4.523 (m, 2H), 4.152-4.102 (m, 1H), 3.955-3.920 (m, 2H), 3.644-3.608 (m, 4H), 2.866-2.677 (m, 6H), 2.562-2.461 (m, 2H) |
| 4H | (S)-3-(3,4-dihydroisoquinolin-2(1H)-yl)-2-hydroxypropyl 3,4-dihydroisoquinoline-2(1H)-carboxylate | 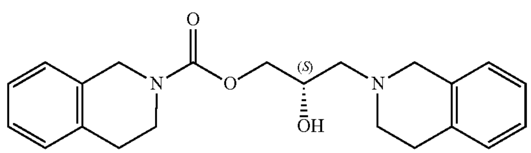 | | | | Method A, Retention Time = 1.802 min, MS: ES+ 367.1 (M + 1) | (400 MHz, DMSO-d$_6$) δ ppm: 7.224-7.173 (m, 4H), 7.125-7.015 (m, 4H), 4.930-4.920 (d, J = 4.0 Hz, 1H), 4.609-4.522 (m, 2H), 4.151-4.120 (m, 1H), 3.956-3.920 (m, 2H), 3.644-3.608 (m, 4H), 2.866-2.677 (m, 6H), 2.562-2.461 (m, 2H) |

| Example | Name | Structure | Reagent A | Reagent B | Reagent C | LC/MS | NMR |
|---|---|---|---|---|---|---|---|
| 4I | 3-(3,4-dihydroisoquinolin-2(1H)-yl)-2-hydroxypropyl 3-hydroxypiperidine-1-carboxylate | 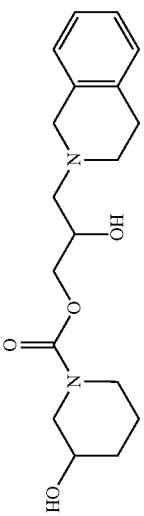 | 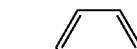 | 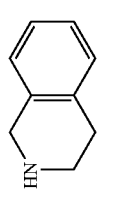 | 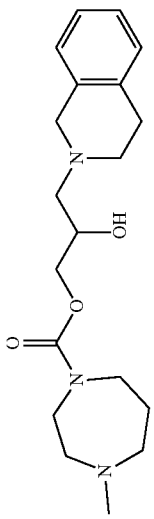 | Method B, Retention Time = 1.241 min, MS: ES+ 335.1 (M + 1) and 1.282 min, MS: ES+ 335.2 (M + 1) | (400 MHz, DMSO-d₆) δ ppm: 7.098-7.032 (m, 4H), 4.889-4.879 (d, J = 4.0 Hz, 1H), 4.870 (br s, 1H), 4.046-4.029 (m, 1H), 3.908-3.866 (m, 2H), 3.794-3.772 (m, 1H), 3.613-3.514 (m, 3H), 3.413-3.371 (m, 2H), 2.896-2.559 (m, 7H), 1.809 (br s, 1H), 1.637 (br s, 1H), 1.310-1.239 (m, 2H) |
| 4J | 3-(3,4-dihydroisoquinolin-2(1H)-yl)-2-hydroxypropyl 4-methyl-1,4-diazepane-1-carboxylate | 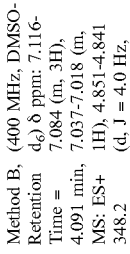 | 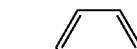 | | | Method B, Retention Time = 4.091 min, MS: ES+ 348.2 (M + 1) | (400 MHz, DMSO-d₆) δ ppm: 7.116-7.084 (m, 3H), 7.037-7.018 (m, 1H), 4.851-4.841 (d, J = 4.0 Hz, 1H), 4.057-4.038 (m, 1H), 3.921-3.900 (m, 2H), 3.609-3.603 (m, 2H), 3.452-3.377 (m, 4H), 2.810-2.686 (m, 5H), 2.474-2.443 (m, 5H), 2.242-2.237 (d, J = 2.0 Hz, 3H), 1.769-1.727 (m, 2H) |

| Example | Name | Structure | Reagent A | Reagent B | Reagent C | LC/MS | NMR |
|---|---|---|---|---|---|---|---|
| 4K | (R)-3-(3,4-dihydro-isoquinolin-2(1H)-yl)-2-hydroxy-propyl (S)-3-phenyl-pyrrolidine-1-carbox-ylate | 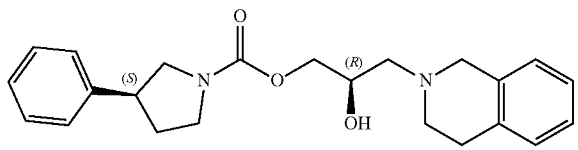 | | | | Method B, Retention Time = 1.919 min, MS: ES+ 381.3 (M + 1) | (400 MHz, DMSO-d₆) δ ppm: 7.341-7.241 (m, 5H), 7.110-7.028 (m, 4H), 4.877 (br s, 1H), 4.081-4.064 (m, 1H), 3.934-3.880 (m, 2H), 3.831-3.786 (m, 1H), 3.751-3.708 (m, 1H), 3.616-3.602 (m, 2H), 3.560-3.453 (m, 2H), 3.391-3.298 (m, 1H), 3.264-3.199 (m, 2H), 2.814-2.729 (m, 3H), 2.536-2.452 (m, 1H), 2.210 (br s, 1H), 1.966-1.918 (m, 1H) |
| 4L | (R)-3-(3,4-dihydro-isoquinolin-2(1H)-yl)-2-hydroxy-propyl (R)-3-phenyl-pyrrolidine-1-carbox-ylate | 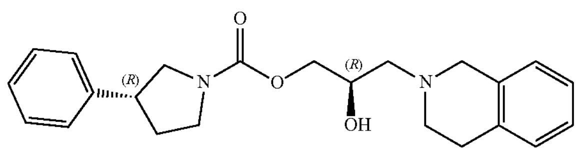 | | | | Method B, Retention Time = 1.850 min, MS: ES+ 381.2 (M + 1) | (400 MHz, DMSO-d₆) δ ppm: 7.350-7.224 (m, 5H), 7.103-7.036 (m, 4H), 4.877 (br s, 1H), 4.110-4.085 (m, 1H), 3.930-3.891 (m, 2H), 3.808-3.783 (m, 1H), 3.742-3.717 (m, 1H), 3.628-3.485 (m, 4H), 3.395-3.301 (m, 1H), 3.270-3.188 (m, 2H), 2.794-2.672 (m, 4H), 2.212-2.197 (m, 1H), 1.981-1.904 (m, 1H) |

| Example | Name | Structure | Reagent A | Reagent B | Reagent C | LC/MS | NMR |
|---|---|---|---|---|---|---|---|
| 4M | 3-(3,4-dihydro-isoquinolin-2(1H)-yl)-2-hydroxypropyl thiomorpholine-4-carboxylate 1-oxide | 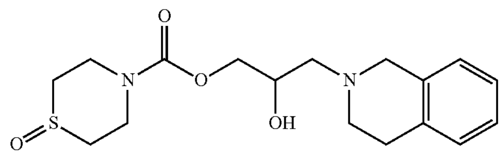 [SMILES: O=C(OCC(O)CN1CCc2ccccc2C1)N1CCS(=O)CC1] | | | | Method C, Retention Time = 3.105 min, MS: ES+ 353.2 (M+1) | (400 MHz, CDCl₃) δ ppm: 7.230-2.144 (m, 3H), 7.069-7.048 (m, 1H), 4.274-4.010 (m, 4H), 3.980-3.739 (m, 4H), 3.118-2.886 (m, 4H), 3.854-3.694 (m, 8H) |
| 4N | 3-(3,4-dihydro-isoquinolin-2(1H)-yl)-2-hydroxypropyl thiomorpholine-4-carboxylate 1,1-dioxide | 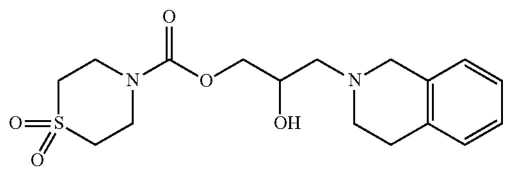 [SMILES: O=C(OCC(O)CN1CCc2ccccc2C1)N1CCS(=O)(=O)CC1] | | | | Method C, Retention Time = 3.084 min, MS: ES+ 369.2 (M+1) | (400 MHz, DMSO-d₆) δ ppm: 7.118-7.070 (m, 3H), 7.041-7.021 (m, 1H), 4.978 (br s, 1H), 4.164-4.132 (m, 1H), 3.973-3.896 (m, 2H), 3.808 (br s, 4H), 3.655-3.563 (m, 2H), 3.155 (br s, 4H), 2.975-2.672 (m, 4H), 2.471-2.423 (m, 2H) |
| 4O | (R)-3-(3,4-dihydro-isoquinolin-2(1H)-yl)-2-hydroxypropyl 4-(dimethylcarbamoyl)piperidine-1-carboxylate | 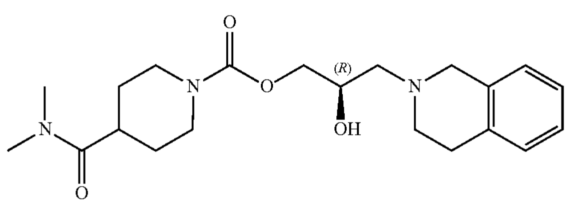 | | | | Method B, Retention Time = 4.120 min, MS: ES+ 390.1 (M+1) | (400 MHz, DMSO-d₆) δ ppm: 7.115-7.082 (m, 3H), 7.041-7.029 (m, 1H), 4.901-4.889 (d, J = 4.8 Hz, 1H), 4.071-4.014 (m, 3H), 3.930-3.911 (m, 2H), 3.607-3.602 (m, 2H), 3.029 (s, 3H), 2.855-2.781 (m, 7H), 2.760-2.732 (m, 1H), 2.718-2.682 (m, 2H), 2.472-2.440 (m, 2H), 1.625-1.593 (m, 2H), 1.410 (br s, 2H) |

| Example | Name | Structure | Reagent A | Reagent B | Reagent C | LC/MS | NMR |
|---|---|---|---|---|---|---|---|
| 4P | (R)-3-(3,4-dihydroisoquinolin-2(1H)-yl)-2-hydroxypropyl 4-(morpholine-4-carbonyl)piperidine-1-carboxylate | 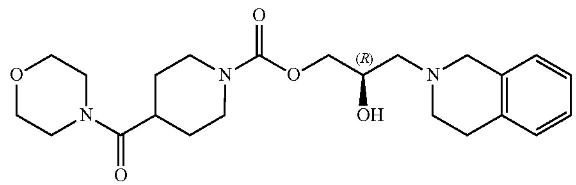 | | | | Method B, Retention Time = 1.387 min, MS: ES+ 432.5 (M + 1) | (400 MHz, DMSO-d₆) δ ppm: 7.114-1.082 (m, 3H), 7.039-7.020 (m, 1H), 4.900-4.889 (d, J = 4.4 Hz, 1H), 4.071-4.008 (m, 3H), 3.943-3.911 (m, 2H), 3.644-3.523 (m, 8H), 3.442-4.431 (m, 2H), 2.849-2.758 (m, 5H), 2.747-2.666 (m, 2H), 2.470-2.438 (m, 2H), 1.622-1.591 (m, 2H), 1.428 (br s, 2H) |
| 4Q | (R)-3-(3,4-dihydroisoquinolin-2(1H)-yl)-2-hydroxypropyl 4-(3-oxa-8-azabicyclo[3.2.1]octane-8-carbonyl)piperidine-1-carboxylate | 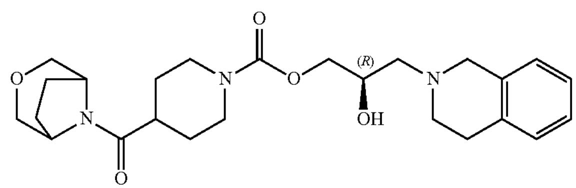 | | | | Method B, Retention Time = 1.774 min, MS: ES+ 458.2 (M + 1) | (400 MHz, DMSO-d₆) δ ppm: 7.115-7.067 (m, 3H), 7.040-7.021 (m, 1H), 4.893-4.882 (d, J = 4.4 Hz, 1H), 4.381-4.317 (m, 2H), 4.072-4.020 (m, 3H), 3.945-3.914 (m, 2H), 3.608-3.432 (m, 6H), 2.809-2.682 (m, 7H), 2.474-2.442 (m, 2H), 1.911-1.817 (m, 2H), 1.745-1.655 (m, 2H), 1.582-1.420 (m, 4H) |

| Example | Name | Structure | Reagent A | Reagent B | Reagent C | LC/MS | NMR |
|---|---|---|---|---|---|---|---|
| 4R | (R)-3-(3,4-dihydroisoquinolin-2(1H)-yl)-2-hydroxypropyl 3-(pyridin-2-yl)pyrrolidine-1-carboxylate | 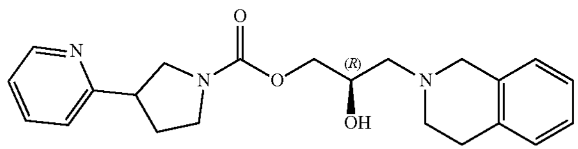 | | | | Method B, Retention Time = 4.410 min, MS: ES+ 382.1 (M + 1) | (400 MHz, DMSO-d₆) δ ppm: 8.533-8.521 (d, J = 4.8 Hz, 1H), 7.769-7.731 (t, J = 7.6 Hz, 1H), 7.355-7.335 (d, J = 8.0 Hz, 1H), 7.279-7.248 (m, 1H), 7.099-7.030 (m, 4H), 4.887 (m, 1H), 4.094-4.058 (m, 1H), 3.919-3.883 (m, 2H), 3.793-3.773 (m, 1H), 3.711-3.694 (m, 1H), 3.615-3.411 (m, 7H), 2.789-2.678 (m, 4H), 2.225 (br s, 1H), 2.097-2.053 (m, 1H) |
| 4S | 3-(3,4-dihydroisoquinolin-2(1H)-yl)-2-hydroxypropyl 3-(dimethylcarbamoyl)azetidine-1-carboxylate | 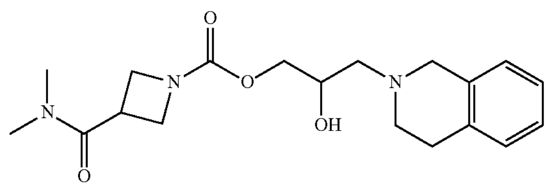 [SMILES: CN(C)C(=O)C1CN(C(=O)OCC(O)CN2CCc3ccccc3C2)C1] | | | | Method B, Retention Time = 4.059 min, MS: ES+ 362.1 (M + 1) | (400 MHz, DMSO-d₆) δ ppm: 7.118-7.083 (m, 3H), 7.040-7.028 (m, 1H), 4.881-4.869 (d, J = 4.8 Hz, 1H), 4.048-3.851 (m, 7H), 3.653-3.601 (m, 2H), 2.839-2.828 (m, 6H), 2.815-2.779 (m, 2H), 2.729-2.673 (m, 2H), 2.475-2.452 (m, 2H) |

| Example | Name | Structure | Reagent A | Reagent B | Reagent C | LC/MS | NMR |
|---|---|---|---|---|---|---|---|
| 4T | 3-(3,4-dihydro-isoquinolin-2(1H)-yl)-2-hydroxy-propyl 3-(morpholine-4-carbonyl) azetidine-1-carboxylate | 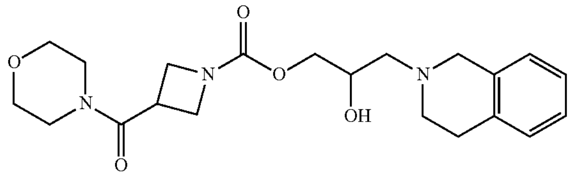 [SMILES: O=C(OCC(O)CN1CCc2ccccc2C1)N1CC(C(=O)N2CCOCC2)C1] | | | | Method B, Retention Time = 3.991 min, MS: ES+ 404.1 (M + 1) | (400 MHz, DMSO-d$_6$) δ ppm: 7.184-7.076 (m, 4H), 5.083-4.832 (m, 1H), 4.053-3.903 (m, 6H), 3.704-3.652 (m, 2H), 3.563-3.539 (m, 4H), 3.481-3.458 (m, 3H), 3.274-3.250 (m, 3H), 2.859-2.802 (m, 4H), 2.557-2.522 (m, 2H) |
| 4U | 3-(3,4-dihydro-isoquinolin-2(1H)-yl)-2-hydroxy-propyl 3-(3-oxa-8-azabicyclo-[3.2.1]-octane-8-carbonyl)-azetidine-1-carboxylate | 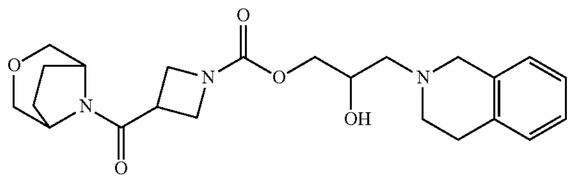 [SMILES: O=C(OCC(O)CN1CCc2ccccc2C1)N1CC(C(=O)N2C3CCC2COC3)C1] | | | | Method B, Retention Time = 1.383 min, MS: ES+ 430.5 (M + 1) | (400 MHz, DMSO-d$_6$) δ ppm: 7.105-7.093 (m, 3H), 7.040-7.028 (m, 1H), 4.888-4.878 (m, 1H), 4.401-3.386 (m, 1H), 4.054-4.036 (m, 2H), 3.981-3.970 (m, 2H), 3.883-3.843 (m, 2H), 3.673-3.602 (m, 3H) 3.558-3.426 (m, 5H), 2.829-2.661 (m, 5H), 2.591-2.424 (m, 2H), 1.878-1.836 (m, 3H), 1.778-1.725 (m, 1H) |

| Example | Name | Structure | Reagent A | Reagent B | Reagent C | LC/MS | NMR |
|---|---|---|---|---|---|---|---|
| 4V | 3-(3,4-dihydroisoquinolin-2(1H)-yl)-2-hydroxypropyl 4-acetyl-1,4-diazepane-1-carboxylate | 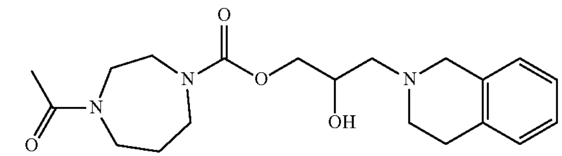 [SMILES: CC(=O)N1CCCN(C(=O)OCC(O)CN2CCc3ccccc3C2)CC1] | | | | Method B, Retention Time = 4.092 min, MS: ES+ 376.1 (M + 1) | (400 MHz, DMSO-d₆) δ ppm: 7.116-7.069 (m, 3H), 7.041-7.030 (m, 1H), 4.911-4.850 (m, 1H), 4.071-4.044 (m, 1H), 3.927-3.909 (m, 2H), 3.647-3.397 (m, 10H), 2.795-2.780 (m, 2H), 2.714-2.673 (m, 2H), 2.599-2.335 (m, 2H), 2.015-1.970 (m, 3H), 1.760-1.589 (m, 2H) |
| 4W | 1-(3-(3,4-dihydroisoquinolin-2(1H)-yl)-2-hydroxypropyl) 4-methyl 1,4-diazepane-1,4-dicarboxylate | 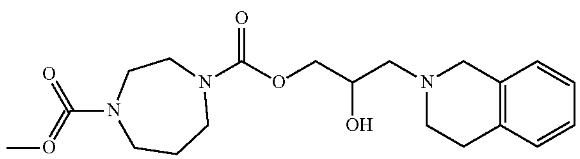 | | | | Method B, Retention Time = 1.729 min, MS: ES+ 392.3 (M + 1) | (400 MHz, DMSO-d₆) δ ppm: 7.116-7.068 (m, 3H), 7.039-7.020 (m, 1H), 4.866-4.855 (d, J = 4.4 Hz, 1H), 4.059-4.026 (m, 1H), 3.926-3.897 (m, 2H), 3.606-3.544 (m, 5H), 3.518-3.430 (m, 5H), 3.371-3.345 (m, 3H), 2.808-2.673 (m, 4H), 2.548-2.2.474 (m, 2H), 1.700-1.642 (m, 2H) |

-continued

| Example | Name | Structure | Reagent A | Reagent B | Reagent C | LC/MS | NMR |
|---|---|---|---|---|---|---|---|
| 4X | (S)-3-(3,4-dihydroisoquinolin-2(1H)-yl)-2-hydroxypropyl 4-(3-oxa-8-azabicyclo[3.2.1]octane-8-carbonyl)-piperidine-1-carboxylate | 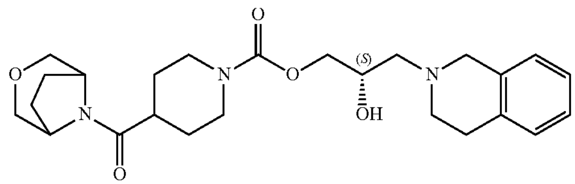 | | | | Method B, Retention Time = 1.420 min, MS: ES+ 458.4 (M + 1) | (400 MHz, DMSO-$d_6$) δ ppm: 7.129-7.067 (m, 3H), 7.040-7.021 (m, 1H), 4.906-4.896 (d, J = 4.0 Hz, 1H), 4.380-4.319 (m, 2H), 4.071-4.051 (m, 3H), 3.916 (br s, 2H), 3.647-3.356 (m, 6H), 2.805-2.667 (m, 7H), 2.472-2.440 (m, 2H), 1.910-1.802 (m, 3H), 1.759-1.655 (m, 2H), 1.585-1.420 (m, 3H) |
| 4Y | 3-(6,7-dihydrothieno[3,2-c]pyridin-5(4H)-yl)-2-hydroxypropyl 3,4-dihydroquinoline-1(2H)-carboxylate | 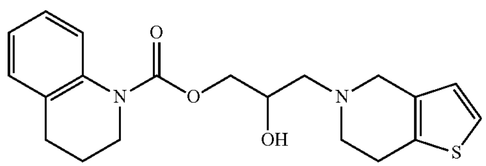 [SMILES: O=C(OCC(O)CN1CCc2sccc2C1)N1CCCc2ccccc21] | | | | Method A, Retention Time = 1.781 min, MS: ES+ 373.1 (M + 1) | (400 MHz, DMSO-$d_6$) δ ppm: 7.674-7.654 (d, J = 8.0 Hz, 1H), 7.274-7.261 (d, J = 5.2 Hz, 1H), 7.142-7.108 (m, 2H), 7.018-6.978 (m, 1H), 6.791-6.778 (d, J = 5.2 Hz, 1H), 4.969-4.958 (d, J = 4.4 Hz, 1H), 4.212-4.177 (dd, J = 3.6, 10.4 Hz, 1H), 4.038-3.951 (m, 2H), 3.718-3.688 (t, J = 6.0 Hz, 2H), 3.572-3.530 (m, 2H), 2.777 (br s, 4H), 2.742-2.710 (d, J = 6.4 Hz, 2H), 2.598-2.531 (m, 2H), 1.878-1.815 (quin, J = 6.4 Hz, 2H) |

| Example | Name | Structure | Reagent A | Reagent B | Reagent C | LC/MS | NMR |
|---|---|---|---|---|---|---|---|
| 4Z | 3-(4,7-dihydrothieno[2,3-c]pyridin-6(5H)-yl)-2-hydroxypropyl 3,4-dihydroquinoline-1(2H)-carboxylate | 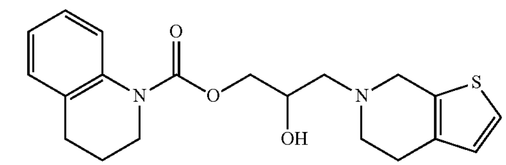 [SMILES: O=C(OCC(O)CN1CCc2ccsc2C1)N1CCCc2ccccc21] | | | | Method A, Retention Time = 2.855 min, MS: ES+ 373.1 (M + 1) | (400 MHz, CDCl₃) δ ppm: 7.608 (br s, 1H), 7.291-7.263 (m, 1H), 7.111-7.030 (m, 3H), 6.890 (br s, 1H), 5.367 (br s, 1H), 4.612 (br s, 2H), 4.302 (br s, 2H), 3.792-3.504 (m, 3H), 3.151 (br s, 4H), 2.792 (br s, 2H), 2.031-1.980 (m, 4H) |
| 4AA | 3-(6,7-dihydrothieno[3,2-c]pyridin-5(4H)-yl)-2-hydroxypropyl 3,4-dihydroisoquinoline-2(1H)-carboxylate | 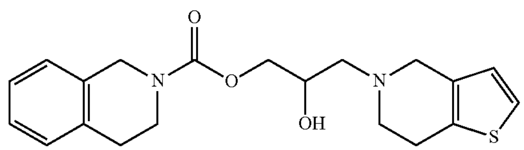 [SMILES: O=C(OCC(O)CN1CCc2sccc2C1)N1CCc2ccccc2C1] | | | | Method A, Retention Time = 1.698 min, MS: ES+ 373.2 (M + 1) | (400 MHz, DMSO-d₆) δ ppm: 7.501-7.489 (d, J = 4.8 Hz, 1H), 7.190 (br s, 4H), 6.942-6.929 (d, J = 5.2 Hz, 1H), 6.564 (br s, 1H), 4.629-4.542 (m, 3H), 4.322 (br s, 2H), 4.063-4.051 (m, 2H), 3.840 (br s, 1H), 3.662-3.609 (m, 2H), 3.472 (br s, 1H), 3.260-3.130 (m, 4H), 2.817 (br s, 2H) |
| 4AB | 3-(4,7-dihydrothieno[2,3-c]pyridin-6(5H)-yl)-2-hydroxypropyl 3,4-dihydroisoquinoline-2(1H)-carboxylate | 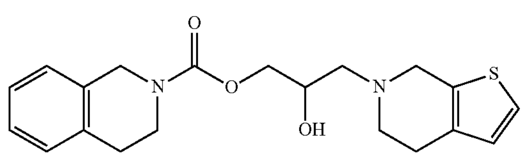 [SMILES: O=C(OCC(O)CN1CCc2ccsc2C1)N1CCc2ccccc2C1] | | | | Method A, Retention Time = 1.738 min, MS: ES+ 373.1 (M + 1) | (400 MHz, DMSO-d₆) δ ppm: 7.286-7.273 (d, J = 5.2 Hz, 1H), 7.174 (br s, 4H), 6.815-6.803 (d, J = 4.8 Hz, 1H), 4.931-4.920 (d, J = 4.4 Hz, 1H), 4.602-4.524 (m, 2H), 4.138-4.087 (m, 1H), 3.962-3.927 (m, 2H), 3.663-3.620 (m, 4H), 2.808-2.743 (m, 4H), 2.619-2.541 (m, 4H) |

| Example | Name | Structure | Reagent A | Reagent B | Reagent C | LC/MS | NMR |
|---|---|---|---|---|---|---|---|
| 4AC | 3-(6,7-dihydrothieno[3,2-c]pyridin-5(4H)-yl)-2-hydroxypropyl 3-phenylpiperidine-1-carboxylate | 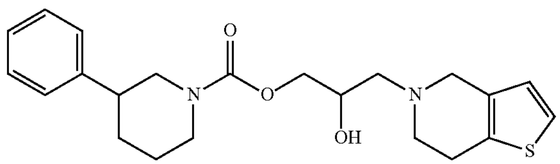 [SMILES: O=C(OCC(O)CN1CCc2sccc2C1)N1CCCC(c2ccccc2)C1] | | | | Method A, Retention Time = 3.096 min, MS: ES+ 401.2 (M + 1) | (400 MHz, DMSO-d$_6$) δ ppm: 7.394-7.350 (m, 2H), 7.271-7.207 (m, 4H), 6.778-6.752 (t, J = 5.2 Hz, 1H), 5.375 (br s, 1H), 4.879 (br s, 1H), 4.090-3.945 (m, 3H), 3.890 (br s, 1H), 3.491 (br s, 1H), 3.442 (br s, 1H), 2.793-2.673 (m, 5H), 2.548-2.471 (m, 2H), 2.340-2.311 (m, 1H), 1.839-1.758 (m, 1H), 1.574-1.546 (m, 2H), 1.434-1.392 (m, 1H), 1.299-1.242 (m, 1H) |
| 4AD | 3-(4,7-dihydrothieno[2,3-c]pyridin-6(5H)-yl)-2-hydroxypropyl 3-phenylpiperidine-1-carboxylate | 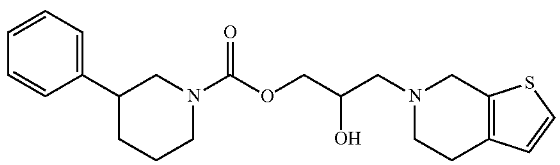 [SMILES: O=C(OCC(O)CN1CCc2ccsc2C1)N1CCCC(c2ccccc2)C1] | | | | Method A, Retention Time = 1.983 min, MS: ES+ 401.2 (M + 1) | (400 MHz, DMSO-d$_6$) δ ppm: 7.394-7.351 (m, 2H), 7.289-7.207 (m, 4H), 6.818-6.800 (dd, J = 2.4, 4.8 Hz, 1H), 5.375 (br s, 1H), 4.885 (br s, 1H), 4.058-3.885 (m, 4H), 3.631-3.583 (m, 2H), 2.770-2.603 (m, 5H), 2.563-2.458 (m, 2H), 2.309 (br s, 1H), 1.816-1.783 (m, 1H), 1.574-1.546 (m, 2H), 1.435-1.392 (m, 1H), 1.277-1.242 (m, 1H) |

| Example | Name | Structure | Reagent A | Reagent B | Reagent C | LC/MS | NMR |
|---|---|---|---|---|---|---|---|
| 4AE | 3-(6,7-dihydrothieno[3,2-c]pyridin-5(4H)-yl)-2-hydroxypropyl 3-phenylpyrrolidine-1-carboxylate | 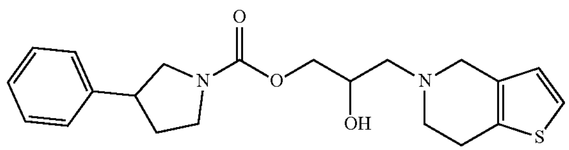 [SMILES: O=C(OCC(O)CN1CCc2sccc2C1)N1CCC(c2ccccc2)C1] | | | | Method A, Retention Time = 1.784 min, MS: ES+ 387.0 (M + 1) | (400 MHz, DMSO-d₆) δ ppm: 7.351-7.223 (m, 6H), 6.798-6.766 (dd, J = 2.8, 7.6 Hz, 1H), 4.873-4.848 (m, 1H), 4.093-4.038 (m, 1H), 3.910-3.901 (m, 2H), 3.826-3.721 (m, 1H), 3.557-3.488 (m, 3H), 3.419-3.170 (m, 3H), 2.821-2.744 (m, 4H), 2.547-2.474 (m, 2H), 2.232-2.203 (m, 1H), 1.949 (br s, 1H) |
| 4AF | 3-(4,7-dihydrothieno[2,3-c]pyridin-6(5H)-yl)-2-hydroxypropyl 3-phenylpyrrolidine-1-carboxylate | 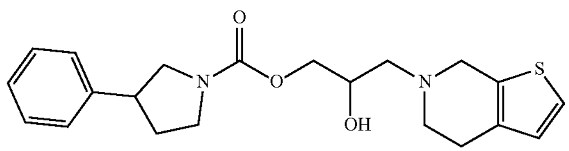 [SMILES: O=C(OCC(O)CN1CCc2ccsc2C1)N1CCC(c2ccccc2)C1] | | | | Method A, Retention Time = 1.792 min, MS: ES+ 387.1 (M + 1) | (400 MHz, DMSO-d₆) δ ppm: 7.352-7.224 (m, 6H), 6.829-6.804 (m, 1H), 4.878 (br s, 1H), 4.078-4.048 (m, 1H), 3.928-3.901 (m, 2H), 3.826-3.486 (m, 5H), 3.447-3.244 (m, 3H), 2.752-2.700 (m, 2H), 2.632-2.557 (m, 3H), 2.229-2.185 (m, 1H), 1.964-1.923 (m, 1H) |

| Example | Name | Structure | Reagent A | Reagent B | Reagent C | LC/MS | NMR |
|---|---|---|---|---|---|---|---|
| 4AG | 3-(3,4-dihydroisoquinolin-2(1H)-yl)-2-hydroxypropyl 3,4-dihydroquinoline-1(2H)-carboxylate | 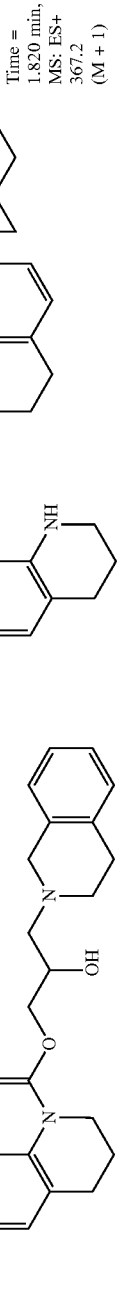 | | | | Method A, Retention Time = 1.820 min, MS: ES+ 367.2 (M + 1) | (400 MHz, DMSO-d6) δ ppm: 7.677-7.656 (d, J = 8.4 Hz, 1H), 7.143-7.066 (m, 5H), 7.038-6.978 (m, 2H), 4.968-4.956 (d, J = 4.8 Hz, 1H), 4.214-4.180 (m, 1H), 4.042-3.976 (m, 2H), 3.719-3.689 (t, J = 6.0 Hz, 2H), 3.650-3.562 (m, 2H), 2.808-2.762 (m, 2H), 2.739-2.670 (m, 4H), 2.571-2.468 (m, 2H), 1.875-1.812 (quin, J = 6.4 Hz, 2H) |
| 4AH | 3-(3,4-dihydroisoquinolin-2(1H)-yl)-2-hydroxypropyl 3-phenylpiperidine-1-carboxylate | 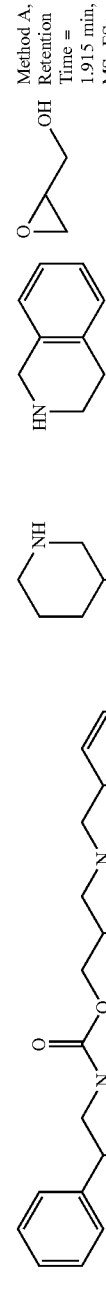 | | | | Method A, Retention Time = 1.915 min, MS: ES+ 295.2 (M + 1) | (400 MHz, DMSO-d6) δ ppm: 7.346-7.217 (m, 5H), 7.108 (br s, 3H), 7.038 (br s, 1H), 4.915-4.887 (m, 1H), 4.087-4.063 (m, 3H), 3.938-3.915 (m, 2H), 3.637 (br s, 2H), 2.813 (br s, 6H), 2.530-2.517 (m, 2H), 1.905-1.875 (m, 1H), 1.706-1.617 (m, 3H), 1.517-1.457 (m, 1H) |

Example 5

Chiral HPLC was used to isolate single distereoisomers (Examples 5A to 5H) of some of the diastereoisomeric mixtures, prepared in Examples 1-4 above.

| Example | Parent Diastereoisomer | Chiral HPLC Method | Name | Structure | LC/MS | NMR |
|---|---|---|---|---|---|---|
| 5A | 1AG | A | (S)-N-((S)-3-(3,4-dihydroisoquinolin-2(1H)-yl)-2-hydroxypropyl)-3-phenylpiperidine-1-carboxamide or (R)-N-((S)-3-(3,4-dihydroisoquinolin-2(1H)-yl)-2-hydroxypropyl)-3-phenylpiperidine-1-carboxamide | | Method A, 2.905 min, MS: ES+ 394.3 (M + 1) | (400 MHz, DMSO-$d_6$) δ ppm: 7.370-7.332 (m, 2H), 7.240-7.096 (m, 7H), 6.760 (br s, 1H), 5.323 (br s, 1H), 4.374-4.343 (m, 1H), 3.912-3.838 (m, 3H), 3.232-3.178 (m, 3H), 3.103-3.038 (m, 1H), 2.885 (br s, 3H), 2.682-2.558 (m, 4H), 2.335-2.232 (m, 1H), 1.943-1.874 (m, 1H), 1.741-1.673 (m, 1H), 1.534-1.289 (m, 2H). |
| 5B | 1AG | A | (S)-N-((S)-3-(3,4-dihydroisoquinolin-2(1H)-yl)-2-hydroxypropyl)-3-phenylpiperidine-1-carboxamide or (R)-N-((S)-3-(3,4-dihydroisoquinolin-2(1H)-yl)-2-hydroxypropyl)-3-phenylpiperidine-1-carboxamide | | Method B, 4.781 min, MS: ES+ 394.1 (M + 1) | (400 MHz, DMSO-$d_6$) δ ppm: 7.364-7.327 (m, 2H), 7.237-7.039 (m, 7H), 6.679 (br s, 1H), 5.306 (br s, 1H), 4.832 (br s, 1H), 3.844-3.810 (m, 2H), 3.589 (br s, 2H), 3.168-3.119 (m, 2H), 2.783 (br s, 2H), 2.682-2.612 (m, 3H), 3.562-2.407 (m, 3H), 2.255-2.226 (m, 1H), 1.8011.620 (m, 1H), 1.751-1.668 (m, 1H), 1.5241.209 (m, 2H). |
| 5c | 1BJ | A | (S)-N-((S)-3-(3,4-dihydroisoquinolin-2(1H)-yl)-2-hydroxypropyl)-2-phenylthiomorpholine-4-carboxamide or (R)-N-((S)-3-(3,4-dihydroisoquinolin-2(1H)-yl)-2-hydroxypropyl)-2-phenylthiomorpholine-4-carboxamide | | Method B, Retention Time = 1.766 min, MS: ES+ 412.3 (M + 1); | (400 MHz, DMSO-$d_6$) δ ppm: 7.368-7.324 (m, 4H), 7.315-7.303 (m, 1H), 7.294-7.206 (m, 4H), 6.889 (br s, 1H), 5.792 (br s, 1H), 4.502 (br s, 1H), 4.352-4.277 (m, 3H), 4.050 (br s, 1H), 3.881-3.854 (m, 1H), 3.705 (br s, 1H), 3.240-3.133 (m, 5H), 3.041- 2.981 (m, 2H), 2.836-2.767 (m, 1H), 2.596-2.563 (m, 2H) |
| 5D | 1BJ | A | (S)-N-((S)-3-(3,4-dihydroisoquinolin-2(1H)-yl)-2-hydroxypropyl)-2-phenylthiomorpholine-4-carboxamide or (R)-N-((S)-3-(3,4-dihydroisoquinolin-2(1H)-yl)-2-hydroxypropyl)-2-phenylthiomorpholine-4-carboxamide | | Method B, 1.775 min, MS: ES+ 412.3 (M + 1) | (400 MHz, DMSO-$d_6$) δ ppm: 7.370-7.294 (m, 5H), 7.225-7.150 (m, 4H), 6.854 (br s, 1H), 5.569 (br s, 1H), 4.347-4.204 (m, 4H), 3.998 (br s, 1H), 3.909-3.876 (dd, J = 2.4, 10.8 Hz, 1H), 3.231-3.169 (m, 2H), 3.148-3.122 (m, 3H), 3.024-2.965 (m, 6H), 2.807-2.738 (m, 1H), 2.568-2.534 (m, 2H) |

| Example | Parent Diastereo-isomer | Chiral HPLC Method | Name | Structure | LC/MS | NMR |
|---|---|---|---|---|---|---|
| 5E | 1BQ | B | (S)-N-((S)-3-(3,4-dihydroisoquinolin-2(1H)-yl)-2-hydroxypropyl)-3-(pyridin-2-yl)piperidine-1-carboxamide or (R)-N-((S)-3-(3,4-dihydroisoquinolin-2(1H)-yl)-2-hydroxypropyl)-3-(pyridin-2-yl)piperidine-1-carboxamide | | Method B, 1.691 min, MS: ES+ 395.0 (M + 1) | (400 MHz, DMSO-d$_6$) δ ppm: 8.507-8.488 (m, 1H), 7.743-7.700 (m, 1H), 7.296-7.277 (d, J = 7.6 Hz, 1H), 7.244-7.210 (m, 1H), 7.102-7.007 (m, 4H), 6.641-6.615 (m, 1H), 4.853 (br s, 1H), 4.086-4.053 (m, 1H), 3.943-3.911 (m, 1H), 3.784-3.772 (m, 1H), 3.613-3.581 (m, 2H), 3.182-3.136 (m, 1H), 3.067-3.019 (m, 1H), 2.872-2.736 (m, 3H), 2.717-2.620 (m, 4H), 2.463-2.376 (m, 2H), 1.920-1.892 (m, 1H), 1.690-1.652 (m, 2H), 1.478-1.356 (m, 1H) |
| 5F | 1BQ | B | (S)-N-((S)-3-(3,4-dihydroisoquinolin-2(1H)-yl)-2-hydroxypropyl)-3-(pyridin-2-yl)piperidine-1-carboxamide or (R)-N-((S)-3-(3,4-dihydroisoquinolin-2(1H)-yl)-2-hydroxypropyl)-3-(pyridin-2-yl)piperidine-1-carboxamide | | Method B, 1.710 min, MS: ES+ 395.0 (M + 1) | (400 MHz, DMSO-d$_6$) δ ppm: 8.507-8.489 (m, 1H), 7.743-7.700 (m, 1H), 7.298-7.279 (d, J = 7.6 Hz, 1H), 7.243-7.210 (m, 1H), 7.101-7.058 (m, 3H), 7.027-7.014 (m, 1H), 6.624 (br s, 1H), 4.854-4.843 (d, J = 4.4 Hz, 1H), 4.091-4.059 (d, J = 12.8 Hz, 1H), 3.942-3.909 (d, J = 13.2 Hz, 1H), 3.779-3.753 (m, 1H), 3.639-3.544 (m, 2H), 3.206-3.160 (m, 1H), 3.043-2.996 (m, 1H), 2.888-2.773 (m, 3H), 2.754-2.605 (m, 4H), 2.468-2.370 (m, 2H), 1.922-1.894 (m, 1H), 1.693-1.582 (m, 2H), 1.429-1.397 (m, 1H) |
| 5G | 1BZ | C | (R)-N-((S)-3-(3,4-dihydroisoquinolin-2(1H)-yl)-2-hydroxypropyl)-3-(tetrahydro-2H-pyran-4-yl)piperidine-1-carboxamide compound or (S)-N-((S)-3-(3,4-dihydroisoquinolin-2(1H)-yl)-2-hydroxypropyl)-3-(tetrahydro-2H-pyran-4-yl)piperidine-1-carboxamide | | Method B, 2.112 min, MS: ES+ 402.2 (M + 1) | (400 MHz, DMSO-d$_6$) δ ppm: 7.123-7.061 (m, 3H), 7.029-7.011 (m, 1H), 6.562-6.536 (t, J = 5.2 Hz, 1H), 3.881-3.816 (m, 4H), 3.771-3.716 (m, 2H), 3.640-3.540 (m, 2H), 3.249-3.131 (m, 3H), 3.027-3.012 (m, 1H), 2.795-2.781 (m, 2H), 2.724-2.664 (m, 2H), 2.596-2.541 (m, 2H), 2.459-2.414 (m, 4H), 1.742-1.719 (m, 1H), 1.599-1.505 (m, 3H), 1.267-1.155 (m, 2H), 1.071-1.055 (m, 2H) |
| 5H | 1BZ | C | (R)-N-((S)-3-(3,4-dihydroisoquinolin-2(1H)-yl)-2-hydroxypropyl)-3-(tetrahydro-2H-pyran-4-yl)piperidine-1-carboxamide compound or (S)-N-((S)-3-(3,4-dihydroisoquinolin-2(1H)-yl)-2-hydroxypropyl)-3-(tetrahydro-2H-pyran-4-yl)piperidine-1-carboxamide | | Method B, 2.113 min, MS: ES+ 402.2 (M + 1) | (400 MHz, DMSO-d$_6$) δ ppm: 7.108-7.076 (m, 3H), 7.029-7.010 (m, 1H), 6.567-6.540 (t, J = 5.2 Hz, 1H), 3.876-3.816 (m, 4H), 3.767-3.722 (m, 2H), 3.639-3.537 (m, 2H), 3.247-3.116 (m, 3H), 3.041-3.009 (m, 1H), 2.795-2.782 (m, 2H), 2.722-2.659 (m, 2H), 2.600-2.522 (m, 2H), 2.462-2.362 (m, 2H), 1.739-1.714 (m, 1H), 1.587-1.500 (m, 3H), 1.224-1.153 (m, 4H), 1.090-1.040 (m, 2H). |

Example 6

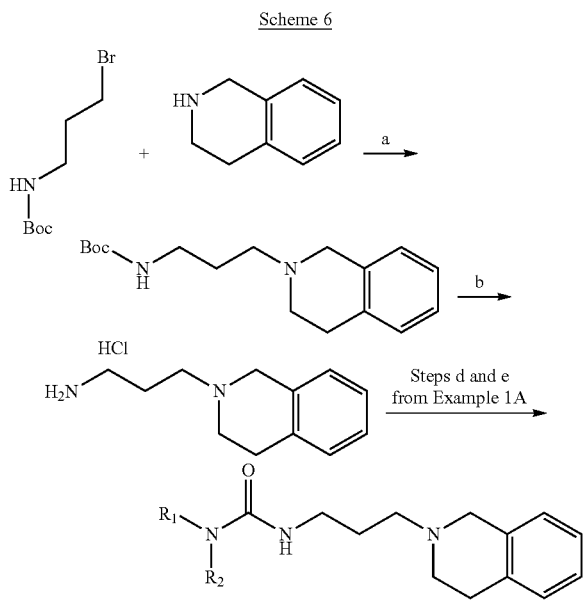

Reagent and conditions: a) NaH, THF, 6 h. b) HCl in dioxane, dioxane

Example 6A N-(3-(3,4-dihydroisoquinolin-2(1H)-yl)propyl)-3-phenyl pyrrolidine-1-carboxamide (prepared according to Scheme 6)

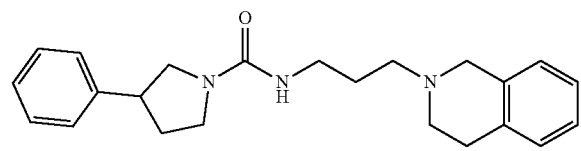 [SMILES: O=C(NCCCN1CCc2ccccc2C1)N1CCC(c2ccccc2)C1]

Step-a

To a stirred suspension of sodium hydride (60% dispersion in mineral oil) (CAS no. 7646-69-7, spectrochem) (0.33 g, 8.25 mmol) in THF (10 ml) was added tetrahydroisoquinoline (CAS no. 91-21-4; alfa aesar) (1 g, 7.50 mmol) at 0° C. temperature under nitrogen atmosphere and allowed to stirred for 10 min. To this, was added tert-butyl (3-bromopropyl)carbamate (CAS no. 83948-53-2, combi blocks) (1.96 g, 7.50 mmol) in THF (20 ml) was added drop wise manner at 0° C. temperature under nitrogen atmosphere. The resulting reaction mixture was allowed to stir at room temperature for 6 h. The reaction mixture was diluted with water (20 ml) and extracted with ethyl acetate (3×20 ml). The combined organic phase was dried over anhydrous $Na_2SO_4$, filtered and concentrated under reduce pressure yielding tert-butyl (3-(3,4-dihydroisoquinolin-2(1H)-yl)propyl)carbamate (0.297 g, 1.02 mmol); which was used directly in the next step without further purification. LCMS: Method A, 1.622 min; MS: ES+291.1 (M+1).

Step-b

To a stirred solution of tert-butyl(3-(3,4-dihydroisoquinolin-2(1H)-yl)propyl)carbamate (1.13 g, 3.89 mmol) in dioxane (5 ml) was added 20 ml of 4N HCl in dioxane at 0° C. under $N_2$ atmosphere. Then reaction mixture was stirred for 1 h at room temperature. The reaction mixture was concentrated under reduce pressure yielding 3-(3,4-dihydroisoquinolin-2(1H)-yl)propan-1-amine hydrochloride (0.9 g, 3.10 mmol); which was used directly in the next step without further purification. LCMS: Method A, 1.875 min; MS: ES+191.23 (M+1).

The title compound was synthesised, following Example-1A, steps d and e to afford N-(3-(3,4-dihydroisoquinolin-2(1H)-yl)propyl)-3-phenyl pyrrolidine-1-carboxamide, LCMS: Method A, Retention Time=2.122 min, MS: ES+364.3 (M+1); $^1H$ NMR: (400 MHz, DMSO-$d_6$) δ ppm: 7.353-7.299 (m, 2H), 7.250-7.209 (m, 3H), 7.107-7.034 (m, 4H), 6.272-6.245 (t, J=5.2 Hz, 1H), 3.662-3.619 (m, 1H), 3.546 (s, 2H), 3.435-3.391 (m, 1H), 3.322-3.190 (m, 2H), 3.126-3.080 (m, 3H), 2.189-2.791 (t, J=5.6 Hz, 2H), 2.667-2.638 (t, J=6.0 Hz, 2H), 2.487-2.469 (m, 2H), 2.185-2.128 (m, 1H), 1.930-1.854 (m, 1H), 1.719-1.651 (m, 2H).

Using the route depicted above, the following compounds were also prepared:

| Example | Name | Structure | $R_1R_2N$ | LC/MS | NMR |
|---|---|---|---|---|---|
| 6B | N-(3-(3,4-dihydroisoquinolin-2(1H)-yl)propyl)-3-phenyl-piperidine-1-carboxamide | 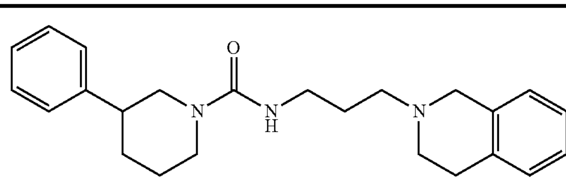 | | Method A, Retention Time = 2.289 min, MS: ES+ 378.3 (M + 1) | (400 MHz, DMSO-$d_6$) δ ppm: 7.362-7.324 (t, J = 7.6 Hz, 2H), 7.231-7.196 (t, J = 7.2 Hz, 1H), 7.140-7.032 (m, 6H), 6.746-6.721 (t, J = 5.2 Hz, 1H), 5.277 (br s, 1H), 3.821-3.789 (m, 1 H), 3.563-3.485 (m, 2H), 3.166-3.118 (m, 2H), 2.781-2.722 (m, 2H), 2.731-2.569 (m, 3H), 2.484-2.450 (m, 2H), 2.228-2.195 (m, 1H), 1.718-1.650 (quin, J = 6.8 Hz, 2H), 1.513-1.482 (m, 1H), 1.416-1.240 (m, 4H) |

Example 7 3-(3,4-dihydroisoquinolin-2(1H)-yl)propyl 3-phenylpyrrolidine-1-carboxylate

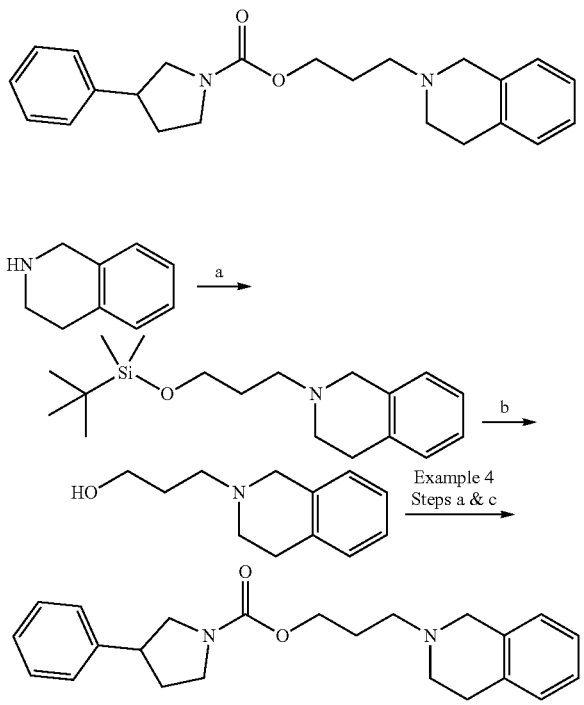

Reagents and conditions: a) (3-bromopropoxy)(tert-butyl)dimethylsilane, KI, acetonitrile b) HCl in dioxane, dioxane Step-a To a stirred solution of tetrahydroisoquinoline (CAS no. 91-21-4; alfa aesar) (0.26 g, 1.954 mmol), in acetonitrile (5 ml) was added (3-bromopropoxy)(tert-butyl)dimethylsilane (CAS no. 29681-57-0; combi blocks) (0.5 g, 1.95 mmol), potassium iodide (CAS no. 7681-11-0; merck chemicals) (0.64 g, 3.904 mmol) at room temperature and the resulting reaction mixture was heated to reflux temperature for 5 h. The reaction mixture was cooled to ambient temperature. The reaction was poured in cold water (25 ml) and extracted using ethyl acetate (3×20 ml). The combined organic phase was brine washed; dried over anhydrous $Na_2SO_4$ and concentrated under reduce pressure. The crude material thus isolated was purified using flash chromatography (25% ethyl acetate in hexane) to afford 2-(3-((tert-butyldimethylsilyl) oxy)propyl)-1,2,3,4-tetrahydroisoquinoline (0.49 g, 1.605 mmol). LCMS: Method A; 2.133 min. MS: ES+306.2 (M+1).

Step-b

To a stirred solution of 2-(3-((tert-butyldimethylsilyl)oxy) propyl)-1,2,3,4-tetrahydroisoquinoline (0.49 g, 1.605 mmol) in dioxane (5 ml) was added 4N HCl in dioxane (10 ml) under nitrogen atmosphere at 0° C. temperature. The resulting reaction mixture was stirred for 1 h at room temperature. The reaction mixture was concentrated under reduce pressure yielding 3-(3,4-dihydroisoquinolin-2(1H)-yl)propan-1-ol hydrochloride (0.26 g, 1.142 mmol) which was used without further purification. LCMS: Method B; 3.885 min. MS: ES+192.1 (M+1).

The synthesis of 3-(3,4-dihydroisoquinolin-2(1H)-yl)propyl 3-phenylpyrrolidine-1-carboxylate was completed by following Example 4A, steps a and c. 3-(3,4-dihydroisoquinolin-2(1H)-yl)propyl 3-phenylpyrrolidine-1-carboxylate, LCMS: Method A, Retention Time=2.230 min, MS: ES+365.3 (M+1); $^1$H NMR (400 MHz, DMSO-$d_6$) δ ppm: 7.347-7.220 (m, 5H), 7.110-7.042 (m, 4H), 4.096-4.054 (dd, J=6.0, 10.8 Hz, 2H), 3.784-3.717 (m, 1H), 3.580-3.488 (m, 3H), 3.330-3.286 (m, 2H), 3.245-3.173 (m, 1H), 2.805-2.776 (m, 2H), 2.664-2.616 (m, 2H), 2.550-2.532 (m, 2H), 2.218-2.191 (m. 1H), 1.973-1.896 (m, 1H), 1.864-1.813 (m, 2H).

Biological Activity of Compounds

A PRMT5 chemiluminescent assay was used to measure the IC50 activity of PRMT5 of the compounds of Examples 1A to 7 above. Biotinylated histone peptides were synthesized and attached to 384-well plates. Compound serial dilutions were performed and added to the assay plate. Histone H4 monomethyl $R_3$ antibody was obtained from Abcam. A master mix for each well was prepared and human PRMT5/MEP50 (expressed in HEK293 cells) diluted in assay buffer to a concentration of 5 ng/µL. The reaction was incubated and slowly rotated for 60 minutes at the point of PRMT5/MEP50 addition. The supernatant from the wells was removed and blocking buffer was added to each well and rotated for 10 minutes. The primary antibody was diluted and added to every well for 60 minutes, before it was removed and the wells washed. The horse raddish peroxidase (HRP)-coupled secondary antibody was diluted and added to each well with an incubation time of 30 minutes. The HRP chemiluminescent substrate was added to every well. The plate was read on a Flourstar Omega BMG Labtech instrument (Ortenberg, Germany) and the analysis of IC50 was performed using the Flourstar Omega BMG Labtech software.

Results

| Example | IC50 (nM) |
|---|---|
| 1A | 290 |
| 1B | 9910 |
| 1C | 1235 |
| 1D | 1872 |
| 1E | 8 |
| 1F | 457 |
| 1G | 568 |
| 1H | 267 |
| 1I | 208 |
| 1J | 320 |
| 1K | 412 |
| 1L | 1645 |
| 1M | 6866 |
| 1N | 2385 |
| 1O | 51 |
| 1P | 221 |
| 1Q | 276 |
| 1R | 11 |
| 1S | 95 |
| 1T | 40 |
| 1U | 896 |
| 1V | 8544 |
| 1W | 7388 |
| 1X | 376 |
| 1Y | 236 |
| 1Z | 639 |
| 1AA | 342 |
| 1AB |  |
| 1AC | 384 |
| 1AD | 652 |
| 1AE | 72 |
| 1Af | 749 |
| 1AG | 185 |
| 1AI | 3224 |
| 1AJ | 80 |
| 1AK | 5983 |

-continued

| Example | IC50 (nM) |
| --- | --- |
| 1AL | 30 |
| 1AM | 1501 |
| 1AN | 14 |
| 1AO | 9 |
| 1AP | 484 |
| 1AQ | 77 |
| 1AR | 658 |
| 1AS | 112 |
| 1AT | 691 |
| 1AU | 31211 |
| 1AV | 3142 |
| 1AW | 7022 |
| 1AX | 588 |
| 1AY | 311 |
| 1AZ | 159 |
| 1BA | 97 |
| 1BB | 51849 |
| 1BC | 33124 |
| 1BD | 58160 |
| 1BE | 3082 |
| 1BF | 5600 |
| 1BG | 3940 |
| 1BH | 167 |
| 1BI | 399 |
| 1BJ | 108 |
| 1BK | 396 |
| 1BL | 4436 |
| 1BM | 1276 |
| 1BN | 104 |
| 1BO | 1816 |
| 1BP | 7326 |
| 1BQ | 48 |
| 1BR | 490 |
| 1BS | 237 |
| 1BT | 127 |
| 1BU | 12 |
| 1BV | 57 |
| 1BW | 2862 |
| 1BX | 634 |
| 1BY | 2650 |
| 1BZ | 270 |
| 1CA | 58 |
| 1CB | 337 |
| 1CC | 1643 |
| 1CD | 12293 |
| 1CE | 3101 |
| 1CF | 376 |
| 1CG | 422 |
| 1CH | 1918 |
| 1CI | 27 |
| 1CJ | 58 |
| 1CK | 329 |
| 1CL | 436 |
| 1CM | 125 |
| 1CN | 1101 |
| 1CO | 17 |
| 2A | 87 |
| 2B | 8500 |
| 3A | 192 |
| 3B | 613 |
| 3C | 9561 |
| 3D | 15 |
| 4A | 477 |
| 4B | 75 |
| 4C | 25 |
| 4D | 173 |
| 4E | 19 |
| 4F | 49 |
| 4G | 8 |
| 4H | 539 |
| 4I | 8830 |
| 4J | 246 |
| 4K | 20 |
| 4L | 13 |
| 4M | 2222 |
| 4N | 212517 |
| 4O | 2714 |
| 4P | 225 |
| 4Q | 160 |
| 4R | 81 |
| 4S | 5030 |
| 4T | 1855 |
| 4U | 2983 |
| 4V | 38936 |
| 4W | 10754 |
| 4X | 809 |
| 4Y | 1457 |
| 4Z | 448 |
| 4AA | 46 |
| 4AB | 1011 |
| 4AC | 374 |
| 4AD | 223 |
| 4AE | 41 |
| 4AF | 21 |
| 4AG | 360 |
| 4AH | 75 |
| 5A | 26 |
| 5B | 599 |
| 5C | 17 |
| 5D | 101 |
| 5E | 81 |
| 5F | 97 |
| 5G | 394 |
| 5H | 511 |
| 6A | 939 |
| 6B | 1704 |
| 7 | 342 |

REFERENCES

Chung, J. et al. Protein arginine methyltransferase 5 (PRMT5) inhibition induces lymphoma cell death through reactivation of the retinoblastoma tumor suppressor pathway and polycomb repressor complex 2 (PRC2) silencing. *J. Biol. Chem.* 288, 35534-35547 (2013).

Wei, L. et al. Protein arginine methyltransferase 5 is a potential oncoprotein that upregulates G1 cyclins/cyclin-dependent kinases and the phosphoinositide 3-kinase/AKT signaling cascade. *Cancer Sci.* 103, 1640-1650 (2012).

Powers, M. A. et al. Protein arginine methyltransferase 5 accelerates tumor growth by arginine methylation of the tumor suppressor programmed cell death 4. *CancerRes.* 71, 5579-5587 (2011).

Cho, E. C et al. Arginine methylation controls growth regulation by E2F1. *EMBO J.* 31, 1785-1797 (2012).

Pal, S. et al. Low levels of miR-92b/96 induce PRMT5 translation and H3R8/H4R3 methylation in mantle cell lymphoma. *EMBO J.* 26, 3558-3569 (2007).

Elayne, C. P et al. Selective inhibitor of PRMT5 with in vivo and in vitro potency in MCL models. *Nature chemical biology.* 11, 432-437 (2015).

The PRMT5 arginine methyltransferase: many roles in development, cancer and beyond. Stopa N, Krebs J E, Shechter D. Cell Mol Life Sci. 2015 June; 72(11):2041-59. doi: 10.1007/s00018-015-1847-9. Review.

A TGFβ-PRMT5-MEP50 axis regulates cancer cell invasion through histone H3 and H4 arginine methylation coupled transcriptional activation and repression H Chen[1], B Lorton[1], V Gupta[2] and D Shechter[1] *Oncogene* (2017) 36, 373-386; doi:10.1038/onc.2016.205; published online 6 Jun. 2016

MTAP deletion confers enhanced dependency on the PRMT5 arginine methyltransferase in cancer cells Gregory V. Kryukov[1] et al,[2],*, Science 11 Feb. 2016: DOI: 10.1126/science.aad5214

Targeting methyltransferase PRMT5 eliminates leukemia stem cells in chronic myelogenous leukemia Yanli Jin Ruibao Ren, Jingxuan Pan J Clin Invest. 2016; 126(10):3961-3980. doi:10.1172/JC185239.

Y K Banasavadi-Siddegowda, L Russell, E Frair, V A Karkhanis, T Relation, J Y Yoo, J Zhang, S Sif, J Imitola, R Baiocchi, B Kaur. PRMT5-PTEN molecular pathway regulates senescence and self-renewal of primary glioblastoma neurosphere cells. ONCOGENE, 2016; DOI: 10.1038/onc2016.199

Protein arginine methyltransferases and cancer Y Yang, MT Bedford Nature Reviews. Cancer, 13, 37-50, 2013

High Expression of PRMT5 and Cyclin D1 is Associated With Poor Outcome in Oropharyngeal Squamous Cell Carcinoma (OPSCC) Patients and Is Inversely Associated With p16 Status; Kumar, B. et al. International Journal of Radiation Oncology 88, 2, 513-514

Karkhanis V, Hu Y J, Baiocchi R A, et al. Versatility of PRMT5-induced methylation in growth control and development[J]. Trends Biochem Sci, 2011, 36(12):633-641

Zhang H T, Zhang D, Zha Z G, et al. Transcriptional activation of PRMT5 by NF-Y is required for cell growth and negatively regulated by the PKC/c-Fos signaling in prostate cancer cells[J]. Biochim Biophys Acta, 2014, 1839(11):1330-1340

Powers M A, Fay Factor R E, et al. Protein arginine methyltransferase 5 accelerates tumor growth by arginine methylation of the tumor suppressor programmed cell death 4. Cancer Res, 2011, 71MM, (16):5579-5587.

Yan F, Alinari L, Lustberg M E, et al. Genetic validation of the protein arginine methyltransferase PRMT5 as a candidate therapeutic target in glioblastoma. Cancer Res, 2014, 74(6):1752-1765

Ibrahim R, Matsubara D, Osman W, et al. Expression of PRMT5 in lung adenocarcinoma and its significance in epithelial-mesenchymal transition. Hum Pathol, 2014, 45(7):1397-1405

Gu Z, Gao S, Zhang F, et al. Protein arginine methyltransferase 5 is essential for growth of lung cancer cells[J]. Biochem J, 2012, 446(2):235-241.

Yang F, Wang J, Ren H Y, et al. Proliferative role of TRAF4 in breast cancer by upregulating PRMT5 nuclear expression[J]. Tumour Biol, 2015, 36(8):5901-5911

Pak M G, Lee H W, Roh M S. High nuclear expression of protein arginine methyltransferase-5 is a potentially useful marker to estimate submucosal invasion in endoscopically resected early colorectal carcinoma. Pathol Int, 2015, 65(10):541-548.

Gu Z, Li Y, Lee P, et al. Protein arginine methyltransferase 5 functions in opposite ways in the cytoplasm and nucleus of prostate cancer cells. PLoS One, 2012, 7(8):e44033.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

The invention claimed is:

1. A compound of formula I, or a salt, solvate or hydrate thereof,

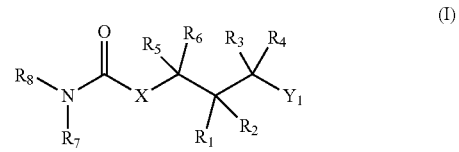

(I)

wherein, $R_1$, $R_3$, $R_4$, $R_5$ and $R_6$ are each hydrogen;

$R_2$ is OH;

X is O or $NR_9$, where $R_9$ is hydrogen or a $C_{1-3}$ alkyl;

$Y_1$ is

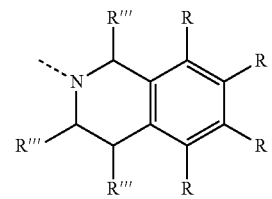

wherein each R and R''' is selected from H and $C_1$ to $C_3$ alkyl;

$R_7$ and $R_8$ are taken together with the intervening nitrogen atom to form a 3-12 membered heterocycloalkyl ring, wherein the 3-12 membered heterocycloalkyl ring is optionally substituted with one or more $R_{10}$; and/or optionally fused to one or more $C_{6-12}$ aryl, $C_{5-12}$ heteroaryl, $C_{3-8}$ cycloalkyl and 3-12 membered heterocycloalkyl rings, wherein each fused $C_{6-12}$ aryl, $C_{5-12}$ heteroaryl, $C_{3-8}$ cycloalkyl and 3-12 membered heterocycloalkyl ring is optionally substituted with one or more $R_{14}$;

$R_{10}$ is selected from a group of the formula $L_1$-$L_2$-$R_{11}$ or $L_2$-$L_1$-$R_{11}$, where $L_1$ is a linker of the formula —[$CR_{12}R_{13}$]$_n$—, where n is an integer of from 0 to 3 and $R_{12}$ and $R_{13}$ are in each instance each independently selected from H and $C_1$ to $C_2$ alkyl, wherein $R^{10}$ is not $C_{1-3}$alkyl;

where $L_2$ is absent or a linker that is selected from O, S, SO, $SO_2$, N(R'), C(O), C(O)O, [O(CH$_2$)r]d$_s$, [(CH$_2$)$_r$O]$_s$, OC(O), CH(OR'), C(O)N(R'), N(R')C(O), N(R')C(O)N(R'), $SO_2$N(R') or N(R')$SO_2$, where R' and R" are each independently selected from hydrogen and a $C_1$ to $C_2$ alkyl, and where r is 1 or 2 and s is 1 to 4;

$R_{11}$ is independently selected from hydrogen, CN, $NO_2$, hydroxyl, =O, halogen, $C_{1-6}$ haloalkyl, $C_{1-6}$ haloalkoxy, $C_{1-6}$ alkyl, O—$C_{1-6}$ alkyl, $C_{3-6}$ cycloalkyl, $C_{6-12}$ aryl, $C_{5-12}$ heteroaryl, 3-10 membered heterocycloalkyl, —C(=O)R$^d$, —C(=O)OR$^d$, —C(=O)NR$^e$R$^d$, —C(O)C(=O)R$^d$, —NR$^e$R$^d$, —NR$^e$C(=O)R$^d$, —NR$^e$C(=O)OR$^d$, —NR$^e$C(=O)NR$^e$R$^d$, —NR$^e$S(=O)$_2$R$^d$, —NR$^e$S(=O)$_2$NR$^e$R$^d$, —OR$^d$, —SR$^d$, —OC(=O)R$^d$, —OC(=O)NR$^e$R$^d$, —OC(=O)OR$^d$, —S(=O)$_2$R$^d$, —S(=O)R$^d$, —OS(=O)R$^d$, —OS(=O)$_2$R$^d$, —OS(=O)$_2$R$^d$, —S(=O)NR$^e$R$^d$, —OS(=O)$_2$NR$^e$R$^d$, and —S(=O)$_2$NR$^e$R$^d$, wherein, where R$_{11}$ is independently selected from C$_{3-6}$ cycloalkyl, C$_{6-12}$ aryl, C$_{5-12}$ heteroaryl and 3-10 membered heterocycloalkyl, each C$_{3-6}$ cycloalkyl, C$_{6-12}$ aryl, C$_{5-12}$ heteroaryl and 3-10 membered heterocycloalkyl is optionally substituted with one or more R$_{14}$;

each R$^a$ and R$^b$ is independently selected from hydrogen and C$_{1-6}$ alkyl;

each R$^d$ is independently selected from hydrogen, hydroxyl, halogen, CN, C$_{1-6}$ haloalkyl, 3-7 membered heterocycloalkyl, C$_{3-6}$ cycloalkyl, C$_{1-6}$ alkyl, O—C$_{1-6}$ alkyl and C$_{6-11}$ aryl, wherein said C$_{1-6}$ alkyl, C$_{6-11}$ aryl, 3-7 membered heterocycloalkyl and C$_{3-6}$ cycloalkyl are optionally substituted with one or more groups selected from hydroxyl, =O, halogen, CN, COR$^a$, NR$^a$R$^b$, C$_{1-6}$ haloalkyl, C$_{3-6}$ cycloalkyl, C$_{6-11}$ aryl, 3-7 membered heterocycloalkyl, C$_{1-6}$ alkyl and O—C$_{1-6}$ alkyl;

each R$^e$ is independently selected from hydrogen, hydroxyl, halogen, CN, C$_{1-6}$ haloalkyl, C$_{3-6}$ cycloalkyl, C$_{1-6}$ alkyl and O—C$_{1-6}$ alkyl; or R$^e$ and R$^d$, when attached to the same atom, together with the atom to which they are attached form a 3-7 membered heterocycloalkyl ring, optionally substituted with one or more substituent selected from hydroxyl, =O, halogen, CN, COR$^a$, NR$^a$R$^b$, C$_{1-6}$ haloalkyl, C$_{3-6}$ cycloalkyl, C$_{6-11}$ aryl, 3-7 membered heterocycloalkyl, C$_{1-6}$ alkyl and O—C$_{1-6}$ alkyl; and R$^{14}$ is independently selected from halo, CN, NO$_2$, hydroxyl, =O, halogen, C$_{1-6}$ haloalkyl, C$_{1-6}$ haloalkoxy, C$_{1-6}$ alkyl, O—C$_{1-6}$ alkyl, C$_{3-6}$ cycloalkyl, C$_{6-12}$ aryl, 5-6 membered heteroaryl, 3-7 membered heterocycloalkyl, C$_{1-6}$alkylC$_{6-12}$aryl, —C(=O)R$^d$, —C(=O)OR$^d$, —C(=O)NR$^e$R$^d$, —C(O)C(=O)R$^d$, —NR$^e$R$^d$, —NR$^e$C(=O)R$^d$, —NR$^e$C(=O)OR$^d$, —NR$^e$C(=O)NR$^e$R$^d$, —NR$^e$S(=O)$_2$R$^d$, —NR$^e$S(=O)$_2$NR$^e$R$^d$, —OR$^d$, —SR$^d$, —OC(=O)R$^d$, —OC(=O)NR$^e$R$^d$, —OC(=O)OR$^d$, —S(=O)$_2$R$^d$, —S(=O)R$^d$, —OS(=O)R$^d$, —OS(=O)$_2$R$^d$, —OS(=O)$_2$OR$^d$, —S(=O)NR$^e$R$^d$, —OS(=O)$_2$NR$^e$R$^d$, and —S(=O)$_2$NR$^e$R$^d$.

2. A compound according to claim 1, or a salt, solvate or hydrate thereof, wherein X is NH.

3. A compound according to claim 1, or a salt, solvate or hydrate thereof, wherein X is O.

4. A compound according to claim 1, or a salt, solvate or hydrate thereof, wherein the 3-12 membered heterocycloalkyl ring formed by R$_7$ and R$_8$ taken together with the intervening nitrogen atom is a 4-7 membered heterocycloalkyl ring.

5. A compound according to claim 4, or a salt, solvate or hydrate thereof, wherein the intervening nitrogen atom is the sole heteroatom in the 4-7 membered heterocycloalkyl ring.

6. A compound according to claim 4, or a salt, solvate or hydrate thereof, wherein 4-7 membered heterocycloalkyl ring comprises a second heteroatom selected from O, S and N.

7. A compound claim 1, or a salt, solvate or hydrate thereof, wherein the 3-12 membered heterocycloalkyl ring formed by R$_7$ and R$_8$ taken together with the intervening nitrogen atom is a 4-7 membered heterocycloalkyl ring is unsubstituted.

8. A compound according to claim 1, or a salt, solvate or hydrate thereof, wherein the 3-12 membered heterocycloalkyl ring formed by R$_7$ and R$_8$ taken together with the intervening nitrogen atom is a 4-7 membered heterocycloalkyl ring is substituted with one or more R$_{10}$.

9. A compound according to claim 8, wherein R$_{11}$ is independently selected from hydroxyl, C$_{1-6}$ alkyl, C$_{6-12}$ aryl, C$_{5-12}$ heteroaryl and —C(=O)R$^d$, wherein, where R$_{11}$ is selected from C$_{6-12}$ aryl and/or C$_{5-12}$ heteroaryl, the C$_{6-12}$ aryl and/or C$_{5-12}$ heteroaryl is optionally substituted with R$_{14}$.

10. A compound according to claim 1, or a salt, solvate or hydrate thereof, wherein L$_1$ is a linker of the formula —[CR$_{12}$R$_{13}$]$_n$—, where n is an integer of from 0 to 3, and R$_{12}$ and R$_{13}$ are in each instance each independently selected from H or C$_1$ to C$_2$ alkyl, and where L$_2$ is absent or a linker that is selected from O.

11. A compound according to claim 1, or a salt, solvate or hydrate thereof, wherein the 3-12 membered heterocycloalkyl ring formed by R$_7$ and R$_8$ taken together with the intervening nitrogen atom is fused to one or more C$_{6-12}$ aryl, C$_{5-12}$ heteroaryl, C$_{3-8}$ cycloalkyl and 3-12 membered heterocycloalkyl rings, wherein each fused C$_{6-12}$ aryl, C$_{5-12}$ heteroaryl, C$_{3-8}$ cycloalkyl and 3-12 membered heterocycloalkyl ring is optionally substituted with R$_{14}$.

12. A compound according to claim 11, or a salt, solvate or hydrate thereof, wherein R$_{14}$ is absent or selected from C$_{1-3}$ alkyl, halo or hydroxyl.

13. A compound according to claim 1, or a salt, solvate or hydrate thereof, wherein R$_7$ and R$_8$ are taken together with the intervening nitrogen atom to form a 4-7 membered heterocycloalkyl ring, wherein the 4 to 7 membered heterocycloalkyl ring is unsubstituted.

14. A compound according to claim 1, selected from:

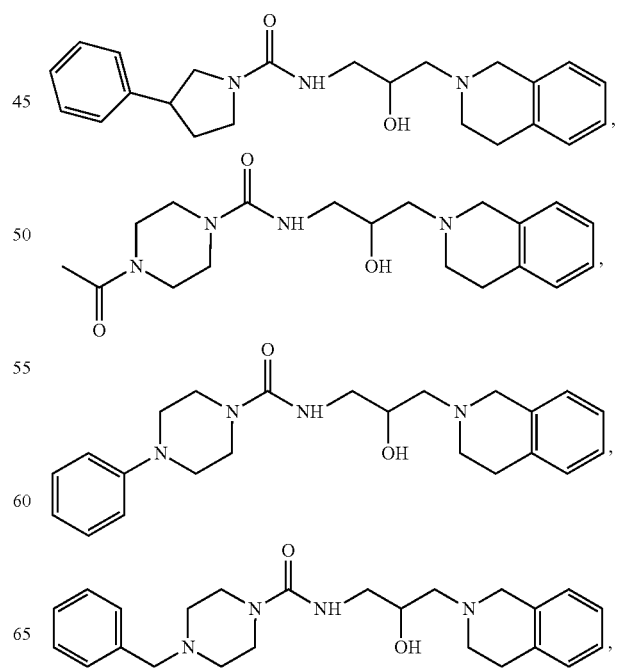

207
-continued
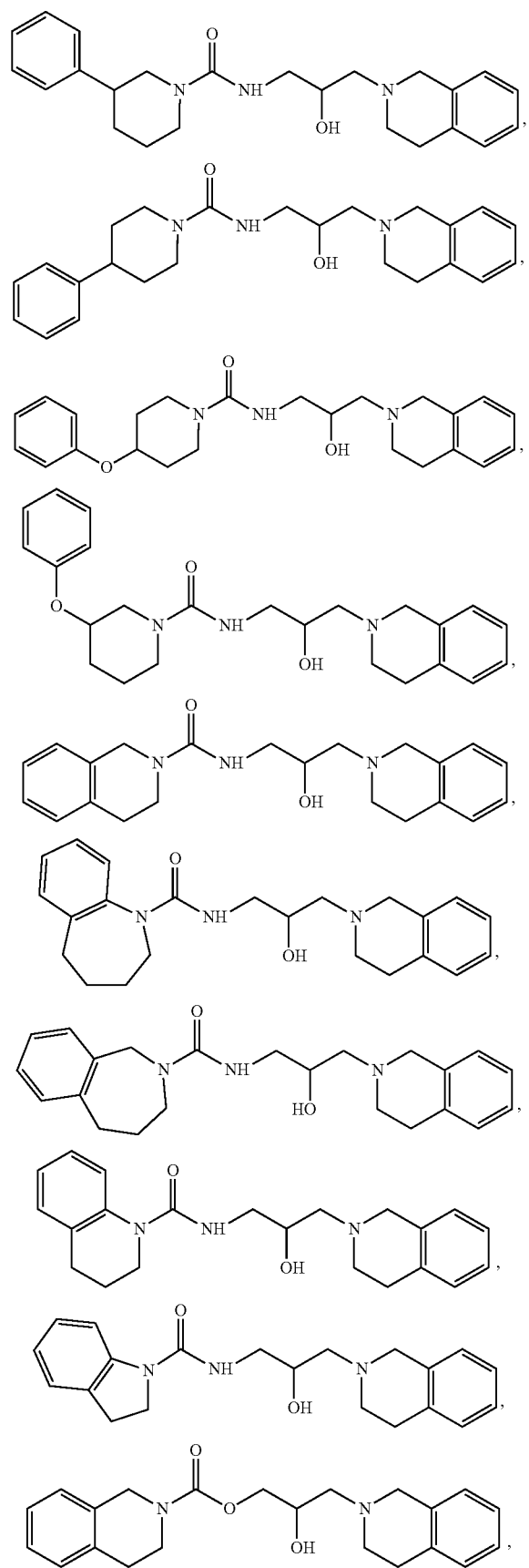
208
-continued
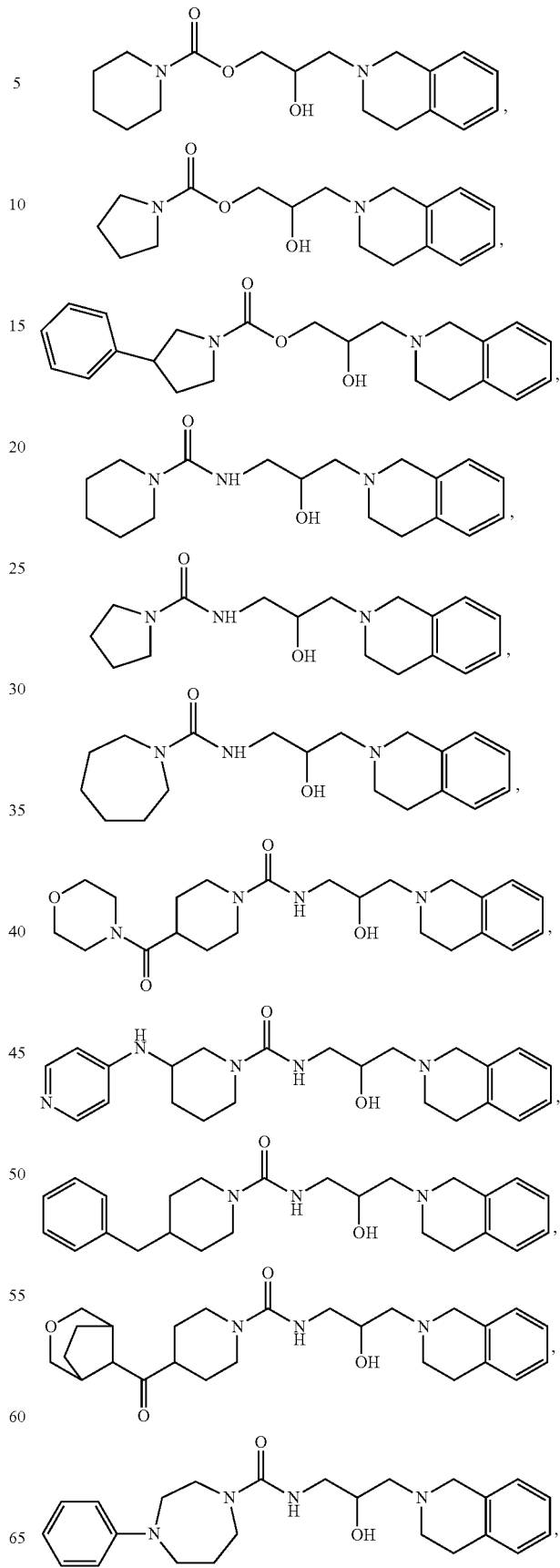

209
-continued
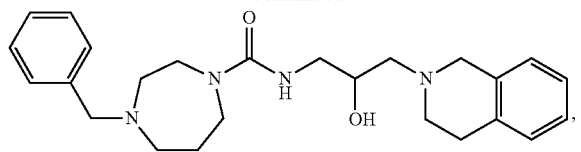
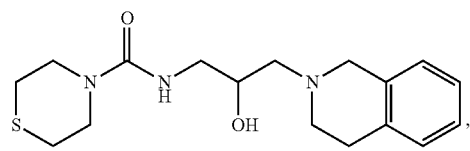
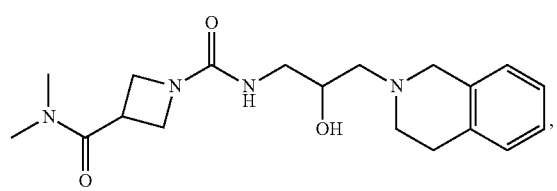
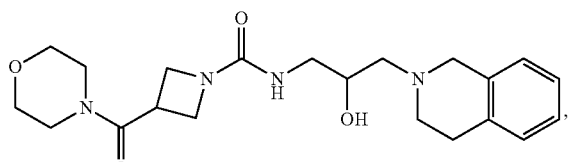
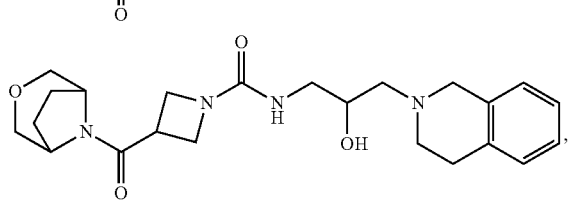
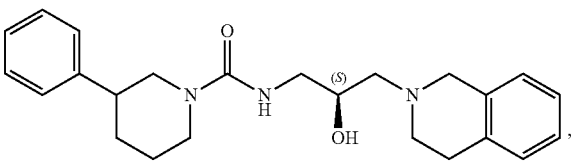
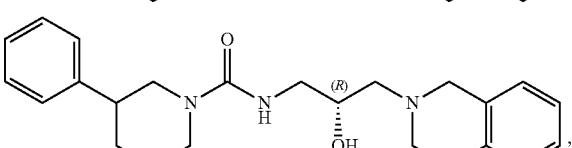
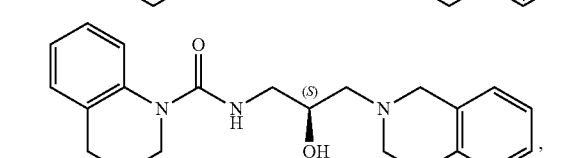
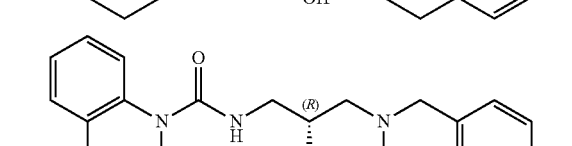
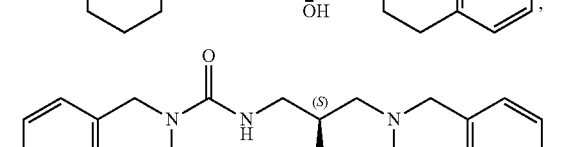
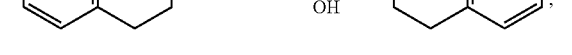
210
-continued
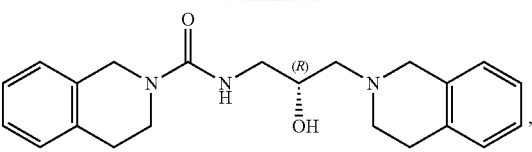
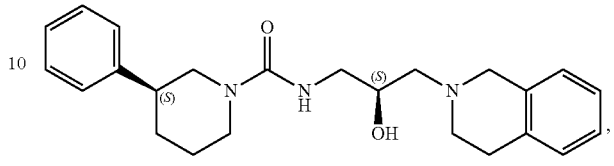
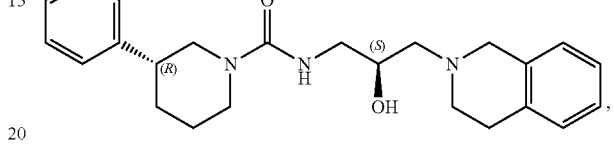
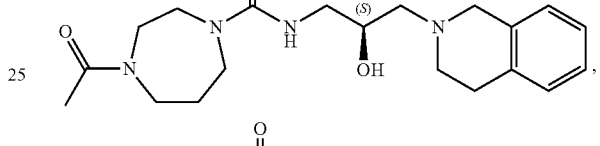
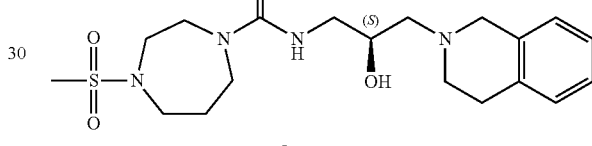
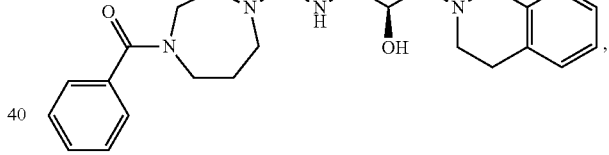
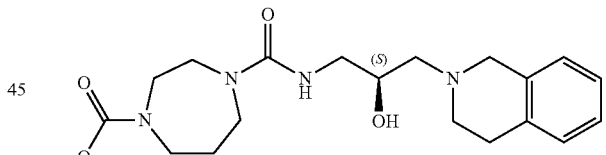
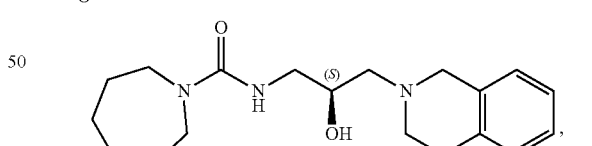
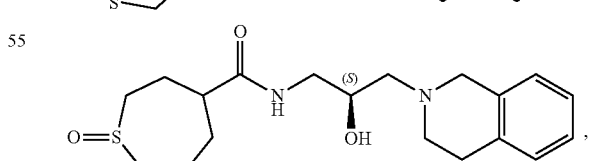
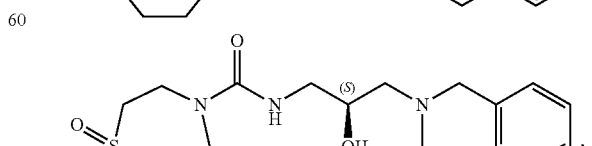

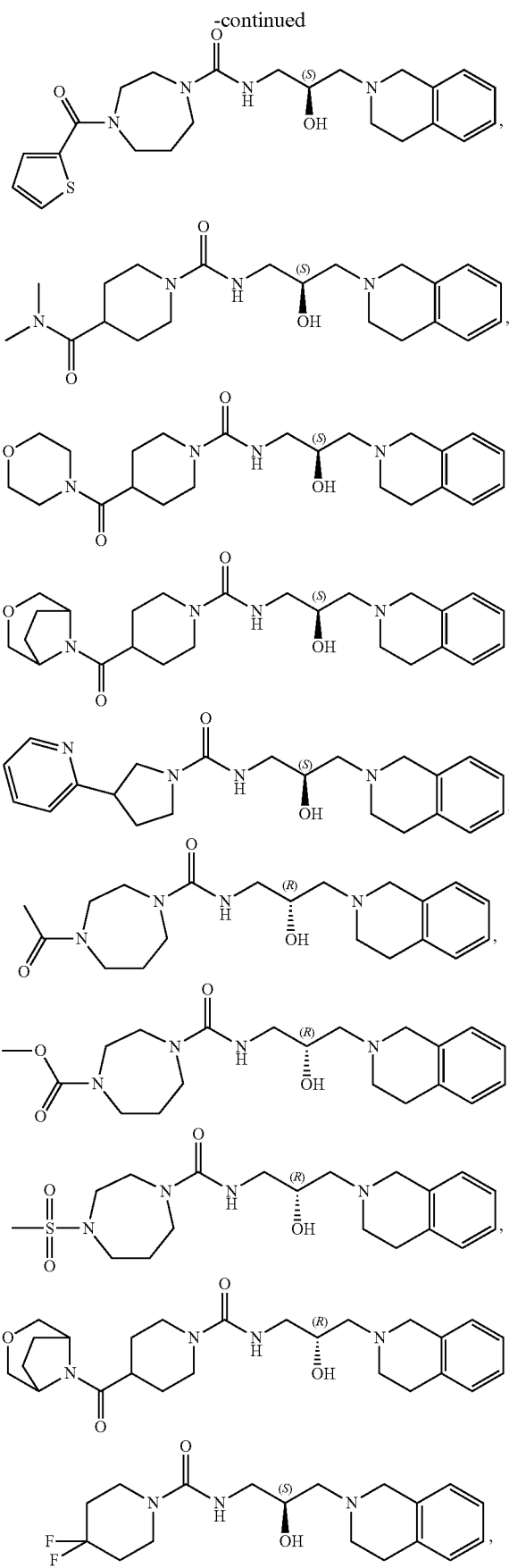
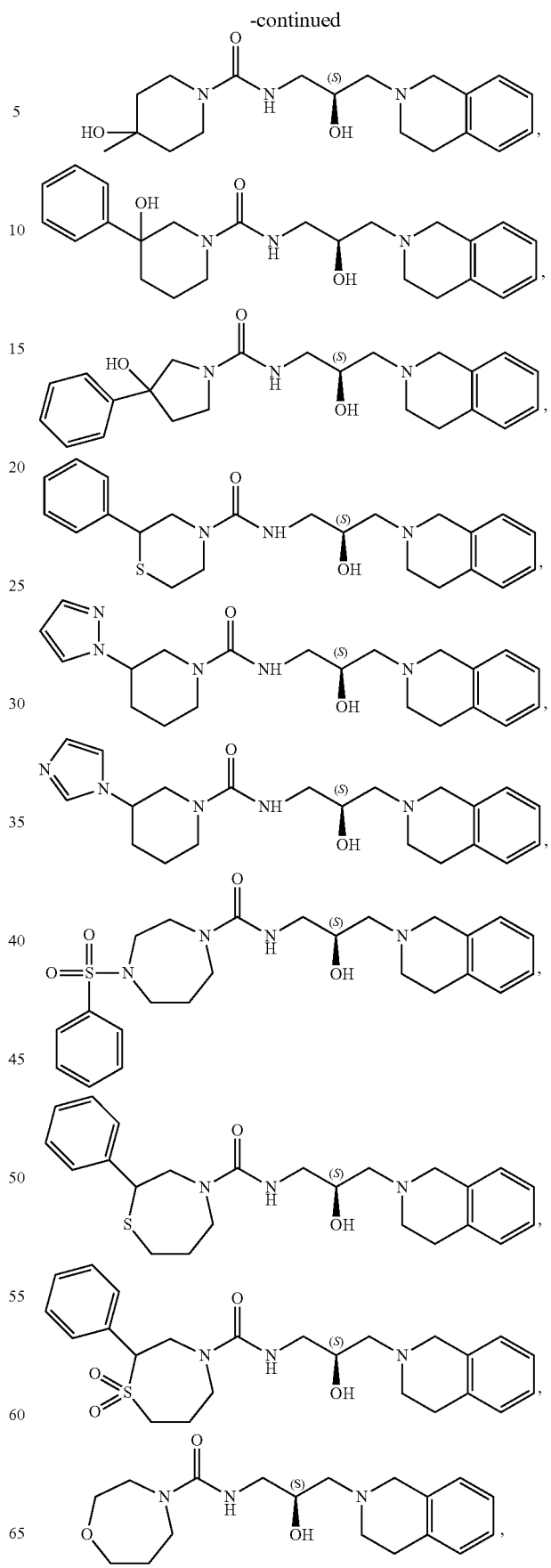

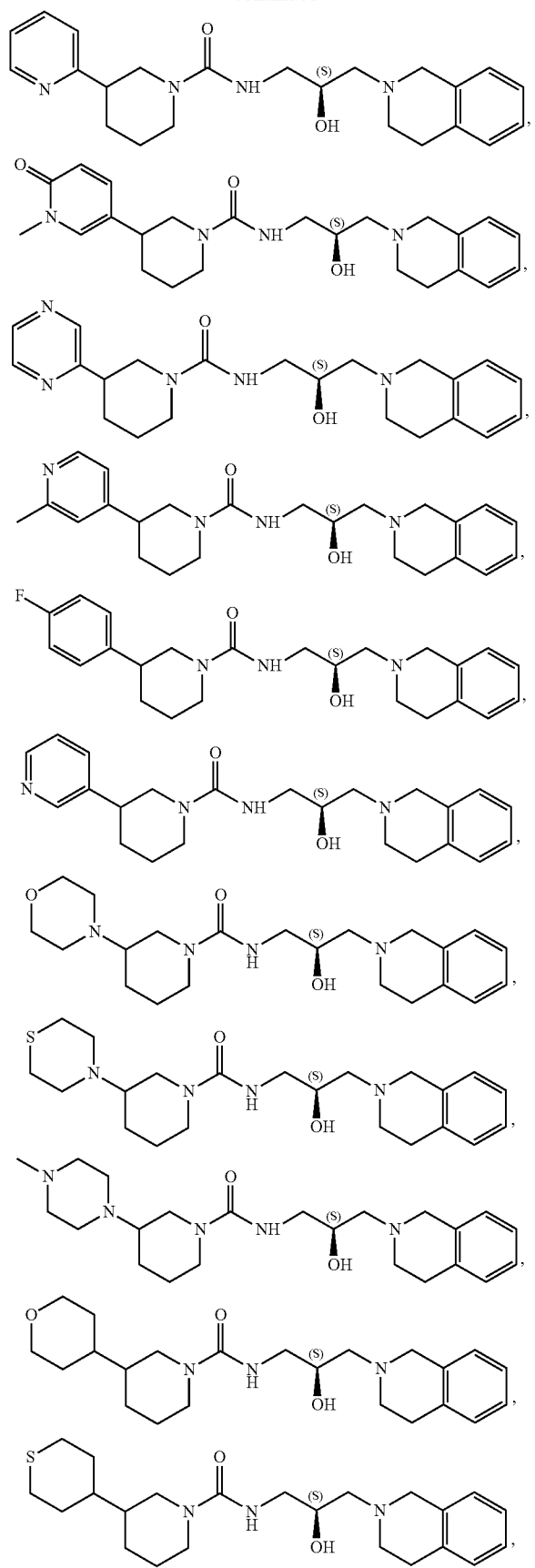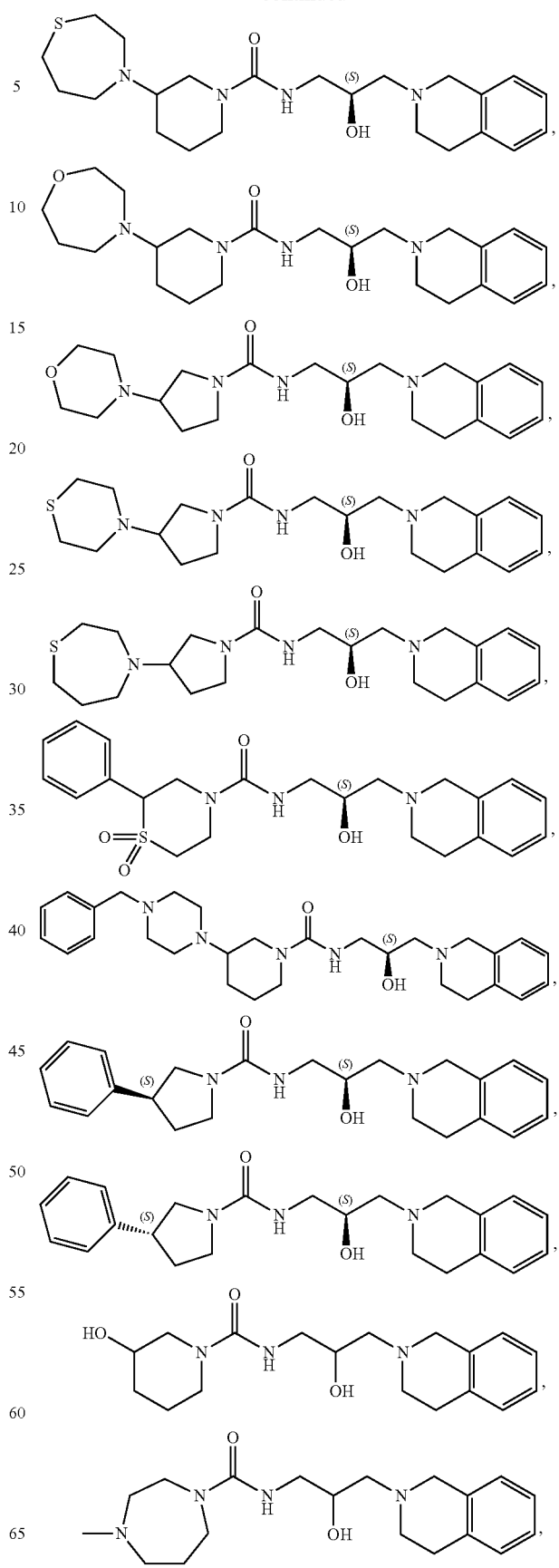

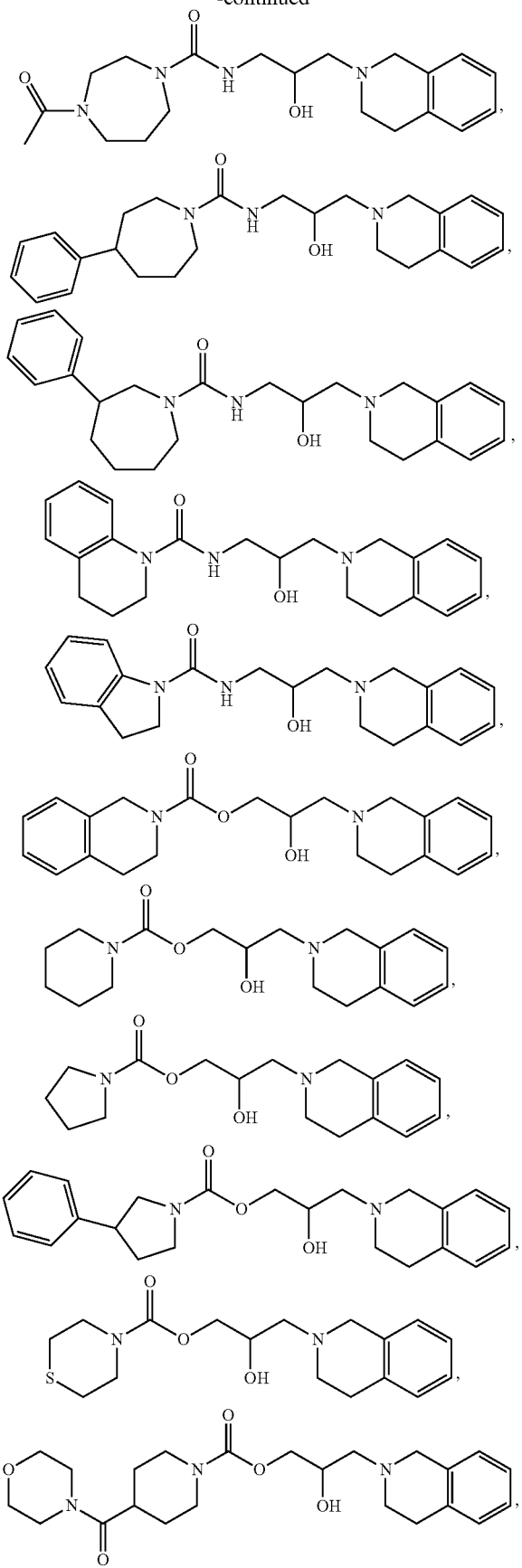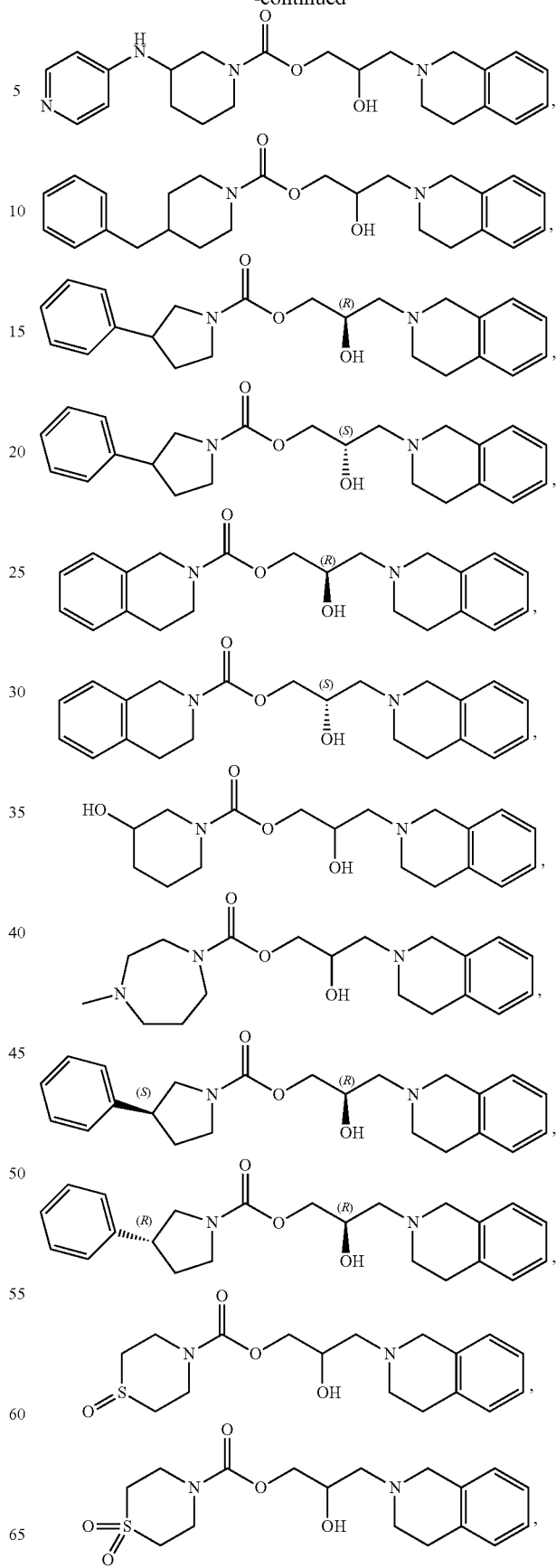

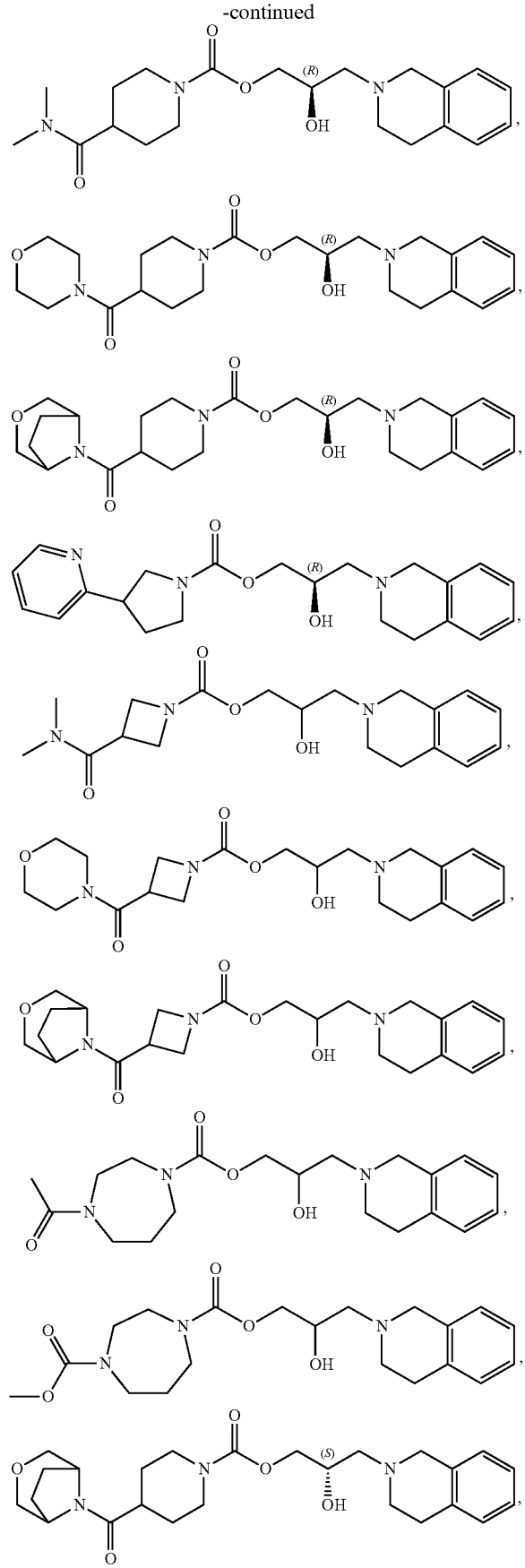
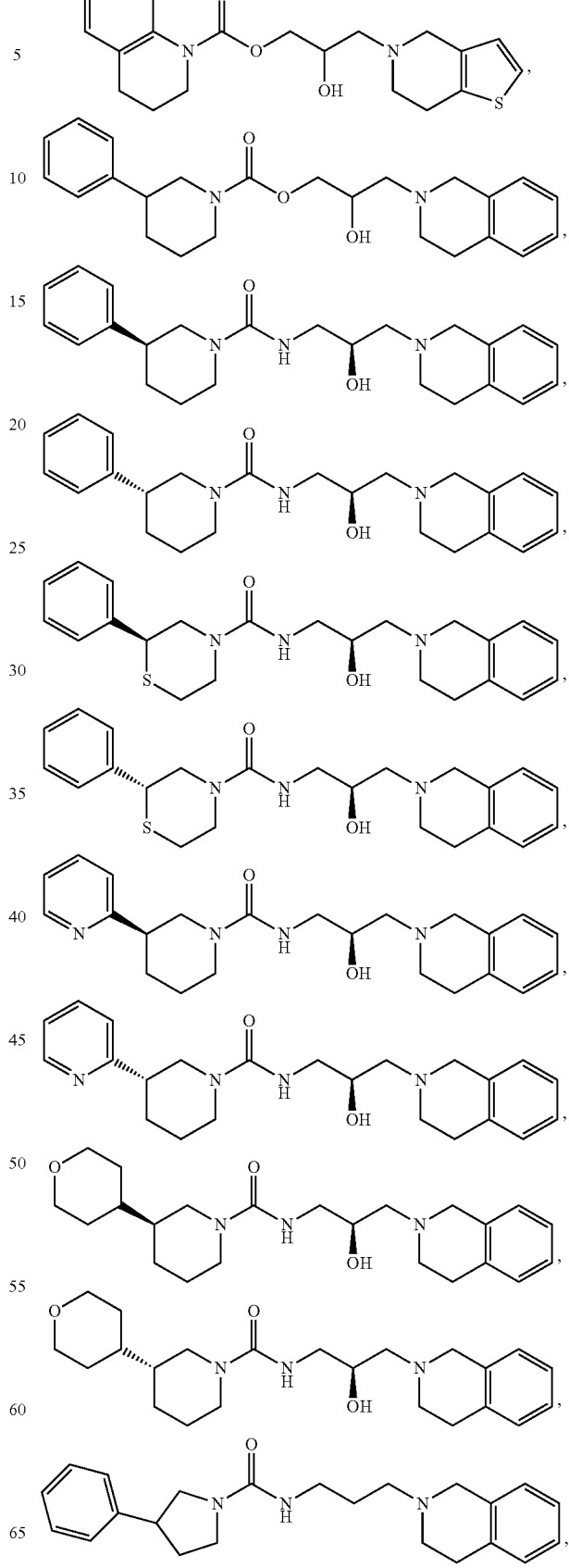

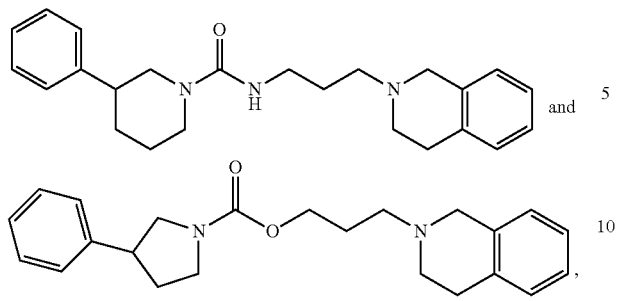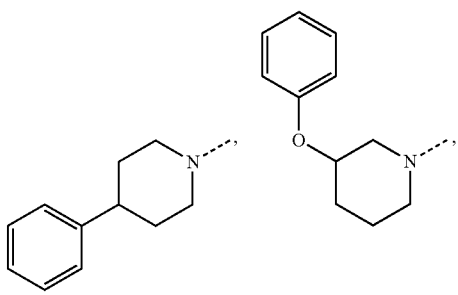

or a salt, solvate or hydrate thereof.

15. A compound according to claim 1, or a salt, solvate or hydrate thereof, wherein $R_7$ and $R_8$ are taken together with the intervening nitrogen atom to form a 4-7 membered heterocycloalkyl ring, wherein the 4 to 7 membered heterocycloalkyl ring is substituted with at least one $R_{10}$, where $R_{10}$ is $L_1$-$L_2$-$R_{11}$ or $L_2$-$L_1$-$R_{11}$, where $L_1$ is a linker of the formula —$[CR_{12}R_{13}]_n$—, where n is an integer of from 0 to 3 and $R_{12}$ and $R_{13}$ are in each instance each independently selected from H or $C_1$ to $C_2$ alkyl, and where $L_2$ is absent or a linker that is selected from O, C(O) or N(R'), where R' is H or $C_1$ to $C_2$ alkyl, and $R_{11}$ is —S(=O)$_2$R$_d$, $C_{6-12}$ aryl, 3-10 membered heterocycloalkyl or $C_{5-12}$ heteroaryl, wherein the $C_{6-12}$ aryl, 3-10 membered heterocycloalkyl and/or $C_{5-12}$ heteroaryl is optionally substituted with one or more $R_{14}$.

16. A compound according to claim 1, or a salt, solvate or hydrate thereof, wherein $R_7$ and $R_8$ are taken together with the intervening nitrogen atom to form a 4-7 membered heterocycloalkyl ring, wherein the 4 to 7 membered heterocycloalkyl ring is fused to at least one $C_{6-12}$ aryl or $C_{5-12}$ heteroaryl; wherein the $C_{6-12}$ aryl and/or $C_{5-12}$ heteroaryl is optionally substituted with one or more $R_{14}$.

17. A compound according to claim 1, or a salt, solvate or hydrate thereof, wherein $R_7$ and $R_8$ are taken together with the intervening nitrogen atom to form a group selected from:

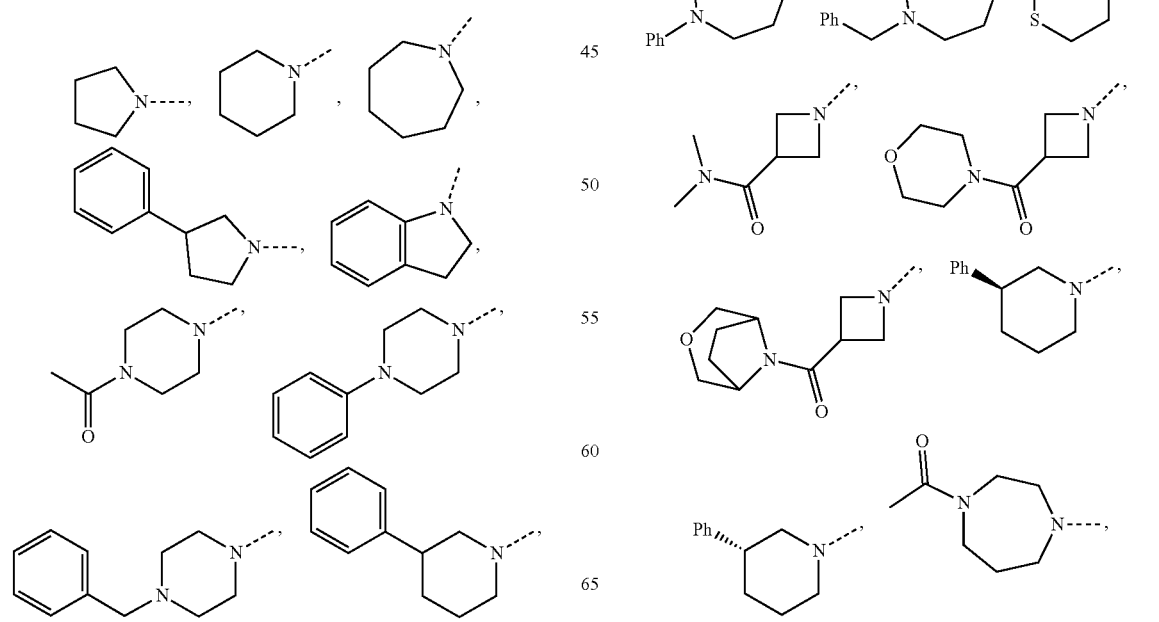

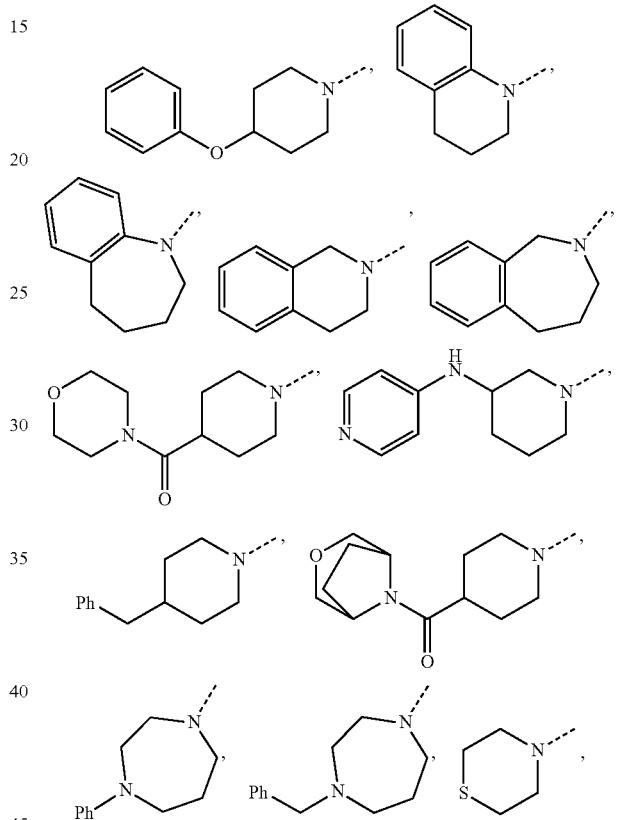

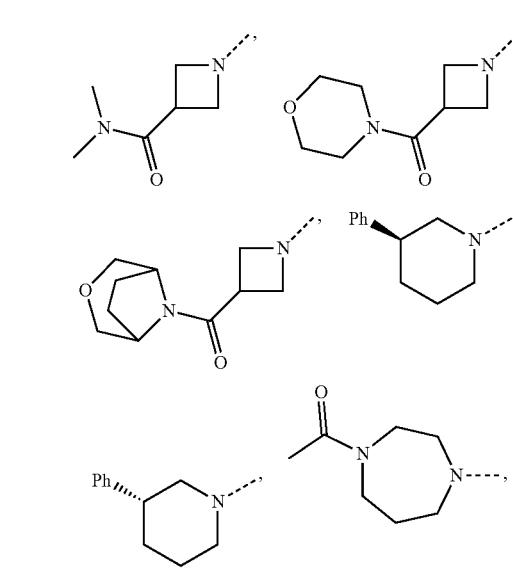

221
-continued
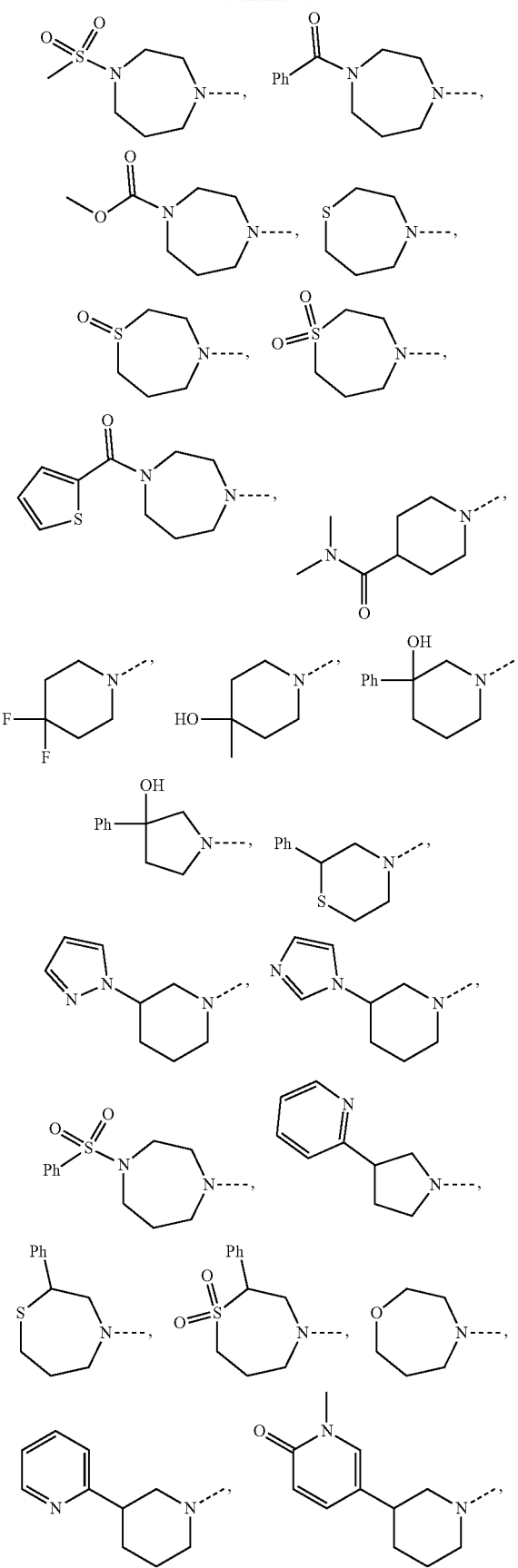
222
-continued
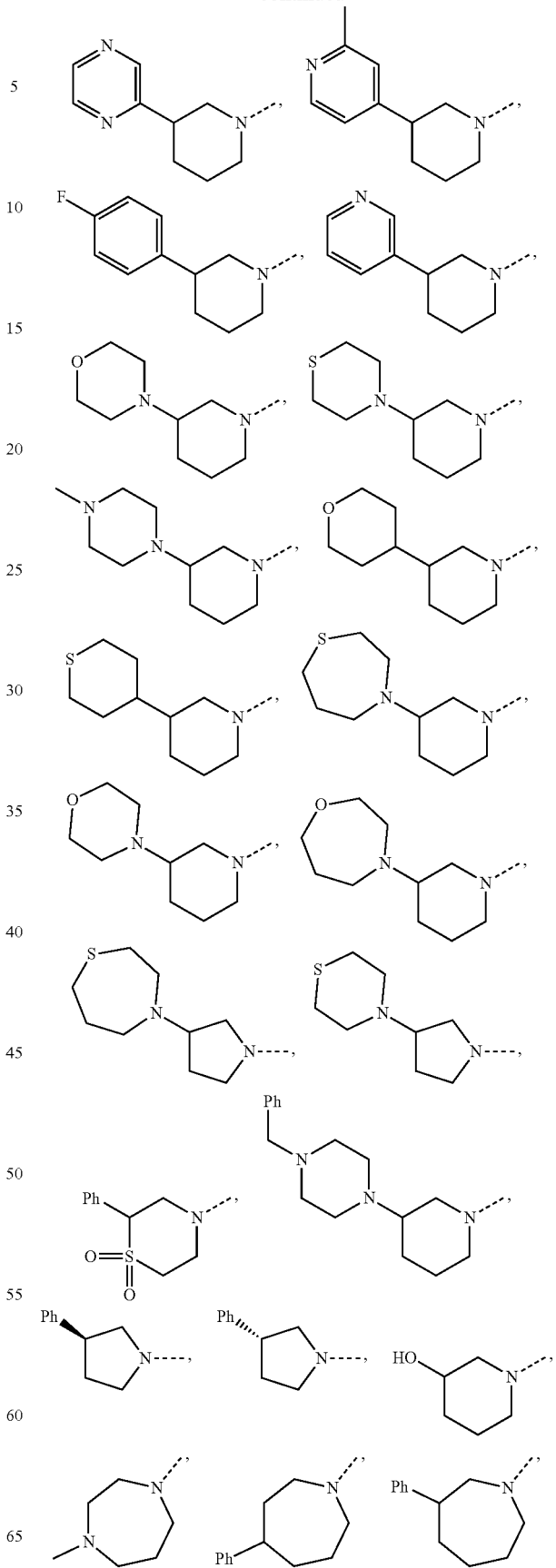

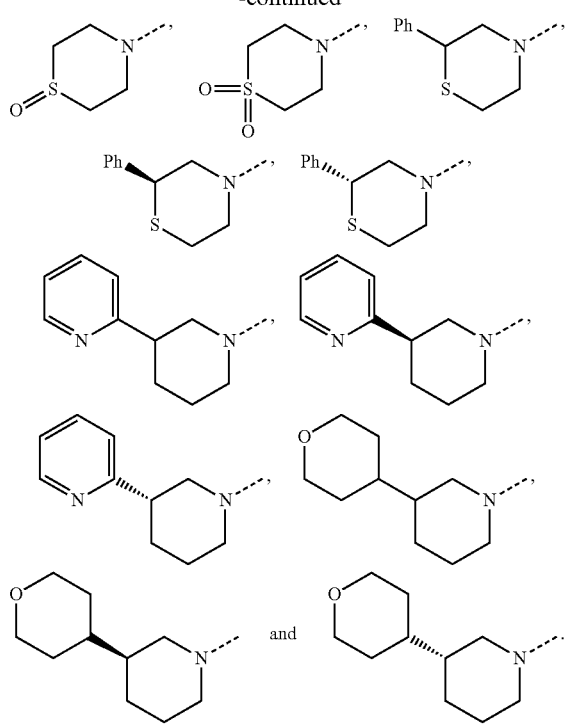

18. A pharmaceutical composition which comprises a compound according to claim 1, or a pharmaceutically acceptable salt, hydrate or solvate thereof, and one or more pharmaceutically acceptable excipients.

19. A method of treating a PRMT5-mediated disorder, said method comprising administering to a subject in need thereof an effective amount of a compound according to claim 1, or a pharmaceutically acceptable salt, hydrate or solvate thereof.

20. A compound of formula I, or a salt, solvate or hydrate thereof,

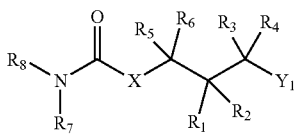

(I)

wherein, $R_1$, $R_3$, $R_4$, $R_5$ and $R_6$ are each hydrogen;
$R_2$ is OH;
X is O or $NR_9$, where $R_9$ is hydrogen or a $C_{1-3}$ alkyl;
$Y_1$ is

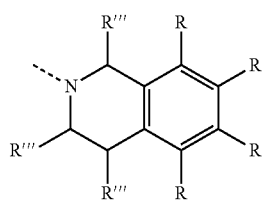

wherein each R and R''' is selected from H and $C_1$ to $C_3$ alkyl;

$R_7$ and $R_8$ are taken together with the intervening nitrogen atom to form a 3-12 membered heterocycloalkyl ring, wherein the 3-12 membered heterocycloalkyl ring is optionally substituted with one or more $R_{10}$; and/or optionally fused to one or more $C_{6-12}$ aryl, $C_{5-12}$ heteroaryl, $C_{3-8}$ cycloalkyl and 3-12 membered heterocycloalkyl rings, wherein each fused $C_{6-12}$ aryl, $C_{5-12}$ heteroaryl, $C_{3-8}$ cycloalkyl and 3-12 membered heterocycloalkyl ring is optionally substituted with one or more $R_{14}$;

$R_{10}$ is selected from a group of the formula $L_1$-$L_2$-$R_{11}$ or $L_2$-$L_1$-$R_{11}$, where $L_1$ is a linker of the formula —$[CR_{12}R_{13}]_n$—, where n is an integer of from 0 to 3 and $R_{12}$ and $R_{13}$ are in each instance each independently selected from H and $C_1$ to $C_2$ alkyl; wherein if $R_{10}$ is $C_{1-3}$akyl, the 3-12 member heterocycloalkyl ring is substituted with one $R_{10}$;

where $L_2$ is absent or a linker that is selected from O, S, SO, $SO_2$, N(R'), C(O), C(O)O, $[O(CH_2)r]d_s$, $[(CH_2)_rO]_s$, OC(O), CH(OR'), C(O)N(R'), N(R')C(O), N(R')C(O)N(R'), $SO_2N(R')$ or $N(R')SO_2$, where R' and R'' are each independently selected from hydrogen and a $C_1$ to $C_2$ alkyl, and where r is 1 or 2 and s is 1 to 4;

$R_{11}$ is independently selected from hydrogen, CN, $NO_2$, hydroxyl, =O, halogen, $C_{1-6}$ haloalkyl, $C_{1-6}$haloalkoxy, $C_{1-6}$ alkyl, O—$C_{1-6}$ alkyl, $C_{3-6}$ cycloalkyl, $C_{6-12}$ aryl, $C_{5-12}$ heteroaryl, 3-10 membered heterocycloalkyl, —C(=O)$R^d$, —C(=O)O$R^d$, —C(=O)N$R^e R^d$, —C(O)C(=O)$R^d$, —N$R^e R^d$, —N$R^e$C(=O)$R^d$, —N$R^e$C(=O)O$R^d$, —N$R^e$C(=O)N$R^e R^d$, —N$R^e$S(=O)$_2 R^d$, —N$R^e$S(=O)$_2$N$R^e R^d$, —O$R^d$, —S$R^d$, —OC(=O)$R^d$, —OC(=O)N$R^e R^d$, —OC(=O)O$R^d$, —S(=O)$_2 R^d$, —S(=O)$R^d$, —OS(=O)$R^d$, —OS(=O)$_2 R^d$, —OS(=O)$_2$O$R^d$, —S(=O)N$R^e R^d$, —OS(=O)$_2$N$R^e R^d$, and —S(=O)$_2$N$R^e R^d$, wherein, where $R_{11}$ is independently selected from $C_{3-6}$ cycloalkyl, $C_{6-12}$ aryl, $C_{5-12}$ heteroaryl and 3-10 membered heterocycloalkyl, each $C_{3-6}$ cycloalkyl, $C_{6-12}$ aryl, $C_{5-12}$ heteroaryl and 3-10 membered heterocycloalkyl is optionally substituted with one or more $R_{14}$;

each $R^a$ and $R^b$ is independently selected from hydrogen and $C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, =O, halogen, CN, CO$R^a$, N$R^a R^b$, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl;

each $R^e$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl; or $R^e$ and $R^d$, when attached to the same atom, together with the atom to which they are attached form a 3-7 membered heterocycloalkyl ring, optionally substituted with one or more substituent selected from hydroxyl, =O, halogen, CN, CO$R^a$, N$R^a R^b$, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; and $R^{14}$ is independently selected from halo, CN, $NO_2$, hydroxyl, =O, halogen, $C_{1-6}$ haloalkyl, $C_{1-6}$ haloalkoxy, $C_{1-6}$ alkyl, O—$C_{1-6}$ alkyl, $C_{3-6}$ cycloalkyl, $C_{6-12}$ aryl, 5-6 membered heteroaryl, 3-7 membered heterocycloalkyl, $C_{1-6}$alkyl$C_{6-12}$aryl, —C(=O)$R^d$, —C(=O)O$R^d$, —C(=O)N$R^e R^d$, —C(O)C(=O)$R^d$, —NR$^e$R$^d$, —NR$^e$C(=O)R$^d$, —NR$^e$C(=O)OR$^d$, —NR$^e$C(=O)NR$^e$R$^d$, —NR$^e$S(=O)$_2$R$^d$, —NR$^e$S(=O)$_2$NR$^e$R$^d$, —OR$^d$, —SR$^d$, —OC(=O)R$^d$, —OC(=O)NR$^e$R$^d$, —OC(=O)OR$^d$, —S(=O)$_2$R$^d$, —S(=O)R$^d$, —OS(=O)R$^d$, —OS(=O)$_2$R$^d$, —OS(=O)$_2$OR$^d$, —S(=O)NR$^e$R$^d$, —OS(=O)$_2$NR$^e$R$^d$, and —S(=O)$_2$NR$^e$R$^d$.

\* \* \* \* \*